United States Patent
Zheng et al.

(10) Patent No.: US 11,905,564 B2
(45) Date of Patent: *Feb. 20, 2024

(54) METHODS FOR THE DETECTION OF CERVICAL CANCER AND CERVICAL INTRAEPITHELIAL NEOPLASIA

(71) Applicant: The United States of America, As Represented by the Secretary, Department of Health and Human Services, Bethesda, MD (US)

(72) Inventors: Zhi-Ming Zheng, Rockville, MD (US); Junfen Xu, Frederick, MD (US); Jun Zhu, Potomac, MD (US); Yanqin Yang, Bethesda, MD (US); Xiaohong Wang, Germantown, MD (US)

(73) Assignee: The United States of America, as Represented by the Secretary, Department of Health and Human Services, Bethesda, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/816,656

(22) Filed: Aug. 1, 2022

(65) Prior Publication Data

US 2023/0122007 A1 Apr. 20, 2023

Related U.S. Application Data

(63) Continuation of application No. 16/595,564, filed on Oct. 8, 2019, now abandoned, which is a continuation of application No. 15/270,774, filed on Sep. 20, 2016, now Pat. No. 10,487,365.

(51) Int. Cl.
C12Q 1/6886 (2018.01)

(52) U.S. Cl.
CPC ...... *C12Q 1/6886* (2013.01); *C12Q 2600/112* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 6,399,364 B1 | 6/2002 | Reeve et al. | |
| 6,582,908 B2 | 6/2003 | Fodor et al. | |
| 7,526,387 B2 | 4/2009 | Baker et al. | |
| 7,659,062 B2 | 2/2010 | Santin | |
| 7,927,795 B2 | 4/2011 | Santin | |
| 7,939,261 B2 | 5/2011 | Baker et al. | |
| 7,939,263 B2 | 5/2011 | Clarke et al. | |
| 7,943,306 B2 | 5/2011 | Chang et al. | |
| 8,110,358 B2 | 2/2012 | Liew | |
| 8,669,058 B2 | 3/2014 | Liew | |
| 8,741,574 B2 | 6/2014 | Ried et al. | |
| 8,855,941 B2 | 10/2014 | Noguchi et al. | |
| 10,487,365 B2 | 11/2019 | Zheng et al. | |
| 2003/0225528 A1 | 12/2003 | Baker et al. | |
| 2007/0141618 A1 | 6/2007 | Dressman et al. | |
| 2008/0227663 A1 | 9/2008 | Tisone et al. | |
| 2008/0286781 A1 | 11/2008 | Monahan et al. | |
| 2009/0136486 A1 | 5/2009 | Pyeon et al. | |
| 2009/0215054 A1 | 8/2009 | Carter et al. | |
| 2010/0316990 A1 | 12/2010 | Dynan et al. | |
| 2011/0244459 A1 | 10/2011 | Bertucci et al. | |
| 2012/0015827 A1 | 1/2012 | Wirtz | |
| 2012/0129705 A1 | 5/2012 | Iftner et al. | |
| 2013/0102488 A1 | 4/2013 | Barrie et al. | |
| 2013/0190197 A1 | 7/2013 | Liew | |
| 2013/0280258 A1 | 10/2013 | D'Andrea et al. | |
| 2014/0024539 A1 | 1/2014 | Craig et al. | |
| 2014/0162254 A1 | 6/2014 | Miller et al. | |
| 2014/0235479 A1 | 8/2014 | Depinho et al. | |
| 2014/0342946 A1 | 11/2014 | Kuriakose et al. | |
| 2015/0051103 A1 | 2/2015 | Barrie et al. | |

OTHER PUBLICATIONS

Chen et al (Biomedicine & Pharmacotherapy. May 2015. 72: 83-90 (Year: 2015).

Xu et al RNA. May 2015. The Twentieth Annual Meeting of the RNA Society, Abstract 178, available via URL kmasociety.org/wp-content/uploads/2015/05/RNA-2015-Abstract-Book-print-150505.pdf> (Year: 2015).

Xu et al., "Genome-Wide Profiling of Cervical RNA-Binding Proteins Identifies Human Papillomavirus Regulation of RNASEH2A Expression by Viral E7 and E2F1", American Society for Microbiology, vol. 10, No. 1, Jan./Feb. 2019, 16 pages.

Liu, H. et al.; "HPV oncoproteins promote expression of long noncoding RNA lnc-FANCI-2 via YY1 and miR-29A"; presented at "DNA 2018. Molecular Biology of DNA Tumor Viruses Conference", held Jul. 31-Aug. 4, 2018., Schedule Available via URL: <conferences.union.wisc.edu/dna/program-info/schedule/>, printed on Jan. 19, 2021. (Year: 2021); 17 pages.

Fu et al Med Sci Manito. May 2015. 21: 1276-1287 (Year: 2015).

Gibb et al Int J Gynecol Cancer. 2012. 22: 1557-1563 (Year: 2012).

Camargo et al.; "GWAS Reveals New Recessive Loci Asociated with Non-syndromic Facial Clefting"; Eur J Med Genet.; 55(10); pp. 510-514; (2012).

Expression of GLB1L2 in cancer—Summary—The Human Protein Atlas; printed May 6, 2015; 1 page; http://www.t>roteinatlas.org/ENSG0OOO0 149328-GLB 1 L2/cancer.

Flanagan et al.; "Genomics Screen in Transformed Stem Cell Reveals RNASEH2A, PPAP2C, and ADARB1 as Putative Anticancer Drug Targets"; Mal Cancer Ther; 8(1 ); pp. 249-260; (2009).

(Continued)

*Primary Examiner* — Carla J Myers

(74) *Attorney, Agent, or Firm* — McDonnell Boehnen Hulbert & Berghoff LLP

(57) ABSTRACT

Described herein are biomarkers for HPV-associated precancers and cancers such as cervical cancer and cervical intraepithelial neoplasia. The RNA binding protein (RBP) and long-noncoding RNA (lnc-RNA) biomarkers can be detected and used to diagnose HPV-associated pre-cancers and cancers. In addition, early diagnosis of HPV-associated pre-cancers and cancers can facilitate therapeutic intervention in patients, particularly in the pre-cancer stage which can delay or prevent progression to cancer.

12 Claims, 11 Drawing Sheets
(2 of 11 Drawing Sheet(s) Filed in Color)

Specification includes a Sequence Listing.

(56) References Cited

OTHER PUBLICATIONS

Itoh et al.; "Role of Growth Factor Receptor—Bound Protein 7 in Hepatocellular Carcinoma"; Mal Cancer Res; 5(7); t>p. 667-673; (2007).

Nadler et al.; "Growth Factor Receptor-bound Protein-7 (Grb7) as a Prognostic Marker and Therapeutic Target in Breast Cancer"; Annals of Oncology; 21; pp. 466-473; (2010).

Takahashi et al.; Manuscript: Significance of Polypyrimidine Tract Binding Protein 1 Expression in Colorectal Cancer; Published OnlineFirst Apr. 22, 2015; DOI: 10.1158/1535-7163.MCT-14-0142; 50 pages (2015)_downloaded from met. iiacrjournals.org on Apr. 24, 2015.

Wang et al.; "Differential Functions of Growth Factor Receptor-Bound Protein 7 (GRB7) and Its Variant GRB7v in Pvarian Carcinogenesis"; Clin Cancer Res; 16; pp. 2529-2539; (2010).

Williams et al_; "A Systems Genetics Approach Identifies CXCL 14, ITGAX, and LPCAT2 as Novel Aggressive Prostate Cancer Susceptibility Genes"; PLoS Genet; 10(11): e1004809; 15 pages; (2014).

Yang et al.; "Identification of Genes with Correlated Patterns oNariations in DNA Copy Number and Gene Expression Level in Gastric Cancer"; Genomics; 89; pp. 451-459; (2007).

Zhang et al.; "High Expression of Neuro-Oncological Ventral Antigen 1 Correlates with Poor Prognosis in Hepatocellular Carcinoma"; PLoS ONE; 9(3); c90955; 11 pages (2014).

Liu et al. PNAS. Jan. 13, 2021. 118(3) e2014195118, p. 1-12 and Supplementary Methods p. 1-19 (Year: 2021).

Sigma-Aldrich (qPCR Technical Guide. 2008 Available via url: <gene-quantification.com/SIAL-qPCR-Technical-Guide.pdf> (Year: 2008).

Schedule for the meeting "DNA 2018. Molecular Biology of DNA Tumor Viruses Conference", held Jul. 31-Aug. 4, 2018., available via URL: <conferences.union .wisc.edu/dna/program-info/schedule/>, printed on Jan. 19, 2021. (Year: 2021).

LncRNAWiki Database for Lnc-FANCI-2: 1, available via URL: <lncrna.big.ac.cn/index.php/Lnc-FANCI-2: 1 >, Oct. 2014 (Year: 2014).

lnc-Fanconi Anemia, Complementation Group I
lnc-β-Galactosidase-1-Like Protein 2

METHODS FOR THE DETECTION OF CERVICAL CANCER AND CERVICAL INTRAEPITHELIAL NEOPLASIA

CROSS-REFERENCE TO RELATED APPLICATIONS

This application is a continuation of U.S. application Ser. No. 16/595,564 filed on Oct. 8, 2019, which is a continuation of U.S. application Ser. No. 15/270,774 filed on Sep. 20, 2016, which are incorporated herein by reference in their entirety.

STATEMENT REGARDING FEDERALLY SPONSORED RESEARCH & DEVELOPMENT

This invention was made in part with government support from the National Institutes of Health. The government has certain rights in this invention.

REFERENCE TO AN ELECTRONIC SEQUENCE LISTING

A computer readable form of the Sequence Listing is filed with this application by electronic submission and is incorporated into this application by reference in its entirety. The sequence listing submitted herewith is contained in the file created Aug. 1, 2022, entitled "21-0945-US-CON2_SequenceListing.xml" and is 302 kilobytes in size.

FIELD OF THE DISCLOSURE

The present disclosure is related to novel polynucleotide biomarkers which can be detected and can be used for the diagnosis of HPV-associated pre-cancers and HPV-associated cancers such as cervical cancer and cervical intraepithelial neoplasia as well as methods of treatment of HPV-associated pre-cancers and HPV-associated cancers.

BACKGROUND

High-risk HPV persistent infection leads to the development of certain types of cancers in the cervix, anus, and oropharynx, for example. Fifteen mucosal HPV types are identified as oncogenic or high-risk (HR) HPVs, with HPV16 and HPV18 being particularly associated with invasive cervical cancer. Cervical cancer is the second most common cancer among women worldwide. Approximately 500,000 incident cases of cervical cancer and approximately 320,000 cervical cancer deaths are estimated each year and more than 80% of the cases arise in developing countries.

There is a need for diagnostic markers that can be detected and used for early diagnosis of high-risk HPV infection, HPV-associated pre-cancer and HPV-associated cancer and for the development of intervention strategies for treatment of HPV-induced cancers.

SUMMARY

In one aspect, a method of determining if a test patient has stage 1, stage 2, or stage 3 cervical intraepithelial neoplasia or cervical cancer comprises
determining an expression level of a first polynucleotide biomarker in a sample containing cells from the test patient's cervix with one or more first polynucleotides that hybridizes to the first polynucleotide biomarker, wherein the first polynucleotide biomarker is lnc-FANCI-2, lnc-GLB1L2-1, GRB7 (SEQ ID NOs: 8-11 and 94), NOVA1 (SEQ ID NOs: 14, 15 and 95), RNASEH2A (SEQ ID NO: 19), CDKN2A (SEQ ID NOs: 1-4), ELAVL2 (SEQ ID NOs: 5-7), HSPB1 (SEQ ID NO: 12), KHSRP (SEQ ID NO: 13), PTBP1 (SEQ ID NOs: 16-18), or a combination thereof,
correlating the expression level of the first polynucleotide biomarker in the sample containing cells from the test patient's cervix to a reference expression level of the first polynucleotide biomarker in a reference sample, wherein the reference sample is
  a control sample from a patient or patients with no evidence of cervical cancer,
  a control sample from a cervical cancer patient or patients, or
  a control sample from a patient or patients with stage 1, stage 2, or stage 3 cervical intraepithelial neoplasia, and
determining, based on said correlation, if the test patient has cervical cancer, or stage 1, stage 2, or stage 3 cervical intraepithelial neoplasia.

In another aspect, the method of determining if a test patient has stage 1, stage 2, or stage 3 cervical intraepithelial neoplasia or cervical cancer comprises
determining an expression level of a first polynucleotide biomarker in a sample containing cells from the test patient's cervix with one or more first polynucleotides that hybridizes to the first polynucleotide biomarker, wherein the first polynucleotide biomarker is GRB7 (SEQ ID NOs: 8-11 and 84), NOVA1 (SEQ ID NOs: 14, 15 and 95), RNASEH2A (SEQ ID NO: 19), or a combination thereof, and/or
determining an expression level of a second polynucleotide biomarker in the sample containing cells from the test patient's cervix with one or more second polynucleotides that hybridizes to the second polynucleotide biomarker, wherein the second polynucleotide biomarker is lnc-FANCI-2, lnc-GLB1L2-1, or a combination thereof.

In a further aspect, a method of quantitating an expression level of a first polynucleotide biomarker in a sample containing cells from a test patient's cervix with one or more first polynucleotides that hybridizes to the first polynucleotide biomarker comprises
contacting the sample containing cells from test patient's cervix with the one or more first polynucleotides, and
detecting the level of hybridization of the one or more first polynucleotides to the first polynucleotide biomarker, wherein the first polynucleotide biomarker is lnc-FANCI-2, lnc-GLB1L2-1, GRB7 (SEQ ID NOs: 8-11 and 94), NOVA1 (SEQ ID NOs: 14, 15 and 95), RNASEH2A (SEQ ID NO: 19), CDKN2A (SEQ ID NOs: 1-4), ELAVL2 (SEQ ID NOs: 5-7), HSPB1 (SEQ ID NO: 12), KHSRP (SEQ ID NO: 13), PTBP1 (SEQ ID NOs: 16-18), or a combination thereof.

In a yet further aspect, a method of treating a test patient in need of treatment for stage 1, stage 2, or stage 3 cervical intraepithelial neoplasia or cervical cancer comprises
determining an expression level of a first polynucleotide biomarker in a sample containing cells from the test patient's cervix with one or more first polynucleotides that hybridizes to the first polynucleotide biomarker, wherein the first polynucleotide biomarker is lnc-FANCI-2, lnc-GLB1L2-1, GRB7 (SEQ ID NOs: 8-11 and 94), NOVA1 (SEQ ID NOs: 14, 15 and 95), RNASEH2A (SEQ ID NO: 19), CDKN2A (SEQ ID NOs: 1-4), ELAVL2 (SEQ ID NOs: 5-7), HSPB1 (SEQ ID NO: 12), KHSRP (SEQ ID NO: 13), PTBP1 (SEQ ID NOs: 16-18), or a combination thereof,
correlating the expression level of the first polynucleotide biomarker in the sample containing cells from the test patient's cervix to a reference expression level of the first polynucleotide biomarker in a reference sample, wherein the reference sample is
a control sample from a patient or patients with no evidence of cervical cancer,
a control sample from a cervical cancer patient or patients, or
a control sample from a patient or patients with stage 1, stage 2, or stage 3 cervical intraepithelial neoplasia, and
administering a therapeutic intervention for the treatment of stage 1, stage 2, or stage 3 cervical intraepithelial neoplasia, or cervical cancer when it is determined, based on said expression levels, that the test patient has stage 1, stage 2, or stage 3 cervical intraepithelial neoplasia.

In a still further aspect, a method of determining if a test patient has an HPV-associated pre-cancer or an HPV-associated cancer comprises
determining an expression level of a first polynucleotide biomarker in a sample containing cells from a tissue of the test patient with one or more first polynucleotides that hybridizes to the first polynucleotide biomarker,
correlating the expression level of the first polynucleotide biomarker in the sample containing cells from the tissue of the test patient to a reference expression level of the first polynucleotide biomarker in a reference sample, wherein the reference sample is
a control sample from a patient or patients with no evidence of HPV-associated pre-cancer or HPV-associated cancer,
a control sample from a patient or patients with HPV-associated pre-cancer, or
a control sample from a patient or patients with HPV-associated cancer, and
determining, based on said correlation, if the test patient has HPV-associated pre-cancer or HPV-associated cancer,
wherein the first polynucleotide biomarker is lnc-FANCI-2, lnc-GLB1L2-1, GRB7 (SEQ ID NOs: 8-11 and 94), NOVA1 (SEQ ID NOs: 14, 15 and 95), RNASEH2A (SEQ ID NO: 19), CDKN2A (SEQ ID NOs: 1-4), ELAVL2 (SEQ ID NOs: 5-7), HSPB1 (SEQ ID NO: 12), KHSRP (SEQ ID NO: 13), PTBP1 (SEQ ID NOs: 16-18), or a combination thereof.

In another aspect, a method of quantitating an expression level of a first polynucleotide biomarker in a sample containing cells from a tissue of the test patient with one or more first polynucleotides that hybridizes to the first polynucleotide biomarker comprises
contacting the sample containing cells from a tissue of the test patient with the one or more first polynucleotides, and
detecting the level of hybridization of the one or more first polynucleotides to the first polynucleotide biomarker,
wherein the first polynucleotide biomarker lnc-FANCI-2, lnc-GLB1L2-1, is GRB7 (SEQ ID NOs: 8-11 and 94), NOVA1 (SEQ ID NOs: 14, 15 and 95), RNASEH2A (SEQ ID NO: 19), CDKN2A (SEQ ID NOs: 1-4), ELAVL2 (SEQ ID NOs: 5-7), HSPB1 (SEQ ID NO: 12), KHSRP (SEQ ID NO: 13), PTBP1 (SEQ ID NOs: 16-18), or a combination thereof.

In a yet further aspect, a method of treating a test patient in need of treatment for an HPV-associated pre-cancer or an HPV-associated cancer comprises
determining an expression level of a first polynucleotide biomarker in a sample containing cells from a tissue of the test patient with one or more first polynucleotides that hybridizes to the first polynucleotide biomarker,
correlating the expression level of the first polynucleotide biomarker in the sample containing cells from the tissue of the test patient to a reference expression level of the first polynucleotide biomarker in a reference sample, wherein the reference sample is
a control sample from a patient or patients with no evidence of HPV-associated pre-cancer or HPV-associated cancer,
a control sample from a patient or patients with HPV-associated pre-cancer, or
a control sample from a patient or patients with HPV-associated cancer, and
administering a therapeutic intervention for the treatment of HPV-associated pre-cancer or HPV-associated cancer when it is determined, based on said expression levels, that the test patient has HPV-associated pre-cancer or an HPV-associated cancer, wherein the first polynucleotide biomarker is lnc-FANCI-2, lnc-GLB1L2-1, GRB7 (SEQ ID NOs: 8-11 and 94), NOVA1 (SEQ ID NOs: 14, 15 and 95), RNASEH2A (SEQ ID NO: 19), CDKN2A (SEQ ID NOs: 1-4), ELAVL2 (SEQ ID NOs: 5-7), HSPB1 (SEQ ID NO: 12), KHSRP (SEQ ID NO: 13), PTBP1 (SEQ ID NOs: 16-18), or a combination thereof.

BRIEF DESCRIPTION OF THE DRAWINGS

The patent or application file contains at least one drawing executed in color. Copies of this patent or patent application publication with color drawings will be provided by the Office upon receipt and payment of the necessary fee.

Figure 1:
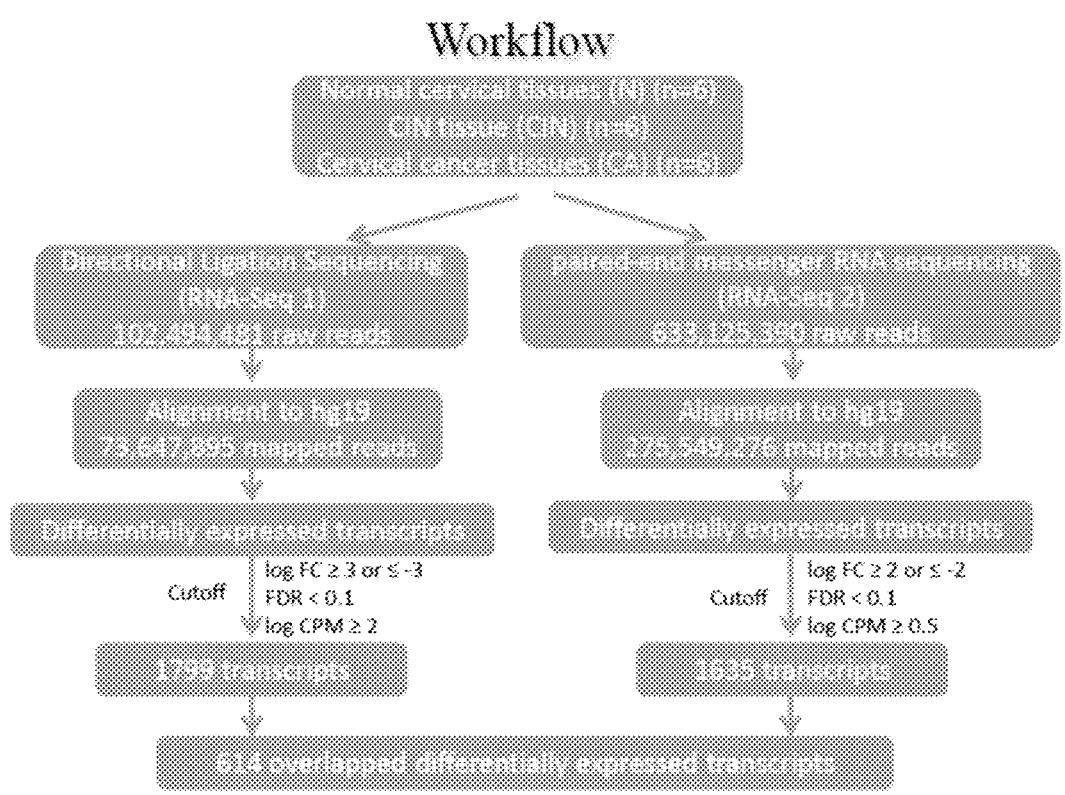
FIG. 1 is a flowchart of the RNA-sequencing (RNA-Seq) analyses for RNA-binding proteins (RBPs).

The above-described and other features will be appreciated and understood by those skilled in the art from the following detailed description, drawings, and appended claims.

DETAILED DESCRIPTION

Using an RNA-sequencing (RNA-Seq) approach, the inventors of the present application examined seven normal cervical tissues and seven cervical cancer tissues for their expression landscapes of approximately 19,000 coding and 113,513 noncoding RNAs. 614 differentially expressed coding transcripts enriched in cancer related pathways were identified, with 95 of them encoding RNA-binding proteins (RBPs) from the analyzed 1502 human RBPs. Moreover, 209 differentially, abundantly expressed long-noncoding RNAs (lnc-RNAs) from normal cervix to cervical cancer were identified. Validation of the altered expression of 26 candidates, including 8 RBP genes by using TaqMan® real-time PCR in a cohort of 47 human cervical tissue samples, including 24 normal cervical tissues and 23 cervical cancer tissues, showed that they are broadly involved in cervical carcinogenesis. Many of the identified RBP candidates had not been previously reported. Using human vaginal keratinocyte-derived raft culture tissues with or without HPV16 and HPV18 infection, it was further corroborated that these RBP candidates, including CDKN2A, ELAVL2, GRB7, HSPB1, KHSRP, PTBP1, RNASEH2A, and NOVA1, are regulated by HPV infection. Further, the inventors found that lnc-FANCI-2 was increasingly expressed along with cervical lesion progression from cervical intraepithelial neoplasia (CIN) to cervical cancer, when compared to the normal tissues. In contrast, lncGLB1L2-1 was gradually decreased along with the lesion progression, when compared to the normal tissues. In addition, FAM83A, SEMA3F, CLDN10, ASRGL1, which are not RBPs, were also found to have altered expression in cervical cancer compared to normal tissue, with FAM83A and SEMA3F being increased in cervical cancer and CLDN10 and ASRGL1 being decreased in cervical cancer. The results presented herein provide the first comprehensive expression atlas of RBPs and lnc-RNAs in normal cervix and cervical cancer, which can be detected to provide better diagnosis and treatment of patients with cervical cancer.

More specifically, an increase of lnc-FANCI-2 RNA, including all of its 35 isoforms, and a decrease of lnc-GLB1L2-1, including its 21 isoforms, were identified in cervical cancer. Fanconi anemia (FA) frequently develops squamous cell carcinoma at sites that are associated with HPV-driven cancer including the female reproductive tract, and is caused by mutations in one of 15 genes in the FA pathway (including FANCA, FANCD2, and FANCI). Loss of FA pathway components FANCA and FANCD2 stimulates E7 protein accumulation in human keratinocytes, and loss of FANCD2 stimulates HPV DNA replication. Both FANCI and lnc-FANCI-2 are expressed from the same location at chromosome 15q26.1. Further, both GLB1L2 (galactosidase, beta 1-like 2) and lnc-GLB1L2-1 are expressed from Chromosome 11q25, with unknown function in cancer development. By using TaqMan® qRT-PCR validation of lnc-FANCI-2 and lnc-GLB1L2-1 in 24 normal, 25 CIN 2-3, and 23 cervical cancer tissues, it was confirmed that altered expression of these lnc-RNAs is remarkably related to cervical lesion progression from CIN to cancer. Moreover, the altered changes of lnc-FANCI-2 could be attributed to HPV16 and HPV18 infection in raft cultures and viral E7 expression. These lnc-RNAs are biomarkers for early diagnosis of high-risk HPV infection with high risk of progression and for development of intervention strategies to treat HPV-induced cancers.

As used herein, a non-coding RNA (ncRNA) is an RNA transcript that does not encode a protein. ncRNAs include short ncRNAs and long ncRNAs (lnc-RNAs). Short ncRNAs are ncRNAs that are generally 18-200 nucleotides (nt) in length. Examples of short ncRNAs include, but are not limited to, microRNAs (miRNAs), piwi-associated RNAs (piRNAs), short interfering RNAs (siRNAs), promoter-associated short RNAs (PASRs), transcription initiation RNAs (tiRNAs), termini-associated short RNAs (TASRs), antisense termini associated short RNAs (aTASRs), small nucleolar RNAs (snoRNAs), transcription start site antisense RNAs (TSSa-RNAs), small nuclear RNAs (snRNAs), retroposon-derived RNAs (RE-RNAs), 3'UTR-derived RNAs (uaRNAs), x-ncRNA, human Y RNA (hY RNA), unusually small RNAs (usRNAs), small NF90-associated RNAs (snaRs), vault RNAs (vtRNAs), small Cajal body-specific RNAs (scaRNAs), and telomere specific small RNAs (tel-sRNAs). lnc-RNAs are cellular RNAs, exclusive of rRNAs, greater than 200 nucleotides in length and having no obvious protein-coding capacity. Lnc-RNAs include, but are not limited to, large or long intergenic ncRNAs (lincR-NAs), transcribed ultraconserved regions (T-UCRs), pseudogenes, GAA-repeat containing RNAs (GRC-RNAs), long intronic ncRNAs, antisense RNAs (aRNAs), promoter-associated long RNAs (PALRs), promoter upstream transcripts (PROMPTs), and long stress-induced non-coding transcripts (LSINCTs).

An RNA-binding protein is a protein that binds single or double stranded RNA to form ribonucleoprotein complexes. RBPs contain conserved structural motifs such as the RNA recognition motif (RRM), dsRNA binding domain, zinc finger domain, and others.

The biomarkers for detection and diagnosis of CIN and cervical cancer include the RBP and lnc-RNA biomarkers of Tables 1-3:

TABLE 1

RBP biomarkers

| SEQ ID NO: | chr | start | end | refseqID | Symbol | description |
|---|---|---|---|---|---|---|
| 1 | chr9 | 21967750 | 21975132 | NM_000077 | CDKN2A | cyclin-dependent kinase inhibitor 2A (CDKN2A), transcript variant 1, mRNA. |
| 2 | chr9 | 21967750 | 21975132 | NM_001195132 | CDKN2A | *Homo sapiens* cyclin-dependent kinase inhibitor 2A (CDKN2A), transcript variant 5, mRNA. |
| 3 | chr9 | 21967750 | 21994490 | NM_058195 | CDKN2A | cyclin-dependent kinase inhibitor 2A (CDKN2A), transcript variant 4, mRNA. |
| 4 | chr9 | 21967750 | 21974826 | NM_058197 | CDKN2A | cyclin-dependent kinase inhibitor 2A (CDKN2A), transcript variant 3, mRNA. |
| 5 | chr9 | 23690102 | 23821843 | NM_001171195 | ELAVL2 | *Homo sapiens* ELAV (embryonic lethal, abnormal vision, *Drosophila*)-like 2 (Hu antigen B) (ELAVL2), transcript variant 2, mRNA. |
| 6 | chr9 | 23690102 | 23821478 | NM_001171197 | ELAVL2 | *Homo sapiens* ELAV (embryonic lethal, abnormal vision, *Drosophila*)-like 2 (Hu antigen B) (ELAVL2), transcript variant 3, mRNA. |
| 7 | chr9 | 23690102 | 23826063 | NM_004432 | ELAVL2 | ELAV (embryonic lethal, abnormal vision, *Drosophila*)-like 2 (Hu antigen B) (ELAVL2), transcript variant 1, mRNA. |
| 8 | chr17 | 37894575 | 37903538 | NM_001030002 | GRB7 | growth factor receptor-bound protein 7 (GRB7), transcript variant 2, mRNA. |
| 9 | chr17 | 37895023 | 37903538 | NM_001242442 | GRB7 | *Homo sapiens* growth factor receptor-bound protein 7 (GRB7), transcript variant 4, mRNA. |
| 10 | chr17 | 37896219 | 37903538 | NM_001242443 | GRB7 | *Homo sapiens* growth factor receptor-bound protein 7 (GRB7), transcript variant 3, mRNA. |
| 11 | chr17 | 37894161 | 37903538 | NM_005310 | GRB7 | growth factor receptor-bound protein 7 (GRB7), transcript variant 1, mRNA. |
| 94 | chr17 | | | NM_001330207.1 | GRB7 | growth factor receptor-bound protein 7 (GRB7), transcript variant 5, mRNA. |
| 12 | chr7 | 75931874 | 75933614 | NM_001540 | HSPB1 | heat shock 27 kDa protein 1 (HSPB1), mRNA. |
| 13 | chr19 | 6413118 | 6424822 | NM_003685 | KHSRP | KH-type splicing regulatory protein (KHSRP), mRNA. |
| 14 | chr14 | 26915088 | 27066960 | NM_002515 | NOVA1 | neuro-oncological ventral antigen 1 (NOVA1), transcript variant 1, mRNA. |
| 15 | chr14 | 26915088 | 27066960 | NM_006489 | NOVA1 | neuro-oncological ventral antigen 1 (NOVA1), transcript variant 2, mRNA. |
| 95 | chr14 | | | NM_006491.2 | NOVA1 | neuro-oncological ventral antigen 1 (NOVA1), transcript variant 3, mRNA. |
| 16 | chr19 | 797391 | 812327 | NM_002819 | PTBP1 | polypyrimidine tract binding protein 1 (PTBP1), transcript variant 1, mRNA. |
| 17 | chr19 | 797391 | 812327 | NM_031990 | PTBP1 | polypyrimidine tract binding protein 1 (PTBP1), transcript variant 2, mRNA. |
| 18 | chr19 | 797391 | 812327 | NM_031991 | PTBP1 | polypyrimidine tract binding protein 1 (PTBP1), transcript variant 3, mRNA. |
| 19 | chr19 | 12917427 | 12924462 | NM_006397 | RNASEH2A | ribonuclease H2, subunit A (RNASEH2A), mRNA. |

TABLE 2 lnc-FANCI-2 isoforms

| Transcript ID | SEQ. ID NO: | Location (hg19) | Length |
|---|---|---|---|
| lnc-FANCI-2: 1 | 20 | chr15: 89904810-89938553 | 1613 |
| lnc-FANCI-2: 10 | 21 | chr15: 89921280-89938544 | 606 |
| lnc-FANCI-2: 11 | 22 | chr15: 89921331-89938354 | 551 |
| lnc-FANCI-2: 12 | 23 | chr15: 89921347-89939471 | 1877 |
| lnc-FANCI-2: 13 | 24 | chr15: 89921362-89938500 | 561 |
| lnc-FANCI-2: 14 | 25 | chr15: 89921794-89931745 | 786 |
| lnc-FANCI-2: 15 | 26 | chr15: 89922355-89938350 | 569 |
| lnc-FANCI-2: 16 | 27 | chr15: 89922468-89941720 | 3779 |
| lnc-FANCI-2: 17 | 28 | chr15: 89922495-89941719 | 3670 |
| lnc-FANCI-2: 18 | 29 | chr15: 89923111-89941720 | 3784 |
| lnc-FANCI-2: 19 | 30 | chr15: 89925731-89938271 | 779 |
| lnc-FANCI-2: 2 | 31 | chr15: 89904810-89938551 | 1611 |
| lnc-FANCI-2: 20 | 32 | chr15: 89929827-89939471 | 2718 |
| lnc-FANCI-2: 21 | 33 | chr15: 89930671-89941720 | 3723 |

TABLE 2-continued lnc-FANCI-2 isoforms

| Transcript ID | SEQ. ID NO: | Location (hg19) | Length |
|---|---|---|---|
| lnc-FANCI-2: 22 | 34 | chr15: 89904810-89941718 | 4778 |
| lnc-FANCI-2: 23 | 35 | chr15: 89911330-89941718 | 4113 |
| lnc-FANCI-2: 24 | 36 | chr15: 89911399-89941721 | 3936 |
| lnc-FANCI-2: 25 | 37 | chr15: 89912393-89941683 | 4026 |
| lnc-FANCI-2: 26 | 38 | chr15: 89921102-89941708 | 4334 |
| lnc-FANCI-2: 27 | 39 | chr15: 89921273-89941718 | 3868 |
| lnc-FANCI-2: 28 | 40 | chr15: 89922232-89941683 | 3978 |
| lnc-FANCI-2: 29 | 41 | chr15: 89923021-89941683 | 3837 |
| lnc-FANCI-2: 3 | 42 | chr15: 89905705-89922463 | 571 |
| lnc-FANCI-2: 30 | 43 | chr15: 89929880-89941721 | 4915 |
| lnc-FANCI-2: 31 | 44 | chr15: 89930027-89941721 | 4687 |
| lnc-FANCI-2: 32 | 45 | chr15: 89930389-89931372 | 706 |
| lnc-FANCI-2: 33 | 46 | chr15: 89930557-89941683 | 3922 |
| lnc-FANCI-2: 34 | 47 | chr15: 89931724-89941721 | 3690 |
| lnc-FANCI-2: 35 | 48 | chr15: 89932071-89941708 | 4093 |
| lnc-FANCI-2: 4 | 49 | chr15: 89905718-89938562 | 957 |
| lnc-FANCI-2: 5 | 50 | chr15: 89911330-89941718 | 2124 |
| lnc-FANCI-2: 6 | 51 | chr15: 89912386-89931074 | 576 |
| lnc-FANCI-2: 7 | 52 | chr15: 89918593-89941720 | 6547 |
| lnc-FANCI-2: 8 | 53 | chr15: 89921220-89941692 | 3814 |
| lnc-FANCI-2: 9 | 54 | chr15: 89921273-89941718 | 4198 |

TABLE 3 lnc-GLB1L2-1 isoforms

| Transcript ID | SEQ ID NO: | Location (hg19) | Length |
|---|---|---|---|
| lnc-GLB1L2-1: 1 | 55 | chr11: 134306367-134337169 | 1402 bp |
| lnc-GLB1L2-1: 10 | 56 | chr11: 134350719-134372941 | 295 bp |
| lnc-GLB1L2-1: 11 | 57 | chr11: 134352524-134373110 | 374 bp |
| lnc-GLB1L2-1: 12 | 58 | chr11: 134306376-134375555 | 2737 bp |
| lnc-GLB1L2-1: 13 | 59 | chr11: 134339378-134360125 | 15706 bp |
| lnc-GLB1L2-1: 14 | 60 | chr11: 134339400-134373384 | 744 bp |
| lnc-GLB1L2-1: 15 | 61 | chr11: 134339400-134375553 | 1129 bp |
| lnc-GLB1L2-1: 16 | 62 | chr11: 134343291-134373078 | 1843 bp |
| lnc-GLB1L2-1: 17 | 63 | chr11: 134344051-134357809 | 1160 bp |
| lnc-GLB1L2-1: 18 | 64 | chr11: 134346572-134375009 | 572 bp |
| lnc-GLB1L2-1: 19 | 65 | chr11: 134349193-134375555 | 4435 bp |
| lnc-GLB1L2-1: 2 | 66 | chr11: 134306469-134308558 | 374 bp |
| lnc-GLB1L2-1: 20 | 67 | chr11: 134349983-134375009 | 1245 bp |
| lnc-GLB1L2-1: 21 | 68 | chr11: 134350411-134401542 | 537 bp |
| lnc-GLB1L2-1: 3 | 69 | chr11: 134306629-134374934 | 1863 bp |
| lnc-GLB1L2-1: 4 | 70 | chr11: 134336079-134357809 | 3679 bp |
| lnc-GLB1L2-1: 5 | 71 | chr11: 134336079-134357809 | 3620 bp |
| lnc-GLB1L2-1: 6 | 72 | chr11: 134344060-134350796 | 720 bp |
| lnc-GLB1L2-1: 7 | 73 | chr11: 134349193-134375507 | 4387 bp |
| lnc-GLB1L2-1: 8 | 74 | chr11: 134349731-134352843 | 1398 bp |
| lnc-GLB1L2-1: 9 | 75 | chr11: 134350086-134367700 | 939 bp |

In additional aspects, the biomarker includes FAM83A (SEQ ID NO: 86; KJ895067.1), SEMA3F (SEQ ID NOs: 87-89; NM_004186.4; NM_001318800.1; NM_001318798.1), CLDN10 (SEQ ID NO: 90-91; NM_182848.3; NM_006984.4), ASRGL1 (SEQ ID NO: 92, 93; NM_001083926.1; NM_025080.3), or a combination thereof.

An RBP, lnc-RNA, or additional RNA biomarker is differentially expressed between two samples if the amount of the RBP, lnc-RNA, or additional RNA biomarker in one sample is statistically significantly different from the amount of the RBP, lnc-RNA, or additional RNA biomarker in the other sample. The expression level of an RBP, lnc-RNA, or additional RNA biomarker can be increased or decreased in a test sample relative to a reference sample. For example, an RBP gene, lnc-RNA, or additional RNA biomarker is differentially expressed in two samples if it is present at least about 120%, at least about 130%, at least about 150%, at least about 180%, at least about 200%, at least about 300%, at least about 500%, at least about 700%, at least about 900%, or at least about 1000% greater than it is present in the other sample, or if it is detectable in one sample and not detectable in the other.

Alternatively or additionally, an RBP gene, lnc-RNA, or additional RNA biomarker is differentially expressed in two sets of samples if the frequency of detecting the RBP gene, lnc-RNA, or additional RNA biomarker in samples is statistically significantly higher or lower than in the control samples. For example, an RBP gene, lnc-RNA, or additional RNA biomarker is differentially expressed in two sets of samples if it is detected at least about 120%, at least about 130%, at least about 150%, at least about 180%, at least about 200%, at least about 300%, at least about 500%, at least about 700%, at least about 900%, or at least about 1000% more frequently or less frequently observed in one set of samples than the other set of samples.

A test amount and a control amount of a biomarker can be either an absolute amount (e.g., number of copies/ml, nanogram/ml or microgram/ml) or a relative amount (e.g., relative intensity of signals).

Diagnostic samples for use in the methods described herein comprise nucleic acids suitable for providing polynucleotide, e.g., RNA, expression information. The sample contains cells from a tissue of the test patient. For example, when the HPV-associated pre-cancer or HPV-associated cancer is anal cancer, the tissue of the test patient contains anal cells; when the HPV-associated pre-cancer or HPV-associated cancer is vulvovaginal cancer, the tissue of the test patient contains vulvovaginal cells; when the HPV-associated pre-cancer or HPV-associated cancer is penile cancer, the tissue of the test patient contains penal cells; or when the HPV-associated pre-cancer or HPV-associated cancer is oropharyngeal cancer, the tissue of the test patient contains oropharyngeal cells.

In one aspect, samples for the methods disclosed herein contain cells from a patient's cervix. Exemplary test samples include a PAP smear, a vaginal wash, or a cervical biopsy sample. In certain aspects, the methods described herein include obtaining from the test patient the sample containing cells from the test patient's cervix.

In certain aspects, the test patient is a patient at risk for an HPV-associated pre-cancer or an HPV-associated cancer, such as a patient diagnosed with HPV infection or a patient at high risk for HPV infection.

In certain aspects, the test patient is a patient at high risk for cervical cancer such as a woman at high risk for HPV infection, a woman with a diagnosed HPV infection, a woman with a history of DES exposure, a woman with a previous history of gynecological cancer, a woman with an abnormal PAP test, a woman immunosuppressed due to AIDS or therapy following organ transplantation, or a woman with abnormal endometrial cells.

In certain aspects, the methods disclosed herein comprise detecting the expression level of one or more biomarkers as disclosed herein.

In addition, the methods disclosed herein include the comparison/correlation of the expression levels of biomarkers in the diagnostic sample from the test patient to a reference sample. Exemplary reference samples include a control sample from a patient or patients with no evidence of HPV-associated pre-cancer or HPV-associated cancer, a control sample from a patient or patients with HPV-associated pre-cancer, and a control sample from a patient or patients with HPV-associated cancer. Additional exemplary reference samples include a control sample from a patient or patients with no evidence of cervical cancer, a control sample from a cervical cancer patient or patients, or a control sample from a patient or patients with stage 1, stage 2, or stage 3 cervical intraepithelial neoplasia. The reference sample can be a single sample from a control patient with a known disease state, or preferably samples from a plurality of subjects such that the reference expression level is averaged over the expression levels for a population of known disease state. Useful population sizes for a reference population are greater than 100 subjects, specifically about 500 subjects for each reference group (CIN 1, 2, 3 and cervical cancer), for example.

RNA can be extracted and purified from biological samples using suitable techniques that are known in the art, and several are commercially available (e.g., FormaPure® nucleic acid extraction kit, Agencourt® Biosciences, Beverly Mass., High Pure FFPE RNA Micro Kit, Roche Applied Science, Indianapolis, Ind.). RNA can be extracted from frozen tissue sections using TRIzol® (Invitrogen, Carlsbad, Calif.) and purified using RNeasy® Protect kit (Qiagen, Valencia, Calif.). RNA can be further purified using DNase I treatment (Ambion, Austin, Tex.) to eliminate any contaminating DNA. RNA concentrations can be made using a NanoDrop ND-1000 spectrophotometer (NanoDdrop Technologies, Rockland, Del.). RNA can be further purified to eliminate contaminants that interfere with cDNA synthesis by cold sodium acetate precipitation. RNA integrity can be evaluated by running electropherograms, and RNA integrity number (RIN, a correlative measure that indicates intactness of mRNA) can be determined using the RNA 6000 PicoAssay for the Bioanalyzer 2100 (Agilent Technologies, Santa Clara, Calif.).

Following sample collection and nucleic acid extraction, the nucleic acid portion of the sample comprising RNA that is or can be used to prepare the target polynucleotide(s) of interest can be subjected to one or more preparative reactions. These preparative reactions can include in vitro transcription (IVT), labeling, fragmentation, amplification, and other reactions. mRNA can first be treated with reverse transcriptase and a primer to create cDNA prior to detection, quantitation, or amplification; this can be done in vitro with purified mRNA or in situ, e.g., in cells or tissues affixed to a slide.

By "amplification" is meant a process of producing at least one copy of a nucleic acid, in this case an expressed RNA, and in many cases produces multiple copies. An amplification product can be RNA or DNA, and may include a complementary strand to the expressed target sequence. DNA amplification products can be produced initially through reverse transcription and then optionally from further amplification reactions. The amplification product may include all or a portion of a target sequence, and may optionally be labeled. A variety of amplification methods are suitable for use, including polymerase-based methods and ligation-based methods.

The expression level of a polynucleotide biomarker can be determined by reverse transcriptase-polymerase chain reaction (RT-PCR) methods, quantitative real-time RT-PCR (RT-qPCR), microarray, serial analysis of gene expression (SAGE), next-generation RNA sequencing (deep sequencing), gene expression analysis by massively parallel signature sequencing (MPSS), immunoassays such as ELISA, in situ hybridization (ISH) formulations that allow histopathological analysis, mass spectrometry (MS) methods, transcriptomics, RNA pull-down and chromatin isolation by RNA purification (ChiRP), proteomics-based identification of lncRNA, detection of single nucleotide polymorphisms (SNPs), measurement of DNA methylation or unmethylation, measurement of siRNA silencing or miRNA silencing, or measurement of downstream targets.

As used herein, the terms "quantitative real time polymerase chain reaction," "real-time polymerase chain reaction," and "qPCR" are synonymous and refer to a laboratory technique based on a polymerase chain reaction used to amplify and simultaneously quantify a targeted DNA molecule. Frequently, real-time PCR is combined with reverse transcription to quantify messenger RNA and non-coding RNA in cells or tissues, e.g., RT-qPCR.

Additional methods for detecting and/or quantifying a polynucleotide biomarker can comprise single-molecule sequencing (e.g., Illumina®, PacBio, ABI SOLID™), in situ hybridization, bead-array technologies (e.g., Luminex xMAP®, Illumina® BeadChips), branched DNA technology (e.g., Affymetrix®, Genisphere®), and Ion Torren™. In some instances, methods for detecting and/or quantifying a target sequence comprise transcriptome sequencing techniques. Transcription sequencing (e.g., RNA-seq, "Whole Transcriptome Shotgun Sequencing" (WTSS)) may comprise the use of high-throughput sequencing technologies to sequence cDNA in order to get information about a sample's RNA content. Transcriptome sequencing can provide information on differential expression of genes, including gene alleles and differently spliced transcripts, non-coding RNAs, post-transcriptional mutations or editing, and gene fusions.

Included herein is a method for measuring the expression levels of biomarkers for HPV-associated pre-cancers and cancers as described herein. The methods optionally include identifying HPV-associated pre-cancer or cancer status of a test subject (e.g., cervical cancer). The data obtained from the expression profiles of a population (e.g., normal, CIN1-3, or cervical cancer) can be evaluated using one or more pattern recognition algorithms. In addition, the results of imaging tests or histological evaluation may optionally be combined with expression profiles generated using the genes disclosed herein.

In one aspect, the methods include
comparing (correlating) the expression level of the first polynucleotide biomarker in the sample containing cells from a tissue of the test patient to a reference expression level of the first polynucleotide biomarker in a reference sample, wherein the reference sample is
a control sample from a patient or patients with no evidence of HPV-associated pre-cancer or HPV-associated cancer,
a control sample from a patient or patients with HPV-associated pre-cancer, or
a control sample from a patient or patients with HPV-associated cancer, and
determining, based on said correlation, if the test patient has HPV-associated pre-cancer or HPV-associated cancer In another aspect, the methods comprise
predicting (or determining), based on the expression level of one or more polynucleotide biomarkers in the containing cells from a tissue of the test patient and a reference expression level of the one or more polynucleotide biomarkers in a reference sample that the patient has no HPV-associated pre-cancer or cancer, that the test patient has HPV-associated pre-cancer, or that the patient has HPV-associated cancer, wherein the reference sample is a control sample from a patient or patients with no evidence of HPV-associated pre-cancer or HPV-associated cancer, a control sample from a patient or patients with HPV-associated pre-cancer, or a control sample from a patient or patients with HPV-associated cancer.

In a further aspect, the methods include classifying the patient as having no cervical cancer or cervical intraepithelial neoplasia, or as having HPV-associated pre-cancer or cancer based on the expression level of one or more polynucleotide biomarkers in the sample containing cells from a tissue of the test patient and a reference expression level of the one or more polynucleotide biomarkers in a reference sample, wherein the reference sample is a control sample from a patient or patients with no evidence of HPV-associated pre-cancer or HPV-associated cancer, a control sample from a patient or patients with HPV-associated pre-cancer, or a control sample from a patient or patients with HPV-associated cancer.

In one aspect, the methods include comparing (or correlating) the expression level of one or more polynucleotide biomarkers in the sample containing cells from the test patient's cervix to a reference expression level of the one or more polynucleotide biomarkers in a reference sample, wherein the reference sample is a control sample from a patient or patients with no evidence of cervical cancer, a control sample from a cervical cancer patient or patients, or a control sample from a patient or patients with stage 1, stage 2, or stage 3 cervical intraepithelial neoplasia, and determining, based on said comparison, if the test patient has cervical cancer, or stage 1, stage 2, or stage 3 cervical intraepithelial neoplasia.

In another aspect, the methods comprise predicting (or determining), based on the expression level of one or more polynucleotide biomarkers in the sample containing cells from the test patient's cervix and a reference expression level of the one or more polynucleotide biomarkers in a reference sample that the patient has no cervical cancer or cervical intraepithelial neoplasia, that the test patient has cervical cancer, or that the patient has stage 1, stage 2, or stage 3 cervical intraepithelial neoplasia, wherein the reference sample is a control sample from a patient or patients with no evidence of cervical cancer, a control sample from a cervical cancer patient or patients, or a control sample from a patient or patients with stage 1, stage 2, or stage 3 cervical intraepithelial neoplasia.

In a further aspect, the methods include classifying the patient as having no cervical cancer or cervical intraepithelial neoplasia, as having cervical cancer, or as having stage 1, stage 2, or stage 3 cervical intraepithelial neoplasia based on the expression level of one or more polynucleotide biomarkers in the sample containing cells from the test patient's cervix and a reference expression level of the one or more polynucleotide biomarkers in a reference sample, wherein the reference sample is a control sample from a patient or patients with no evidence of cervical cancer, a control sample from a cervical cancer patient or patients, or a control sample from a patient or patients with stage 1, stage 2, or stage 3 cervical intraepithelial neoplasia.

Analysis methods may be used to form a predictive model, and then the predictive model may be used to classify test data. For example, one convenient and particularly effective method of classification employs multivariate statistical analysis modeling, first to form a model (a "predictive mathematical model") using data ("modeling data") from samples of known class (e.g., from subjects known to have, or not have, a particular grade of CIN or cervical cancer), and second to classify an unknown sample (e.g., "test data"), according to HPV-associated (e.g., cervical) cancer status.

Pattern recognition (PR) is the use of multivariate statistics, both parametric and non-parametric, to analyze spectroscopic data, and hence to classify samples and to predict the value of some dependent variable based on a range of observed measurements. There are two main approaches. One set of methods is termed "unsupervised" and these simply reduce data complexity in a rational way and also produce display plots which can be interpreted by the human eye. The other approach is termed "supervised" whereby a training set of samples with known class or outcome is used to produce a mathematical model and is then evaluated with independent validation data sets.

Unsupervised PR methods are used to analyze data without reference to any other independent knowledge. Examples of unsupervised pattern recognition methods include principal component analysis (PCA), hierarchical cluster analysis (HCA), and non-linear mapping (NLM).

Alternatively, and in order to develop automatic classification methods, it has proved efficient to use a "supervised" approach to data analysis. Here, a "training set" of biomarker expression data is used to construct a statistical model that predicts correctly the "class" of each sample. This training set is then tested with independent data (referred to as a test or validation set) to determine the robustness of the computer-based model. These models are sometimes termed "expert systems," but may be based on a range of different mathematical procedures. Supervised methods can use a data set with reduced dimensionality (for example, the first few principal components), but typically use unreduced data, with all dimensionality. In all cases the methods allow the quantitative description of the multivariate boundaries that characterize and separate each class, for example, each class of cervical cancer in terms of its biomarker expression profile. It is also possible to obtain confidence limits on any predictions, for example, a level of probability to be placed on the goodness of fit. The robustness of the predictive models can also be checked using cross-validation, by leaving out selected samples from the analysis.

It is often useful to pre-process data, for example, by addressing missing data, translation, scaling, weighting, etc. Multivariate projection methods, such as principal component analysis (PCA) and partial least squares analysis (PLS), are so-called scaling sensitive methods. By using prior knowledge and experience about the type of data studied, the quality of the data prior to multivariate modeling can be enhanced by scaling and/or weighting. Adequate scaling and/or weighting can reveal important and interesting variation hidden within the data, and therefore make subsequent multivariate modeling more efficient. Scaling and weighting may be used to place the data in the correct metric, based on knowledge and experience of the studied system, and therefore reveal patterns already inherently present in the data.

The methods described herein may be implemented and/or the results recorded using a device capable of implementing the methods and/or recording the results. Examples of devices that may be used include but are not limited to electronic computational devices, including computers of all types. When the methods described herein are implemented and/or recorded in a computer, the computer program that may be used to configure the computer to carry out the steps of the methods may be contained in any computer readable medium capable of containing the computer program. Examples of computer readable medium that may be used include but are not limited to diskettes, CD-ROMs, DVDs, ROM, RAM, and other memory and computer storage devices. The computer program that may be used to configure the computer to carry out the steps of the methods and/or record the results may also be provided over an electronic network, for example, over the internet, an intranet, or other network.

The process of comparing a measured value and a reference value can be carried out in a convenient manner appropriate to the type of measured value and reference value for the discriminative gene at issue. "Measuring" can be performed using quantitative or qualitative measurement techniques, and the mode of comparing a measured value and a reference value can vary depending on the measurement technology employed. For example, when a qualitative colorimetric assay is used to measure expression levels, the levels may be compared by visually comparing the intensity of the colored reaction product, or by comparing data from densitometric or spectrometric measurements of the colored reaction product (e.g., comparing numerical data or graphical data, such as bar charts, derived from the measuring device). However, it is expected that the measured values used in the methods will most commonly be quantitative values. In other examples, measured values are qualitative. As with qualitative measurements, the comparison can be made by inspecting the numerical data, or by inspecting representations of the data (e.g., inspecting graphical representations such as bar or line graphs).

The process of comparing may be manual (such as visual inspection by the practitioner of the method) or it may be automated. For example, an assay device (such as a luminometer for measuring chemiluminescent signals) may include circuitry and software enabling it to compare a measured value with a reference value for a biomarker. Alternately, a separate device (e.g., a digital computer) may be used to compare the measured value(s) and the reference value(s). Automated devices for comparison may include stored reference values for the biomarker(s) being measured, or they may compare the measured value(s) with reference values that are derived from contemporaneously measured reference samples (e.g., samples from control subjects).

As will be apparent to those of skill in the art, when replicate measurements are taken, the measured value that is compared with the reference value is a value that takes into account the replicate measurements. The replicate measurements may be taken into account by using either the mean or median of the measured values as the "measured value."

When it has been determined that the test patient has HPV-pre-cancer or cancer, the methods optionally include HPV detection and or typing.

When it has been determined that the test patient has CIN 1, 2, or 3 cervical cancer, the methods optionally include HPV detection and or typing, for example, using the Cobas® HPV test marketed by Roche Diagnostics.

Also included herein are methods of treating the test patient with an interventional strategy for HPV-associated pre-cancer or cancer.

Interventional therapies for anal, vulvovaginal, penile, and oropharyngeal cancer include radiation therapy, surgery, and chemotherapy.

Further included herein are methods of treating the test patient with an interventional strategy for CIN or cervical cancer. When the patient is determined to have stage 1 CIN, the interventional strategy may include screening for further cervical changes, screening the patient for HPV infection, HPV typing, or a combination thereof. Exemplary tests for the detection of HPV infection include detection of HPV infection via DNA/RNA amplification with PCR using, for example, the Cobas® HPV test marketed by Roche Diagnostics. Advantageously, early identification of CIN 1 optionally coupled with determining the HPV infection type will provide critical information regarding the type of intervention required to treat the patient. Early diagnosis and treatment at stage CIN 1 could prevent or slow progression to later disease stages.

When the patient is determined to have stage 2 or stage 3 CIN, interventional strategies may include, in addition to monitoring, cryosurgery to freeze abnormal cells, laser therapy to remove abnormal tissue, loop electrosurgical procedure excision, surgery to remove abnormal tissue, or hysterectomy. At early stages, for example, low cost outpatient procedures such as loop electrosurgical excision are 90-95% effective. Thus, a benefit to the methods disclosed herein is the ability to use minor surgical intervention before CIN progresses to cervical cancer.

Interventional strategies for the treatment of cervical cancer include surgery, radiation therapy, chemotherapy, targeted therapy, or a combination thereof. Surgery involves removal of the cancer and may include conization to remove tissue from the cervix and/or cervical canal or hysterectomy such as total, radical, modified radical hysterectomy. Radiation therapy includes internal and external radiation therapy in addition to intensity-modulated radiation therapy. Chemotherapy involves the use of drugs to inhibit the growth of cancer calls and can involve systemic or regional chemotherapy. Drugs approved for the treatment of cervical cancer include bleomycin, cisplatin, topotecan hydrochloride, and gemcitabine-cisplatin. Targeted therapy involves the use of drugs that identify and attack specific cancer cells without harming normal cells. Targeted therapy includes antibody therapy such as bevacizumab therapy.

Further disclosed herein, is a probe set for diagnosing, predicting, and/or monitoring cervical cancer in a subject. The probe set comprises a plurality of polynucleotide probes capable of detecting an expression level of at least one biomarker for CIN or cervical cancer, wherein the expression level determines the CIN or cervical cancer status of the subject.

In one aspect, a probe set comprises
one or more polynucleotides that hybridizes to a first polynucleotide biomarker, wherein the first polynucleotide biomarker is GRB7 (SEQ ID NOs: 8-11), NOVA1 (SEQ ID Nos: 14 and 15), RNASEH2A (SEQ ID NO: 19), or a combination thereof, and
one or more polynucleotides that hybridizes to a second polynucleotide biomarker, wherein the second polynucleotide biomarker is lnc-FANCI-2, lnc-GLB1L2-1, or a combination thereof.

In certain aspects, the probe set is attached to a solid support, and/or each member of the probe set comprises a detectable moiety.

One skilled in the art understands that the nucleotide sequence of the polynucleotide probe need not be identical to its target sequence in order to specifically hybridize thereto. The polynucleotide probes, therefore, comprise a nucleotide sequence that is at least about 65%, 70%, 75%, 80%, 85%, 90%, 95%, or more identical to a region of the coding target or non-coding target. Methods of determining sequence identity are known in the art and can be determined, for example, by using the BLASTN program of the University of Wisconsin Computer Group (GCG) software or provided on the NCBI website. The nucleotide sequence of the polynucleotide probes may exhibit variability by differing (e.g. by nucleotide substitution, including transition or transversion) at one, two, three, four or more nucleotides from the sequence of the coding target or non-coding target.

Primers/probes based on the nucleotide sequences of target sequences can be used in amplification of the target sequences. For use in amplification reactions such as PCR, a pair of primers can be used. The exact composition of the primer sequences is selected so that the primers hybridize to specific sequences of the probe set under stringent conditions, particularly under conditions of high stringency. The pairs of primers are usually chosen so as to generate an amplification product of at least about 50 nucleotides, more usually at least about 100 nucleotides. Algorithms for the selection of primer sequences are generally known, and are available in commercial software packages. These primers may be used in standard quantitative or qualitative PCR-based assays to assess transcript expression levels of RNAs defined by the probe set. Alternatively, these primers may be used in combination with probes, such as molecular beacons in amplifications using real-time PCR.

The polynucleotide probes or primers can incorporate moieties useful in detection, isolation, purification, or immobilization, if desired. Such moieties are detectable labels, such as radioisotopes, fluorophores, chemiluminophores, enzymes, colloidal particles, and fluorescent microparticles, as well as antigens, antibodies, haptens, avidin/streptavidin, biotin, haptens, enzyme cofactors/substrates, enzymes, and the like. A label can optionally be attached to or incorporated into a probe or primer polynucleotide to allow detection and/or quantitation of a target polynucleotide representing the target sequence of interest.

In some embodiments, one or more polynucleotide probes/primers provided herein can be provided on a substrate. The substrate can comprise a wide range of material, either biological, nonbiological, organic, inorganic, or a combination of any of these. For example, the substrate may be a polymerized Langmuir Blodgett film, functionalized glass, Si, Ge, GaAs, GaP, $SiO_2$, $SiN_4$, modified silicon, or any one of a wide variety of gels or polymers such as (poly)tetrafluoroethylene, (poly)vinylidenedifluoride, polystyrene, cross-linked polystyrene, polyacrylic, polylactic acid, polyglycolic acid, poly(lactide coglycolide), polyanhydrides, poly(methyl methacrylate), poly(ethylene-co-vinyl acetate), polysiloxanes, polymeric silica, latexes, dextran polymers, epoxies, polycarbonates, or combinations thereof. Conducting polymers and photoconductive materials can be used.

Substrates can be planar crystalline substrates such as silica based substrates (e.g., glass, quartz, or the like), or crystalline substrates used in, e.g., the semiconductor and microprocessor industries, such as silicon, gallium arsenide, indium doped GaN and the like, and include semiconductor nanocrystals.

The substrate can take the form of an array, a photodiode, an optoelectronic sensor such as an optoelectronic semiconductor chip or optoelectronic thin-film semiconductor, or a biochip. The location(s) of probe(s) on the substrate can be addressable; this can be done in highly dense formats, and the location(s) can be microaddressable or nanoaddressable.

The substrate can be a plate, slide, bead, pellet, disk, particle, microparticle, nanoparticle, strand, precipitate, optionally porous gel, sheets, tube, sphere, capillary, film, chip, multiwell plate or dish, optical fiber, etc. The substrate can be a form that is rigid or semi-rigid. The substrate may contain raised or depressed regions on which an assay component is located. The surface of the substrate can be etched using known techniques to provide for desired surface features, for example trenches, v-grooves, mesa structures, or the like.

Surfaces on the substrate can be composed of the same material as the substrate or can be made from a different material, and can be coupled to the substrate by chemical or physical means. Such coupled surfaces may be composed of any of a wide variety of materials, for example, polymers, plastics, resins, polysaccharides, silica or silica-based materials, carbon, metals, inorganic glasses, membranes, or any of the above-listed substrate materials. The surface can be optically transparent and can have surface Si—OH functionalities, such as those found on silica surfaces.

The substrate and/or its optional surface can be chosen to provide appropriate characteristics for the synthetic and/or detection methods used. The substrate and/or surface can be transparent to allow the exposure of the substrate by light applied from multiple directions. The substrate and/or its surface is generally resistant to, or is treated to resist, the conditions to which it is to be exposed in use, and can be optionally treated to remove any resistant material after exposure to such conditions.

The substrate or a region thereof may be encoded so that the identity of the sensor located in the substrate or region being queried may be determined. A suitable coding scheme can be used, for example optical codes, RFID tags, magnetic codes, physical codes, fluorescent codes, and combinations of codes.

The invention is further illustrated by the following non-limiting examples.

EXAMPLES

Materials and Methods

Human patient samples: Samples for RNA sequencing, containing 7 normal cervical tissues, 7 pre-cancer tissues and 7 cervical cancer tissues, and samples for validation, including 24 normal cervical tissues, 25 CIN 2-3 tissues, and 23 cervical cancer tissues, were all collected from the Women's Hospital, School of Medicine, Zhejiang University. All the human samples were used in accordance with the Institutional Review Board procedures of the hospital. Informed consent was obtained from each participant prior to the study. Samples were snap-frozen and stored at −80° C. until use.

RNA isolation: RNA was isolated from each human tissue sample by TRIzol® (Invitrogen, CA, USA) according to the instructions provided by the manufacturer. Total RNA quality and quantity were verified spectrophotometrically (NanoDrop ND-1000 spectrometer; Thermo Scientific, DE, USA) and electrophoretically (Bioanalyzer 2100; Agilent Technologies, CA, USA).

RNA sequencing and mapping: RNA-seq libraries were prepared using TruSeq® Stranded Total RNA Sample Preparation Kit with Ribo-Zero™ depletion and sequenced on an Illumina® HiSeq™-2500 platform as paired-end reads. In brief, high-quality of human total RNA (1 µg) was Ribo-Zero™ depleted, fragmented, and then reverse transcribed. The double-stranded cDNA were A-tailed and ligated with Illumia® sequencing adapters. Subsequently, the ligated products were enriched by PCR and size-selected by agarose gel electrophoresis. The products of approximately 200-400-bp in size were sequenced by the Illumina® HiSeq™-2500 platform. The raw data in fastq format were mapped to the human reference genome (hg19, GRCh37) by Tophat v2.0.11(-g 1), which had the aligner Bowtie (v2.2.1.0) with the parameter settings (-N 0, -L 20, -i S,1,1.25, -n-ceil L,0,0.15 and -gbar 4). The mapping results were further sorted in coordination position by samtools (v0.1.19.0) (Robinson M D, Oshlack A., "A scaling normalization method for differential expression analysis of RNA-seq data," *Genome Biology*, 11:R25 (2010); Robinson M D, McCarthy D J and Smyth G K., "edgeR: a Bioconductor package for differential expression analysis of digital gene expression data," *Bioinformatics*, 26, pp. 139-140 (2010)). The latest annotation of LncRNA was downloaded from the publicly available lncipedia database version 3.0. The mapped reads in individual lncRNA region of each sample were counted by bedtools (v2.19.0). The R Bioconductor edgeR package was used to normalize raw reads by the scaling method. Differentially expressed lncRNAs were identified by one-way ANOVA method with 10% false discovery rate (FDR) and four-fold changes between the conditions. The FDR was controlled by the Benjamini-Hochberg (BH) procedure. RNA-binding protein genes were compiled from the literature (Alfredo Castello, et al., "Insights into RNA Biology from an Atlas of Mammalian mRNA-Binding Proteins," *Cell*, 149, pp. 1393-1406 (2012); Alfredo Castello, et al., "RNA-binding proteins in Mendelian disease," *Trends in Genetics*, 29, pp. 318-327 (2013)). The normalized reads from the multiple transcripts of each gene were averaged to represent composite gene expression. The expression results were clustered using unsupervised hierarchical clustering analysis, in which the Euclidean Distance is used as the similarity measure.

Human primary keratinocytes and organotypic (raft) epithelial cultures: Total RNA extracted from various raft tissues were leftovers from previous studies (Wang, X. et al., "Oncogenic HPV infection interrupts the expression of tumor-suppressive miR-34a through viral oncoprotein E6," *RNA*, 15, pp. 637-647 (2009); Wang, X., et al., "microRNAs are biomarkers of oncogenic human papillomavirus infections," *Proc. Natl. Acad. Sci. USA*, 111, pp. 4262-4267 (2014)). Briefly, primary human foreskin keratinocytes (HFK) and primary human vaginal keratinocytes (HVK) were isolated from newborn circumcision and adult vaginectomy tissue specimens, respectively, as previously described (Meyers, C., Mayer, T. J., and Ozbun, M. A., "Synthesis of infectious human papillomavirus type 18 in differentiating epithelium transfected with viral DNA," *J. Virol.*, 71, pp, 7381-7386 (1997)). Keratinocytes were grown in monolayer culture by using epithelial (E) medium plus epidermal growth factor (5 ng/ml) in the presence of mitomycin C (4 µg/ml)-treated J2 3T3 feeder cells. Keratinocyte lines stably maintaining HPV16 and HPV18 DNA following electroporation were subcloned by limiting dilutions of cells. Organotypic (raft) epithelial culture tissues derived from HPV16 and HPV18-immortalized HFK or HVK were prepared as described previously (McLaughlin-Drubin, M. E. and Meyers, C., "Propagation of infectious, high-risk HPV in organotypic "raft" culture," *Methods Mol. Med.*, 119, pp. 171-186 (2005)). The stratified and differentiated raft culture epidermal tissues were collected free from collagen (no fibroblasts) on day 10 and frozen on dry ice for total cell RNA preparation. Additional productive HPV18 raft cultures of HFKs were obtained by Cre-loxP-mediated recombination as described (Wang, H. K., Duffy, A. A., Broker, T. R., and Chow, L. T., "Robust production and passaging of infectious HPV in squamous epithelium of primary human keratinocytes", *Genes Dev.*, 23, pp. 181-194 (2009)), and the derived raft cultures were collected on day 8, day 12, and day 16.

Plasmid pLJd-HPV-18URR-E6, pLC-HPV-18URR-E7, and pLJd-HPV-18URR-E6E7 have been described (Cheng, S., Schmidt-Grimminger, D. C., Murant, T., Broker, T. R., and Chow, L. T., "Differentiation-dependent up-regulation of the human papillomavirus E7 gene reactivates cellular DNA replication in suprabasal differentiated keratinocytes," *Genes Dev.*, 9, pp. 2335-2349 (1995); Genovese, N.J., Banerjee, N. S., Broker, T. R., and Chow, L. T., "Casein kinase II motif-dependent phosphorylation of human papillomavirus E7 protein promotes p130 degradation and S-phase induction in differentiated human keratinocytes," *J. Virol.*, 82, pp. 4862-4873 (2008)). Retroviruses derived from the above vectors were prepared as described (Banerjee, N. S., Chow, L. T., and Broker, T. R., "Retrovirus-mediated gene transfer to analyze HPV gene regulation and protein functions in organotypic "raft" cultures," *Methods Mol. Med.*, 119, pp. 187-202 (2005)). Primary HFKs were acutely infected with the retroviruses and selected with G-418 (300 µg/mL). The selected HFKs were used to establish epithelial raft cultures and harvested on day 11.

TaqMan® real-time quantitative PCR assays: Quantitative validation of genes in clinical samples and raft tissues was analyzed by real-time PCR TaqMan® gene expression assays (Applied Biosystems). In brief, 2 µg of total RNA from each sample was reversely transcribed using Superscript® First-stand Synthesis kit (Invitrogen) according to the manufacturer's instructions. TaqMan® gene expression assays for RNA-binding protein gene expression were obtained from life technologies and lncRNA primers for RT-qPCR were designed as given in Example 2.

The TaqMan® assay probes that span over exon-exon junctions were designed to amplify spliced RNA products to avoid detection of any contaminated residual genomic DNA in our RNA samples. After reverse transcription, PCR products were amplified from the cDNA samples using TaqMan® gene expression Master Mix (Applied Biosystems) together with TaqMan® gene expression assays on a StepOne Plus™ Real-Time PCR system (Applied Biosystems). Gene enrichment was calculated using the $2^{-\Delta\Delta Ct}$ method in relation to the housekeeping gene GAPDH. The mean Ct value of a given gene from 24 normal cervical tissues after normalization was served as a basal level to calculate a relative level of the gene detected in each clinical sample. Data are presented as a bar graph with mean±SE for each group. Significance of mRNA levels among clinical tissue groups was analyzed using the nonparametric Mann-Whitney U-test, while significance of the mRNA levels between raft culture tissue groups was analyzed by Student t-test.

Example 1: Identification of Altered Expression of RNA-Binding Protein Genes in Cervical Cancer Using RNA-sequencing (RNA-Seq) approach, seven normal cervical tissues and seven cervical cancer tissues were examined for their expression landscapes of approximately 19,000 coding and 113,513 noncoding RNAs. We identified 614 differentially expressed coding transcripts enriched in cancer related pathways and 95 of them encoding RNA-binding proteins (RBPs) from the analyzed 1502 human RBPs. Moreover, we identified 34 differentially, abundantly expressed lnc-RNAs from normal cervix to cervical cancer. Table 4 shows the two RNA-Seq analyses of 14 different clinical cervical tissues with two different RNA-seq platforms, each containing normal cervical tissues without HPV infection and cervical cancer tissues with HPV infection. The right column of the table shows the raw reads of individual samples from each RNA-Seq platform.

TABLE 4

RNA-Seq detection from 14 cervical tissue samples

| Sample No. | Age (yr) | Pathology | HPV infection | Total reads |
|---|---|---|---|---|
| RNA-Seq-1 | | | | |
| 1 | 27 | N | No | 13,171,863 |
| 2 | 38 | N | No | 12,028,762 |
| 3 | 42 | N | No | 31,143,321 |
| 4 | 40 | SCC | Yes | 12,422,476 |
| 5 | 42 | SCC | Yes | 11,425,454 |
| 6 | 24 | SCC | Yes | 22,302,605 |
| RNA-Seq-2 | | | | |
| 7 | 42 | N | No | 85,255,279 |
| 8 | 37 | N | No | 83,376,820 |
| 9 | 52 | N | No | 80,265,055 |
| 10 | 44 | N | No | 81,954,460 |
| 11 | 48 | SCC | Yes | 66,982,821 |
| 12 | 45 | SCC | Yes | 74,819,347 |
| 13 | 47 | SCC | Yes | 93,579,886 |
| 14 | 49 | SCC | Yes | 66,891,722 |

Figure 2:
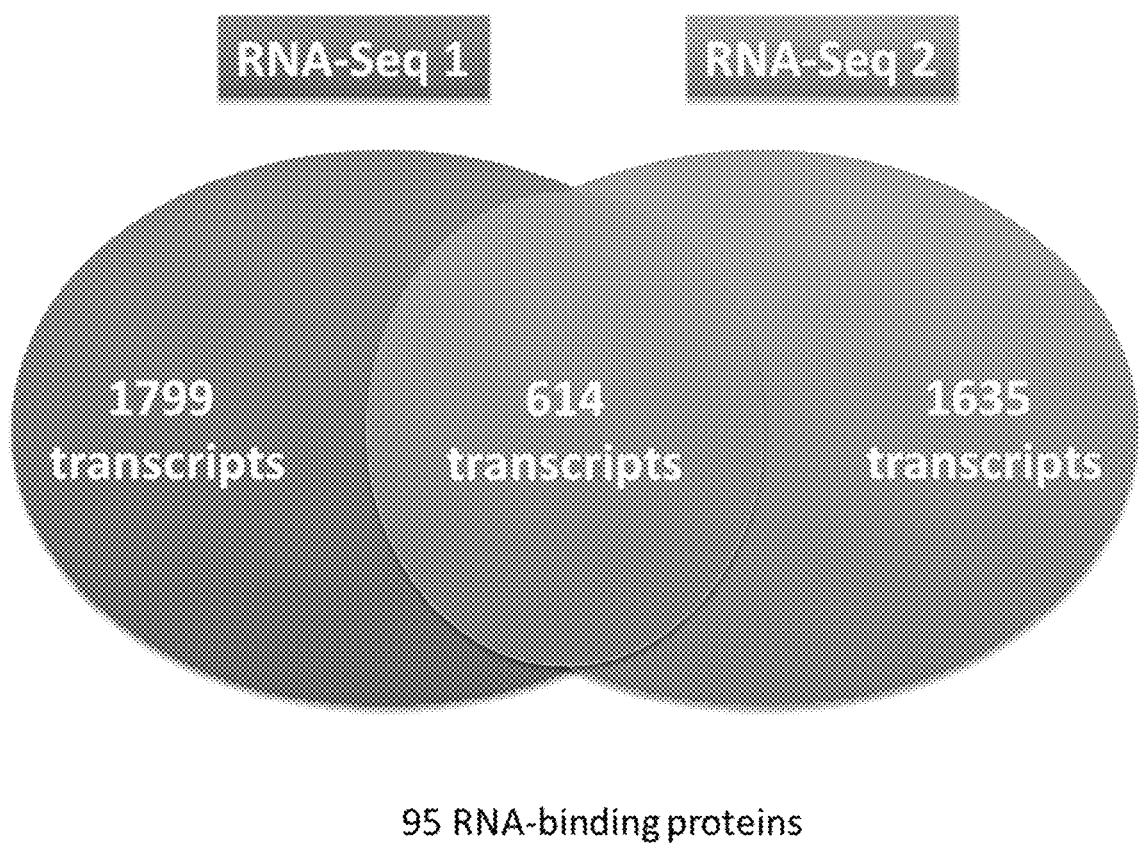
FIG. 2 shows Venn diagrams showing 95 differentially expressed RBP genes being identified from two separate RNA-seq analyses of cervical cancer, pre-cancer to normal cervical tissues.
Figure 3:
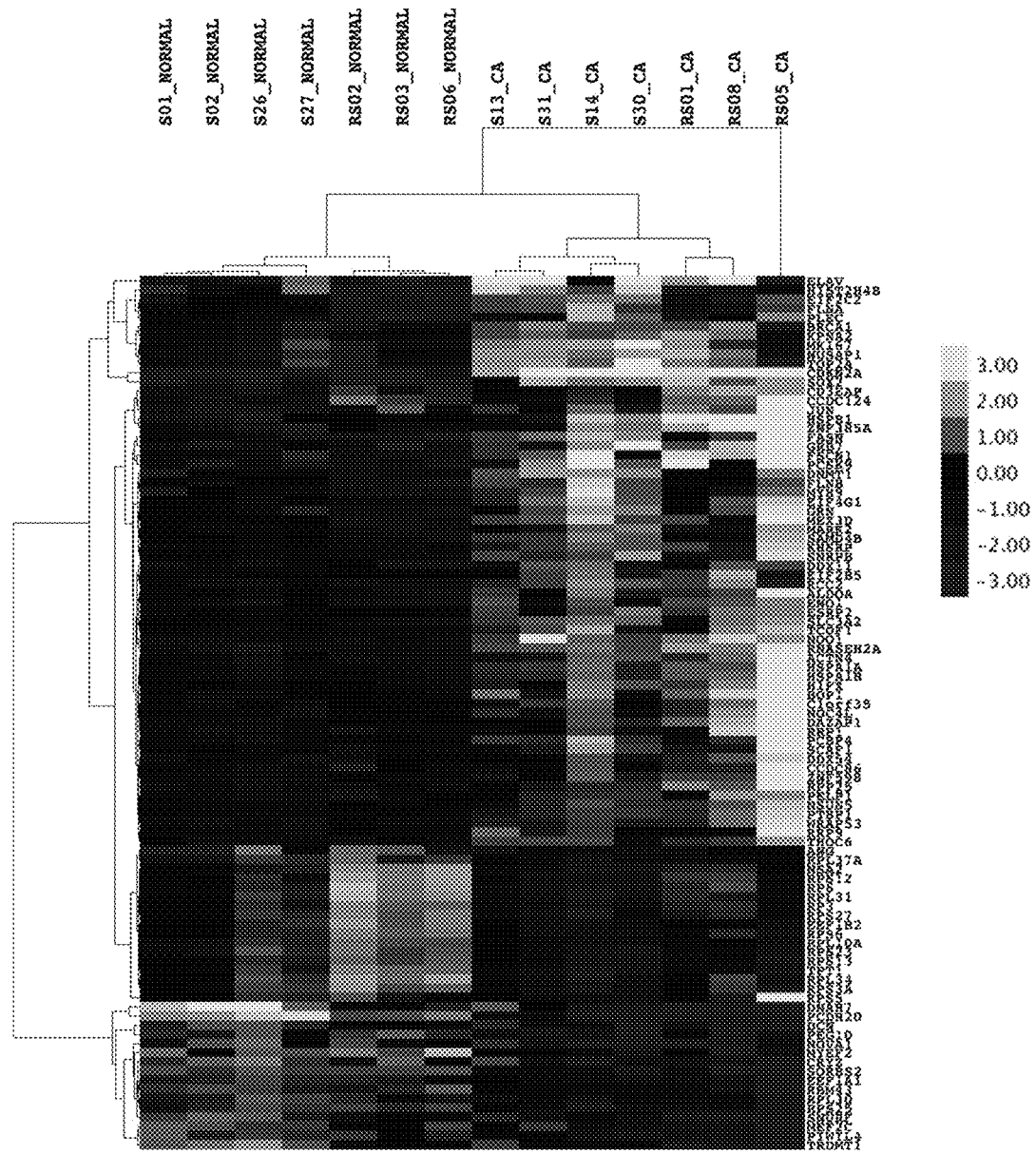
FIG. 3 shows a heat map comparing 95 differentially expressed RBP genes in cervical cancer to normal cervical tissues.

FIG. 1 is a flowchart of the RNA-Seq analyses. FIG. 2 shows Venn diagrams and FIG. 3 shows a heat map showing 95 differentially expressed RNA-binding protein genes in cervical cancer (n=7) compared to normal cervical tissues (n=7). Table 5 summarizes the 8 RBPs with expression changes between normal and cancer tissues by RNA-Seq. (CPM: Counts per Million)

TABLE 5

RNA-Seq data of the 8 RBP genes between normal and cancer tissues

| RNA-binding protein genes | Description | Normal (log$_2$ CPM, mean ± SD) | Cancer (log$_2$ CPM, mean ± SD) |
|---|---|---|---|
| CDKN2A | Cyclin-dependent kinase inhibitor 2A | −0.24 ± 0.88 | 6.3 ± 1.12 |
| ELAVL2 | ELAV like neuron-specific RNA binding protein 2 | −3.38 ± 1.89 | 0.17 ± 3.54 |
| GRB7 | Growth factor receptor-bound protein 7 | 0.9 ± 0.96 | 4.07 ± 1.22 |
| HSPB1 | Heat shock 27 kDa protein 1 | 5.74 ± 1.09 | 8.84 ± 2.49 |
| KHSRP | KH-type splicing regulatory protein | 4.35 ± 0.18 | 5.85 ± 0.78 |
| NOVA1 | Neuro-oncological ventral antigen 1 | 2.82 ± 0.55 | 0.1 ± 1.55 |
| PTBP1 | Polypyrimidine tract binding protein 1 | 5.74 ± 0.21 | 7.18 ± 0.83 |
| RNASEH2A | Ribonuclease H2, subunit A | 2.32 ± 0.47 | 5.01 ± 0.72 |

Table 6 provides the TaqMan® probe information of each RBP.

TABLE 6

TaqMan ® probe information of each RBP

| Company | Order name | Cat No | ID No |
|---|---|---|---|
| Applied Biosystems ® | Single Tube TaqMan ® Assay for GRB7 | Cat. # 4331182 | Hs00918009_g1 |
| Applied Biosystems ® | Single Tube TaqMan ® Assay for ELAVL2 | Cat. # 4331182 | Hs00270011_m1 |
| Applied Biosystems ® | Single Tube TaqMan ® Assay for RNASEH2A | Cat. # 4331182 | Hs00958451_g1 |
| Applied Biosystems ® | Single Tube TaqMan ® Assay for KHSRP | Cat. # 4351372 | Hs01100863_g1 |
| Applied Biosystems ® | Single Tube TaqMan ® Assay for NOVA1 | Cat. # 4351372 | Hs01103130_m1 |
| Applied Biosystems ® | Single Tube TaqMan ® Assay for PTBP1 | Cat. # 4351372 | Hs00914687_g1 |
| Applied Biosystems ® | Single Tube TaqMan ® Assay for CDKN2A | Cat. # 4331182 | Hs00923894_m1 |
| Applied Biosystems ® | Single Tube TaqMan ® Assay for HSPB1 | Cat. # 4331182 | Hs03044127_g1 |

Figure 4:
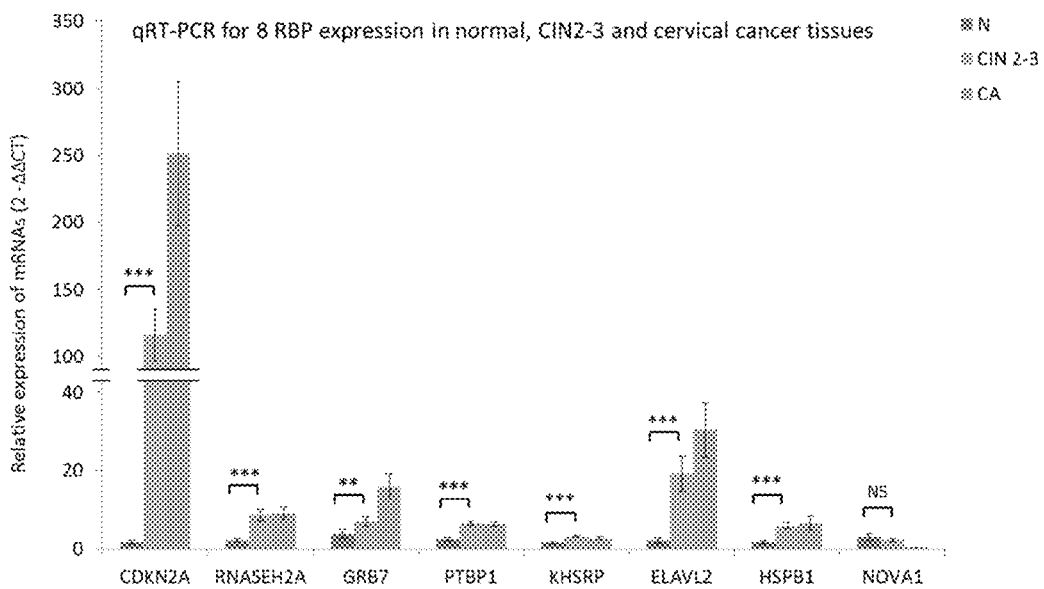
FIG. 4 shows the TaqMan® RT-qPCR validation of the 8 selected RBPs.

FIG. 4 shows the TaqMan® RT-qPCR validation confirming that all 8 RBPs significantly increased (7 RBPs) or decreased (1 RBP) in cervical cancer tissues (n=23), compared to normal cervical tissues (n=24). 7 increased RBP genes in cervical cancer were also shown higher expression in pre-cancerous lesions (CIN 2-3, n=25) when compared to the normal tissues, indicating these changes appear even at the early stage of cervical carcinogenesis. P<0.01; *, P<0.001; NS, no statistics significance.

Figure 5:
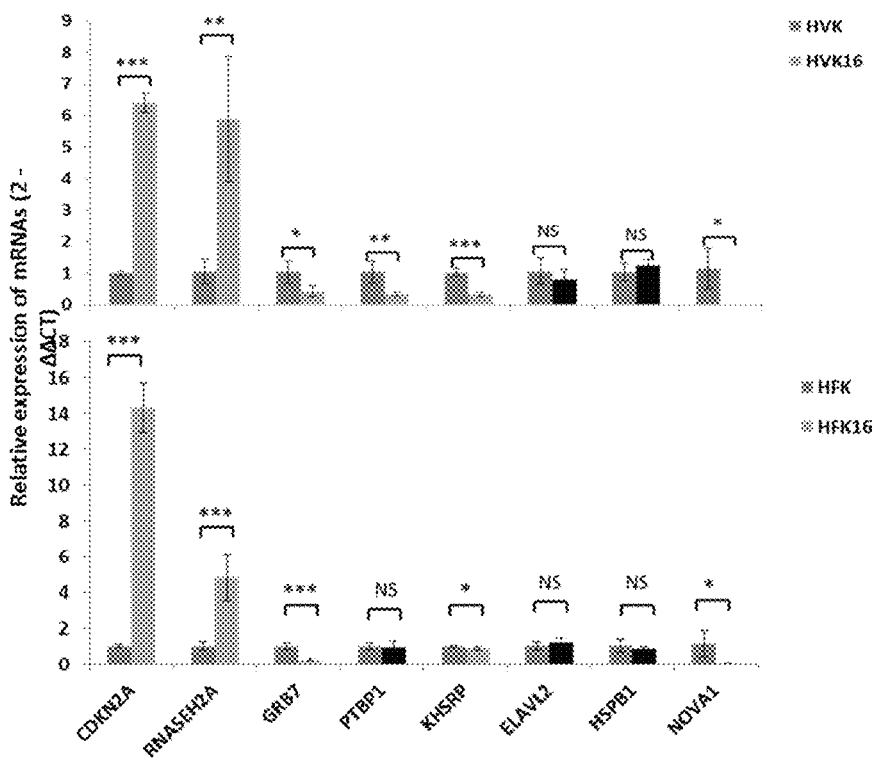
FIG. 5 shows that high-risk HPV16 infection affects the expression of RBPs. Total RNA extracted from human vaginal keratinocyte (HVK)-derived raft cultures with (HVK16) or without (HVK) productive HPV16 infection and human foreskin keratinocyte (HFK) derived raft cultures with (HFK16) or without (HFK) productive HPV16 infection were examined by TaqMan® RT-qPCR for the expression of 8 RBPs.
Figure 6:
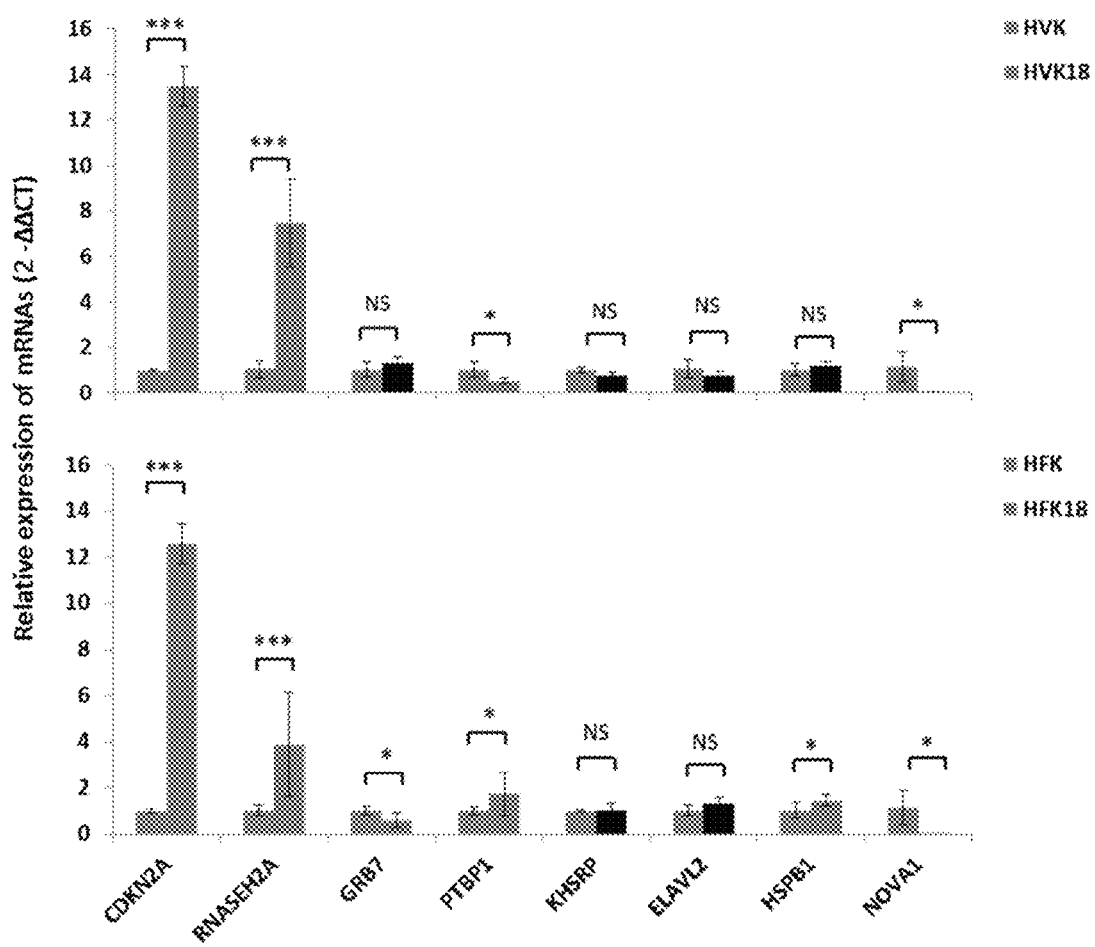
FIG. 6 shows that high-risk HPV18 infection affects the expression of RBPs. Total RNA extracted from human vaginal keratinocyte (HVK)-derived raft cultures with (HVK18) or without (HVK) productive HPV18 infection and human foreskin keratinocyte (HFK) derived raft cultures with (IFK18) or without (HFK) productive HPV18 infection were examined by TaqMan® RT-qPCR for the expression of 8 RBPs.
Figure 7:
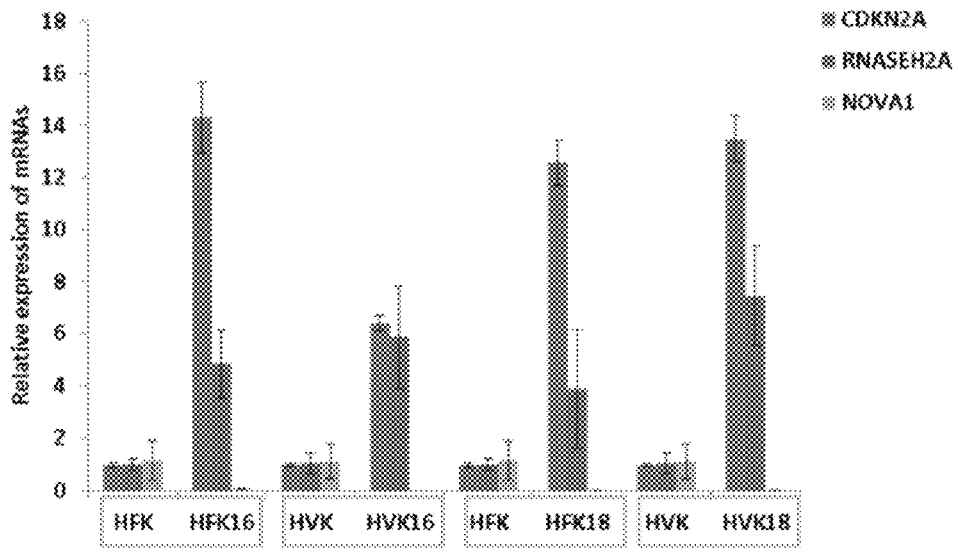
FIG. 7 shows that both HPV16 and HPV18 increase the expression of CDKN2A and RNASEH2A, but decrease the expression of NOVA1 in HFK- and HVK-derived rafts.
Figure 8:
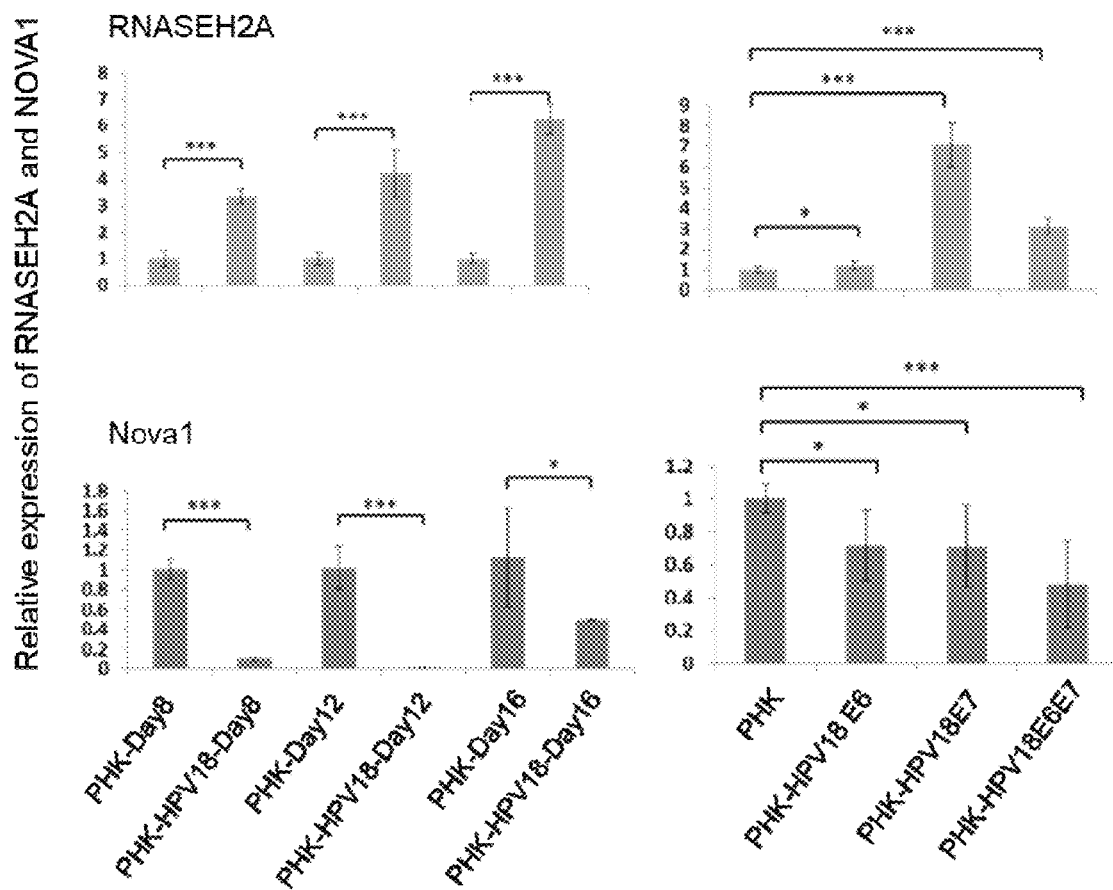
FIG. 8 shows that HPV18 infection and viral E6 and/or E7 affect the expression of RNASEH2A and Nova1. The expression of RNASEH2A and NOVA1 in primary human keratinocytes (PHK)-derived raft tissues with or without HPV18 infection on day 8, day 12, and day 16 or PHK rafts transduced with a retrovirus expression HPV18 E6, E7 or E6E7 or with an empty control retrovirus were further validated by TaqMan® RT-qPCR.

FIGS. 5 and 6 show that high-risk HPV16 and HPV18 infection affects the expression of RBPs. FIG. 5 shows Total RNA extracted from human vaginal keratinocyte (HVK)-derived raft cultures with (HVK6) or without (HVK) productive HPV16 infection and human foreskin keratinocyte (HFK) derived raft cultures with (HFK16) or without (HFK) productive HPV16 infection were examined by TaqMan® RT-qPCR for the expression of 8 RBPs. *, P<0.05; P<0.01; *, P<0.001; NS, no statistics significance. FIG. 6 shows Total RNA extracted from human vaginal keratinocyte (HVK)-derived raft cultures with (HVK18) or without (HVK) productive HPV18 infection and human foreskin keratinocyte (HFK) derived raft cultures with (HFK18) or without (HFK) productive HPV18 infection were examined by TaqMan® RT-qPCR for the expression of 8 RBPs. *, P<0.05; ***, P<0.001; NS, no statistics significance. FIG. 7 shows that both HPV16 and HPV18 increase the expression of CDKN2A and RNASEH2A, but decrease the expression of NOVA1 in HFK- and HVK-derived rafts. In this experiment, total RNA was used to determine the relative levels of individual proteins by TaqMan® RT-qPCR. FIG. 8 shows that HPV18 infection and viral E6 and/or E7 affect the expression of RNASEH2A and Nova1. The expression of RNASEH2A and NOVA1 in primary human keratinocytes (PHK)-derived raft tissues with or without HPV18 infection on day 8, day 12, and day 16 or PHK rafts transduced with a retrovirus expression HPV18 E6, E7 or E6E7 or with an empty control retrovirus were further validated by TaqMan® RT-qPCR. These results demonstrate that RNASEH2A and NOVA1 respond to HPV18 infection and their altered expression in cervical cancer could be attributed to viral oncoprotein E6 and/or E7. *, P<0.05; ***, P<0.001; NS, no statistics significance.

Figure 9:
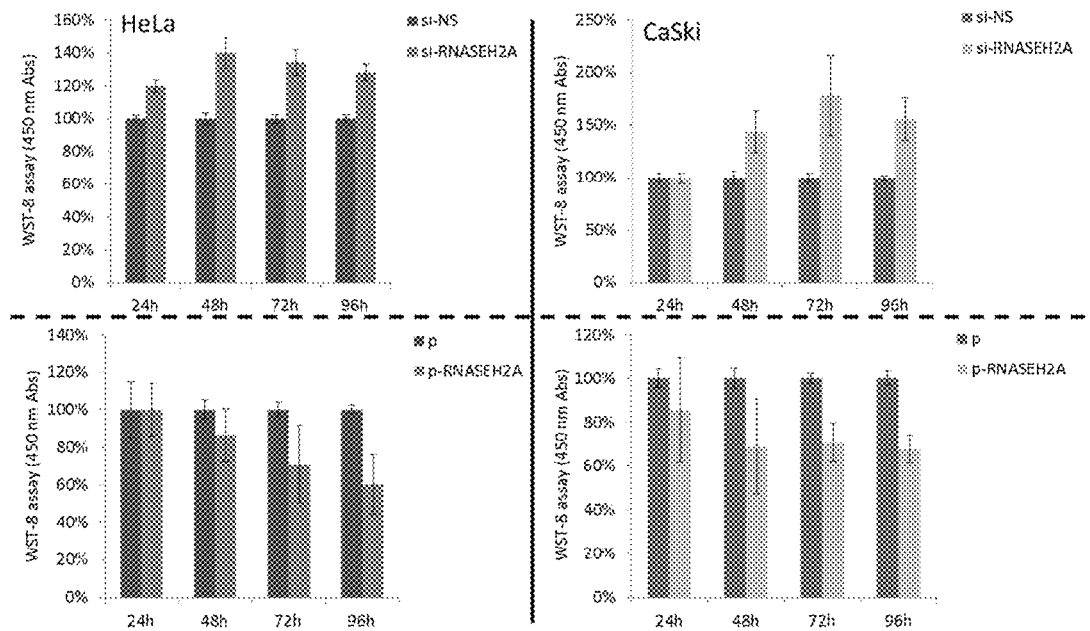
FIG. 9 shows that knockdown or overexpression of RNASEH2A in HeLa or CaSki cells affects cell proliferation. Specific-siRNA knockdown or ectopic expression of RNASEH2A from a mammalian expression vector in HeLa or CaSki cells on cell proliferation was evaluated by Cell Counting Kit-8 (CCK-8) assay
Figure 10:
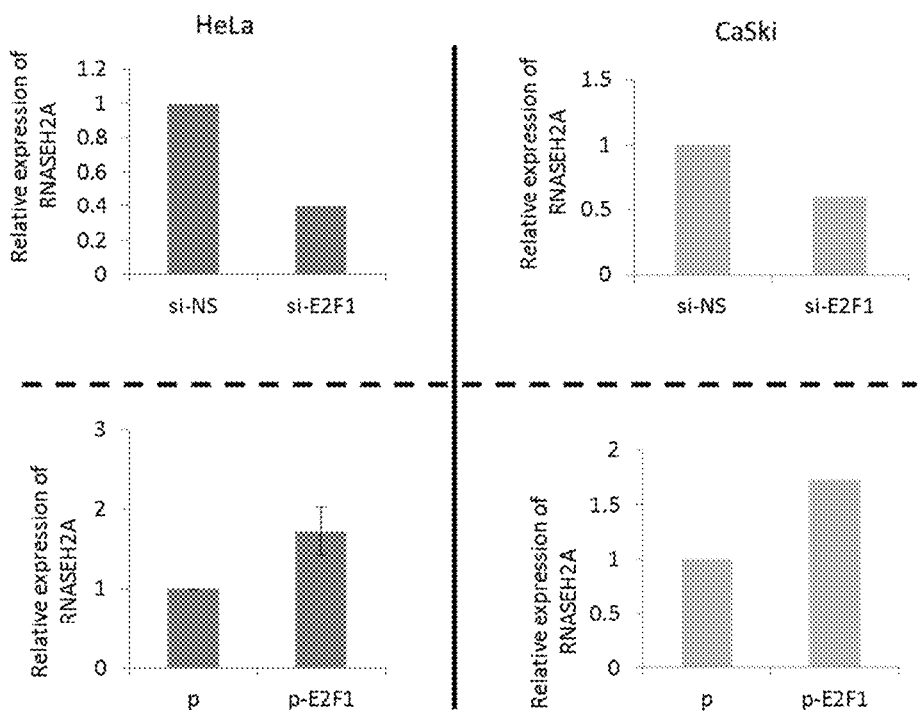
FIG. 10 shows HPV oncoprotein E7 regulates the expression of RNASEH2A via E2F1. Specific-siRNA knockdown or ectopic expression of E2F1 from a mammalian expression vector in HeLa or CaSki cells on RNASEH2A was evaluated by Western blot.

FIG. 9 shows that knockdown or overexpression of RNASEH2A in HeLa or CaSki cells affects cell proliferation. Specific-siRNA knockdown or ectopic expression of RNASEH2A from a mammalian expression vector in HeLa or CaSki cells on cell proliferation was evaluated by Cell Counting Kit-8 (CCK-8) assay at time indicated. si-NS, non-specific siRNA; siRNASEH2A, RNASEH2A-specific siRNA; P, control vector; p-RNASEH2A, RNASEH2A-expression vector. FIG. 10 shows HPV oncoprotein E7 regulates the expression of RNASEH2A via E2F1. Specific-siRNA knockdown or ectopic expression of E2F1 from a mammalian expression vector in HeLa or CaSki cells on RNASEH2A was evaluated by Western blot using anti-RNASEH2A antibody. si-NS, non-specific siRNA; si-E2F1, E2F1-specific siRNA; P, control vector; p-E2F1, E2F1-expression vector.

Figure 11:
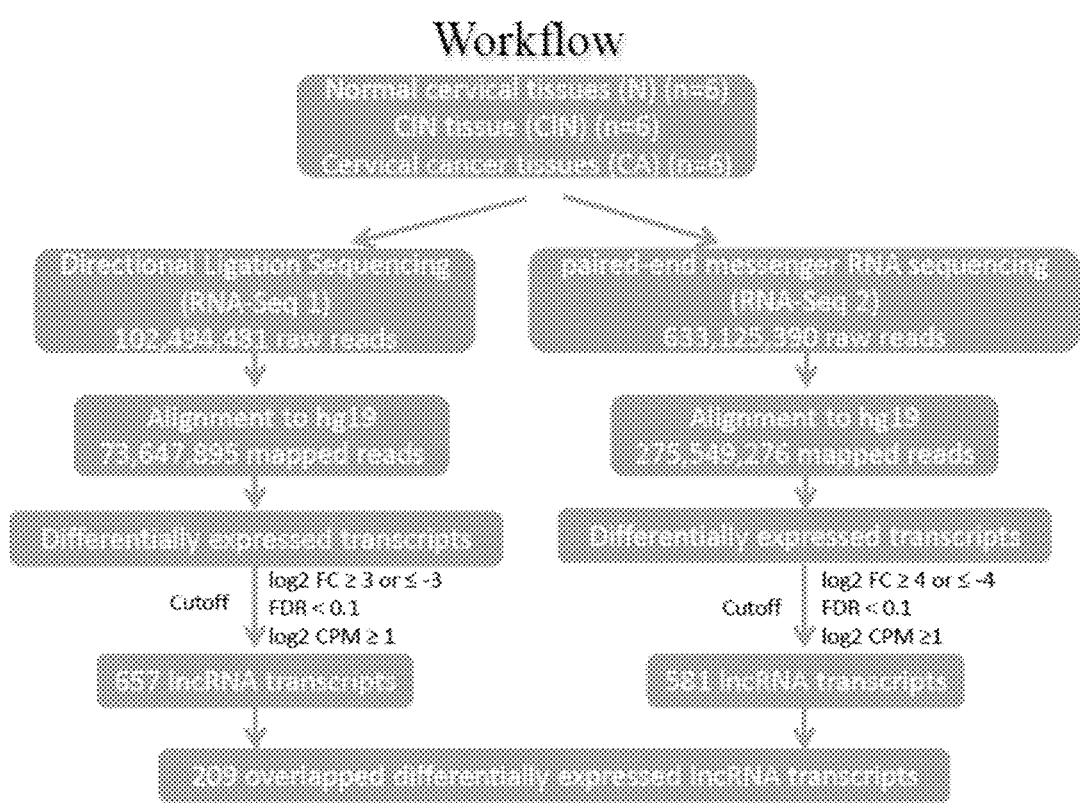
FIG. 11 is a flowchart of the RNA-Seq analyses for long-noncoding RNAs (lnc-RNAs).
Figure 12:
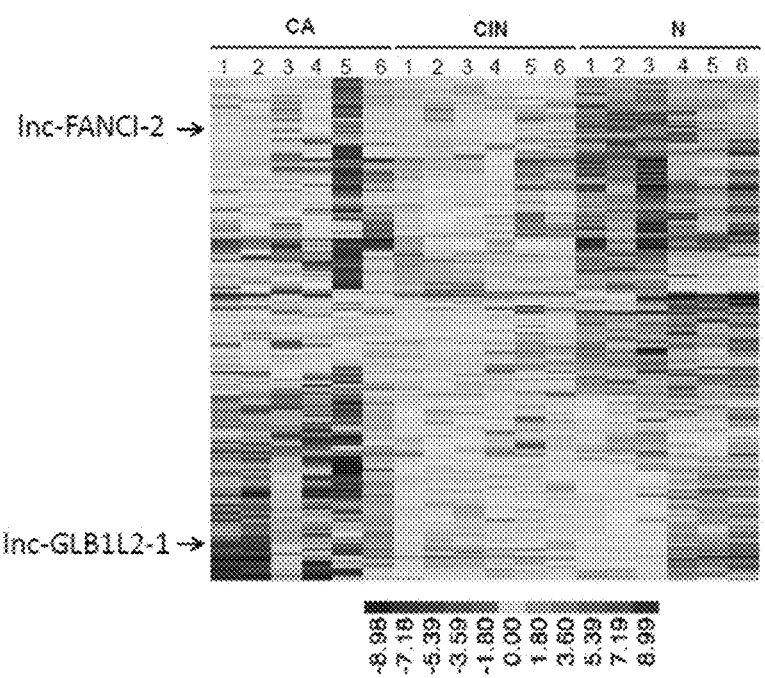
FIG. 12 is a heat map showing 209 overlapped, differentially expressed lnc-RNAs from cervical cancer, pre-cancer to normal cervical tissues.

Example 2: The Expression Profile of Long Noncoding RNAs Distinguishes Normal Cervix from and Cancerous Cervix RNA was extracted from each sample using Trizol® reagent (Life technologies). RNAseq libraries were prepared using TruSeq® Stranded Total RNA Kit with Ribo-Zero depletion and sequenced on an Illumina HiSeq™ 2000 platform as paired-end reads. The fastq data were mapped to human reference genome (hg19, GRCh37) by Bowtie (v2.2.1.0), and the mapping results were further filtered by samtools (v0.1.19.0). The latest annotation of LncRNA was downloaded from lncipedia database version 3.0. We counted the mapped reads in individual lncRNA region of each sample by bedtools (v2.19.0). The R Bioconductor edgeR package was used to normalize raw reads by the scaling method. The differentially expressed lncRNAs were detected by one-way ANOVA method with 10% false discovery rate (FDR) and four fold changes between the conditions. FIG. 11 is a flow chart of the RNA-Seq analysis. FIG. 12 is a heat map showing 34 overlapped, differentially expressed lnc-RNAs in cervical cancer compared to normal cervical tissues. lnc-FANCI-2 and lnc-GLB1L2-1 were specifically identified as associated with cervical cancer. Tables 2 and 3 list all of the isoforms of these two lnc-RNAs.

```
Taqman® primer design for lnc-FANCI-2
Exon 6:
                                           (SEQ ID NO: 76)
CTGGAAAGGAGGAGAACATGAAACATTGCTTGAAGACAATGGCCGAG
ACAGCAGGTCCCACCCTGCACAGCCACCAGCATCTCTCCCCTCAGCC
CTGTCTCCTCTTCTGCAGTTGGGATCTGCACATTTAAGCCTGAA Exon 7:
                                           (SEQ ID NO: 77)
ATTGTCCTGTGAAGTGAAGTATGATCGGACAGCCTCTTTTCAGCTTT
TATGACAATGGAGACAGAGGAATTGTGGCTCTTGCCAAGGTCACAGG
ATTGGAATACAGAGCCAAGCCACCCCAGGACATGCAAGAGCCTCAGA
AGGGAA Primers for RT-qPCR
Forward:
                                           (SEQ ID NO: 78)
5'-ACAGCCACCAGCATCTCTC-3'

Probe:
                                           (SEQ ID NO: 79)
5'-TGAAGTGAAGTATGATCGGACAGCCTC-3'

Reverse:
                                           (SEQ ID NO: 80)
5'-CCACAATTCCTCTGTCTCCATT-3'

TaqMan® primer design for lnc-GLB1L2-1:
Last Exon 3:
                                           (SEQ ID NO: 81)
TCTCTCATCTGTGTTTTCAGGGCATGGACTGGAACTCCCAATACCCC
TGACATGGGCTGAGTCAACGTGGTCATGAACATGTGACAGGAG Last Exon 2:
                                           (SEQ ID NO: 82)
GCAGCAGAAGTTGCAGAGAAGAGTGAGGCACGTTTGAAAAAGGCTGA
AAAATGTTTCTGTCCAGGCAAGGGTGTGTGCTGAATGACTCAAGGAT
TTTTTGG Primers for RT-qPCR
Forward:
                                           (SEQ ID NO: 83)
5'-CATGGACTGGAACTCCCAATA-3'

Probe:
                                           (SEQ ID NO: 84)
5'-TGCAGAGAAGAGTGAGGCACGTTTG-3'

Reverse:
                                           (SEQ ID NO: 85)
5'-CCTTGCCTGGACAGAAACATT-3'
```

Figure 13:
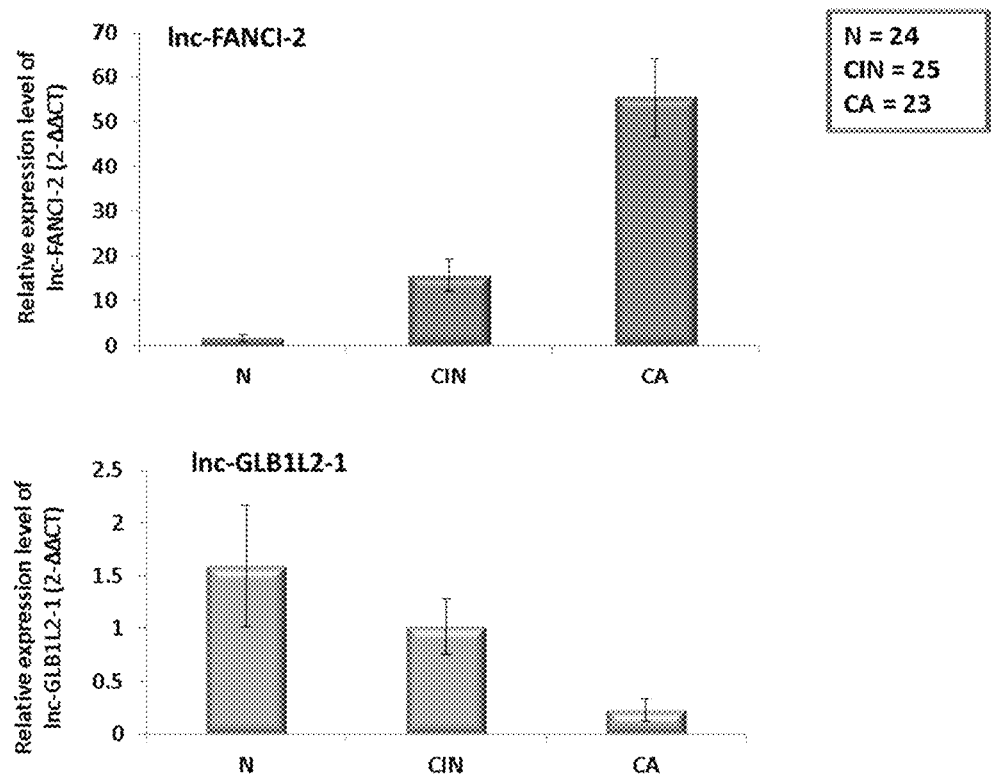
FIG. 13 shows an increase of lnc-FANCI-2, and decrease of lnc-GLB1L2-1 expression along with the cervical lesion progression from normal cervix. Lnc-FANCI-2 and lnc-GLB1L2-1 RNA expression was examined by RT-qPCR in 24 normal, 25 CIN 2-3, and 23 cancer tissues.
Figure 14:
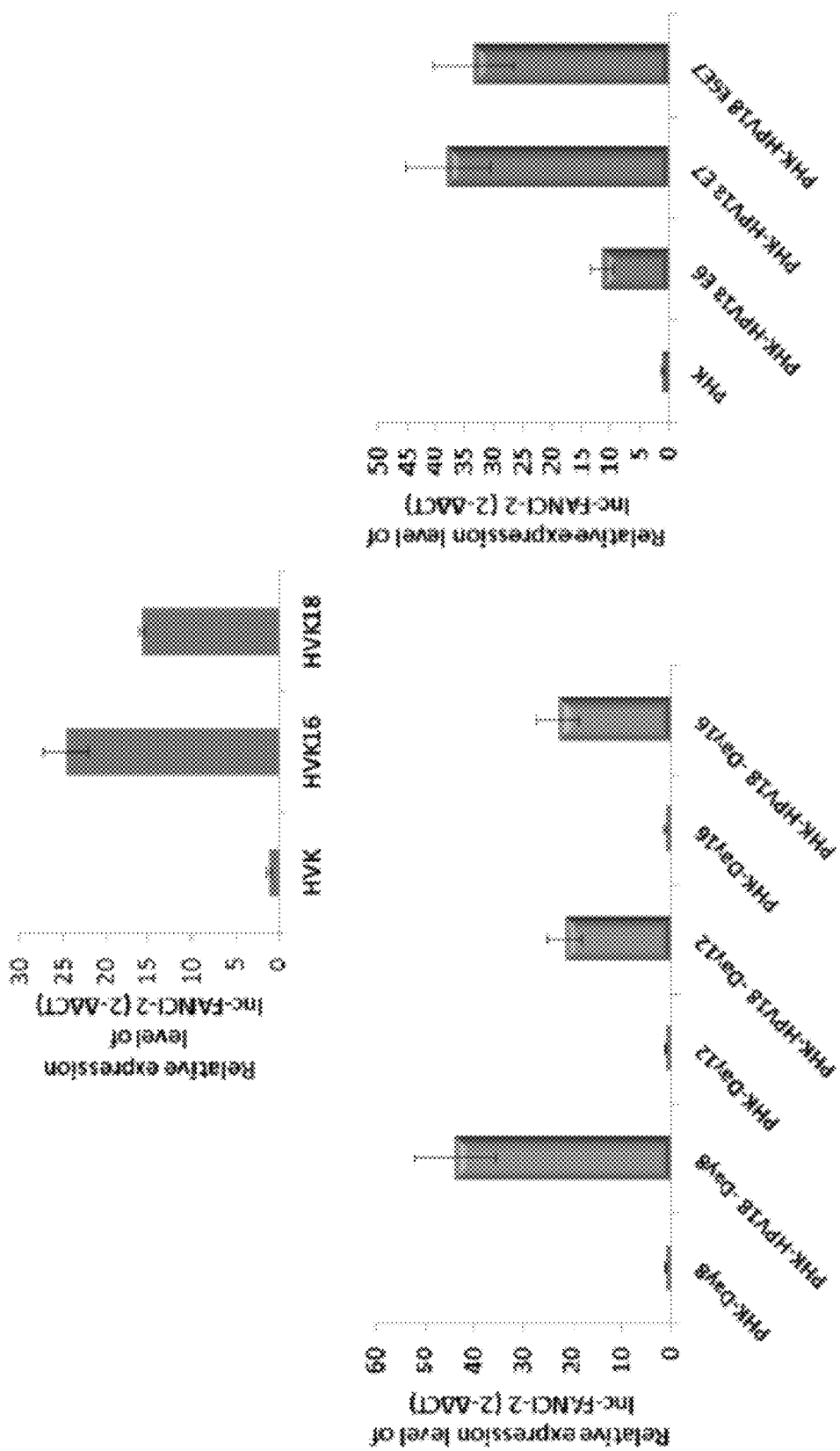
FIG. 14 shows that HPV infection increases lnc-FANCI-2 expression in HVK- and PHK-derived rafts and viral E7 or E6 is responsible for the increase. The expression of lnc-FANCI-2 in human vaginal keratinocytes (HVK)-derived raft tissues without (HVK) or with HPV16 (HVK16) or HPV18 (HVK18) infection or primary human keratinocytes (PHK)-derived raft tissues without or with HPV18 infection.

FIG. 13 shows an increase of lnc-FANCI-2, and decrease of lnc-GLB1L2-1 expression along with the cervical lesion progression from normal cervix. Lnc-FANCI-2 and lnc-GLB1L2-1 RNA expression was examined by RT-qPCR in 24 normal, 25 CIN 2-3, and 23 cancer tissues. FIG. 14 shows that HPV infection increases lnc-FANCI-2 expression in HVK- and PHK-derived rafts and viral E7 or E6 is responsible for the increase. The expression of lnc-FANCI-2 in human vaginal keratinocytes (HVK)-derived raft tissues without (HVK) or with HPV16 (HVK16) or HPV18 (HVK18) infection or primary human keratinocytes (PHK)-derived raft tissues without or with HPV18 infection on day 8, day 12, and day 16 or PHK rafts transduced with a retrovirus expressing HPV18 E6, E7 or E6E7 or with an empty control retrovirus were further validated by RT-qPCR. These results demonstrate that lnc-FANCI-2 expression responds to HPV18 infection and viral oncoprotein E6 and/or E7.

In data not shown, lnc-FANCI-2 was upregulated in isolated keratinocyte lines infected by high-risk HPVs, but not low risk HPV11 and epidermodysplasia verruciformis-associated HPV5 and 10.

The term "polynucleotide" as used herein refers to a polymer of greater than one nucleotide in length of ribonucleic acid (RNA), deoxyribonucleic acid (DNA), hybrid RNA/DNA, modified RNA or DNA, or RNA or DNA mimetics, including peptide nucleic acids (PNAs). The polynucleotides may be single- or double-stranded. The term includes polynucleotides composed of naturally-occurring nucleobases, sugars, and covalent internucleoside (backbone) linkages as well as polynucleotides having non-naturally-occurring portions which function similarly. Such modified or substituted polynucleotides are well known in the art and are referred to as "analogues."

"Complementary" or "substantially complementary" refers to the ability to hybridize or base pair between nucleotides or nucleic acids, such as, for instance, between a sensor peptide nucleic acid or polynucleotide and a target polynucleotide. Complementary nucleotides are, generally, A and T (or A and U), or C and G. Two single-stranded polynucleotides or PNAs are said to be substantially complementary when the bases of one strand, optimally aligned and compared and with appropriate insertions or deletions, pair with at least about 80% of the bases of the other strand, usually at least about 90% to 95%, and more preferably from about 98 to 100%.

Alternatively, substantial complementarity exists when a polynucleotide may hybridize under selective hybridization conditions to its complement. Typically, selective hybridization may occur when there is at least about 65% complementarity over a stretch of at least 14 to 25 bases, for example at least about 75%, or at least about 90% complementarity.

The term "homologous region" refers to a region of a nucleic acid with homology to another nucleic acid region. Whether a "homologous region" is present in a nucleic acid molecule is determined with reference to another nucleic acid region in the same or a different molecule.

Hybridization conditions typically include salt concentrations of less than about 1M, more usually less than about 500 mM, for example, less than about 200 mM. In the case of hybridization between a peptide nucleic acid and a polynucleotide, the hybridization can be done in solutions containing little or no salt. Hybridization temperatures can be as low as 5° C., but are typically greater than 22° C., and more typically greater than about 30° C., for example in excess of about 37° C. Longer fragments may require higher hybridization temperatures for specific hybridization as is known in the art. Other factors may affect the stringency of hybridization, including base composition and length of the complementary strands, presence of organic solvents and extent of base mismatching, and the combination of parameters used is more important than the absolute measure of any one alone. Other hybridization conditions which may be controlled include buffer type and concentration, solution pH, presence and concentration of blocking reagents to decrease background binding such as repeat sequences or blocking protein solutions, detergent type(s) and concentrations, molecules such as polymers which increase the relative concentration of the polynucleotides, metal ion(s) and their concentration(s), chelator(s) and their concentrations, and other conditions known in the art.

As used herein, a "probe" is a polynucleotide capable of selectively hybridizing to a target sequence, a complement thereof, a reverse complement thereof, or to an RNA version of the target sequence, the complement thereof, or the reverse complement thereof. A probe may comprise ribonucleotides, deoxyribonucleotides, peptide nucleic acids, and combinations thereof. A probe may optionally comprise one or more labels. In some embodiments, a probe may be used to amplify one or both strands of a target sequence or an RNA form thereof, acting as a sole primer in an amplification reaction or as a member of a set of primers. In one aspect, probes include nucleotide sequences of 10 to 1,000 nucleotides. In other embodiments, the probes are 10-200, 10-30, 10-40, 20-50, 40-80, 50-150, or 80-120 nucleotides in length.

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

The invention claimed is:

1. A method of quantitating an expression level of a lnc-FANCI-2 polynucleotide in a sample containing cells from a test patient's cervix with one or more first polynucleotides that hybridizes to the lnc-FANCI-2 polynucleotide, the method comprising
   contacting the sample containing cells from the test patient's cervix with the one or more first polynucleotides, and
   detecting the level of hybridization of the one or more first polynucleotides to the lnc-FANCI-2 polynucleotide,
   comparing the level of hybridization in the sample containing cells from the test patient's cervix to a control level of hybridization in a control sample of normal cervical tissues, and
   determining differential expression of the lnc-FANCI-2 polynucleotide in the sample containing cells from the test patient's cervix when the level of hybridization for the sample containing cells from the test patient's cervix is at least about 150% of the control level of hybridization in the control sample,
   wherein the one or more first polynucleotides are SEQ ID NOs: 78, 79 and 80.

2. The method of claim 1, wherein detecting the level of hybridization of the one or more first polynucleotides to the lnc-FANCI-2 polynucleotide is done with real-time RT-PCR.

3. The method of claim 1, wherein the sample containing cells from the test patient's cervix comprises a PAP smear, a vaginal wash, or a cervical biopsy sample.

4. The method of claim 1, wherein differential expression of the lnc-FANCI-2 polynucleotide in the sample containing cells from the test patient's cervix is determined when the level of hybridization for the sample containing cells from the test patient's cervix is at least about 180% of the control level of hybridization for the control sample.

5. The method of claim 1, wherein differential expression of the lnc-FANCI-2 polynucleotide in the sample containing cells from the test patient's cervix is determined when the level of hybridization for the sample containing cells from the test patient's cervix is at least about 200% of the control level of hybridization for the control sample.

6. A method of determining if a test patient has stage 1, stage 2, or stage 3 cervical intraepithelial neoplasia, cervical cancer, HPV-associated pre-cancer, or HPV-associated cancer, the method comprising
   contacting the sample containing cells from the test patient's cervix with one or more first polynucleotides, and
   determining an expression level of a lnc-FANCI-2 polynucleotide in the sample by detecting the level of hybridization of the one or more first polynucleotides to the lnc-FANCI-2 polynucleotide,
   correlating the expression level of the lnc-FANCI-2 polynucleotide in the sample to a reference expression level of the lnc-FANCI-2 polynucleotide in a reference sample that is
      a control sample from a patient or patients with no evidence of cervical cancer,
      a control sample from a cervical cancer patient or patients,
      a control sample from a patient or patients with stage 1, stage 2, or stage 3 cervical intraepithelial neoplasia,
      a control sample from a patient or patients with no evidence of HPV-associated pre-cancer or HPV-associated cancer,
      a control sample from a patient or patients with HPV-associated pre-cancer, or
      a control sample from a patient or patients with HPV-associated cancer; and
   determining, based on said correlation, whether the test patient has cervical cancer, stage 1, stage 2, or stage 3 cervical intraepithelial neoplasia, HPV-associated pre-cancer, or HPV-associated cancer,
   wherein the one or more first polynucleotides are SEQ ID NOs: 78, 79 and 80.

7. The method of claim 6, wherein the determination is whether the test patient has HPV-associated pre-cancer.

8. The method of claim 6, wherein the determination is whether the test patient has HPV-associated cancer.

9. The method of claim 6, wherein the determination is whether the test patient has cervical cancer.

10. The method of claim 6, wherein the determination is whether the test patient has stage 1, stage 2, or stage 3 cervical intraepithelial neoplasia.

11. The method of claim 6, wherein the reference sample is a control sample from a cervical cancer patient or patients.

12. The method of claim 6, wherein the detecting the level of hybridization of the one or more first polynucleotides to the lnc-FANCI-2 polynucleotide is done with real-time RT-PCR.

* * * * *

SEQUENCE LISTING

```
Sequence total quantity: 95
SEQ ID NO: 1          moltype = DNA  length = 1267
FEATURE               Location/Qualifiers
source                1..1267
                      mol_type = other DNA
                      organism = Homo sapiens
SEQUENCE: 1
cgagggctgc ttccggctgg tgcccccggg ggagacccaa cctggggcga cttcaggggt    60
gccacattcg ctaagtgctc ggagttaata gcacctcctc cgagcactcg ctcacggcgt   120
ccccttgcct ggaaagatac cgcggtccct ccagaggatt tgagggacag ggtcggaggg   180
ggctcttccg ccagcaccgg aggaagaaag aggaggggct ggctggtcac cagagggtgg   240
ggcggaccgc gtgcgctcgg cggctgcgga gaggggggaga gcaggcagcg ggcggcgggg   300
agcagcatgg agccggcggc ggggagcagc atggagcctt cggctgactg gctggccacg   360
gccgcggccc ggggtcgggt agaggaggtg cgggcgctgc tggaggcggg ggcgctgccc   420
aacgcaccga atagttacgg tcggaggccg atccaggtca tgatgatggg cagcgcccga   480
gtggcggagc tgctgctgct ccacgcgcgc gagcccaact gcgccgaccc cgccactctc   540
```

```
acccgacccg tgcacgacgc tgcccgggag ggcttcctgg acacgctggt ggtgctgcac    600
cggggccgggg cgcggctgga cgtgcgcgat gcctggggcc gtctgcccgt ggacctggct    660
gaggagctgg gccatcgcga tgtcgcacgg tacctgcgcg cggctgcggg gggcaccaga    720
ggcagtaacc atgcccgcat agatgccgcg gaaggtccct cagacatccc cgattgaaag    780
aaccagagag gctctgagaa acctcaggaa acttagatca tcagtcaccg aaggtcctac    840
agggccacaa ctgcccccgc cacaacccac cccgctttcg tagttttcat ttagaaaata    900
gagcttttaa aaatgtcctg ccttttaacg tagatatatg ccttcccca ctaccgtaaa    960
tgtccattta tatcattttt tatatattct tataaaaatg taaaaagaa aaacaccgct   1020
tctgccttt cactgtgttg gagttttctg gagtgagcac tcacgcccta agcgcacatt   1080
catgtgggca tttcttgcga gcctcgcagc ctccggaagc tgtcgacttc atgacaagca   1140
ttttgtgaac tagggaagct caggggggtt actggcttct cttgagtcac actgctagca   1200
aatggcagaa ccaaagctca aataaaaata aataattttt cattcattca ctcaaaaaaa   1260
aaaaaaa                                                             1267

SEQ ID NO: 2           moltype = DNA    length = 1464
FEATURE                Location/Qualifiers
source                 1..1464
                       mol_type = other DNA
                       organism = Homo sapiens
SEQUENCE: 2
cgagggctgc ttccggctgg tgcccccggg ggagacccaa cctggggcga cttcaggggt     60
gccacattcg ctaagtgctc ggagttaata gcacctcctc cgagcactcg ctcacggcgg    120
cccccttgcct ggaaagatac cgcggtccct ccagaggatt tgaggacag ggtcggaggg    180
ggctcttccg ccagcaccgg aggaagaaag aggaggggct ggctggtcac cagagggtgg    240
ggcggaccgc gtgcgctcgg cggctgcgga gaggggggaga gcaggcagcg ggcggcgggg    300
agcagcatgg agccggccgc ggggacagc atggagcctt cgctgactg gctggccacg    360
gccgcgggccc gggtcgggt agaggaggtg cgggcgctgc tggaggcggg ggcgctgccc    420
aacgcaccga atagttacgg tcggaggccg atccaggtca tgatgatggg cagcgcccga    480
gtggcggagc tgctgctgct ccacggcgcg gagcccaact cgccgacccc cgccactctc    540
acccgaccg tgcacgacgc tgcccgggag ggcttcctgg acacgctggt ggtgctgcac    600
cggggccgggg cgcggctgga cgtgcgcgat gcctggggcc gtctgcccgt ggacctggct    660
gaggagctgg gccatcgcga tgtcgcacgg tacctgcgcg cggctgcggg gggcaccaga    720
ggcagtaacc atgcccgcat agatgccgcg gaaggtccct cagaaatgat cggaaaccat    780
ttgtgggttt gtagaagcag gcatgcgtag ggaagctacg ggattccgcc gaggagcgcc    840
agagcctgag gcgccctttg gttatcgcaa gctggctggc tcactccgca ccaggtgcaa    900
aagatgcctg gggatgcggg aagggaaagg ccatctcttc acgccttcgc gcctggcatt    960
acatccccga ttgaaagaac cagagaggct ctgagaaacc tcgggaaact tagatcatca   1020
gtcaccgaag gtcctacagg gccacaactg ccccgccac aacccacccc gctttcgtag   1080
ttttcattta gaaatagag cttttaaaaa tgtcctgcct tttaacgtag atatatgcct   1140
tcccccacta ccgtaaatgt ccatttatat cattttttat atattcttat aaaaatgtaa   1200
aaaagaaaaa caccgcttct gccttttcac tgtgttggag ttttctggag tgagcactca   1260
cgccctaagc gcacattcat gtgggcattt cttgcgagcc tcgcagcctc cggaagctgt   1320
cgacttcatg acaagcattt tgtgaactag ggaagctcag gggggttact ggcttctctt   1380
gagtcacact gctagcaaat ggcagaacca aagctcaaat aaaaataaaa taattttcat   1440
tcattcactc aaaaaaaaaa aaaa                                          1464

SEQ ID NO: 3           moltype = DNA    length = 1164
FEATURE                Location/Qualifiers
source                 1..1164
                       mol_type = other DNA
                       organism = Homo sapiens
SEQUENCE: 3
cgctcaggga aggcgggtgc gcgcctgcgg ggcggagatg ggcaggggc ggtgcgtggg     60
tcccagtctg cagttaaggg ggcaggagtg gcgctgctca cctctggtgc caaagggcgg    120
cgcagcggct gccgagctcg ggcctggagg cggcgagaac atggtgcga ggttcttggt    180
gaccctccgg attcggcgcg cgtgcgggcc gccgcgagtg aggggtttcg tggttcacat    240
cccgcggctc acggggagt gggcagcgcc aggggcgccc gccgctgtgg ccctcgtgct    300
gatgctactg aggagccagc gtctagggca gcagccgctt cctagaagac caggtcatga    360
tgatgggcag cgcccgagtg gcggagctgc tgctgctcca cggcgcggag cccaactgcg    420
ccgaccccgc cactctcacc cgacccgtgc acgacgctgc cggggaggcc ttcctggaca    480
cgctggtggt gctgcaccgg gccggggcgc ggctggacgt gcgcgatgcc tggggccgtc    540
tgcccgtgga cctggctgag gagctgggcc atcgcgatgt cgcacggtac ctgcgcgcgg    600
ctgcgggggg caccagaggc agtaaccatg cccgcataga tgccgcggaa ggtccctcag    660
acatccccga ttgaaagaac cagagaggct ctgagaaacc tagatcatca              720
gtcaccgaag gtcctacagg gccacaactg ccccgccac aacccacccc gctttcgtag    780
ttttcattta gaaatagag cttttaaaaa tgtcctgcct tttaacgtag atatatgcct    840
tcccccacta ccgtaaatgt ccatttatat cattttttat atattcttat aaaaatgtaa    900
aaaagaaaaa caccgcttct gccttttcac tgtgttggag ttttctggag tgagcactca    960
cgccctaagc gcacattcat gtgggcattt cttgcgagcc tcgcagcctc cggaagctgt   1020
cgacttcatg acaagcattt tgtgaactag ggaagctcag gggggttact ggcttctctt   1080
gagtcacact gctagcaaat ggcagaacca aagctcaaat aaaaataaaa taattttcat   1140
tcattcactc aaaaaaaaaa aaaa                                          1164

SEQ ID NO: 4           moltype = DNA    length = 1235
FEATURE                Location/Qualifiers
source                 1..1235
                       mol_type = other DNA
                       organism = Homo sapiens
SEQUENCE: 4
```

```
atggagccgg cggcggggag cagcatggag ccttcggctg actggctggc cacggccgcg    60
gcccggggtc gggtagagga ggtgcgggcg ctgctggagg cggggcgct gcccaacgca    120
ccgaatagtt acggtcggag gccgatccag gtgggtagag ggtctgcagc gggagcaggg    180
gatggcgggc gactctggag gacgaagttt gcagggaat tggaatcagg tagcgcttcg    240
attctccgga aaaagggag gcttcctcgg gagttttcaa aaggggtttg taatcacaga    300
cctcctcctg gcgacgccct gggggcttgg gaagccaagg aagaggaatg aggagccacg    360
cgcgtacaga tctctcgaat gctgagaaga tctgaagggg ggaacatatt tgtattagat    420
ggaagtcatg atgatgggca gcgcccgagt ggcggagctg ctgctgctcc acggcgcgga    480
gcccaactgc gccgacccccg ccactctcac ccgaccccgtg cagcacgctg cccgggaggg    540
cttcctggac acgctggtgg tgctgcaccg ggcgggggcg cggctggacg tgcgcgatgc    600
ctggggccgt ctgcccgtgg acctggctga ggagctgggc catcgcgatg tcgcacggta    660
cctgcgcgcg gctgcggggg gcaccagagg cagtaaccat gcccgcatag atgccgcgga    720
aggtccctca gacatcccccg attgaaagaa ccagagaggc tctgagaaac ctcgggaaac    780
ttagatcatc agtcaccgaa ggtcctacag ggccacaact gccccccgcca caacccaccc    840
cgctttcgta gtttttcattt agaaaataga gcttttaaaa atgtcctgcc ttttaacgta    900
gatatatgcc ttcccccact accgtaaatg tccatttata tcattttta tatattctta    960
taaaaatgta aaaagaaaa acaccgcttc tgccttttca ctgtgttgga gttttctgga   1020
gtgagcactc acgccctaag cgcacattca tgtgggcatt tcttgcgagc ctcgcagcct   1080
ccggaagctg tcgacttcat gacaagcatt ttgtgaacta gggaagctca gggggggttac   1140
tggcttctct tgagtcacac tgctagcaaa tggcagaacc aaagctcaaa taaaaataaa   1200
ataatttca ttcattcact caaaaaaaaa aaaaa                              1235

SEQ ID NO: 5              moltype = DNA   length = 3756
FEATURE                   Location/Qualifiers
source                    1..3756
                          mol_type = other DNA
                          organism = Homo sapiens
SEQUENCE: 5
aacggcggga ccgcggcgcc tgggcgtcac tgaggcagta gccggccggg tgaggagggc    60
ggttgccggc gcggcgcggc gcggcgcggg tggggcgggg gttccgccgg cttccagtcc    120
ccttccccgc cgccgccgcc gccaccgcct ctccgcggga ctcgccccga gcgactcctc    180
cgcggcagtg ctgacggcca gcggcacgag ccgtagtagc tgcagcttcg agtcacagca    240
gcaggtaatt gctgccatgg aaacacaact gtctaatggg ccaacttgca ataacacagc    300
caatggtcca accaccataa acaacaactg ttcgtcactg gttgactctg ggaacacaga    360
agacacgcaag accaacttaa tagtcaacta ccttcctcag aacatgacac aggaggaact    420
aaagagtctc tttgggagca ttggtgaaat agagtcctgt aagcttgtaa gagacaaaat    480
aacagggcag agcttgggat atggcttttgt gaactacatt gaccccaagg atgcagaaaa    540
agctatcaac accctgaatg gattgagact tcaaaccaaa acaataaaaag tttcctatgc    600
tcgcccaagt tcagcttcta tcagagatgc aaattttatat gtcagcggac ttccaaaac    660
aatgaccccag aaggagttgg aacagctttt ttcacaatat ggacgcatta ttacttctcg    720
tattcttgtc gaccaggtca ctggcatatc aaggggtgta gggtttattc gatttgacaa    780
gcgaattgag gcagaagaag ctatcaaagg cctaaatggc cagaaacctc ccgtgccac    840
ggagccactc actgtaaagt ttgctaataa cccaagcaaa aaaaccaatc aggccatcct    900
tcccagctg taccagtctc caaacagaag gtatccagga ccgctagctc agcaggcaca    960
gcgttttagg ttttctccaa tgaccattga cggaatgacc agtttggctg gaattaatat   1020
ccctgggcac cctggaacag ggtggtgtat atttgtgtac aacctggctc ctgacgcaga   1080
tgagagtatc ctgtgggcaaa tgttggggcc ttttggagct gtcaccaatg tgaaggtcat   1140
ccgtgacttt aacaccaata aatgcaaagg ttttggattt gtgactatga caaactatga   1200
tgaggctgcc atggcgatag ctagcctcaa tggatacgt ctgggagaca gagtactgca   1260
ggtctccttt aagacaaaca aaacgcacaa agcctaatga gctcttgtcc tcagtccatt   1320
tatatatgaa aactatacaa caaaggcaag ttaagagaaa cttttatacat tagtaaatgt   1380
ctttgtaagt cagtgttgag atgggggataa aatgactact tagcatccta agaaatatgt   1440
gagatttttt attgctagta tttgaattaa aacttcttaa atatctttta tgtttgaata   1500
tggacaagag gtacagggtt tttacctgtc acattgcatt ctattgcctt ctttgaagaa   1560
ggtggacctt ttaaagtgtt tcagctaagg gaagacattt cttttcttt tacataactg   1620
ccttgaacct gtgagtaaat attgaggctt tgtgttgtaa ttcttcagtt ggttgtgtct   1680
tttttttccc ccctttttt ccttttctgt attagctttg tgtttggttt acatttaaag   1740
cattgctgtt atgtctgttt aagaaaagta ttttgaagtt tacatttta tttatgaagt   1800
ttaaaacagt atttattttg taattatgat ttgggttggg aagggggggg ctacattata   1860
aacgcttatt gtaagaatac tggaaacttt tccgtaaagc agtaccttgc caaaggata   1920
agagcctctt tgatgtgggt ttaaaaaaag catctatttt tataaaaaag aaaatttgga   1980
gaaacttttc actggtcctg gaacaaatat tttgacttga atactttgag aaatctcttc   2040
atatgacacc tagtgagctt ttaaaatttta ccaggaaatt tgcagcggtt ggaaaattta   2100
gaaagattta tggtgtagaa aatacttttg agatctttgt atgaaaggag tagaatcaat   2160
gggggggaaac actgctggtt tcattttgt aatcaccagt ggagcgtctg atcatcctgg   2220
ttattatgtg ataggtggct cacattgatt tgtgattttg aaacaaataa aaaaaattta   2280
caaaagaata tataagagca ggcaagaaat ttaaattacc gagagatggg ggaaaaaatc   2340
tgttcttcct aaagaaatcc cttcagatag gcttcatggt gtttagtgat gtacttgcag   2400
tattgtttga agaattgttt tgtcttaagg aaaaaagacg ttgcacatga tttgtactgc   2460
agcaaatcag caaaagtgat ctgagttgga tatattttga aggtattttga aagttacgtt   2520
caaggctaac acctgagctt tgtgtaatgt aaataagacc ttgtgtttat gaacctttca   2580
gctaatttaa ttttttttcc cttacatgcc aagtgatgtt caggttttga atgttttgt   2640
atcagttttt tcctttgtaa atggcattaa cattgttact tgaggtcttg cttaatcact   2700
tttgttgtcc tgaggacttg aatttacagt gcatcagatt tgtgcaaat tttgctgtta   2760
gatagtctag cttcagctgt ttatggtgat gctacatttt cgtttataaa tatgtttgtg   2820
gtataaaaaa atgagtataa ccataggttt tgaacaaatt tccttacatt tttcatacaa   2880
aaatcataaa tatctgtatg ctattgaaat ttaactttgt atgatgctta aaaaccacta   2940
tttgggaaa taataaaata agtctttacc atgtatgaaa gaaattttaa aaaatacaaa   3000
atattttctg attagcatct agcttataat aaattttcaa aaagctgaa ggcaaaaatg   3060
```

```
cccttcatcag gatgcactga gaactatata gttacgtcct gcttttttgta taaactgaga   3120
tgctcacatg cttcccctta gaacaggcaa tgtgctatgc ataacatagt tgtacattat    3180
ctttgcggtt gctttgagtt ttatttttta ttatttaaaa ttgtagttat aaaattttc     3240
agtatagtac agtacatata ctgtgaggcg cgtgctaaag tgaataagcg agttttcatg    3300
ctgacccact caatgctatt cagaaatcaa ttggcttagc acttctct at atccttaggt   3360
gcatttagat tgccagagtt aaccttctgc gtttaaaaaa agaaaaacac taaaaaataa    3420
aatacatgta tatacttaaa aaaaaataat aaggtttccc tcaagggaaa acagcagcta    3480
catgcttctt tcctatacta ctgtagcaaa ccaaggcatt gatgagggg catgcaaatt     3540
gtgcttcact ttacagtgtt ttatcagagc acttaataaa atgtaaggct ggtatttatt   3600
tgaagttgta cagtatgact taattcacat ctgttggaat agaaaatata ttctgttgag   3660
tatttaagag gctgtacatg tttttctttg tgtttggatt ctttgtactt tttcatgttc   3720
agtacatcaa taaacaaagt tgaagggaaa aaaaaa                              3756

SEQ ID NO: 6          moltype = DNA   length = 3769
FEATURE               Location/Qualifiers
source                1..3769
                      mol_type = other DNA
                      organism = Homo sapiens
SEQUENCE: 6
agtccgaact ctgggcggga acactggtgg gggcggcgga ggttgtgccc gcgaagttcc    60
tagagctcag cccgttgcgg cgggagtaga gagaattggg cgcctcggga ggtggcaccg    120
ccctcccgt gggcacaagc aggttggggg cggcgggagc cgagcgggga cagtcgcgcc     180
tggcagcgtg cacgggcgtg gacgtgcccg ggtgcggccg cgtgtagcgc aagaaggaaa    240
ctgttgagac gcagcaggta attgctgcca tggaaacaca actgtctaat gggccaactt    300
gcaataacac agccaatggt ccaaccacca taaacaacaa ctgttcgtca ccagttgact    360
ctgggaacac agaagacagc aagaccaact taatagtcaa ctaccttcct cagaacatga    420
cacaggagga actaaagagt ctctttggga gcattggtga aatagagtcc tgtaagcttg    480
taagagacaa aataacaggg cagagcttgg gatatggctt tgtgaactac attgacccca    540
aggatgcaga gaaagctatc aacaccctga atggattgag acttcaaacc aaaacaataa    600
aagtttccta tgctcgccca agttcagctt ctatcagaga tgcaaattta tatgtcaggg    660
gacttccaaa aacaatgacc cagaaggagt tggaacagct ttttttcacaa tatgacgca   720
ttattacttc tcgtattctt gtcgaccagg tcactggcat atcaaggggt gtagggttta   780
ttcgatttga caagcgaatt gaggcagaag aagctatcaa aggcctaaat ggccagaaac   840
ctcccggtgc cacggagcca atcactgtaa agtttgctaa taacccaagc caaaaaaccc   900
atcaggccat cctttcccag ctgtaccagt ctccaaacag aaggtatcca ggaccgctag    960
ctcagcaggc acagcgtttt aggttttctc caatgaccat tgacggaatg accagtttgg   1020
ctggaattaa tatccctggg caccctggaa cagggtggtg tatatttgtg tacaacctgg   1080
ctcctgacgc agatgagagt atcctgtggc aaatgtttgg gccttttgga gctgtcacca   1140
atgtgaaggt catccgtgac tttaacacca ataatgcaaa aggttttgga tttgtgacta   1200
tgacaaacta tgatgaggct gccatggcga tagctagcct caatggatac cgtctgggag   1260
acagagtact gcaggtctcc tttaagacaa acaaaacgca caaagcctaa tgagctcttg   1320
tcctcagtcc atttatatat gaaaactata caacaaaggc aagttaagag aaactttata   1380
cattagtaaa tgtctttgta agtcagtgtt gagatgggga taaatgact attagcatc    1440
ctaagaaata tgtgagattt tttattgcta gtatttgaat taaaacttct taatatctt   1500
ttatgtttga atatggacaa gaggtacagg gttttttacct gtcacattgc attctattgc   1560
cttctttgaa gaaggtggac cttttaaagt gtttcagcta agggaagaca tttctttct   1620
ttttacataa ctgcttgaa cctgtgagta aatattgagg ctttgtgttg taattcttca   1680
gttggttgtg tctttttttt cccccctttt tttcctttt ctgattagct ttgtgtttgg   1740
tttacattta aagcattgct gttatgtctg tttaagaaaa gtattttgaa gtttacattt   1800
ttatttatga agttttaaaac agtatttatt ttgtaattat gatttgggtt ggggaagggg   1860
gggctacatt ataaacgctt atttgtaagaa tactggagac ctttttcgtaa agcagtcaat   1920
tgccaaagag ataagagcct ctttgatgtg ggttttaaaa aagcatctat ttttataaaa   1980
aagaaaattt ggagaaactt tttactggtc ctggaacaaa tattttgact tgaatacttt   2040
gagaaatctc ttcatatgac acctagtgag cttttaaaat ttaccaggaa atttgcagcg   2100
gttggaaaat ttagaaagat ttatggtgta gaaaatactt ttgagatctt tgtatgaaag   2160
gagtagaatc aatgggggga aacactgctg gtttcatttt tgtaatcacc agtggagcgt   2220
ctgatcatcc tggttattat gtgataggtg gctcacattg atttgtgatt ttgaaacaaa   2280
taaaaaaaat ttacaaaga atatataaga gcaggcaaga aatttaaatt accgagagat   2340
gggggaaaaa atcgttctt cctaaagaaa tcccttcaga tagagctcat ggtgtttagt   2400
gatgtacttg cagtattgtt tgaagaattg ttttgtctta aggaaaaaag acgttgcaca   2460
tgatttgtac tgcagcaaat cagcaaaagt gatctgagtt ggatatattt gaaggtattt   2520
tgaaagttac gttcaaggct aacacctgag ctttgtgtaa tgtaaataag accttgtgtt   2580
tatgaacctt tcagctaatt taatttttt tcccttacat gccaagtgat gttcaggttt   2640
tgaatgtttt tgtatcagtt tttctttg taaatgggcat taacattgtt acttgagtc    2700
ttgcttaatc actttgttg tcctgaggac ttgaattac agtgcatcag atttgttgca    2760
aattttgtct gtagatagtc tagcttcagc tgtttatggt gatgctacat tttcgtttat   2820
aaatatgttt gtggtataaa aaaatgagta taaccatagg ttttgaacaa atttccttac   2880
atttttcata caaaaatcat aaaatatctgt atgcattga aatttaactt tgtatgatgc   2940
ttaaaaaccaa ctatttgggg aaataataaa ataagtcttt accatgtatg aaagaaattt   3000
taaaaaaatac aaaatatttt ctgattagca tctagcttat aataaatttt caaaaaagct   3060
gaaggcaaaa atgccttcat caggatgcac tgagaactat atagttacgt cctgcttttt   3120
gtataaactg agatgctcac atgcttcccc ttagaacagg caatgtgcta tgcataacat   3180
agttgtacat tatctttgcg gttgctttga gttttattttt ttatttatta aaattgtagt   3240
tataaaaattt tcagtatag tacagtacat atactgtgag gcgcgtgcta aagtgaataa   3300
gcgagttttc atgctgaccc actcaatgct attcagaaat caattggctt agcacttct    3360
catatcctta ggtgcattta gattgccaga gttaaccttc tgcgtttaaa aaagaaaaa    3420
cactaaaaaa taaatacat gtatatactt aaaaaaaaat aataaggttt ccctcaaggg   3480
aaaacagcag ctacatgctt ctttcctata ctactgtagc aaaccaaggc attgatgaga   3540
gggcatgcaa attgtgcttc actttacagt gttttatcag agcacttaat aaaatgtaag   3600
```

```
SEQ ID NO: 7              moltype = DNA   length = 3814
FEATURE                   Location/Qualifiers
source                    1..3814
                          mol_type = other DNA
                          organism = Homo sapiens
SEQUENCE: 7
caataggagg gtagtctctc cgtcttttta aactctttt taagtttccc ctccccttc    60
atatttttt tcgccatttc ttttagcatt ggactttggg gtcgaaagcg tttcttttta  120
tttgcttctt ttaagccgag cacagtttag gtttcgtgct gtcttaagag aactatccag  180
cagcttcttg ctcatcctta ttgggagaac tgcaccgtta ctttaaaaac acacatacac  240
aaaaaaccta agggagaaag caggtaattg ctgccatgga aacacaactg tctaatgggc  300
caacttgcaa taacacagcc aatggtccaa ccaccataaa caacaactgt tcgtcaccag  360
ttgactctgg gaacacagaa gacagcaaga ccaacttaat agtcaactac cttcctcaga  420
acatgacaca ggaggaacta aagagtctct ttgggagcat tggtgaaata gagtcctgta  480
agcttgtaag agacaaaata acagggcaga gcttgggata tggctttgtg aactacattg  540
acccccaagga tgcagagaaa gctatcaaca ccctgaatgg attgagactt caaaccaaaa  600
caataaaagt ttcctatgct cgcccaagtt cagcttctat cagagatgca aatttatatg  660
tcagcggact tccaaaaaca atgacccaga aggagttgga cagctttt tcacaatatg   720
gacgcattat tacttctcgt attcttgtcg accaggtcac tggcatatca agggtgtag  780
ggtttattcg atttgacaag cgaattgagg cagaagaagc tatcaaaggc ctaaatggcc  840
agaaaccctcc cggtgccacg gagccaatca ctgtaaagtt tgctaataac ccaagccaaa  900
aaaccaatca ggccatcctt tcccagctgt accagtctcc aaacagaagg tatccaggac  960
cgctagctca gcaggcacag cgttttaggt tggacaatct gctcaatatg gcttatggag 1020
taaagaggtt ttctccaatg accattacgg gaatgaccag tttggctgga attaatatcc 1080
ctgggcaccc tggaacaggg tggtgtatat tgtgtacaa cctggctcct gacgcagatg 1140
agagtatcct gtggcaaatg tttgggcctt ttggagctgt caccaatgg aaggtcatcc 1200
gtgactttaa caccaataaa tgcaaaggtt ttggatttgt gactatgaca aactatgatg 1260
aggctgccat ggcgatagct agcctcaatg gataccgtct gggagacaga gtactgcagg 1320
tctccttaa gacaaacaaa acgcacaaag cctaatgagc tcttgtcctc agtccattta 1380
tatatgaaaa ctatacaaca aggcaagtt aagagaact ttatacatta gtaaatgtct 1440
ttgtaagtca gtgttgagat ggggataaaa tgactactta gcatcctaag aaatatgtga 1500
gattttttat tgctagtatt tgaattaaaa cttcttaaat atcttttatg tttgaatatg 1560
gacaagaggt acagggtttt tacctgtcac attgcattct attgccttct ttgaagaagg 1620
tggacctttt aaagtgtttc agctaaggga agacatttct tttctttta cataactgcc 1680
ttgaacctgt gagtaaatat tgaggctttg tgttgtaatt cttcagttgg ttgtgtcttt 1740
tttttccccc ctttttttcc tttttctgat tagcttgtg tttggtttac atttaaagca 1800
ttgctgttat gtctgtttaa gaaaagtatt ttgaagttta cattttatt tatgaagttt 1860
aaaacagtat ttattttgta attatgattt gggttgggga aggggggct acattataaa 1920
cgctattgt aagaatactg gagaacttttc cgtaaagcag tacctttgcca aagagataag 1980
agcctctttg atgtgggttt aaaaaaagca tctattttta taaaaagaa aatttggaga 2040
aactttttac tggtcctgga acaaatattt tgacttgaat actttgagaa atctcttcat 2100
atgacaccta gtgagcttt aaaatttacc aggaaatttg cagcggttgg aaaatttaga 2160
aagatttatg gtgtagaaaa tacttttgag atctttgtat gaaaggagta gaatcaatgg 2220
ggggaaacac tgctggtttc atttttgtaa tcaccagtgg agcgtctgat catcctggtt 2280
attatgtgat aggtggctca cattgatttg tgattttgaa acaaataaaa aaaatttaca 2340
aaagaatata taagagcagg caagaaattt aaattaccga gagatggggg aaaaaatctg 2400
ttcttcctaa agaaatccct tcagatagag ctcatggtgt ttagtgatgt acttgcagg 2460
ttgtttgaag aattgttttg tcttaaggaa aaaagacgtt gcacatgatt tgtactgcag 2520
caaatcagca aaagtgatct gagttggata tatttgaagg tattttgaaa gttacgttca 2580
aggctaacac ctgagctttg tgtaatgtaa ataagacctt gtgtttatga acctttcagc 2640
taatttaatt tttttttccct tacatgccaa gtgatgttca ggttttgaat gttttttgtat 2700
cagtttttc ctttgtaaat ggcattaaca ttgttacttg aggtcttgct taatcacttt 2760
tgttgtcctg aggacttgaa tttacagtgc atcagatttg ttgcaaattt tgtctgtaga 2820
tagtctagct tcagctgttt atggtgatgc tacattttcg tttataaata tgtttgtggt 2880
ataaaaaaat gagtataacc ataggttttg aacaaatttc cttacatttt tcatacaaaa 2940
atcataaata tctgtatgct attgaaattt aactttgtat gatgcttaaa aaccactatt 3000
tggggaaata ataaaataag tcttaccat gtatgaaaga aattttaaaa aatacaaaat  3060
attttctgat tagcatctag cttataataa attttcaaaa aagctgaagg caaaaatgcc 3120
ttcatcagga tgcactgaga actatatagt tacgtcctgc ttttgtata aactgagatg 3180
ctcacatgct tccccttaga acaggcaatg tgctatgcat acatagttg tacattatct 3240
ttgcggttgc tttgagtttt atttttatt atttaaaatt gtagttataa aatttttcag 3300
tatagtacag tacatatact gtgaggcgcg tgctaaagtg aataagcgag ttttcatgct 3360
gacccactca atgctattca gaaatcaatt ggcttagcac tttctcatat ccttaggtgc 3420
atttagattg ccagagttaa ccttctgcgt ttaaaaaag aaaaacacta aaaaataaaa 3480
tacatgtata tacttaaaaa aaaataataa ggtttccctc aagggaaaac agcagctaca 3540
tgcttcttt ctatactact gtagcaaacc aaggcattga tgagagggca tgcaaattgt 3600
gcttcacttt acagtgtttt atcagagcac ttaataaaat gtaaggctgg tatttatttg 3660
aagttgtaca gtatgactta attcacatct gttggaatag aaaatatatt ctgttgagta 3720
tttaagaggc tgtacatgtt tcttttgtg tttggattcc ttgtacttt tcatgttcag 3780
tacatcaata aacaaagttg aagggaaaaa aaaa                             3814

SEQ ID NO: 8              moltype = DNA   length = 2130
FEATURE                   Location/Qualifiers
source                    1..2130
                          mol_type = other DNA
```

```
                    organism = Homo sapiens
SEQUENCE: 8
agttaagggc ctggcgtctc cctccctgaa gacgtggtcc cagccgggtg tcctgacgct    60
cggggttcag gacaagggca cacaactggt tccgttaagc ccctctctcg ctcagacgcc   120
atggagctgg atctgtctcc acctcatctt agcagctctc cggaagacct ttgcccagcc   180
cctgggaccc ctcctgggac tccccggccc cctgataccc ctctgcctga ggaggtaaag   240
aggtcccagc ctctcctcat cccaaccacc ggcaggaaac ttcgagagga ggagaggcgt   300
gccacctccc tcccctctat ccccaacccc ttccctgagc tctgcagtcc tccctcacag   360
agcccaattc tcgggggccc ctccagtgca aggggctgc tccccgcga tgccagccgg    420
ccccatgtag taaaggtgta cagtgaggat ggggcctgca ggtctgtgga ggtggcagca   480
ggtgccacag ctcgccacgt gtgtgaaatg ctggtgcagc gagctcacgc cttgagcgac   540
gagacctggg ggctggtgga gtgccacccc cacctagcac tggagcgggg tttgaggac    600
cacgagtccg tggtggaagt gcaggctgcc tggcccgtgg gcggagatag ccgcttcgtc   660
ttccggaaaa acttcgccaa gtacgaactg ttcaaggagct ccccacactc cctgttccca   720
gaaaaaatgg tctccagctg tctcgatgca cacactggta tatcccatga agacctcatc   780
cagaacttcc tgaatgctgg cagctttcct gagatccagg gctttctgca gctgcggggt   840
tcaggacgga agctttggaa acgcttttc tgcttcttgc gccgatctgg cctctattac    900
tccaccaagg gcacctctaa ggatccgagg cacctgcagt acgtggcaga tgtgaacgag   960
tccaacgtgt acgtggtgac gcagggccgc aagctctacg gatgccacc tgacttcggt   1020
ttctgtgtca gcccaacaa gcttcgaaat ggccacaagg ggcttcggat cttctgcagt   1080
gaagatgagc agagccgcac ctgctggctg gctgccttcc gcctcttcaa gtacggggtg   1140
cagctgtaca agaattacca gcaggcacag tctcgccatg tcatccatc ttgtttgggc   1200
tccccaccct tgagaagtgc ctcagataat accctggtgg ccatggactt ctctggccat   1260
gctgggcgtg tcattgagaa ccccgggag gctctgagtg tggccctgga ggaggcccag   1320
gcctggagga agaagacaaa ccaccgcctc agcctgccca tgccagcctc cggcacgagc   1380
ctcagtgcag ccatccaccg cacccaactc tggttccaga gcgcatttc ccgtgaggag   1440
agccagcggc ttattggaca caggggcttg gtagacaggc cgttcctggt ccggagagt   1500
cagcggaacc cccagggctt tgtcctctct ttgtgccacc tgcagaaagt gaagcattat   1560
ctcatcctgc cgagcgagga ggagggccgc ctgtacttca gcatggatga tggccagacc   1620
cgcttcactg acctgctgca gctcgtggag ttccaccagc tgaaccgcgg catcctgccg   1680
tgcttgctgc gccattgctg cacgcgggtg gccctctgac caggccgtgg actggctcat   1740
gcctcagccc gccttcaggc tgcccgccgc ccctccaccc atccagtgga ctctggggcg   1800
cggccacagg gacgggatg aggagcggga gggttccgcc actccagttt tctcctctgc   1860
ttctttgcct ccctccagata gaaaacagcc cccactcctg tccactcctg accccctctc   1920
tcaagggaag gccttgggtg gccccctctc cttctcctag ctctggaggt gctgctctag   1980
ggcagggaat tatgggagaa gtggggcag cccaggcggt ttcacgcccc acacttgta    2040
cagaccgaga ggcagttga tctgctctgt tttatactag tgacaataaa gattattttt    2100
tgatacaaaa aaaaaaaaa aaaaaaaaa                                      2130

SEQ ID NO: 9          moltype = DNA   length = 2214
FEATURE               Location/Qualifiers
source                1..2214
                      mol_type = other DNA
                      organism = Homo sapiens
SEQUENCE: 9
tgcgggctgc ggggagatgt ggggagggcc ccctccactt tggagggcag tgaaggagag     60
ggatcctcta aattgtcgag gcttcatctc tccagattgt atgcccttct cagcaacacc   120
gcctccggcc ctccgatggg aaagtggagg ccgggacaag ggcacacaac tggttccgtt   180
aagcccctct ctcgctcaga cgccatggag ctggatctgt ctccacctca tcttagcagc   240
tctccggaag acctttgccc agccctgg acccctcctg ggactccccg gccccctgat    300
accctctgca gtcctgaggagt aaagaggtcc cagcctctc tcatcccaac caccggccac   360
aaacttcgag aggaggagag gcgtgccacc tccctcccct ctatccccaa ccccttccct   420
gagctctgca gtcctccctc acagagccca attctcgggg gccccctcag tgcaagggg    480
ctgctccccc gcgatgccag ccgccccat gtagtaaagg tgtacagtga ggatggggcc   540
tgcaggtctg tggaggtggc agcaggtgcc acagctcgcc acgtgtgtga aatgctggtg   600
cagcgagctc acgccttgag cgacgagacc tggggctgg tggagtgcca ccccacccta   660
gcactggagc ggggtttgga ggaccacgag tccgtggtgg aagtgcaggc tgcctggccc   720
gtgggcggag atagccgctt cgtcttccgg aaaaacttcg ccaagtacga actgttcaag   780
agctccccac actcccctgtt cccagaaaaa atggtctcca gctgtctcga tgcacacact   840
ggtatatccc atgaagacct catccagaac ttcctgaatg ctggcagctt tcctgagatc   900
cagggctttc tgcagctgcg gggttcagga cggaagcttt ggaaacgctt tttctgcttc   960
ttgcgccgat ctgcctcta ttactccacc aagggcacct ctaaggatcc gaggcacctg  1020
cagtacgtgg cagatgtgaa cgagtccaac gtgtacgtgg tgacgcaggg ccgcaagctc   1080
tacggatgcc ccactgactt cggtttctgt gtcaagccca acaagcttcg aaatggccac   1140
aaggggcttc ggatcttctg cagtgaagat gagcagagcc gcacctgctg gctggctgcc   1200
ttccgcctct tcaagtacgg ggtgcagctg tacaagaatt accagcaggc acagtctcgc   1260
catctgcatc atcttgttt gggctcccca cccttgagaa gtgcctcaga taatacccctg   1320
gtggccatgg acttctctgg ccatgctggg cgtgtcattg agaaccccg ggaggctctg    1380
agtgtggccc tggaggaggc ccaggcctg gaggaagaag acaaaccacc gcctcagcc    1440
cccatgccag cctccggcac gagcctcagt gcagccatcc accgcaccca actctggttc   1500
cacgggcgca tttcccgtga ggagagccag cggcttattg gacagcaggg cttggtagac   1560
ggcctgttcc tggtccggga gagtcagcgg aaccccagg gctttgtcct ctctttgtgc    1620
cacctgcaga aagtgaagca ttatctcatc ctgccgagcg aggaggaggg ccgcctgtac   1680
ttcagcatgg atgatggcca gacccgcttc actgacctgc tgcagctcgt ggagttccac   1740
cagctgaacc gcggcatcct gccgtgcttg ctgcgccatt gctgcacgcg ggtggccctc   1800
tgaccaggcc gtgactggc tcatgcctca gcccgccttc aggctgcccg ccgcccctcc   1860
acccatccag tggactctgg ggcgcggcca ggggacgg gatgagagc gggagggttc    1920
cgccactcca gttttctcct ctgctttctt tgcctccctc agatagaaaac agcccccact   1980
ccagtccact cctgaccct ctcctcaagg gaaggccttg ggtggccccc tctccttctc    2040
```

```
ctagctctgg aggtgctgct ctagggcagg gaattatggg agaagtgggg gcagcccagg  2100
cggtttcacg ccccacactt tgtacagacc gagaggccag ttgatctgct ctgttttata  2160
ctagtgacaa taaagattat ttttttgatac aaaaaaaaaa aaaaaaaaaa aaaa        2214

SEQ ID NO: 10            moltype = DNA   length = 2275
FEATURE                  Location/Qualifiers
source                   1..2275
                         mol_type = other DNA
                         organism = Homo sapiens
SEQUENCE: 10
aggcaaaccc cagccttgga ctggccctct ctgatctctg aggccaggct ctaatgtgat    60
ttgaatctac ttctaacccc ttccaagcac tgccctcccg aattctctgc tcctctcccc   120
accccactgt tggtctgtga tttcgaggca ggcgtggccc cctgcagcct ggaatgaagt   180
cactggggct gttttggagac cggggctgtt tggaggacaa ctggttccgt                240
taagcccctc tctcgctcag acgccatgga gctggatctg tctccacctc atcttagcag   300
ctctccggaa gacctttgcc cagcccctgg gacccctcct gggactcccc ggccccctga   360
taccccctctg cctgaggagg taaagaggtc ccagcctctc ctcatcccaa ccaccggcag   420
gaaacttcga gaggaggaga ggcgtgccac ctccctcccc tctatcccca acccctttccc  480
tgagctctgc agtcctccct cacagagccc aattctcggg ggcccctcca gtgcaagggg   540
gctgctcccc cgcgatgcca gccgccccca tgtagtaaag gtgtacagtg aggatggggc   600
ctgcaggtct gtggaggtgg cagcaggtgc cacagctcgc cacgtgtgtg aaatgctggt   660
gcagcgagct cacgccttga gcgacgagac ctggggggctg gtggagtgcc acccccacct  720
agcactggag cggggttttgg aggaccacga gtccgtggtg gaagtgcagg ctgcctggcc  780
cgtgggcgga gatagccgct tcgtcttccg gaaaaacttc gccaagtacg aactgttcaa   840
gagctcccca cactccctgt tcccagaaaa aatggtctcc agctgtctcg atgcacacac   900
tggtatatcc catgaagacc tcatccagaa cttcctgaat gctggcagct ttcctgagat   960
ccagggcttt ctgcagctgc ggggttcagg acggaagctt tggaaacgct tttttctgctt 1020
cttgcgccga tctggcctct attactccac caagggcacc tctaaggatc cgaggcacct  1080
gcagtacgtg gcagatgtga acgagtccaa cgtgtacgtg gtgacgcagg ccgcaagct   1140
ctacgggatg cccactgact tcggtttctg tgtcaagccc aacaagcttc gaaatggcca  1200
caagggggctt cggatcttct gcagtgaaga tgagcagagc cgcacctgct ggctggctgc  1260
cttccgcctc ttcaagtacg gggtgcagct gtacaagaat taccagcagg cacagtctcg  1320
ccatctgcat ccatcttgtt tgggctcccc acccttgaga agtgcctcag ataatacct    1380
ggtggccatg gacttctctg gccatgctgg gcgtgtcatt gagaaccccc ggggggctct  1440
gagtgtggcc ctgaggagg cccaggcctg gaggaagaag acaaaccacc gcctcagcgt   1500
gcccatgcca gcctccggca cgagcctcag tgcagccatc caccgcaccc aactctggtt  1560
ccacgggcgc atttccgtg aggagagcca gcggcttatt ggacagcagg gcttggtaga   1620
cggcctgttc ctggtccggg agagtcagcg gaaaccccca ggctttgtcc tctctttgtg  1680
ccacctgcag aaagtgaagc attatctcat cctgccgagc gaggaggagg gccgcctgta  1740
cttcagcatg gatgatggcc agacccgctt cactgacctg ctgcagctcg tggagttcca  1800
ccagctgaac cgcggcatcc tgccgtgctt gctgcgccat tgctgcacgc gggtggccct  1860
ctgaccaggc cgtggactgg ctcatgcctc agcccgcctt caggctgccc gccgccctc   1920
cacccatcca gtggactctg ggggcgcggcc acagggacgg ggatgaggag cgggagggtt  1980
ccgccactcc agttttctcc tctgcttctt tgcctcccctc agatagaaaa cagccccac   2040
tccagtccac tcctgacccc tctcctcaag ggaaggcctt gggtgccccc ctctccttct  2100
cctagctctg gaggtgctgc tctagggcag ggaattatgg gagaagtggg ggcagcccag  2160
gcggtttcac ccccacact ttgtacagac cgagaggcca gttgatctgc tctgttttat   2220
actagtgaca ataaagatta ttttttgata caaaaaaaaa aaaaaaaaaa aaaaa        2275

SEQ ID NO: 11            moltype = DNA   length = 2285
FEATURE                  Location/Qualifiers
source                   1..2285
                         mol_type = other DNA
                         organism = Homo sapiens
SEQUENCE: 11
acccgccccc atctgcccaa gataatttta gttccttgg gcctggaatc tggacacaca     60
gggctccccc ccgcctctga cttctctgtc cgaagtcggg acaccctcct accacctgta   120
gagaagcggg agtggatctg aaataaaatc caggaatctg ggggttccta gacggagcca   180
gacttcggaa cgggtgtcct gctactcctg ctggggctcc tccaggacaa gggcacacaa   240
ctggttccgt taagcccctc tctcgctcag acgccatgga gctggatctg tctccacctc   300
atcttagcag ctctccggaa gacctttgcc cagcccctgg gacccctcct gggactcccc   360
ggccccctga taccccctctg cctgaggagg taaagaggtc ccagcctctc ctcatcccaa  420
ccaccggcag gaaacttcga gaggaggaga ggcgtgccac ctccctcccc tctatcccca   480
acccctttccc tgagctctgc agtcctccct cacagagccc aattctcggg ggcccctcca  540
gtgcaagggg gctgctcccc cgcgatgcca gccgccccca tgtagtaaag gtgtacagtg   600
aggatggggc ctgcaggtct gtggaggtgg cagcaggtgc cacagctcgc cacgtgtgtg   660
aaatgctggt gcagcgagct cacgccttga gcgacgagac ctggggggctg gtggagtgcc  720
acccccacct agcactggag cggggttttgg aggaccacga gtccgtggtg gaagtgcagg  780
ctgcctggcc cgtgggcgga gatagccgct tcgtcttccg gaaaaacttc gccaagtacg   840
aactgttcaa gagctcccca cactccctgt tcccagaaaa aatggtctcc agctgtctcg   900
atgcacacac tggtatatcc catgaagacc tcatccagaa cttcctgaat gctggcagct   960
ttcctgagat ccagggcttt ctgcagctgc ggggttcagg acggaagctt tggaaacgct  1020
tttttctgctt cttgcgccga tctggcctct attactccac caagggcacc tctaaggatc 1080
cgaggcacct gcagtacgtg gcagatgtga acgagtccaa cgtgtacgtg gtgacgcagg  1140
ccgcaagct ctacgggatg cccactgact tcggtttctg tgtcaagccc aacaagcttc   1200
gaaatggcca caagggggctt cggatcttct gcagtgaaga tgagcagagc cgcacctgct 1260
ggctggctgc cttccgcctc ttcaagtacg gggtgcagct gtacaagaat taccagcagg  1320
cacagtctcg ccatctgcat ccatcttgtt tgggctcccc acccttgaga agtgcctcag  1380
ataatacct ggtggccatg gacttctctg gccatgctgg gcgtgtcatt gagaaccccc  1440
```

```
gggaggctct gagtgtggcc ctggaggagg cccaggcctg gaggaagaag acaaaccacc   1500
gcctcagcct gcccatgcca gcctccggca cgagcctcag tgcagccatc caccgcaccc   1560
aactctggtt ccacgggcgc atttcccgtg aggagagcca gcggcttatt ggacagcagg   1620
gcttggtaga cggcctgttc ctggtccggg agagtcagcg gaaccccag ggctttgtcc    1680
tctctttgtg ccacctgcag aaagtgaagc attatctcat cctgccgagc gaggaggagg   1740
gccgcctgta cttcagcatg gatgatggcc agacccgctt cactgacctg ctgcagctcg   1800
tggagttcca ccagctgaac cgcggcatcc tgccgtgctt gctgcgccat tgctgcacgc   1860
gggtggccct ctgaccaggc cgtggactgg ctcatgcctc agcccgcctt caggctgccc   1920
gccgcccctc cacccatcca gtggactctg gggcgcggcc acaggggacg ggatgaggag   1980
cgggagggtt ccgccactcc agttttctct tctgcttctt tgcctccctc agatagaaaa   2040
cagccccac tccagtccac tcctgacccc tcctcaag ggaaggcctt gggtggcccc      2100
ctctccttct cctagctctg gaggtgctgc tctagggcag ggaattatgg gagaagtggg   2160
ggcagcccag gcggtttcac gccccacact tgtacagac cgagaggcca gttgatctgc    2220
tctgttttat actagtgaca ataaagatta ttttttgata caaaaaaaaa aaaaaaaaa    2280
aaaaa                                                                2285

SEQ ID NO: 12          moltype = DNA   length = 914
FEATURE                Location/Qualifiers
source                 1..914
                       mol_type = other DNA
                       organism = Homo sapiens
SEQUENCE: 12
gcatggggag gggcggccct caaacgggtc attgccatta atagagacct caaacaccgc   60
ctgctaaaaa tacccgactg gaggagcata aaagcgcagc cgagcccagc gccccgcact   120
tttctgagca gacgtccaga gcagagtcag ccagcatgac cgagcgccgc gtcccctcct   180
cgctcctgcg gggcccagc tgggacccct ccgcgacctg gtaccgcat agccgcctct    240
tcgaccaggc cttcgggctg ccccggctgc cggaggagtg gtcgcagtgg ttaggcggca   300
gcagctggcc aggctacgtg cgcccctgc ccccgccgc catcgagagc cccgcagtgg    360
ccgcgcccgc ctacagccgc gcgctcagcc ggcaactcag cagcggggtc tcggagatcc   420
ggcacactgc ggaccgctgg cgcgtgtccc tggatgtcaa ccacttcgcc gggacgagg    480
tgacggtcaa gaccaaggat ggcgtggtgg agatcaccgg caagcacgag gagcggcagg   540
acgagcatgg ctacatctcc cggtgcttca cgcggaaata cacgctgccc cccggtgtgg   600
accccaccca agtttcctcc tccctgtccc ctgggggcac actgaccgtg gaggccccca   660
tgcccaagct agccacgcag tccaacgaga tcaccatccc agtcaccttc gagtcgcggg   720
cccagcttgg gggcccagaa gctgcaaaat ccgatgagac tgccgccaag taaagcctta   780
gcccggatgc ccaccctgc tgccgccact ggctgtgcct ccccccgccac ctgtgtgttc    840
ttttgataca tttatcttct gttttttctca aataaagttc aaagcaacca cctgtcaaaa   900
aaaaaaaaaa aaaa                                                       914

SEQ ID NO: 13          moltype = DNA   length = 3262
FEATURE                Location/Qualifiers
source                 1..3262
                       mol_type = other DNA
                       organism = Homo sapiens
SEQUENCE: 13
agagtgctcc gcggccgtgt ggagcgaggc cttgttcccg cgttgagccg ccgccgccgc   60
cgccgcctcc tcagcttcag cctccgcgcc aggcccggcc gccgccgccgc atgtcggact   120
acagcacggg aggaccccgc cccgggccgc cgccgcccgc cggcggggc gggggagccg    180
gaggcgccgg gggaggccct ccgccgggcc gccaggcgc gggggaccgg ggcggcggcg    240
gtcccggcg cggcggcccg ggcggggggt cggccggggg ccctctcag ccacccggcg     300
gaggcgcccc gggaatccgc aaggacgctt tcgccgacgc cgtgcagcgg gccgccaaga   360
ttgcagccaa aattggaggc gatgctgcca cgacagtgaa taacagcact cctgattttg   420
gttttggggg ccaaaagaga cagttggaag atgagatcca accggagagc aagaagctgg   480
cttcccaggg agactcaatc agttctcaac ttggacccat ccatcctccc caaggacttt   540
caatgacaga agagtacagg gtcccagacg gcatggtgag cctgatcatt ggcagaggag   600
gtgaacaaat taacaaaatc caacaggatt caggctgcaa agtacagatt tctcccagaca   660
gcggtggcct acccgagcgc agtgtgtcct tgacaggagc cccagaatct gtccagaaag   720
ccaagatgat gctggatgac attgtgtctc ggggtcgtgg ggccccccca ggacagttcc   780
acgacaacgc caacggggc cagaaccgtg gatcatgac cccgcgggca                840
aggccggcct ggtcattgcc aagggcgggg agaccattga gcagctgcag gaacgcgctg   900
gagtgaagat gatcttaatt caggacggat ctcagaatac gaatgtggac aaacctctcc   960
gcatcattgg ggatccttac aaagtgcagc aagcctgtga tggtgatg acatcctcc     1020
gggaacgtga ccaaggcggc tttggggacc ggaatgagta cggatctcgg attggcgag   1080
gcatcgatgt gccagtgccc aggcattctg ttggcgtgct cattggccgg agtggagaa   1140
tgatcaagaa gatccagaat gatgctggcc tgcggataca gttcaagcaa gatgacggga   1200
cagggccga agattgct catataatgg ggccccaga caggtgcgag cacgcagccc      1260
ggatcatcaa cgacctcctc agagcctca ggagtggtcc cccaggtcct ccaggggtc     1320
caggcatgcc cccgggggc cgaggccgag aagaggcca aggcaattgg ggtcccctg      1380
gcggggagat gaccttctcc atccccactc acaagtgtgg gctggtcatc ggccgagggtg   1440
gcgagaatgt gaaagccata aaccagcaga cgggagcctt cgtagagatc tccccggcagc  1500
tgccacccaa cggggacccc aacttcaagt tgttcatcat ccgggggttca cccccagcaga  1560
ttgaccacgc caagcagctt atcgaggaaa agatcgaggg tcctctcgc ccagttggac    1620
caggcccagg tgcccaggc cctgctggcc aatggggcc cttcaatcct gggccttca      1680
accaggggcc acccgggct cccccacatg cggggggcc tcctcccac cagtaccac       1740
cccaggggct gggcaatacc tacccccagt ggcagccgcc tgctcctcat gacccaagca   1800
aagcagctgc agcggccgcg gacccaacg ccgcgtgggc cgcctactac tcacactact   1860
accagcagcc cccgggcccc gtcccgcc ccgcaccggc cctgcgcc ccaccggctc       1920
agggtgagcc cctcagcccc ccaccaccg gccagtcgga ctacactaag gcctgggaag   1980
agtattacaa aaagatcggc cagcagccc agcagcccg agcacccca cagcaggact      2040
```

-continued

```
acacgaaggc ttgggaggag tactacaaga agcaagcgca agtgccacc ggaggggtc    2100
caggagctcc cccaggctcc cagccagact acagtgccgc ctgggcggaa tattacagac   2160
agcaggccgc ttactacgga cagacccag gtcctggcgg cccccagccg ccgcccacgc    2220
agcagggaca gcagcaggct caatgaatcg aatgaatgtg aacttcttca tctgtgaaaa   2280
atcttttttt tttccatttt gttctgtttg ggggcttctc ttttgtttgg cgagagagcg   2340
atggctgccg tggggagtac tggggagccc tcgcggcaag cagggtgggg gggacttggg   2400
ggcatgccgg gccctcactc tctcgcctgt tctgtgtctc acatgctttt tctttcaaaa   2460
ttgggatcct tccatgttga gccagccaga gaagatagcg agatctaaat ctctgccaaa   2520
aaaaaaaaaa aacttaaaaa ttaaaaacac aaagagcaaa gcagaactta taaaattata   2580
tatatatata ttaaaaagtc tctattcttc acccccagc cttcctgaac ctgcctctct    2640
gaggataaag caattcattt tctcccaccc tcggccctct tgttttttaa ataaactttt   2700
aaaaaggaaa aaaaaaagtc actcttgcta tttctttttt ttagttagag gtggaacatt   2760
ccttggacca ggtgttgtat tgcaggaccc cttccccag cagccaagcc ccctcttctc     2820
tccctcccgc cctggctcag ctcccgcggc cccgcccgtc cccctccca ggactggtct    2880
gttgtctttt catctgttca agaggagatt gaaactgaaa acaaaatgag aacaacaaaa   2940
aaaattgtat ggcagttttt acttttatc gctcgttttt aacttcacaa ataaatgata    3000
acaaaacctc cccgtctgcg ggtgctgtct gtctccccc ctttccttcc ctccctgtag    3060
ttttgaagcg gatgtttgtt ctttatagat gttgtttaaa cactggggag tgctagttga   3120
aaatttacaa actttgtgtt tttttttttt taagaaaaat ataaaatagt ttccttcagg   3180
ctcaatgtgc tttcctaacc gtgcccccc cccttttttt tttttgttaa ataaagtgct    3240
ttttgtttaa aaaaaaaaaa aa                                           3262

SEQ ID NO: 14          moltype = DNA   length = 3918
FEATURE                Location/Qualifiers
source                 1..3918
                       mol_type = other DNA
                       organism = Homo sapiens
SEQUENCE: 14
ctctcccttc tccactctct cccctgtct cctttcttct tcttctttca ccctccgtct    60
ctcacacccc ctccattccc ctgtctcctt tctgacactg cactgcagct gctcctcagc   120
cctgcccct cccagtgag aacaaaccag caacattgct ttttttccta aagagattta     180
tattgatccg attaaaaaaa aaaaccttta agaaacccca aacgcaaaaa aaaaaaaaaa   240
aaaaaagaa aaaagaaaag aaaaagccaa acaaagggg agaacttct cccggtagca      300
gcggcaggaa ctgcaaacat gatggcggca gctcccatcc agcagaacgg gacccacact   360
gggggttccca tagacctgga cccgccggac tcgcggaaaa ggccgctgga agccccccct   420
gaagccggca gcaccaagag gaccaatacg ggcgaagacg gccagtattt tctaaaggtt   480
ctcataccta gttatgctgc tggatctata attgggaagg gaggacagac aattgttcag   540
ttgcaaaaag aaactggagc caccatcaag ctgtctaagt ccaaagattt ttacccaggt   600
actactgagc gagtgtgctt gatccaggga acggttgaaa cactgaagac agttcatgga   660
ttcattgcag aaaaaattcg agaaatgccc caaaatgtgg ccaagacaga accagtcagc   720
attctacaac cccagaccac cgttaatcca gatcgcatca acaaacatt gccatcttcc    780
ccaactacca ccaagtcctc tccatctgat cccatgacca cctccagagc taatcaggta   840
aagattatag ttcccaacag cacagcaggt ctgataatag ggaagggagg tgctactgtg   900
aaggctgtaa tggagcagtc aggggcttgg gtgcagcttt cccagaaacc tgatgggatc   960
aacttgcaag agagggttgt cactgtgagt ggagaacctg aacaaaaccg aaaagctgtt   1020
gaacttatca tccagaagat acaagaggat ccacaaagtg gcagctgtct caatatcagt   1080
tatgccaatg tgacaggtcc agtggcaaat tccaatccaa ccggatctcc ttatgcaaac   1140
actgctgaag tgttaccaac tgctgcagca gctgcagggc tattaggaca tgctaacctt   1200
gctggcgttg cagcctttcc agcagttta tctggcttca caggcaatga cctggtggcc    1260
atcacctctg cacttaatac attagccagc tatggatata atctcaacac tttaggttta   1320
ggtctcagtc aagcagcagc aacaggggct ttggctgcag tgccaaccca                1380
gcagcagcag cagccaattt attggccacc tatgccagtg aagcctcagc cagtggcagc   1440
acagctggtg gtacggcggg gacatttgca ttaggtagcc tggctgctgc tactgctgca   1500
accaatggat attttggagc tgcttctccc ctagctgcca gtgccattct aggaacagaa   1560
aagtccacag atggatccaa ggatgtagtt gaaatagcag tgccagaaaa cttagttggt   1620
gcaaatcttg gcaaaggagg gaaaacatta gtggaatacc aggagttgac tggtgcaagg   1680
atacagatct ccaaaaaagg agaattcgta cctggcacaa ggaatcggaa ggtaaccatt   1740
actggaacac cagctgcaac acaggctgct caatatttaa ttacacaaag gatcacatat   1800
gagcaaggag ttcgggctgc caatcctcag aaagtgggtg gagtgcccca gttacacatc   1860
agattgtttt aaccccttcct ttaccccatt ttcaagaagg atgtactgta cttttgcagaa   1920
gtgaagtttt tctgttatta atatataatt atgcaaatga atgcgactat gttgacaatg   1980
tgtatatgta aataatatgt gttttaccag atgtttcata gaaagaattt ttcttgatc    2040
tgttttgttc tctatacttt gcttgtgtat atttgtcaga ggtgtttcta gtgtaagatt    2100
taagcctgcc attttaccag cattattgta gtttaatgat tgatgtgaa cagggatatg    2160
cgtatagttt tcagtattag ttctagataa cactaaatta actactgtta ggttgagtat    2220
ggtggggtca gtgacctaaa atggagtgag gccaaagcac tgtcctgtaa gtcttacttc    2280
ctgcttaggg cacagtgaag taggaaacaa tattttgaaa ataagtttta aatttaaaat   2340
gatcaaaaag caatatagtt gcataaaagc actgtaaaat atttaaaagg ttaaaactgt   2400
ggaaaattat attggtaagt ttacagatca ataaaagcac ctgttctcca tctgaactag   2460
acaatggaaa taatgctgca tgctggccat ggcccattct tcatcatttg taagttcaac    2520
aaaagttctc acatggagtc ccacctcttc agaggtttgt acatttgttt ttaagcactg    2580
aattcactac tgatcccatc gcctggccag tagaacagtc attactccat taacatcctc    2640
actgtttaga cacataactg tggtacagtg tattggaaat tttataaaca aaagtgaaag   2700
tgccaacaaa ttattgatag ctgataatgt ttcattatct gctttatct gataagtatg     2760
ttgcatttta agagcttata attgtgtata atttgttaac actagaaacc tattagtatt    2820
gtgaatgtag attttactgt gaagctatct gtgatttagc tgtttgctcc catgatggag   2880
tctttgcagc atgcgctag cagccaatgc agtttctaat actcggtaat ttgcatgttt    2940
tgtggagcat tttatgtca ccaaccagac agtatttcct gcatgcttat ttagaagagg    3000
cagcttatct tgagaggtag tgttatctac ctttgtcagg cttttttgaca ggtcatttca   3060
```

```
gagtaagcct tgttcccaa gacccaacaa ctgtcaccct cttctgtacc tctcctgagt   3120
gccaactgtc caggccattt gacacaccat ctgttaacct ctgagtttgc ccactcaagg   3180
ccactcatag gggcatccat ccccaagcac ctcctcatgc tgtgcatgca gtcttaaatt   3240
caatggacaa aaataaaatg ctggctacct ctggatcatc tggctgagca actgaattac   3300
aaaagagaat tacttccatc tcaacttcaa cccattgatt acgtccatcc tagcaagcta   3360
aatggcatcc cagctgctcc tttctgtgca accaattaaa gaacaatgag tgtgatgctc   3420
catgtctgaa tttcgtccag cctctctctg aactgtgatc tttgtcctca tgaactttcc   3480
cttttgttca ttgaactata tggactcttc atttcatatt gatttactgt gcaatttact   3540
tttggacatt gagaacttga aatttatttcc tgatcccttc cccttccact attaataatt   3600
catttctgtc aaactgtaag agtagactca tttttttttt tttagttttt aacattggac   3660
tgttatttca tttagagttc tctatctcta aatatttatt tagagaatga ttttaaaagg   3720
gaatgatatg cttgtttaaa tgaaagagaa aagctgtagt aaactgtgtt aattggtaat   3780
gactatttat cgtcgatact ctgtagctgt gtaagttttg acaaatagtg tatctcgtgg   3840
aatcagtggt tagcattgcc gctattatat ttactcattt tatcattata aatgtgctta   3900
gttcatcatg tagcatca                                                 3918

SEQ ID NO: 15          moltype = DNA  length = 3846
FEATURE                Location/Qualifiers
source                 1..3846
                       mol_type = other DNA
                       organism = Homo sapiens
SEQUENCE: 15
ctctcccttc tccactctct cccctgtct  cctttcttct tcttctttca ccctccgtct    60
ctcacacccc ctccattccc ctgtctcctt tctgacactg cactgcagct gctcctcagc   120
cctgcccct  ccccagtgag aacaaaccag caacattgct tttttcta aagagattta     180
tattgatccg attaaaaaaa aaaaaccta agaaaccaaa acaaaaaaaaa aaaaaaaaa    240
aaaaaaagaa aaaagaaaag aaaaagccaa aacaaaaggg agaaccttct cccggtagca   300
gcggcaggaa ctgcaaacat gatggcggca gctcccatcc agcagaacgg gacccacact   360
ggggttccca tagacctgga cccgccggac tcgcggaaaa ggccgctgga agcccccct    420
gaagccggca gcaccaagag gaccaatacg ggcgaagacg gccagtattt tctaaaggtt   480
ctcataccta gttatgctgc tggatctata attgggaagg gaggacagac aattgttcag   540
ttgcaaaaag aaactggagc caccatcaag ctgtctaagt ccaaagattt ttacccaggt   600
actactgagc gagtgtgctt gatccaggga acggttgaag cactgaatgc agttcatgga   660
ttcattgcag aaaaattcg  agaaatgccc caaaatgtgg ccaagacaga accagtcagc   720
attctacac  cccagaccac cgttaatcca gatcgcatca acaagtaaaa gattatagtt   780
cccaacagca cagcaggtct gataataggg aaggaaggtg ctactgtgaa ggctgtaatg   840
gagcagtcag gggcttgggt gcagctttcc cagaaacctg atgggatcaa cttgcaagag   900
agggttgtca ctgtgagtgg agaacctgaa caaaaccgaa aagctgttga acttatcatc   960
cagaagatac aagaggatcc acaaagtggc agctgtctca atatcagtta tgccaatgtg  1020
acaggtccag tggcaaattc caatccaacc ggatctcctt atgcaaacac tgctgaagtg  1080
ttaccaactg ctgcagcagc tgcagggcta ttaggacatg ctaaccttgc tggcgttgca  1140
gcctttccag cagtttatc  tggcttcaca ggcaatgacc tggtggccat cacctctgca  1200
cttaatacat tagccagcta tggatataat ctcaacactt taggtttagg tctcagtcaa  1260
gcagcagcaa caggggcttt ggctgcagca gctgccagtg ccaacccagc agcagcagca  1320
gccaatttat tggccacct  tgccagtgaa gcctcagcca gtggcagcac agctggtggt  1380
acggcgggca catttgcatt aggtagcctg gctgctgcta ctgctgcaac caatggatat  1440
ttgaggactg cttctcccct agctgccagt gccattctag gaacagaaaa gtccacagat  1500
ggatccaagg atgtagttga aatagcagtg ccagaaaact tagttggtgc aatacttggc  1560
aaaggaggga aaacattagt ggaataccag gagttgactg gtgcaaggat acagatctcc  1620
aaaaaaggag aattcgtacc tggcacaagg aatcggaagg taaccattac tggaacacca  1680
gctgcaacac aggctgctca atatttaatt acacaaagga tcacatatga gcaaggagtt  1740
cgggctgcca atcctcagaa agtgggttga gtgccccagt tacacatcag attgtttaa   1800
ccctccttt  accccatttt caagaaggat gtactgtact ttgcagaagt gaagtttttc  1860
tgttattaat atataattat gcaaatgaat gcgactatgt tgacaatgtg tatatgtaaa  1920
taatatgtgt tttaccagat gtttcataga aagaattttt tcttgatctg tttttgttctc 1980
tatactttgc ttgtgtatat ttgtcagagg tgtttctagt gtaagattta agcctgccat  2040
tttaccagca ttattgtagt ttaatgattg aatgtagaca gggatatgcg tatagttttc  2100
agtattagtt ctagataaca ctaaattaac tactgttagg ttgagtatgg tggggtcagt  2160
gacctaaaat ggagtgaggc caaagcactg tcctgtaagt cttacttcct gcttagggca  2220
cagtgaagta ggaaacaata tttgaaaat  aagttttaaa tttaaaatga tcaaaagca   2280
atatagttgc ataaaagcac tgtaaaatat ttaaaaggtt aaaactgtgg aaaattatat  2340
tggtaagttt acagatcaat aaaagcacct gttctccatc tgaactagac aatgaaaata  2400
atgctgcatg ctggccatgg cccattcttc atctttgta  agttcaacaa aagttctcac  2460
atggagtccc acctcttcag aggtttgtac atttgttttt aagcactgaa ttcactactg  2520
atcccatcgc ctggccagta aacagtcat  tactccatta acatcctcac tgtttagaca  2580
cataactgtg gtacagtgta ttggaaattt tataaacaaa agtgaaagtg ccaacaaatt  2640
attgatagct gataatgttt cattatctgc aactgcttga taagtatgtt gcattttaag  2700
agcttataat tgtgtataat ttgttaacac tagaaaccta ttagtattgt gaatgtagat  2760
tttactgtga agctatctgt gatttagctg tttgctccca tgatggagtc tttgcagcat  2820
ggcgctagca gccaatgcag tttctaatac tcggtaattt gcatgtttg  tggagcattt  2880
ttatgtcacc aaccagacag tatttcctgc atgcttattt agaagaggca gcttatcttg  2940
agaggtagtg ttatctacct ttgtcaggct ttttgacagg tcatttcaga gtaagccttt  3000
gttcccaaga cccaacaatc gtcaccctct tctgtacctc tcctgagtgc caactgtcca  3060
ggccatttga cacaccatct gttaacctct gagtttgccc actcaaggcc actcatagg   3120
gcatccatcc caagcacct  cctcatgctg tgcatgcagt cttaaattca atggacaaaa  3180
ataaaatgct ggctacctct ggatcatctg gctgagcaac tgaattacaa aagagaatta  3240
cttccatctc aacttcaacc cattgattac gtccatccta gcaagctaaa tggcatccca  3300
gctgctcctt tctgtgcaac caattaaaga acaatgagt  tgatgctcca tgtctgaatt  3360
tcgtccagcc tctctctgaa ctgtgatctt tgtcctcatg aactttccct tttgttcatt  3420
```

```
gaactatatg gactcttcat ttcatattga tttactgtgc aatttacttt tggacattga    3480
gaacttgaaa ttatttcctg atcccttccc cttccactat taataattca tttctgtcaa    3540
actgtaagag tagactcatt tttttttttt tagtttttaa cattggactg ttatttcatt    3600
tagagttctc tatctctaaa tatttattta gagaatgatt ttaaaaggga atgatatgct    3660
tgtttaaatg aaagagaaaa gctgtagtaa actgtgttaa ttggtaatga ctatttatcg    3720
tcgatactct gtagctgtgt aagttttgac aaatagtgta tctcgtggaa tcagtggtta    3780
gcattgccgc tattatattt actcattttta tcattataaa tgtgcttagt tcatcatgta    3840
gcatca                                                                3846
```

```
SEQ ID NO: 16           moltype = DNA   length = 3340
FEATURE                 Location/Qualifiers
source                  1..3340
                        mol_type = other DNA
                        organism = Homo sapiens
SEQUENCE: 16
tgcgggcgtc tccgccattt tgtgagtcta taactcggag ccgttgggtc ggttcctgct    60
attccggcgc ctccactccg tccccgcgg gtctgctctg tgtgccatgg acggcattgt    120
cccagatata gccgttggta caaagcgggg atctgacgag cttttctcta cttgtgtcac    180
taacggaccg tttatcatga gcagcaactc ggcttctgca gcaaacgaa atgacagcaa    240
gaagttcaaa ggtgacagcc gaagtgcagg cgtcccctct agagtgatcc acatccggaa    300
gctcccccatc gacgtcacgg aggggggaagt catctccctg gggctgccct ttgggaaggt    360
caccaacctc ctgatgctga aggggaaaaa ccaggccttc atcgagatga acacggagga    420
ggctgccaac accatggtga actactacac ctcggtgacc cctgtgctgc gcggccagcc    480
catctacatc cagttctcca accacaagga gctgaagacc gacagctctc ccaaccaggc    540
gcgggcccag gcggccctgc aggcggtgaa ctcggtccag tcggggaacc tggccttggc    600
tgcctcggcg gcggccgtgg acgcagggat ggcgatggcc agagagcc tccgtgctcag    660
gatcatcgtg gagaacctct tctaccctgt gaccctggat gtgctgcacc agatttttctc    720
caagttcggc acagtgttga agatcatcac cttcaccaag aacaaccagt tccaggccct    780
gctgcagtat gcggacccccg tgagcgccca gcacgccaag ctgtcgctgg acgggcagaa    840
catctacaac gcctgctgca cgctgcgcat cgactttttcc aagctcacca gcctcaacgt    900
caagtacaac aatgacaaga gccgtgacta cacacgccca gacctgcctt ccggggacag    960
ccagcccctcg ctggaccaga ccatggccgc ggccttcggt gcacctggta taatctcagc    1020
ctctccgtat gcaggagctg gtttccctcc cacctttgcc attcctcaag ctgcaggcct    1080
ttccgttccg aacgtccacg gcgccctggc ccccctggcc ccccctcgg cggcggcggc    1140
agctgcggcg gcaggtcgga tcgccatccc gggcctggcg ggggcaggaa attctgtatt    1200
gctggtcagc aacctcaacc cagagagagt cacaccccaa agcctcttta ttcttttcgg    1260
cgtctacggt gacgtgcagc gcgtgaagat cctgttcaat aagaaggaga cgccctagt    1320
gcagatggcg gacggcaacc aggcccagct ggccatgagc cacctgaacg ggcacaagct    1380
gcacggggaag cccatccgca tcacgctctc gaagcaccag aacgtgcagc tgccccgcga    1440
gggccaggag gaccagggcc tgaccaagga ctacggcaac tcaccctctgc accgcttcaa    1500
gaagccgggc tccaagaact tccagaacat attcccgccc tcggccacgc tgcacctctc    1560
caacatcccg ccctcagtct ccgaggagga tctcaaggtc ctgttttcca gcaatggggg    1620
cgtcgtcaaa ggattcaagt tcttccagaa ggaccgcaag atggcactga tccagatgcg    1680
ctccgtggag gaggcggtcc aggccctcat tgacctgcac aaccacgacc tcggggagaa    1740
ccaccacctg cgggtctcct tctccaagtc caccatctag gggcacaggc ccccacggcc    1800
gggccccctg gcgacaactt ccatcattcc agagaaaagc cactttaaaa acagctgaag    1860
tgaccttagc agaccagaga tttttatttt ttaaagagaa atcagtttac ctgtttttaa    1920
aaaaattaaa tctagttcac cttgctcacc ctgcggtgac agggacagct caggctcttg    1980
gtgactgtgg cagcgggagt tcccggcctc ccacacccgg ggccagaccc tcggggccat    2040
gccttggtgg ggcctgtgtc gggcgtgggg cctgcaggtg ggcgcccga ccacgacttg    2100
gcttccttgt gccttaaaaa acctgccttc ctgcagccac acacccaccc gggtgtcct    2160
ggggacccaa ggggtgggg ggtcacacca gagagaggca ggggcctgg ccggctcctg    2220
caggatcatg cagctggggc gcggcggccg cggctgcgac acccccaaccc cagccctcta    2280
atcaagtcac gtgattctcc cttcaccccg cccccagggc cttcccttct gccccaggc    2340
gggctcccg ctgctccagc tgcggagctg gtcgacataa tctctgtatt atatactttg    2400
cagttgcaga cgtctgtgcc tagcaatatt tccagttgac caaatattct aatctttttt    2460
catttatatg caaaagaaat agttttaagt aactttttat agcaagatga tacaatggta    2520
tgagtgtaat ctaaacttcc ttgtggtatt accttgtatg ctgttacttt tatttattc    2580
cttgtaatta agtcacaggc aggacccagt ttccagagaa caggcggggc cgcccagtgg    2640
gtcaggcaca gggagccccg gtcctatctt agagccctg agcttcaggg aaggggcggg    2700
cgtgtcgccg cctctggcat cgcctccggt tgccttacac cacgccttca cctgcagtcg    2760
cctagaaaac ttgctctcaa acttcaggt ttttcttcc ttcaaatttt ggaccaaagt    2820
ctcatttctg tgttttgcct gcctctgatg ctgggacccg gaaggcgggc gctcctcctg    2880
tcttctctgt gctctttcta ccgcccccgc gtcctgtccc ctaggatccc                2940
ctttccgtaa aagcgtgtaa caagggtgta aatatttata atttttata cctgttgtga    3000
gacccgaggg gcggcggcgc ggttttttat ggtgacacaa atgtatattt tgctaacagc    3060
aattccaggc tcagtattgt gaccgcgag ccacagggga ccccacgcac attccgttgc    3120
cttacccgat ggcttgtgac gcggagagaa ccgattaaaa ccgtttgaga aactcctccc    3180
ttgtctagcc ctgtgttcgc tgtggacgct gtagaggcag tggccagt ctgtacctcg    3240
acttcgaata aatcttctgt atcctcgctc cgttccgcct taaaaaaaaa aaaaaaaaa    3300
aaaaaaaaa aaaaaaaaaa aaaaaaaaaa aaaaaaaaaa                             3340
```

```
SEQ ID NO: 17           moltype = DNA   length = 3319
FEATURE                 Location/Qualifiers
source                  1..3319
                        mol_type = other DNA
                        organism = Homo sapiens
SEQUENCE: 17
tgcgggcgtc tccgccattt tgtgagtcta taactcggag ccgttgggtc ggttcctgct    60
```

```
attccggcgc ctccactccg tccccgcgg gtctgctctg tgtgccatgg acggcattgt    120
cccagatata gccgttggta caaagcgggg atctgacgag cttttctcta cttgtgtcac    180
taacggaccg tttatcatga gcagcaactc ggcttctgca gcaaacggaa atgacagcaa    240
gaagttcaaa ggtgacagcc gaagtgcagg cgtcccctct agagtgatcc acatccggaa    300
gctccccatc gacgtcacgg aggggaagt catctccctg gggcgccct ttgggaaggt    360
caccaacctc ctgatgctga aggggaaaaa ccaggccttc atcgagatga acacggagga    420
ggctgccaac accatggtga actactacac ctcggtgacc cctgtgctgc gcggccagcc    480
catctacatc cagttctcca accacaagga gctgaagacc gacagctctc caaccaggc    540
gcgggcccag gcgggccctgc aggcggtgaa ctcggtccag tcggggaacc tggccttggc    600
tgcctcggcg gcggccgtgg acgcagggat ggcgatggcc gggcagagcc ccgtgctcag    660
gatcatcgtg gagaacctct ctacccctgt gaccctggat gtgctgcacc agattttctc    720
caagttcggc acagtgttga agatcatcac cttcaccaag aacaaccagt tccaggccct    780
gctgcagtat gcggaccccg tgagcgccca gcacgccaag ctgtcgctgg acgggcagaa    840
catctacaac gcctgctgca cgctgcgcat cgacttttcc aagctcacca gcctcaacgt    900
caagtacaac aatgacaaga gccgtgacta cacacgccca gacctgcctt ccggggacag    960
ccagccctcg ctggaccaga ccatggccgc ggccttcgcc tctccgtatg caggagctgg   1020
tttccctccc acctttgcca ttcctcaagc tgcaggcctt tccgttccga acgtccacgg   1080
cgccctggcc ccctggcca tcccctcggc ggcggccgca gctgcggccg caggtcgga   1140
cgccatcccg ggcctggcgg gggcaggaaa ttctgtattg ctggtcagca acctcaaccc   1200
agagagagtc acaccccaaa gcctctttat tcttttcggc gtctacggtg acgtgcagcg   1260
cgtgaagatc ctgttcaata agaagagaa cgccctagtg cagatggcgg acggcaacca   1320
ggcccagctg gccatgagcc acctgaacgg gcacaagctg cagggaagcc ccatccgcat   1380
cacgctctcg aagcaccaga acgtgcagct gccccgcgag ggccaggagg accagggcct   1440
gaccaaggac tacggcaact caccccctgca ccgcttcaag aagccgggct ccaagaactt   1500
ccagaacata ttccgcccct cggccacgct gcacctctcc aacatcccgc cctcagtctc   1560
cgaggaggat ctcaaggtcc tgttttccag caatgggggc gtcgtcaaag gattcaagtt   1620
cttccagaag gaccgcaaga tggcactgat ccagatgggc tccgtggagg aggcggtcca   1680
ggccctcatt gacctgcaca accacgacct cggggagaac caccacctgc gggtctcctt   1740
ctccaagtcc accatctagg ggcacaggcc cccacgccg ggcccctgg cgacaacttc   1800
catcattcca gagaaaagcc actttaaaaa cagctgaagt gaccttagca gaccagagat   1860
tttatttttt taaagagaaa tcagtttacc tgttttaaa aaattaaat ctagttcacc   1920
ttgctcaccc tgcggtgaca gggacagctc aggctcttgg tgactgtggc agcgggagtt   1980
cccggccctc cacacccggg gccagaccct cggggccatg ccttggtggg gcctgtgtcg   2040
ggcgtggggc ctgcaggtgg gcgccccgac cacgacttgg cttccttgtg ccttaaaaaa   2100
cctgccttcc tgcagccaca caccccaccg gggtgtcctg gggacccaag gggtggggggg   2160
gtcacaccag agagaggcag ggggcctggc cggctcctgc aggatcatgc agctggggcg   2220
cggcggccgc ggctgcgaca ccccaacccc agccctctaa tcaagtcacg tgattctccc   2280
ttcaccccgc ccccagggcc ttcccttctg cccccaggcg ggctccccgc tgctccagct   2340
gcggagctgg tcgacataat ctctgtatta tatcttgc agttgcagac gtctgtgcct   2400
agcaatattt ccagttgacc aaatattcta atctttttc atttatatgc aaaagaaata   2460
gttttaagta acttttata gcaagatgat acaatggtat gagtgtaatc taaacttcct   2520
tgtggtatta ccttgtatgc tgttacttt attttattcc ttgtaattaa gtcacaggca   2580
ggaccagtt tccagagagc aggcgggggcc gcccagtggg tcaggcacag gagccccgg   2640
tcctatctta gagcccctga gcttcaggga aggggcgggc gtgtcgccgc ctctggcatc   2700
gcctccggtt gccttacacc acgccttcac ctgcagtcgc ctagaaaact tgctctcaaa   2760
cttcaggggtt ttttcttcct tcaaattttg gaccaaagtc tcatttctgt gttttgcctg   2820
cctctgatgc tgggacccgg aaggcgggcg ctcctcctgt cttctctgtg tctttttctac   2880
cgccccgcg tcctgtcccg gggctctcc taggatcccc tttccgtaaa agcgtgtaac   2940
aagggtgtaa atatttataa ttttttatac ctgttgtgag accgagggg cggcggcgcg   3000
gtttttatg gtgacacaaa tgtatatttt gctaacagca attccaggct cagtattgtg   3060
accgcgggag cacaggggac cccacgcaca ttccgttgac ttacccgatg gcttgtgacg   3120
cggagagaac cgattaaaac cgtttgaaa actcctccct tgtctagccc tgtgttcgct   3180
gtggacgctg tagaggcagg ttggccagtc tgtacctgga cttcgaataa atcttctgta   3240
tcctcgctcc gttccgcctt aaaaaaaaa aaaaaaaaa aaaaaaaaa aaaaaaaaa   3300
aaaaaaaaa aaaaaaaa                                                   3319

SEQ ID NO: 18         moltype = DNA  length = 3262
FEATURE               Location/Qualifiers
source                1..3262
                      mol_type = other DNA
                      organism = Homo sapiens
SEQUENCE: 18
tgcgggcgtc tccgccattt tgtgagtcta taactcggag ccgttgggtc ggttcctgct     60
attccggcgc ctccactccg tccccgcgg gtctgctctg tgtgccatgg acggcattgt    120
cccagatata gccgttggta caaagcgggg atctgacgag cttttctcta cttgtgtcac    180
taacggaccg tttatcatga gcagcaactc ggcttctgca gcaaacggaa atgacagcaa    240
gaagttcaaa ggtgacagcc gaagtgcagg cgtcccctct agagtgatcc acatccggaa    300
gctccccatc gacgtcacgg aggggaagt catctccctg gggcgccct ttgggaaggt    360
caccaacctc ctgatgctga aggggaaaaa ccaggccttc atcgagatga acacggagga    420
ggctgccaac accatggtga actactacac ctcggtgacc cctgtgctgc gcggccagcc    480
catctacatc cagttctcca accacaagga gctgaagacc gacagctctc caaccaggc    540
gcgggcccag gcgggccctgc aggcggtgaa ctcggtccag tcggggaacc tggccttggc    600
tgcctcggcg gcggccgtgg acgcagggat ggcgatggcc gggcagagcc ccgtgctcag    660
gatcatcgtg gagaacctct ctacccctgt gaccctggat gtgctgcacc agattttctc    720
caagttcggc acagtgttga agatcatcac cttcaccaag aacaaccagt tccaggccct    780
gctgcagtat gcggaccccg tgagcgccca gcacgccaag ctgtcgctgg acgggcagaa    840
catctacaac gcctgctgca cgctgcgcat cgacttttcc aagctcacca gcctcaacgt    900
caagtacaac aatgacaaga gccgtgacta cacacgccca gacctgcctt ccggggacag    960
ccagccctcg ctggaccaga ccatggccgc ggccttcggc ctttccgttc gaacgtcca   1020
```

```
cggcgccctg gcccccctgg ccatcccctc ggcggcggcg gcagctgcgg cggcaggtcg    1080
gatcgccatc ccgggcctgg cggggcagg  aaattctgta ttgctggtca gcaacctcaa    1140
cccagagaga gtcacacccc aaagcctctt tattcttttc ggcgtctacg gtgacgtgca    1200
gcgcgtgaag atcctgttca ataagaagga gaacgcccta gtgcagatgg cggacggcaa    1260
ccaggcccag ctggccatga gccacctgaa cgggcacaaa ctgcacggga agccccatcc    1320
catcacgctc tcgaagcacc agaacgtgca gctgccccgc gagggccagg aggaccaggg    1380
cctgaccaag gactacggca actcaccct  gcaccgcttc aagaagcggg gctccaagaa    1440
cttccagaac atattcccgc cctcggccac gctgcacctc tccaacatcc cgccctcagt    1500
ctccgaggag gatctcaagg tcctgttttc cagcaatggg ggcgtcgtca aaggattcaa    1560
gttcttccag aaggaccgca agatggcact gatccagatg ggctccgtgg aggaggcggt    1620
ccaggccctc attgacctgc acaaccacga cctcggggag aaccaccacc tgcgggtctc    1680
cttctccaag tccaccatct aggggcacag gcccccacgg ccgggccccc tggcgacaac    1740
ttccatcatt ccagagaaaa gccactttaa aaacagctga agtgaccta gcagaccaga    1800
gattttattt ttttaaagag aaatcagttt acctgttttt aaaaaaatta aatctagttc    1860
accttgctca ccctgcgtg  acagggacag ctcaggctct tggtgactgt ggcagcggga    1920
gttcccggcc ctccacaccc ggggccgac  cctcggggcc atgccttggt ggggcctgtg    1980
tcgggcgtgg ggcctgcagg tgggcgcccc gaccacgact tggcttcctt gtgccttaaa    2040
aaacctgcct tcctgcagcc acacacctac ccggggtgtc ctgggggacc aaggggtggg    2100
ggggtcacac cagagagagg caggggggcct ggccggctcc tgcaggatca tgcagctggg   2160
gcgcggcggc cgcggctgcg acaccccaac cccagccctc taatcaagtc acgtgattct    2220
cccttcaccc cgccccagg  gccttccctt ctgccccag  gcgggctccc cgctgctcca    2280
gctgcggagc tggtcgacat aatctctgta ttatatactt tgcagtttga gactgctgtg    2340
cctagcaata tttccagttg accaaatatt ctaatctttt ttcatttata tgcaaaagaa    2400
atagttttaa gtaacttttt atagcaagat gatacaatgg tatgtagtgt  aatctaaactt   2460
ccttgtggta ttaccttgta tgctgttact tttatttat  tccttgtaat taagtcacag    2520
gcaggaccca gtttccagag agcaggcggg gccgcccagt gggtcaggca cagggagccc    2580
cggtcctatc ttagagcccc tgagcttcag ggaaggggcg ggcgtgtcgc cgcctctggc    2640
atcgcctccg gttgccttac accacgcctt cacctgcagt cgcctagaaa acttgctctc    2700
aaacttcagg gttttttctt ccttcaaatt ttggaccaaa gtctcattc  tgtgttttgc    2760
ctgcctctga tgctgggacc cggaaggcgg gcgctcctcc tgtcttctct gtgctcttc    2820
taccgccccc gcgtcctgtc ccgggggctc tcctaggatc ccctttccgt aaaagcgtgt    2880
aacaagggtg taaatattta aatttttta  tacctgttgt gagacccgag gggcggcggc    2940
gcggtttttt atggtgacac aaatgtatat tttgctaaca gcaattccag gctcagtatt    3000
gtgaccgcg  agccacaggg gacccacgc  acattccgtt gccttacccg atggccttgtg   3060
acgcggagag aaccgattaa aaccgtttga gaaactcctc ccttgtctag ccctgtgttc    3120
gctgtggacg ctgtagaggc aggttggcca gtctgtacct ggacttcgaa taaatcttct    3180
gtatcctcgc tccgttccgc cttaaaaaaa aaaaaaaaaa aaaaaaaaaa aaaaaaaaaa    3240
aaaaaaaaaa aaaaaaaaaa aa                                             3262

SEQ ID NO: 19        moltype = DNA   length = 1148
FEATURE              Location/Qualifiers
source               1..1148
                     mol_type = other DNA
                     organism = Homo sapiens
SEQUENCE: 19
gcgccgagac ccgctcctgc agtattagtt cttgcagctg gtggtggcgg ctgaggcggc     60
atggatctca gcgagctgga gagagacaat acaggccgtc gtcgcctgag ttcgcctgtg    120
cccgcggtgt gccgcaagga gccttgcgtc ctgggcgtcg atgaggcggc aggggcccc    180
gtgctgggcc ccatggtcta cgccatctgt tattgtcccc tgcctcgcct ggcagatctg    240
gaggcgctga aagtggcaga ctcaaagacc ctattggaga gcgagcggga aaggctgttt    300
gcgaaaatgg aggacacgga cttttgtcgg ctgggcgctg atgtgctgtc tccaaacctc    360
atctctacca gcatgcttgg gcgggtcaaa tacaactga  actccctgtc acatgataca    420
gccactgggc ttatacagta tgcattggaa caggcgtga acgtcaccca ggtattcgtg    480
gacaccgtag gatgccaga  gacataccag gcgcggctgc agcaaagttt tcccgggatt    540
gaggtgacgg tcaaggccaa agcagatgcc tctacccgg  tggttagtgc tgccagcatc   600
tgtgccaagg tggcccggga ccaggccgtg aagaaatggc agttcgtgga gaaactgcag    660
gacttggata ctgattatgg ctcaggctac cccaatgatc caagacaa  agcgtggttg    720
aaggagcacg tggagcctgt gttcggcttc ccccagtttg tccggttcag ctggcgcacg    780
gcccagacca tcctggagaa agaggcggaa gatgttatat gggaggactc agcatccgag    840
aatcaggagg gactcaggaa gatcacatcc tacttcctca atgaagggtc ccaagccgt    900
ccccgttctt cccaccgata tttcctggaa cgcggcctgg agtcagcaac cagcctctag    960
cagctgcctc tacgcgctct acctgcttcc caacccaga  cattaaaatt gtttaaggag   1020
aaccacacgt aggggatgta cttttgggac agaagcaagg tgggagtgtg ctctgcagcc    1080
gggtccagct acttcctttt ggaaccttaa atagaatggg tgttggttga ttaatttat     1140
ttaaaaaa                                                             1148

SEQ ID NO: 20        moltype = DNA   length = 1613
FEATURE              Location/Qualifiers
source               1..1613
                     mol_type = other DNA
                     organism = Homo sapiens
SEQUENCE: 20
ggagaaaacac acacgggcgg gcggagggga cccggggcga gtcatcaagg gcgcgtggtt     60
cggcgtgcca gcgcgcttgc tctgcctgct ctcttggctt ctgtctccct tcgaccgatc    120
gccccctatc ctgaagcttt ccaatgtcat cttggagccc caaagttttcc tggggcctcc    180
gcgttgtgcg tccagaaacc ccttgcctgc ccctgaggga aacgcggagc catagggcagc   240
ggacgtcgg  gagccagccc aggggaggcc agattcagca tttggacagc ggctctgggg    300
cgcagtcggc ccagcgagtt tgccggtgaa cagcctcggg cacatggcgg gtaggagggc    360
cgcagggctg ctctgggtct tgaagaagca ggacccagcc tagagggcat ccccagctcc    420
```

```
gaatgggaca cgttttcccg agataaaaga tcccttctga gctcacacgg gagcccggg    480
accatccaat ccagcgtgga tatcccagc ctaaccaaca cctgtgctgg ggggaaagat    540
aagacgcccc ctttcagcca ggaggtggac gaccctcatg ccctcagctc tccattcttc    600
ccaaagcagc tcggatccct aagtctggag ctgccagcga ggcttccaac ccgctgcttg    660
ccatcacctc ccaggtcgtt ggtggctccg attactcccc tgctggtgcc tccctccttg    720
gcgcgcttcc cacctgcgat cggcgccctc ttcgcagtca cgaactcgcc agcagctagc    780
agcactgact agtaggaggg cccgccggag gagagccgcg cggcccacag aagcggaacg    840
cgcgtcgaga gcgccctgtc cgctcgcccc agacagatgc ccggttattc attaccgcga    900
ggcctagagg aaaagtggc tgccgtcttc ctgcccacag cccgccggac cctccgtcgc    960
ggctgcccgg tccccggagc cgcagccgcc gagcccggct gtgcgtgtcg tggctgctga   1020
ggagaaagag gcttccggac atgctctgga gtcagaagac agcgaaaaga gaagcagaag   1080
ccccggtggc aagagtctga aggaaggatg actgtagcct gtggattgta ctgcagtagg   1140
aaactgtcct agcaaggctc cactttgccc cagcttcaag ctggaaagga ggagaacatg   1200
aaacattgct tgaagacaat ggccgagaca gcaggtccca ccctgcacag ccaccagcat   1260
ctctcccctc agccctgtct cctcttctgc agttgggatc tgcacattta agcctgaaat   1320
tgtcctgtga agtgaagtat gatcggacag cctcttttca gctttatga caatgagac    1380
agaggaattg tggctcttgc caaggtcaca ggattggaat acagagccaa gccacccag    1440
gacatgcaag agcctcagaa gggaaaaaag cccagcagga aggagaaca agtagcctct   1500
gtcctgaagt tgtaacagcc aggggccagg atgaggagg aggacccat aatctgccca    1560
tctgggactt ggcaggggac ctgggaaaat gtaccccaac ccatccctta agg          1613

SEQ ID NO: 21           moltype = RNA  length = 606
FEATURE                 Location/Qualifiers
source                  1..606
                        mol_type = other RNA
                        organism = Homo sapiens
SEQUENCE: 21
cctgctggtg cctccctcct tggcgcgctt cccacctgcg atcggcgccc tcttcgcagt     60
cacgaactcg ccagcagcta gcagcactga ctagtaggag ggcccgccgg aggagaggac    120
atgctctgga gtcagaagac agcgaaaaga gaagcagaag cccccggtggc aagagtctga   180
agctggaaag gaggagaaca tgaaacattg cttgaagaca atggccgaga cagcaggtcc    240
caccctgcac agccaccagc atctctcccc tcagccctgt ctcctcttct gcagttggga    300
tctgcacatt taagcctgaa attgtcctgt gaagtgaagt atgatcggac agcctctttt    360
cagcttttat gacaatggag acagaggaat tgtggctctt gccaaggtca caggattgga    420
atacagagcc aagccacccc aggacatgca agagcctcag aagggaaaaa agcccagcag    480
gaagggagaa caagtagcct ctgtcctgaa gttgtaacag ccaggggcca ggatgaggag    540
ggaggacccc ataatctgcc catctgggac ttggcagggg acctgggaaa atgtacccca    600
acccat                                                              606

SEQ ID NO: 22           moltype = DNA  length = 551
FEATURE                 Location/Qualifiers
source                  1..551
                        mol_type = other DNA
                        organism = Homo sapiens
SEQUENCE: 22
cttcgcagtc acgaactcgc cagcagctag cagcactgac tagtaggagg gcccgccgga     60
ggagaggaag cccagagag attggtgagg gtgatttccc aggaagacgc agtgtgctct    120
gacttctgtg acagtgagca acgggaccag tggatgtcca gatgctggca atgagacatg    180
ctctggagtc agaagacagc gaaaagagaa gcagaagccc cggtggcaag agtctgaagg    240
aaggatgact gtagcctgtg gattgtactg cagtaggaaa ctgtcctagc aaggctccac    300
tttgccccag cttcaagctg gaaaggagga gaacatgaaa cattgcttga agacaatggc    360
cgagacagca ggtcccaccc tgcacagcca ccagcatctc tcccctcagc cctgtctcct    420
cttctgcagt tgggatctgc acatttaagc ctgaaattgt cctgtgaagt gaagtatgat    480
cggacagcct cttttcagct tttatgacaa tggagacaga ggaattgtgg ctcttgccaa    540
ggtcacagga t                                                        551

SEQ ID NO: 23           moltype = DNA  length = 1877
FEATURE                 Location/Qualifiers
source                  1..1877
                        mol_type = other DNA
                        organism = Homo sapiens
SEQUENCE: 23
tcgccagcag ctagcagcac tgactagtag gagggcccgc cggaggagag ccgcgcggcc     60
cacagaagcg gaacgcgcgt cgagagcgcc ctgtccgctc gccccagaca gatgccccgg    120
tattcattac cgcgaggcct agaggaaaga gtggctgccg tcttcctgcc cacagcccgc    180
cggaccctcc gtcgcggctg cccggtcccc ggagccgcag ccgccgagcc cggctgtgcg    240
tgtcgtggct gctggggaga aagaggcttc cggaagcccc agagagattg gtgagggtga    300
tttccaggga agacgcagtg tgctctgact tctgtgacag tgagcaacgg gaccagtgga    360
tgtccagatg ctggcaatga gacatgctct ggagtcagaa gacagcgaaa agagaagcag    420
aagcccggt ggcaagagtc tgaagcagga aggatgactg tagcctgtgg attgtactgc    480
agtaggaaac tgtcctagca aggctccact ttgccccagc ttcaagctgg aaaggaggag    540
aacatgaaac attgcttgaa gacaatggcc gagacagcag gtcccaccct gcacagccac    600
cagcatctct cccctcagcc ctgtctcctc ttctgcagtt gggatctgca catttaagcc    660
tgaaattgtc ctgtgaagtg aagtatgatc ggacagcctc ttttcagctt ttatgacaat    720
ggagacagag gaattgtggc tcttgccaag gtcacaggat tggaatacag agccaagcca    780
ccccaggaca tgcaagagcc tcagaaggga aaaaagccca gcaggaaggg agaacaagta    840
gcctctgtcc tgaagttgta acagccaggg gccaggatgg aggaggagga cccccataatc    900
tgcccatctg gacttggca ggggacctgg gaaaatgtac cccaacccat cccttaaggg    960
cctttgtctt tggcccattg gcctagcatc tacttcttca ccgtgtctgt tcttgtcaca   1020
```

```
cctagtcagg tctgtttggg tctgaggtgc atggaacatt ctgggtaggc ctccagcaaa   1080
cggaagctct tcaccgtgtt tccagcctgg gaccaagggc agcatactgg caaagttgcc   1140
aaaagcaaggg actccagcct cttaggagtt aatgactccc tctccccagc tgtcctccc   1200
ttggtgctcc tcttcctccc tcctcctgct cacagcaggc agggcctaga cccgggagcc   1260
atgctgctgt gctgttgcca ggggagcacg gaggcagatc tgagctatgc agggaaaagg   1320
cccagcctgt caaagtgtct gagatgaacc gccgccgtcc ctgtgcagct gggctcagac   1380
gtgtctcagc tcttgttctg tgcctgagaa tggcgaaacc cagtgaggtt caagggcaaa   1440
ctcgctattc attagtcagg ggttcttgac gtcccgtctc tcccagggat gagttccccc   1500
ctcctctttc tccccctcct atgacacatt cctgggtgcc tttggtgagg actgcacacc   1560
ctcctcctgc ctagccccct ctccaaaggc ccctgaataa actcccccca aggagaccag   1620
gcagggcaga gacaatggct gcaggaaatc attcaggcgg acatgctggc cctgccctcc   1680
acccagtccc cctgtgggcc ccactccctt ctgattcagg cacccttgg gccccagcc    1740
tatacaggcc tggacaggaa gaaaccactg ggaaccaccc taaggacaac atgctagtcc   1800
agtgccattc ttcgctggct ctgtgggtgc cttttgtggcc tgtaccgact ggctggctaa   1860
ttttgtggtt tctgtac                                                  1877

SEQ ID NO: 24           moltype = DNA   length = 561
FEATURE                 Location/Qualifiers
source                  1..561
                        mol_type = other DNA
                        organism = Homo sapiens
SEQUENCE: 24
agcactgact agtaggaggg cccgccggag gagaggacat gctctggagt cagaagacag    60
cgaaaagaga agcagaagcc ccggtggcaa gagtctgaag caggaaggat gactgtagcc   120
tgtggattgt actgcagtag gaaactgtcc tagcaaggct ccactttgcc ccagcttcaa   180
gctggaaagg aggagaacat gaaacattgc ttgaagacaa tgccgagac agcaggtccc   240
accctgcaca gccaccagca tctctcccct cagccctgtc tcctcttctg cagttgggat   300
ctgcacattt aagcctgaaa ttgtcctgtg aagtgaagta tgatcggaca gcctcttttc   360
agcttttatg acaatggaga cagaggaatt gtggctcttg ccaaggtcac aggattgaa    420
tacagagcca agccacccca ggacatgcaa gagcctcaga agggaaaaaa gcccagcagg   480
aagggagaac aagtagcctc tgtcctgaag ttgtaacagc caggggccag gatggaggag   540
gaggacccca taatctgccc a                                            561

SEQ ID NO: 25           moltype = DNA   length = 786
FEATURE                 Location/Qualifiers
source                  1..786
                        mol_type = other DNA
                        organism = Homo sapiens
SEQUENCE: 25
ctgggagtgg cgcggctgct tcccgcccgc gcaggatcag gccggccccc gcgggcctgg    60
agctggatcc agagctaggg aaactggaaa aacaggcaca aactcggaag ccgcggtacg   120
gcaagagcct aagcaaagaa tccttttcaa gattcacacc tcgtctacac cagggcaccg   180
cctgggccta cggccttccg aacccgaagc gcccgcagcc cagagctggc atcaggccat   240
caggccggga aggtcgtcgc aggccccaga gtgcgggcgc ggggggcgcg cgcccacagg   300
acgcccgggg ttgggtaggc aggagagaag ggcgccagca ggcccgcggc tgtttcccct   360
cggtccgcac agcgggcccg ggaggccatt ttgagagcgc gaagagggcc ggcaagatgg   420
ctgcgtgggc acccggaagg tcgccgcgcc aagggcccgc tgagccccctc ctccattcg   480
tccagccgcg cggcccacag aagcggaacg cgcgtcgaga gcgccctgtc cgctcgcccc   540
agacagatgc ccggttattc attaccgcga ggcctagagg aaaagagtgg ctgccgtcttc   600
ctgcccacag cccgccggac cctccgtcgc ggctgcccgg tccccggagc cgcagccgcc   660
gagcccggct gtgcgtgtcg tggctgctgg ggagaaaagc gcttccggac atgctctgga   720
gtcagaagac agcgaaaaga gaagcagaag ccccggtggc aagagtctga agcaggaagg   780
atgact                                                             786

SEQ ID NO: 26           moltype = DNA   length = 569
FEATURE                 Location/Qualifiers
source                  1..569
                        mol_type = other DNA
                        organism = Homo sapiens
SEQUENCE: 26
ttaccgcgag gcctagagga aagagtggct gccgtcttcc tgcccacagc ccgccggacc    60
ctccgtcgcg gctgcccggt ccccggagcc gcagccgccg agcccggctg tgcgtgtcgt   120
ggctgctggg gagaaagagg cttccggaca tgctctggag tcagaagaca gcgaaaagag   180
aagcagaagc cccggtggca agagtctgaa gggagaaaat aacccagttt gggaaggcaa   240
tttaaaaggg gaaatattag gaaggatgac tgtagcctg tggattgtac tgcagtagga   300
aactgtccta gcaaggctcc actttgcccc agcttcaagc tggaaaggag gagaacatga   360
acattgcttg aagacaatgc cgagacagca ggtcccacc ctgcacagc caccagcatc   420
tctcccctca gccctgtctc ctcttctgca gttgggatct gcacatttaa gcctgaaatt   480
gtcctgtgaa gtgaagtatg atcggacagc ctcttttcag cttttatgac aatggagaca   540
gaggaattgt ggctcttgcc aaggtcaca                                    569

SEQ ID NO: 27           moltype = DNA   length = 3779
FEATURE                 Location/Qualifiers
source                  1..3779
                        mol_type = other DNA
                        organism = Homo sapiens
SEQUENCE: 27
gtgtcgtggc tgctggggag aaagaggctt ccggacatgc tctggagtca gaagacagcg    60
aaaagagaag cagaagcccc ggtggcaaga gtctgaagca ggaaggatga ctgtagcctg   120
```

```
tggattgtac tgcagtagga aactgtccta gcaaggctcc actttgcccc agcttcaagc    180
tggaaaggag gagaacatga aacattgctt gaagacaatg gccgagacag caggtcccac    240
cctgcacagc caccagcatc tctcccctca gccctgtctc ctcttctgca gttgggatct    300
gcacatttaa gcctgaaatt gtcctgtgaa gtgaagtatg atcggacagc ctcttttcag    360
cttttatgac aatggagaca gaggaattgt ggctcttgcc aaggtcacag gattggaata    420
cagagccaag ccaccccagg acatgcaaga gcctcagaag ggaaaaaagc ccagcaggaa    480
gggagaacaa gtagcctctg tcctgaagtt gtaacagcca ggggccagga tgaggagga    540
ggaccccata atctgcccat ctgggacttg gcaggggacc tgggaaaatg taccccaacc    600
catcccttaa gggcctttgt ctttggccca ttggcctagc atctacttct tcaccgtgtc    660
tgttcttgtc acacctagtc aggtctgttt gggtctgagg tgcatggaac attctggtta    720
ggcctccagc aaacggaagc tcttcaccgt gtttccagcc tgggaccaag ggcagcatac    780
tggcaaagtt gccaaagcaa gggactccag cctcttagga gttaatgact ccctctcccc    840
agctgtcctc cccttggtgc tcctcttcct ccctcctcct gctcacagca ggcagggcct    900
agacccggga gccatgctgc tgtgctgttg ccaggggagc acggaggcag atctgagctg    960
tgcagggaaa aggccagcc tgtcaaagtg tctgagatga accgccgccg tccctgtgca   1020
gctgggctca gacgtgtctc agctcttgtt ctgtgcctga gaatgccgaa acccagtgag   1080
gttcaagggc aaactcgcta ttcattagtc agggggtctt gacgtcccgt ctctcccagg   1140
gatgagttcc ccctcctct ttctcccct cctatgacac attcctgggt gcctttggtg   1200
aggactgcac accctcctcc tgcctagccc cctctccaaa gcccctgaa taaactcccc   1260
ccaaggagac caggcagggc agagacaatg gctgcaggaa atcattcagg cgggacatgc   1320
tggcctgccc tccacccagt cccctgtgg gccccactcc cttctgattc agggcaccct   1380
tgggccccca gcctatacag gcctggacag gaagaaacca gggaaccca ccctaaggac   1440
aacatgctag tccagtgcca ttcttcgctg gctctgtggg tgcctttgtg gcctgtaccg   1500
actggctggc taatttttgtg gttctgtac catcacatgc ctatttaag acactctcca   1560
gcactgtcgg ttagggagtg taaatttgc aatattttct gaaatgtggc aatatcaaaa   1620
tgtaaaaggc acacatactt ggtcacaaac aaatggcact atttactctg tgggcatatt   1680
tgtaaaagtt gccaaagaat tatatacaag gatgttcatc agagcattc ttttgaaagc   1740
taaagaaatg gacatgaacc tgtggtccgt tcatacggtg gaatacctat gcagctgtaa   1800
aaatcagtgt ggtagatctc cgtatatgag ttgatgtgga aggttggcca gttcacatga   1860
taaggtgaat agaataagtt acagaacagg ctgtagagta tgatcttatt tgtagatgtt   1920
taaaactgag tcataagtat gcttatatac agatcgtttc tggaagtatg tactggaagt   1980
ctacctctgg ggagtgggga tgggggagtg cactcttcta tactgttata ttttcttttc   2040
atgctcctaa ggtactttta ttggaagatg taaagcggtt caatgtaata ggcttaactt   2100
ctgtcaacta agttggcgtg ggtgctttaa gagggtggta gtgatgttgc tggagaaagt   2160
atcccacagt cactggtggc ttcagccacg ggccattttg gggcctaata atcacatatc   2220
atcatggttg ctagtgttaa tcgaaaacct actaagtgcc aggcttactg tctctgggtc   2280
ttgcttacgt ggatgtcatt tttccagttg caccaaatcg aaagaggtta attggtttgt   2340
tggagttcct ttgtaggtga agggcagagc caggagcttg gctagggaca ggggaggtga   2400
gtgggggatg gtggataggt cttggctccc agtttcctc tgggcagaca ttgcccctct   2460
gccctgagga cctgcttgtt tggggaaga ggcctttaga ggcaccaggg tcatgccagg   2520
tgttggacat ggtgaactgg gaagtgctcc catctggcca cagcgcagaa gtatcaccgt   2580
gctggggat ggggaacagg gctgtgaatg ggcctatttg cataagcagc atgtgtctgg   2640
agagaaagac atcacagagc agaagagtgc gggtgcccag gagtgccactt gccacccta   2700
cttcatccct gaaagagtaa atggcctgga aggtgtctct gagaggtaat ccgcacacc   2760
accctccctg gggcagggt caggctacac ctgcctagg tcgggggctg cagcagcctg   2820
agagctctca gtagggcctc agtagcctgg gagggagcag gggcaggggg cagggaaaga   2880
ggcgtaatgg ggctgtccag aggggcctgg gaaacctggt ccctgaggcc tggcacagc   2940
tacaatcact tcaaattggc tgtgggccaa gtggactggg aaggaaaaaa gcaataagag   3000
tgaccaagtc cagaaggctg tcaggtccca ggtcacatgc cttagtcag tgactcctca   3060
tcatttatg gggtgtgggt gtcgttggta cacccatttt acagatgagg acaccgaggc   3120
ccagaaaagt taagttacat gtcctaagtc acacagcttg taagtgccag aactgagatc   3180
aaaaccaagt ctctttgact ttaaagtctg tactctgacc ccaaagagat cctgtttggc   3240
cacttatagg aggtccctaa agctgcagac tccccttgcc ggcacccaca tatagagaca   3300
ttaaccttc ccctgcaggg tcacctcaaa tagtcttttta gctgggcttc tcctgcaatt   3360
ccacctaatg ccatccctg ggttttgccc aaacctgaac tgggcagtgg ggtgagagga   3420
ggggtttaca gggttacaga gcctcataca gataggagcc catggctgct ggtcatctgc   3480
attcctgcag gattggctgt tccttgggt ccttggcagg aaaatgagga ttgctccgag   3540
gcctgctcca gtacttccca gaggctgcc tggtgtgggg ctctgggaag gctgaggctg   3600
gagaagcgta agtaggaggg cagagatggc actcaggtag cttgaatcac caggacccttt   3660
ccaagcccca caggttctga gggagtacta gggcaggctc tgggagaggt ctcttcctat   3720
gctgtgaacc ccctgccttt cttgcagcct acaacgaata aatttctttt gcaaaggct   3779
```

```
SEQ ID NO: 28          moltype = DNA  length = 3670
FEATURE                Location/Qualifiers
source                 1..3670
                       mol_type = other DNA
                       organism = Homo sapiens
SEQUENCE: 28
cttccggaca tgctctggag tcagaagaca gcgaaaagag aagcagaagc cccggtggca    60
agagtctgaa gctggaaagg aggagaacat gaaacattgc ttgaagacaa tggccgagac   120
agcaggtccc accctgcaca gccaccagca tctctcccct cagccctgtc tcctcttctg   180
cagttgggat ctgcacattt aagcctgaaa ttgtcctgtg aagtgaagta tgatcggaca   240
gcctcttttc agcttttatg acaatggaga cagaggaatt gtggctcttg ccaaggtcac   300
aggattggaa tacagagcca agccaccca ggacatgcaa gagcctcaga agggaaaaaa   360
gcccagcagg aagggagaac aagtagcctc tgtcctgaag ttgtaacagc caggggccag   420
gatgaggag gaggacccca taatctgccc atctgggact tggcagggga cctgggaaaa   480
tgtaccccaa cccatccctt aagggccttt gtctttggcc cattggccta gcatctactt   540
cttcaccgtg tctgttcttg tcacacctag tcaggtctgt ttgggtctga ggtgcatgga   600
acattctggg taggcctcca gcaaacggaa gctcttcacc gtgtttccag cctgggacca   660
```

```
agggcagcat actggcaaag ttgccaaagc aagggactcc agcctcttag gagtttaatga    720
ctccctctcc ccagctgtcc tcccctggt gctcctcttc ctccctcctc ctgctcacag      780
caggcagggc ctagacccgg gagccatgct gctgtgctgt tgccagggga gcacggaggc     840
agatctgagc tatgcaggga aaaggccag cctgtcaaag tgtctgagat gaaccgccgc      900
cgtccctgtg cagctgggct cagacgtgtc tcagctctg ttctgtgcct gagaatggcg      960
aaacccagtg aggttcaagg gcaaactcgc tattcattag tcaggggttc ttgacgtccc    1020
gtctctccca gggatgagtt cccccctcct ctttctcccc ctcctatgac acattcctgg    1080
gtgccttttgg tgaggactgc acaccctcct cctgcctagc cccctctcca aaggcccctg   1140
aataaactcc ccccaaggag accaggcagg gcagagacaa tggctgcagg aaatcattca    1200
ggcgggacat gctggcctgc cctccaccca gtcccctgt gggcccccact cccttctgat    1260
tcagggcacc cttgggcccc cagcctatac aggcctggac aggaagaaac cactgggaac    1320
caccctaagg acaacatgct agtccagtgc cattcttcgc tggctctgtg ggtgcctttg    1380
tggcctgtac cgactggctg gctaatttttg tggtttctgt accatcacat gcctatttta   1440
agacactctc cagcactgtc ggttagggag tgtaaattt gcaatatttt ctgaaatgtg     1500
gcaatatcaa aatgtaaag gcacacatac ttggtcacaa acaaatggca ctatttactc     1560
tgtgggcata tttgtaaaag ttgccaaaga attatataca aggatgttca tcagagcatt    1620
tcttttgaag agtaaagaaa tggacatgaa cctgtggtcc gttcatacgg tggaatacct    1680
atgcagctgt aaaaatcagt gtggtagatc tccgtatatg agttgatgtg gaaggttggc    1740
cagttcacat gataaggtga atagaataag ttacagaaca ggctgtagag tatgatctta    1800
tttgtagatg ttttaaaactg agtcataagt atgcttatat acagatcgtt tctgaagta    1860
tgtactggaa gtctacctct ggggagtggg gatgggggag tgcactcttc tatactgtta    1920
tattttctttt tcatgctctt aaggtacttt tattggaaga tgtaaagcgg ttcaatgtaa   1980
taggcttaac ttctgtcaac taagttggcg tgggtgcttt aagagggtgg tagtgatgtt    2040
gctgagaaa gtatcccaca gtcactggtg gcttcagcca cgggccattt tggggcctaa     2100
taatcacata tcatcatggt tgctagtgtt aatcgaaaac ctactaagtg ccaggcttac    2160
tgtctctggg tcttgcttac gtggatgtca ttttccagt tgcaccaaat cgaaagaggt     2220
taattggttt gttggagttc ctttgtaggt gaagggcaga gccaggagct tggctaggga    2280
cagggaggt gagtgggga tggtggatag gtcttggctc ccagtttcct tctgggcaga     2340
cattgccct ctgccctgag gacctgcttg tttgggggaa gaggccttta gaggcaccag     2400
ggtcatgcca ggtgttggac atggtgaact gggaagtgct cccatctgc cacagcgcag    2460
aagtatcacc gtgctggggg atggggaaca gggctgtgaa tgggcctatt tgcataagca    2520
gcatgtgtct ggagagaaag acatcacaga gcagaagagt gcgggtgccc aggagtgcac   2580
ttgccaccc tacttcatcc ctgaaagagt aaatggcctg gaaggtgtct ctgagaggta    2640
atgccgcaca ccaccctccc tgggggcagg gtcaggctac acctgcctta ggtcgggggc   2700
tgcagcagcc tgagagctct cagtagggcc tcagtagcct gggagggagc aggggcaggg   2760
ggcagggaaa gaggcgtaat ggggctgtcc agagggcct gggaaacctg gtccctgagg    2820
cctgggcaca gctacaatca cttcaaattg gctgtggggc cagtggactg ggaaggaaaa   2880
aagcaataag agtgaccaag tgcagaaggc tgtcaggtcc caggtcacat gccttagtgc    2940
agtgactcct catcatttta tggggtgtgg gtgtcgttgg tacacccatt ttacagatga   3000
ggacaccgag gcccagaaaa gttaagttac atgtcctaag tcacacagct tgtaagtgcc   3060
agaactgaga tcaaaaccaa gtctctttga ctttaaagtc tgtactctga ccccaaagag    3120
atcctgtttg gccacttata ggaggtccct aaagctgcag actcccttg ccggcaccca    3180
catatagaca cattaacct tcccctgcag ggtcacctca aatagtcttt tagctggct    3240
tctcctgcaa ttccacctaa tgccatcccc tgggttttgc ccaaacctga actgggcagt   3300
ggggtgagag gagggttta cagggttaca gagcctcata cagataggag cccatggctg    3360
ctggtcatct gcattcctgc aggattggct gttccttggg gtccttggca ggaaaatgag   3420
gattgctccg aggcctgctc cagtacttcc cagaggctgg ggctggtggg ggctctggga  3480
aggctgaggc tggagaagcg taagtaggag ggcagagatg gcactcaggt agcttgaatc    3540
accaggaccc ttccaagccc cacaggttct gagggagtac tagggccagc tctgggagag   3600
gtctcttcct atgctgtgaa ccccctgcct ttccttgcagc ctacaacgaa taaattttct   3660
ttgcaaaggc                                                         3670
```

| SEQ ID NO: 29 | moltype = DNA  length = 3784 |
|---|---|
| FEATURE | Location/Qualifiers |
| source | 1..3784 |
| | mol_type = other DNA |
| | organism = Homo sapiens |

SEQUENCE: 29

```
gctaacagct tcaggagaat tcagcctcac cttgacagga catgctctgg agtcagaaga    60
cagcgaaaag agaagcagaa gccccggtgg caagagtctg aagcaggaag gatgactgta   120
gcctgtggat tgtactgcag taggaaactg tcctagcaag gctccacttt gccccagctt    180
caagctggaa aggaggagaa catgaaacat gcttgaaga caatggccga cagcaggt    240
cccaccctgc acagccacca gcatctctcc cctcagccct gtctcctctt ctgcagttgg    300
gatctgcaca tttaagcctg aaatttgtcct gtgaagtgaa gtatgatcgg acagcctctg   360
ttcagctttt atgacaatgg agacagagga attgtggctc ttgccaaggt cacaggattg    420
gaatacagag ccaagccacc ccaggacatg caagagcctc agaagggaaa aaagcccagc   480
aggaaggag aacaagtagc ctctgtcctg aagttgtaac agccagggc caggatggag     540
gaggaggacc ccataatctg cccatctggg acttggcagg ggactgggga aaatgtaccc   600
caacccatcc cttaagggcc tttgtctttg gcccattgc ctagcatcta cttcttcaga   660
gtgtctgttc ttgtcacacc tagtcaggtc tgtttgggtc tgaggtgcat ggaacattct    720
gggtaggcct ccagcaaacg gaagctcttc accgtgtttc cagcctggga ccaagggcag   780
catactggca aagttgccaa agcaagggac tccagcctct taggagttaa tgactcctc    840
tccccagctg tccctccccctt ggtgctcctc ttccctcctc ctcctgctca cagcaggcag   900
ggcctagacc cgggagccat gctgctgtgc tgttgccacg agggcagatctg              960
agctatgcag ggaaaaggcc cagcctgtca aagtgtctga gatgaaccgc cgcgtccct    1020
gtgcagctgg gctcagacgt gtctcagctc ttgttctgtg cctgagaatg gcgaacccca   1080
gtgaggttca agggcaaact cgctattcat tagtcagggg ttcttgacgt cccgtctctc   1140
ccaggggatga gttccccccct cctctttctc ccctcctat gacacattcc tgggtgcctt  1200
tggtgaggac tgcacaccct cctcctgcct agccccctct ccaaaggccc ctgaataaac   1260
```

```
tcccccaag gagaccaggc agggcagaga caatggctgc aggaaatcat tcaggcggga  1320
catgctggcc tgccctccac ccagtccccc tgtgggcccc actcccttct gattcagggc  1380
acccttgggc ccccagccta tacaggcctg gacaggaaga aaccactggg aaccacccta  1440
aggacaaact gctagtccag tgccattctt cgctggctct gtgggtgcct tgtggcctg   1500
taccgactgg ctggctaatt ttgtggtttc tgtaccatca catgcctatt ttaagacact  1560
ctccagcact gtcggttagg gagtgtaaat tttgcaatat tttctgaaat gtggcaatat  1620
caaaatgtaa aaggcacaca tacttggtca caaacaaatg gcactattta ctctgtgggc  1680
atatttgtaa aagttgccaa agaattatat acaaggatgt tcatcagagc atttctttg   1740
aagagtaaag aaatggacat gaacctgtgg tccgttcata cggtggaata cctatgcagc  1800
tgtaaaaatc agtgtggtag atctccgtat atgagttgat gtggaaggtt ggccagttca  1860
catgataagg tgaatagaat aagttacaga acaggctgta gagtatgatc ttatttgtag  1920
atgtttaaaa ctgagtcata agtatgctta tatacagatc gtttctggaa gtatgtactg  1980
gaagtctacc tctggggagt ggggatgggg gagtgcactc ttctatactg ttatattttc  2040
ttttcatgct cctaaggtac ttttattgga agatgtaaaa cggttcaatg taataggctt  2100
aacttctgtc aactaagttg gcgtgggtgc tttaagaggg tggtagtgat gttgctggag  2160
aaagtatccc acagtcactg gtggcttcag ccacgggcca ttttgggcc taataatcac   2220
atatcatcat ggttgctagt gttaatcgaa aacctactaa gtgccaggct tactgtctct  2280
gggtcttgct tacgtggatg tcattttttcc agttgcacca aatcgaaaga ggttaattgg  2340
tttgttggag ttccttttgta ggtgaagggc agagccagga gcttggctag ggacagggga  2400
ggtgagtggg ggatggtgga taggtcttgg ctcccagttt ccttctgggc agacattgcc  2460
cctctgccct gaggacctgc ttgtttgggg gaagaggcct ttagaggcac cagggtcatg  2520
ccaggtgttg gacatggtga actgggaagt gctcccatct ggccacagcg cagaagtatc  2580
accgtgctgg gggatgggga acagggctgt gaatgggcct atttgcataa gcagcatgtg  2640
tctggagaga aagacatcac agagcagaag agtgcgggtg cccaggagtg cacttgccac  2700
ccctacttca tccctgaaag agtaaatggc ctggaaggtg tctctgagag gtaatgccgc  2760
acaccaccct ccctgggggc agggtcaggc tacacctgcc ttaggtcggg ggctgcagca  2820
gcctgagagc tctcagtagg gcctcagtag cctgggaggg agcaggggca ggggcaggg   2880
aaagaggcgt aatgggggctg tccagagggg cctgggaaac ctggtccctg aggcctgggc  2940
acagctacaa tcacttcaaa ttggctgtgg ggccagtgga ctgggaagga aaaaagcaat  3000
aagagtgacc aagtgcagaa ggctgtcagg tcccaggtca catgccttag tgcagtgact  3060
cctcatcatt ttatggggtg tgggtgtcgt tggtacaccc attttacaga tgaggacacc  3120
gaggcccaga aaagttaagt tacatgtcct aagtcacaca gcttgtaagt gccagaactg  3180
agatcaaaac caagtctctt tgactttaaa gtctgtactc tgaccccaaa gagatcctgt  3240
ttggccacttt ataggaggtc cctaaagctg cagactcccc ttgccggcac ccacatatag  3300
agacattaac ccttcccctg cagggtcacc tcaaatagtc ttttagctgg gcttctcctg  3360
caattccacc taatgccatc ccctgggttt tgcccaaacc tgaactgggc agtggggtga  3420
gaggagggggg ttacagggtt acagagcctc atacagatag gagcccatgg ctgctggtca  3480
tctgcattcc tgcaggattg gctgttcctt ggggtccttg gcaggaaaat gaggattgct  3540
ccgaggcctg ctccagtact tcccagaggc tggcctggtg tggggctctg ggaaggctga  3600
ggctggagaa gcgtaagtag gagggcagag atggcactca ggtagcttga atcaccagga  3660
cccttccaag ccccacaggt tctgagggag tactagggcc agtctgggga gaggtctctt  3720
cctatgctgt gaacccctg cctttcttgc agcctacaac gaataaattt tctttgcaaa   3780
ggct                                                              3784
```

```
SEQ ID NO: 30          moltype = DNA  length = 779
FEATURE                Location/Qualifiers
source                 1..779
                       mol_type = other DNA
                       organism = Homo sapiens
SEQUENCE: 30
gcacgacttg ttcttgcctt ctaaagcaga gaggagcttt tgtgggtagt tcctacaggg   60
atacatggta gaaaattcac caaacccagt gctggagtgt ttctcttcct cagaagaaat  120
cagatgctgt tcagagcacg aaggctagaa ttttaccctg gttctcatgc taccttgcac  180
ccaggttgga tcctgagtac agttttttggc aggaagcccc agagagattg gtgagggtga  240
tttccagga agacgcagtg tgctctgact tctgtgacag tgagcaacgg gaccagtgga  300
tgtccagatg ctggcaatga gacatgctct gggtcagaa gacagcgaaa agagaagcag  360
aagccccggt ggcaagagtc tgaaggaagg atgactgtag cctgtggatt gtactgcagt  420
aggaaactgt cctagcaagg ctccacttttg ccccagcttc aaggtatatc gtctcaaaat  480
gcaggggact tcagatgagt tttgagcacc ctttctttta ttataaaaaa aattccagac  540
agttcagcca atactgacta agggctgaga ccagttccat gcttttctgt ctccagagca  600
atttgcttcc atctggatgc ctgaaacgct ggaaaggagg agaacatgaa acattgcttg  660
aagacaatgg ccgagacagc aggtcccacc ctgcacagcc accagcatct ctcccctcag  720
ccctgtctcc tcttctgcag ttgggatctg cacatttaag cctgaaattg tcctgtgaa   779

SEQ ID NO: 31          moltype = DNA  length = 1611
FEATURE                Location/Qualifiers
source                 1..1611
                       mol_type = other DNA
                       organism = Homo sapiens
SEQUENCE: 31
ggagaaacac acacgggcgg gcggagggga cccgggggcga gtcatcaagg gcgcgtggtt   60
cggcgtgcca ggcgcgctgc tctgcctgct ctcttggctt ctgtctccct tcgaccgatc  120
gccccctatc ctgaagcttt ccaatgtcat cttggagccc caaagttttcc tggggcctcc  180
gcgttgtgcg tcccagaacc ccttgcctgc ccctgaggga aacgcggagc cataggcagc  240
gggacgtcgg gagccagccc aggggaggcc agattcagca tttggacagc ggctctgggg  300
cgcagtcggc ccagcgagtt tgccggtgaa cagcctcggg cacatggcgg gtaggagggc  360
cgcagggctg ctctgggtct tgaagaagca ggacccagcc tagagggcat ccccagctcc  420
gaatgggaca cgttttcccg agataaaaga tcccttctga gctcacacgg gagccccggg  480
accatccaat ccagcgtgga tatccccagc ctaaccaaca cctgtgctgg ggggaaagat  540
```

```
aagacgcccc ctttcagcca ggaggtggac gaccctcatg ccctcagctc tccattcttc    600
ccaaagcagc tcggatccct aagtctggag ctgccagcga ggcttccaac ccgctgcttg    660
ccatcacctc ccaggtcgtt ggtggctccg attactcccc tgctggtgcc tccctccttg    720
gcgcgcttcc cacctgcgat cggcgccctc ttcgcagtca cgaactcgcc agcagctagc    780
agcactgact agtaggaggg cccgccgagg gagagccgcg cacccccacag aagcggaacg    840
cgcgtcgaga gcgccctgtc cgctcgcccc agacagatgc ccggttattc attaccgcga    900
ggcctagagg aaagagtggc tgccgtcttc ctgcccacag cccgccggac cctccgtcgc    960
ggctgcccgg tccccggagc cgcagccgcc gagcccggct gtgcgtgtcg tggctgctgg   1020
ggagaaagag gcttccggac atgctctgga gtcagaagac agcgaaaaga gaagcagaag   1080
ccccggtggc aagagtctga aggaaggatg actgtagcct gtggattgta ctgcagtagg   1140
aaactgtcct agcaaggctc cactttgccc cagcttcaag ctggaaagga ggagaacatg   1200
aaacattgct tgaagacaat ggccgagaca gcaggtccca ccctgcacag ccaccagcat   1260
ctctcccctc agccctgtct cctcttctgc agttgggatc tgcacattta agcctgaaat   1320
tgtcctgtga agtgaagtat gatcggacag cctcttttca gctttatga caatggagac   1380
agaggaattg tggctcttgc caaggtcaca ggattggaat acagagccaa gccacccag    1440
gacatgcaag agcctcagaa gggaaaaaag cccagcagga agggagaaca gtagcctct    1500
gtcctgaagt tgtaacagcc aggggccagg atggaggagg aggaccccat aatctgccca   1560
tctgggactt ggcaggggac ctgggaaaat gtaccccaac ccatcccta a              1611

SEQ ID NO: 32           moltype = DNA  length = 2718
FEATURE                 Location/Qualifiers
source                  1..2718
                        mol_type = other DNA
                        organism = Homo sapiens
SEQUENCE: 32
atcaagcgat cctcccacct gggcctccca aagtgttgag attacagcat gagccaccac     60
acccagacta aaaggcagtt tgattttaca aatcaaaata gcagtaatct atggagattt    120
acttgtgaga ttggtaggaa acatcttaaa tgtaatcaaa caataactta catcttgatg    180
aattcacgtg taggtttctc ttcctcagaa gaaatcagat gctgttcaga gcacgaaggc    240
tagaatttta ccctggttct catgctacct tgcacccagg ttggatcctg agtacagttt    300
ttggcaggtg ggcctgcata taagttagca atgggggata cccagctgcc tctcttcata    360
cagctgaggt tttggggagt cattcttata gcccctgggt tgggcctagt cctgcaaatg    420
aattcaccag ccctaaagcc caaattgcag cctctgtcat tcaccttcca ggagtggaaa    480
gggcagtaag tttcatctta ttattattgc tattttggtg gttttgttga ggtggttgtg    540
tgtatgttag taagataaag ctctcagaaa ttacataga tttgtcaagg atataagagg    600
gactgtgcca catctggctg tatagaaggt ggttccatat cttaaatag agccccaggt    660
ccttagccac cagaaaggtt ttcaggggaa gtgtgcaccc tcagcagctg ctgctggtgg    720
gcaggatggg cacgcatgga acaggctttc ctctgtggcc aggtgagaag caggtggtga    780
gacacagag agtgctgggc tctgcttctg aagcctccaa cctttccttc cctaggaagc    840
cccagagaga ttggtgaggg tgatttccca ggaagacgca gtgtgctctg acttctgtga    900
cagtgagcaa cgggaccagt ggatgtccag atgctggcaa tgagtaggcc ttccctacgc    960
tgggtggcgt ccacaccctc cggcttccat tgcctgggtc tcctggaggt ggtttgctgg   1020
atgaataccg catgcacaga ggctggcctt gggtttgaat atggcagcca gtggacagca   1080
tgtgcttcag ttatgagact gcccaggaga tgcttcttcc aaggcagagc acgtgcagag   1140
tccagtgctg gagaggccgg gtgcgcagtt gacccatttc cagttctgtt ttccctctca   1200
tgttcctctg tccccatcta ggacatgctc tggagtcaga agacagcgaa aagagaagca   1260
gaagccccgg tggcaagagt ctgaagcagg aaggatgact gtagcctgtg gattgtactg   1320
cagtaggaaa ctgtcctagc aaggctccac tttgccccag cttcaagctg gaaaggagga   1380
gaacatgaaa cattgcttga agacaatggc gagacagca ggtcccaccc tgcacagcca   1440
ccagcatctc tcccctcagc cctgtctcct cttctgcagt tgggatctgc acatttaagc   1500
ctgaaattgt cctgtgaagt gaagtatgat cggacagtct ttttcagct tttatgacaa   1560
tggagacaga ggaattgtgg ctcttgccaa ggtcacagga ttggaataca gagccaagcc   1620
accccaggac atgcaagagc ctcagaaggg aaaaaagccc agcaggaagg gagaacaagt   1680
agcctctgtc ctgaagttgt aacagccagg gccaggatg gaggaggagg accccataat   1740
ctgcccatct gggacttggc aggggacctg ggaaaatgta ccccaaccca tcccttaagg   1800
gcctttgtct ttggcccatt ggcctagcat ctacttcttc accgtgtctg ttcttgtcac   1860
acctagtcag gtctgtttgg gtctgaggtg catggaacat tctgggtagg cctccagcaa   1920
acggaagctc ttcaccgtgt ttccagcctg gaccaaggg cagcatactg gcaaagttgc   1980
caaagcaagg gactccagcc tcttaggagt taatgactcc ctctcccccag ctgtcctccg   2040
cttggtgctc ctcttcctcc ctcctcctgc tcacagcagg cagggcctag accgggagc   2100
catgctgctg tgctgttgcc aggggagcac ggaggcagat ctgagctatg cagggaaaag   2160
gcccagcctg tcaaagtgtc tgagatgaac cgccgccgtc cctgtgcagc tgggctcaga   2220
cgtgtctcag ctcttgttct gtgcctgaga atggcgaaac ccagtgaggt tcaagggcaa   2280
actcgctatt cattagtcag gggttcttga cgtcccgtct ctcccaggga tggttccccc   2340
cctcctcttt ctcccctcc tatgacacat tcctggtgc cttttggtgag gactgcacac   2400
cctcctcctg cctagcccc tctccaaagg cccctgaata aactccccc aaggagacca    2460
ggcagggcag agacaatggc tgcaggaaat cattcaggcg gacatgctg gcctgccctc   2520
cacccagtcc ccctgtgggc cccactccct tctgattcag ggcacccttg ggccccccagc  2580
ctatacaggc ctggacagga gaaaccact gggaaccacc ctaaggacaa catgctagtc   2640
cagtgccatt cttcgctggc tctgtgggtg cctttgtggc ctgtaccgac tggctggcta   2700
attttgtggt ttctgtac                                                  2718

SEQ ID NO: 33           moltype = DNA  length = 3723
FEATURE                 Location/Qualifiers
source                  1..3723
                        mol_type = other DNA
                        organism = Homo sapiens
SEQUENCE: 33
gagagattgg tgagggtgat ttcccaggaa gacgcagtgt gctctgactt ctgtgacaga     60
```

```
catgctctgg agtcagaaga cagcgaaaag agaagcagaa gccccggtgg caagagtctg   120
aagctggaaa ggaggagaac atgaaacatt gcttgaagac aatggccgag acagcaggtc   180
ccaccctgca cagccaccag catctctccc ctcagccctg tctcctcttc tgcagttggg   240
atctgcacat ttaagcctga aattgtcctg tgaagtgaag tatgatcgga cagcctcttt   300
tcagctttta tgacaatgga gacagaggaa ttgtggctct tgccaaggtc aacaggattgg  360
aatacagagc caagccaccc caggacatgc aagagcctca gaagggaaaa aagcccagca   420
ggaagggaga acaagtagcc tctgtcctga gttgtaaca gccaggggcc aggatggagg   480
aggaggaccc cataatctgc ccatctggga cttggcaggg gacctgggaa aatgtacccc   540
aacccatccc ttaagggcct ttgtctttgg cccattggcc tagcatctac ttcttcaccg   600
tgtctgttct tgtcacacct agtcaggtct gtttgggtct gaggtgcatg gaacattctg   660
ggtaggcctc cagcaaacgg aagctcttca ccgtgtttcc agcctgggac caagggcagc   720
atactggcaa agttgccaaa gcaagggact ccagcctctt aggagttaat gactccctct   780
ccccagctgt cctcccctg gtgctcctct tcctccctcc tcctgctcac agcaggcagg   840
gcctagaccc gggagccatg ctgctgtgct gttgccagga gcacggaga gcagatctga    900
gctatgcagg gaaaaggccc agcctgtcaa agtgtctgag atgaaccgcc gccgtccctg    960
tgcagctggg ctcagacgtg tctcagctct tgttctgtgc ctgagaatgg cgaaacccag  1020
tgaggttcaa gggcaaactc gctattcatt agtcaggggt cttgacgtc ccgtctctcc   1080
cagggatgag ttcccccctc ctcttttctcc ccctcctatg acacattcct gggtgccttt  1140
ggtgaggact gcacaccctc ctcctgccta gccccctctc caaaggcccc tgaataaact  1200
cccccccaagg agaccaggca gggcagagac aatggctgca ggaaatcatt caggcgggac  1260
atgctggcct gccctccacc cagtccccct gtgggcccca ctcccttctg attcaggggca 1320
cccttgggcc cccagcctat acaggcctgg acaggaagaa accactggga accaccctaa  1380
ggacaacatg ctagtccagt gccattcttc gctggctctg tgggtgcctt tgtggcctgt  1440
accgactggc tggctaattt tgtggtttct gtaccatcac atgcctattt taagacactc   1500
tccagcactg tcggttaggg agtgtaaatt ttgcaatatt ttctgaaatg tggcaatatc   1560
aaaatgtaaa aggcacacat acttggtcac aaacaaatgg cactatttac tctgtgggca   1620
tatttgtaaa agttgccaaa gaattatata caaggatgtt catcagagca tttctttga    1680
agagtaaaga aatggacatg aacctgtggt ccgttcatac ggtggaatac ctatgcagct   1740
gtaaaaatca gtgtggtaga tctccgtata tgagttgatg tggaaggttg ccagttcac    1800
atgataaggt gaatagaata agttacagaa caggctgtga agtatgatct tatttgtaga  1860
tgtttaaaac tgagtcataa gtatgcttat atacagatcg tttctggaag tatgtactga  1920
aagtctacct ctggggagtg gggatggggg agtgcactct tctatactgt tatattttct  1980
tttcatgctc ctaaggtact tttattggaa gatgtaaagc ggttcaatgt aataggctta  2040
acttctgtca actaagttgg cgtgggtgct ttaagagggt ggtagtgatg ttgctggaga  2100
aagtatccca cagtcactgg tggcttcagc cacgggccat tttggggcct aataatcaca  2160
tatcatcatg gttgctagtg ttaatcgaaa acctactaag tgccaggctt actgtctctg  2220
ggtcttgctt acgtggatgt cattttttcca gttgcaccaa atcgaaagag gttaattggt  2280
ttgttggagt tccttttgtag gtgaaggca gagccaggag cttggctagg gacagggag   2340
gtgagtgggg gatggtggat aggtcttggc tcccagtttc cttctgggca gacattgccc  2400
ctctgccctg aggacctgct tgtttggggg aagaggcctt tagaggcacc agggtcatgc  2460
caggtgttgg acatggtgaa ctgggaagtg ctcccatctg gccacagcgc agaagtatca  2520
ccgtgctggg ggatggggaa cagggctgtg aatgggccta tttgcataag cagcatgtgt  2580
ctggagagaa agacatcaca gagcagaaga gtgcggcgtc ccaggagtgc acttgccacc  2640
cctacttcat ccctgaaaga gtaaatggcc tggaaggtgt ctctgagagg taatgccgca  2700
caccaccctc cctgggggca gggtcaggct acacctgcct taggtcgggg gctgcagcag  2760
cctgagagct ctcagtaggg cctcagtagc ctggagggga gcaggggcag ggggcaggga  2820
aagaggcgta atggggctgt ccagaggggc ctgggaaacc tggtccctga ggcctgggca  2880
cagctacaat cacttcaaat tggctgtggg gccagtggac tgggaaggaa aaaagcaata  2940
agagtgacca agtgcagaag gctgtcaggt cccaggtcac atgccttagt gcagtgactc  3000
ctcatcattt tatggggtgt gggtgtcgtt ggtacaccca ttttacagat gaggacaccg  3060
aggcccagaa aagttaagtt acatgtccta agtcacacag cttgtaagtg ccagaactga  3120
gatcaaaacc aagtgtcttt gactttaaag tctgtactct gacccccaaag agatcctgtt  3180
tggccactta taggaggtcc ctaaagctgc agactcccct tgccggcacc cacatataga  3240
gacattaacc cttcccctgc agggtcacct caaatagtct tttagctggg cttctcctgc  3300
aattccacct agccatcc cctgggttttt gcccaaacct gagtgggca gtggggtgag  3360
aggaggggtt tacagggtta cagagcctca tacagatagg agcccatggc tgctggtcat  3420
ctgcattcct gcaggattgg ctgttccttg gggtccttgg caggaaaatg aggattgctc  3480
cgaggcctgc tccagtactt cccagaggct ggcctggtgt ggggctctgg gaaggctgag  3540
gctggagaag cgtaagtagg agggcagaga tggcactcag gtagcttgaa tcaccaggac  3600
ccttccaagc cccacaggtt ctgagggagt actagggcca gctctgggga aggtctcttc  3660
ctatgctgtg aaccccctgc ctttcttgca gcctacaacg aataaatttt ctttgcaaag  3720
gct                                                                 3723
SEQ ID NO: 34        moltype = RNA   length = 4778
FEATURE              Location/Qualifiers
source               1..4778
                     mol_type = other RNA
                     organism = Homo sapiens
SEQUENCE: 34
ggagaaacac acacgggcgg gcggagggga cccggggcga gtcatcaagg gcgcgtggtt    60
cggcgtgcca ggcgcgctgc tctgcctgct ctcttggctt ctgtctccct tcgaccgatc   120
gcccccatc ctgaagcttt ccaatgtcat cttggagccc caaagtttcc tggggcctcc    180
gcgttgtgcg tcccagaacc ccttgcctgc ccctgaggga aacgcggagc cataggcagc   240
gggacgtcgg gagccagccc aggggaggcc agattcagca tttggacagc ggctctgggg   300
cgcagtcggc ccagcgagtt tgccggtgaa cagcctcggg cacatgcgg gtaggagggc    360
cgcagggctg ctctgggtct tgaagaagca ggacccagcc tagagggcat ccccagctcc   420
gaatgggaca cgttttcccg agataaaaga tccttctga gctcacacgg gagcccggg    480
accatccaat ccagcgtgga tatccccagc ctaaccaaca cctgtgctgg ggggaaagat   540
aagacgcccc ctttcagcca ggaggtggac gaccctcatg ccctcagctc tccattcttc   600
```

```
ccaaagcagc tcggatccct aagtctggag ctgccagcga ggcttccaac ccgctgcttg    660
ccatcacctc ccaggtcgtt ggtggctccg attactcccc tgctggtgcc tccctccttg    720
gcgcgcttcc cacctgcgat cggcgccctc ttcgcagtca cgaactcgcc agcagctagc    780
agcactgact agtaggaggg cccgccggag gagagccgcg cggcccacag aagcggaacg    840
cgcgtcgaga gcgccctgtc cgctcgcccc agacagatgc ccggttattc attaccgcga    900
ggcctagagg aaaagagtgg ctgccgtctt cctgcccacag cccgccggac cctccgtcgc    960
ggctgcccgg tccccggagc cgcagccgcc gagcccggct gtgcgtgtcg tggctgctgg   1020
ggagaaagag gcttccggac atgctctgga gtcagaagac agcgaaaaga gaagcagaag   1080
ccccggtggc aagagtctga aggaaggatg actgtagcct gtggattgta ctgcagtagg   1140
aaactgtcct agcaaggctc cactttgccc cagcttcaag ctggaaagga ggagaacatg   1200
aaacattgct tgaagacaat ggccgagaca gcaggtccca ccctgcacag ccaccagcat   1260
ctctcccctc agccctgtct cctcttctgc agttgggatc tgcacattta agcctgaaat   1320
tgtcctgtga agtgaagtat gatcggacag cctcttttca gcttttatga caatggagac   1380
agaggaattg tggctcttgc caaggtcaca ggattggaat acagagccaa gccaccccag   1440
gacatgcaag agcctcagaa gggaaaaaag cccagcagga agggagaaca agtagcctct   1500
gtcctgaagt tgtaacagcc aggggccagg atggaggagg aggacccat aatctgccca    1560
tctgggactt ggcaggggac ctgggaaaat gtaccccaac ccatccctta agggcctttg   1620
tctttggccc attggcctag catctacttc ttcaccgtgt ctgttcttgt cacacctagt   1680
caggtctgtt tgggtctgag gtgcatggaa cattctgggt aggcctccag caaacggaag   1740
ctcttcaccg tgtttccagc ctgggaccaa gggcagcata ctggcaaagt tgccaaagca   1800
agggactcca gcctcttagg agttaatgac tccctctccc cagctgtcct ccccttggtg   1860
ctcctcttcc tccctcctcc tgctcacagc aggcagggcc tagacccggg agccatgctg   1920
ctgtgctgtt gccaggggag cacgaggca gatctgagct atgcagggaa aaggcccagc    1980
ctgtcaaagt gtctgagatg aaccgccgcc gtccctgtgc agctgggctc agacgtgtct   2040
cagctcttgt tctgtgcctg agaatggcga aacccagtag ggttcaaggg caaactcgct   2100
attcattagt caggggttct tgacgtcccg tctctccgag ggatgagttc ccctctcctc   2160
tttctccccc tcctatgaca cattcctggg tgcctttggt gaggactgca caccctcctc   2220
ctgcctagcc ccctctccaa aggccctga ataaactccc cccaaggaga ccaggcaggg    2280
cagagacaat ggctgcagga aatcattcag gcggacatg ctggcctgcc ctccacccag    2340
tcccctgtg ggcccactc ccttctgatt cagggcaccc ttgggcccc agcctataca     2400
ggcctggaca ggaagaaacc actgggaacc acccctaagga caacatgcta gtccagtgcc   2460
attcttcgct ggctctgtgg gtgccttgt ggctgtacc gactggctgg ctaattttgt     2520
ggtttctgta ccatcacatg cctattttaa gacactctcc agcactgtcg gttagggagt   2580
gtaaatttg caatattttc tgaaatgtgg caatatcaaa atgtaaaagg cacacatact    2640
tggtcacaaa caaatggcac tatttactct gtgggcatat ttgtaaaagt tgccaaagaa   2700
ttatatacaa ggatgttcat cagagcatt cttttgaaga gtaaagaaat ggacatgaac     2760
ctgtggtccg ttcatacggt ggaataccta tgcagctgta aaaatcagtg tggtagatct   2820
ccgtatatga gttgatgtgg aaggttggcc agttcacatg ataaggtgaa tagaataagt   2880
tacagaacag gctgtagagt atgatcttat ttgtagatgt ttaaaactga gtcataagta   2940
tgcttatata cagatcgttt ctggaagtat gtactggaag tctacctctg ggagtgggg   3000
atgggggagt gcactcttct atactgttat atttctttt catgctccta aggtactttt    3060
attggaagat gtaaagcggt tcaatgtaat aggcttaact tctgtcaact aagttggcgt   3120
gggtgcttta agagggtggt agtgatgttg ctggagaaga tatcccacag tcactggtga   3180
cttcagccac gggccatttt ggggcctaat aatcacatat catcatggtt gctagtgtta   3240
atcgaaaacc tactaagtgc caggcttact gtctctgggt cttgcttacg tggatgtcat   3300
ttttccagtt gcaccaaatc gaaagaggtt aattggtttg ttggagttcc tttgtaggtg   3360
aagggcagag ccaggagctt ggctagggac aggggaggtg agtgggggat ggtggataag   3420
tcttggctcc cagtttcctt ctgggcgagac attgccctcg tgccctgagg acctgcttgt   3480
ttgggggaag aggcctttag aggcaccagg gtcatgccag gtgttggaca tggtgaactg   3540
ggaagtgctc ccatctggcc acagcgcaga agtatcaccg tgctgggga tggggaacag    3600
ggctgtgaat gggcctattt gcataagcag catgtgtctg gagagaaaga catcacagag   3660
cagaagagtg cgggtgccca ggagtgcact tgccacccct acttcatccc tgaaagagta   3720
aatggcctgg aaggtgtctc tgagaggtaa tgccgcacac caccctcccct ggggcaggg   3780
tcaggctaca cctgccttag gtcggggggct gcagcagcct gagagctctc agtagggcct   3840
cagtagcctg ggagggagca ggggcagggg gcagggaaaa aggcgtaatg gggctgtcca   3900
gagggggcctg ggaaacctgg tccctgaggc ctgggcacag ctacaatcac ttcaaattgg   3960
ctgtgggggcc agtggactgg gaaggaaaaa agcaataaga gtgaccaagt gcagaaggct   4020
gtcaggtccc aggtcacatg ccttagtgca gtgactcctc atcatttat ggggtgtggg    4080
tgtcgttggt acacccattt tacagatgag gacaccgagg cccagaaaag ttaagttaca   4140
tgtcctaagt cacacagctt gtaagtgcca gaactgagat caaaaccaag tctctttgac   4200
tttaaagtct gtactctgac cccaaagaga tcctgtttgg ccacttatag gaggtcccta   4260
aagctgcaga ctcccttgc cggcacccac atatagagac attaacccctt cctgcagg     4320
gtcacctcaa atagtctttt agctgggcctt ctcctgcaat tccacctaat gccatccct    4380
gggttttgcc caaacctgaa ctgggcagtg gggtgagagg aggggtttac agggttacag   4440
agcctcatac agataggagc ccatggctgc tggtcatctg cattcctgca ggattggctg   4500
ttccttgggg tccttggcag gaaaatgagg attgctccga ggcctgctcc agtacttccc   4560
agaggctggc ctggtgtggg gctctgggaa ggctgaggct ggagaagcgt aagtaggagg   4620
gcagagatgg cactcaggta gcttgaatca ccaggacct tccaagcccc acaggttctg   4680
agggagtact agggccagct ctgggagagg tctcttccta tgctgtgaac cccctgcctt   4740
tcttgcagcc tacaacgaat aaattttctt tgcaaagg                          4778

SEQ ID NO: 35             moltype = RNA   length = 4113
FEATURE                   Location/Qualifiers
source                    1..4113
                          mol_type = other RNA
                          organism = Homo sapiens
SEQUENCE: 35
gattctcaca acttctgcgt gcgagcgccc gccccaccga ccgccccggc ccggcccgca     60
agagccagag gagccgagag gagcccagcg ccggcccagc ggactccagc tcgacggagc    120
```

```
ggccgcgccc cgaccagtta ctcccctgct ggtgcctccc tccttggcgc gcttcccacc    180
tgcgatcggc gccctcttcg cagtcacgaa ctcgccagca gctagcagca ctgactagta    240
ggagggcccg ccggaggaga ggaagcccca gagagattgg tgagggtgat ttcccaggaa    300
gacgcagtgt gctctgactt ctgtgacagt gagcaacggg accagtggat gtccagatgc    360
tggcaatgag acatgctctg gagtcagaag acagcgaaaa gagaagcaga agccccggtg    420
gcaagagtct gaagcaggaa ggatgactgt agcctgtgga ttgtactgca gtaggaaact    480
gtcctagcaa ggctccactt tgccccagct tcaagctgga aaggaggaga acatgaaaca    540
ttgcttgaag acaatggccg agacagcagg tcccaccctg cacagccacc agcatctctc    600
ccctcagccc tgtctcctct tctgcagttg ggatctgcac atttaagcct gaaattgtcc    660
tgtgaagtga agtatgatcg gacagcctct tttcagcttt tatgacaatg gagacagagg    720
aattgtggct cttgccaagg tcacaggatt ggaatacaga gccaagccac cccaggacat    780
gcaagagcct cagaagggaa aaagcccag caggaaggga gaacaagtag cctctgtcct    840
gaagttgtaa cagccagggg ccaggatgga ggaggaggac cccataatct gcccatctgg    900
gacttggcag gggacctggg aaaatgtacc ccaaccatc ccttaagggc ctttgtcttt    960
ggcccattgg cctagcatct acttcttcac cgtgtctgtt cttgtcacac ctagtcaggt   1020
ctgtttgggt ctgaggtgca tggaacattc tgggtaggcc tccagcaaac ggaagctctt   1080
caccgtgttt ccagcctggg accaagggca gcatactggc aaagttgcca aagcaaggga   1140
ctccagcctc ttaggagtta atgactccct ctcccccagct gtcctcccct tggtgctcct   1200
cttcctccct cctcctgctc acagcaggca gggcctagac ccgggagcca tgctgctgtg   1260
ctgttgccag gggagcacgg aggcagatct gagctatgca gggaaaaggc ccagcctgtc   1320
aaagtgtctg agatgaaccg ccgccgtccc tgtgcagctg ggctcagacg tgtctcagct   1380
cttgttctgt gcctgagaat ggcgaaaccc agtgaggttc aagggcaaac tcgctattca   1440
ttagtcaggg gttcttgacg tcccgtctct cccaggatg agttccccc tcctctttct   1500
cccccctccta tgacacattc ctgggtgcct tggtgagga ctgcacaccc tcctcctgcc   1560
tagccccctc tccaaaggcc cctgaataaa ctcccccaa ggagaccagg cagggcagag   1620
acaatggctg caggaaatca ttcaggcggg acatgctgcc ctgccctcca cccagtcccc   1680
ctgtgggccc cactcccttc tgattcaggg cacccttggg ccccagcct atacaggcct   1740
ggacaggaag aaaccactgg gaaccaccct aaggacaaca tgctagtcca gtgccattct   1800
tcgctggctc tgtgggtgcc tttgtggcct gtaccgactg gctggctaat tttgtggttt   1860
ctgtaccatc acatgcctat tttaagacac tctccagcac tgtcggttag gggtgtaaa   1920
ttttgcaata ttttctgaaa tgtggcaata tcaaaatgta aaaggcacac atacttggtc   1980
acaaacaaat ggcactattt actctgtggg catatttgta aaagttgcca agaattata   2040
tacaaggatg ttcatcagag catttctttt gaagagtaaa gaaatggaca tgaacctgtg   2100
gtccgttcat acggtggaat acctatgcag ctgtaaaaat cagtgtggta gatctccgta   2160
tatgagttga tgtggaaggt tggccagttc acatgataag gtgaatagaa taagttacag   2220
aacaggctgt agagtatgat cttatttgta gatgtttaaa actgagtcat aagtatgctt   2280
atatacagat cgtttctgga agtatgtact ggaagtctac ctctggggag tggggatggg   2340
ggagtgcact cttctatact gttatatttt cttttcatgc tcctaaggta ctttttattgg   2400
aagatgtaaa gcggttcaat gtaataggct taacttctgt caactaagtt ggcgtgggtg   2460
ctttaagagg gtggtagtga tgttgctgga gaaagtatcc cacagtcact ggtggcttca   2520
gccacgggcc attttggggc ctaataatca catatcatca tggttgctag tgttaatcga   2580
aaacctacta agtgccaggc ttactgtctc tgggtcttgc ttacgtggat gtcattttc   2640
cagttgccac aaatcgaaag aggttaattg gtttgttgga gttcctttgt aggtgaaggg   2700
cagagccagg agcttggcta gggacagggg aggtgagtgg gggatggtgg ataggtcttg   2760
gctcccagtt tccttctggg cagacattgc ccctctgccc tgaggacctg cttgttgggg   2820
ggaagaggcc tttagaggca ccagggtcat gccaggtgtt ggacatggtg aactgggaag   2880
tgctcccatc tggccacagc gcagaagtat caccgtcgtg gggatgggg aacagggctg   2940
tgaatgggcc tatttgcata agcagcatgt gtctggagag aaagacatca cagagcagaa   3000
gagtgcgggt gcccaggagt gcacttgcca ccccttactttc atccctgaaa gagtaaatgg   3060
cctggaaggt gtctctgaga ggtaatgccg cacaccaccc tccctggggg cagggtcagg   3120
ctacacctgc cttaggtcgg gggctgcagc agcctgcaga ctctcagtag ggcctcagta   3180
gcctggggag gagcagggc aggggcagg gaaagaggcg taatgggct gtccagaggg   3240
gcctgggaaa cctggtccct gaggcctggg cacagctaca atcacttcaa attggctgtg   3300
gggccagtgg actgggaagg aaaaaagcaa taagagtgac caagtgcaga aggctgtcag   3360
gtcccaggtc acatgcctta gtgcagtgac tcctcatcat tttatggggt gtgggtgtcg   3420
ttggtacacc catttacag atgaggacac cgaggcccag aaaagttaag ttacatgtcc   3480
taagtcacac agcttgtaag tgccagaact gagatcaaaa ccaagtctct ttgactttaa   3540
agtctgtact ctgaccccaa agagatcctg tttggccact tataggaggt ccctaaagct   3600
gcagactccc cttgccggca cccacatata gagacattaa ccctccct gcagggtcac   3660
ctcaaatagt cttttagctg ggcttctcct gcaattccac ctaatgccat ccctggtt   3720
ttgcccaaac ctgaactggg cagtggggtg agaggagggg tttacagggt tacagagcct   3780
catacagata ggagcccatg gctgctgtc atctgcattc ctgcaggatt ggctgttcct   3840
tgggtccttt ggcaggaaaa tgaggattgc tccgaggcct gctccagtac ttcccagagg   3900
ctggcctggt gtggggctct gggaaggctg aggctggaga aggtaagta aggtgtaaa   3960
gatggcactc aggtagcttg aatcaccagg acccttccaa gccccacagg ttctgaggga   4020
gtactagggc cagctctggg agaggtctct tcctatgctg tgaacccct gccttttcttg   4080
cagcctacaa cgaataaatt ttctttgcaa agg                                4113

SEQ ID NO: 36        moltype = RNA   length = 3936
FEATURE              Location/Qualifiers
source               1..3936
                     mol_type = other RNA
                     organism = Homo sapiens
SEQUENCE: 36
ggagccgaga ggagcccagc gccggccag cggactccag ctcgacgag cggccgcgc      60
ccgaccagtt actcccctgc tggtgcctcc tccttggcg cgcttcccac ctgcgatcgg    120
cgccctcttc gcagtcacga actcgccagc agctagcagc actgactagt agagggccc    180
gccggaggag aggacatgct ctggagtcag aagacagcga aaagagaagc agaagccccg    240
gtggcaagag tctgaaggaa ggatgactgt agcctgtgga ttgtactgca gtaggaaact    300
```

```
gtcctagcaa ggctccactt tgccccagct tcaagctgga aaggaggaga acatgaaaca   360
ttgcttgaag acaatggccg agacagcagg tcccaccctg cacagccacc agcatctctc   420
ccctcagccc tgtctcctct tctgcagttg ggatctgcac atttaagcct gaaattgtcc   480
tgtgaagtga agtatgatcg gacagcctct tttcagcttt tatgcaatg  gagacagagg   540
aattgtggct cttgccaagg tcacaggatt ggaatacaga gccaagccac cccaggacat   600
gcaagagcct cagaagggaa aaaagcccag caggaaggga gaacaagtag cctctgtcct   660
gaagttgtaa cagccagggg ccaggatgga ggaggaggac cccataatct gcccatctgg   720
gacttggcag gggacctggg aaaatgtacc ccaacccatc ccttaagggc ctttgtcttt   780
ggcccattgg cctagcatct acttcttcac cgtgtctgtt cttgtcacac ctagtcaggt   840
ctgtttgggt ctgaggtgca tggaacattc tgggtagaac tccagcaaac ggaagctctt   900
caccgtgttt ccagcctggg accaagggca gcatactggc aaagttgcca aagcaaggga   960
ctccagcctc ttaggagtta atgactccct ctccccagct gtcctcccct tggtgctcct  1020
cttcctcctc cctcctgctc acagcaggca gggcctagac ccgggagcca tgctgctgtg  1080
tgttgccag  gggagcacgg aggcagatct gagctatgca gggaaaaggc ccagcctgtc  1140
aaagtgtctg agatgaaccg ccgccgtccc tgtgcagctg ggctcagacg tgtctcagct  1200
cttgttctgt gcctgagaat ggcgaaaccc agtgaggttc aagggcaaac tcgctattca  1260
ttagtcaggg gttcttgacg tcccgtctct cccagggatg agttccccc  tcctcttcct  1320
ccccctccta tgacacattc ctgggtgcct ttggtgagga ctgcacaccc tcctcctgcc  1380
tagccccctc tccaaaggcc cctgaataaa ctccccccaa ggagaccagg cagggcagag  1440
acaatggctg caggaaatca ttcaggcggg acatgctggc ctgccctcca cccagtcccc  1500
ctgtgggccc cactcccttc tgattcaggg cacccttggg ccccagcct  ataccaggcct  1560
ggacaggaag aaaccactgg gaaccacct aaggacaaca tgctagtcca gtgccattct  1620
tcgctggctc tgtgggtgcc tttgtggcct gtaccgactg gctggctaat tttgtggttt  1680
ctgtaccatc acatgcctat tttaagacac tctccagcac tgtcgttag  ggagtgtaaa  1740
ttttgcaata ttttctgaaa tgtggcaata tcaaatgta  aaaggcacac atacttggtc  1800
acaaacaaat ggcactattt actctgtggg catatttgta aagaattata               1860
tacaaggatg ttcatcagag catttctttt gaagagtaaa gaaatggaca tgaacctgtg  1920
gtccgttcat acggtggaat acctatgcag ctgtaaaaat cagtgtggta gatctccgta  1980
tatgagttga tgtggaaggt tggccagttc acatgataag gtgaatagaa taagttacag  2040
aacaggctgt agagtatgat cttatttgta gatgtttaaa actgagtcat aagtatgctt  2100
atatacagat cgtttctgga agtatgtact ggaagtctac ctctggggag tggggatggg  2160
ggagtgcact cttctatact gttatatttt cttttcatgc tcctaaggta cttttattgg  2220
aagatgtaaa gcggttcaat gtaataggct taacttctgt caactaagtt ggcgtgggtg  2280
ctttaagagg gtggtagtga tgttgctgga gaaagtatcc acagtcact  ggtggcttca  2340
gccacgggcc attttggggc ctaataatca catatcatca tggttgctag tgttaatcga  2400
aaacctacta agtgccaggc ttactgtctc tgggtcttgc ttacgtggat gtcattttc   2460
cagttgcacc aaatcgaaag aggttaattg gtttgttgga gttcctttgt aggtgaaggg  2520
cagagccagg agcttggcta gggacagggg aggtgagtgg gggatggtgg ataggtcttg  2580
gctcccagtt tccttctggg cagacattgc ccctctgccc taggacctg cttgtttggg   2640
ggaagaggcc tttagaggca ccagggtcat gccaggtgtt ggacatggtg aactgggaag  2700
tgctcccatc tggccacagc gcagaagtat caccgtgctg ggggatgggg aacagggctg  2760
tgaatgggcc tatttgcata agcagcatgt gtctggagag aaagacatca cagagcagaa  2820
gagtgcgggt gcccaggagt gcacttgcca ccctacttc  atccctgaaa gagtaaatgg  2880
cctggaaggt gtctctgaga ggtaatgccg cacaccaccc tccctggggg cagggtcagg  2940
ctacacctgc cttaggtcgg gggctgcagc agcctgagag ctctcagtag ggcctcagta  3000
gcctgggagg gagcaggggc aggggcagg  gaaagaggcg taatgggct gtccagaggg   3060
gcctgggaaa cctggtccct gaggcctggg cacagctaca atcacttcaa attggctgtg  3120
gggccagtgg actgggaagg aaaaaagcaa taagagtgac caagtgcaga aggctgtcag  3180
gtcccaggtc acatgcctta gtgcagtgac tcctcatcat tttatggggt gtgggtgtcg  3240
ttggtacacc cattttacag atgaggacac cgaggcccag aaaagttaag ttacatgtcc  3300
taagtcacac agcttgtaag tgccagaact gagatccaag tctctt tgacttta        3360
agtctgtact ctgaccccaa agagatcctg tttggccact tataggaggt ccctaaagct  3420
gcagactccc cttgccggca cccacatata gagacattaa cccttcccct gcagggtcac  3480
ctcaaatagt cttttagctg ggcttctcct gcaattccac ctaatgccat cccctgggtt  3540
ttgcccaaac ctgaactggg cagtggggtg agaggagggg tttacagggt tacagagcct  3600
catacagata ggagcccatg gctgctggtc atctgcattc ctgcaggatt ggctgttcct  3660
tggggtcctt ggcaggaaaa tgaggattgc tccgaggcct gctccagtac ttcccagagg  3720
ctggcctggt gtggggctct gggaaggctg aggctggaga agcgtaagta ggagggcaga  3780
gatggcactc aggtagcttg aatcaccagg acccttccaa gccccacagg ttctgaggga  3840
gtactagggc cagctctggg agaggtctct tcctatgctg tgaacccct  gcctttcttg   3900
cagcctacaa cgaataaatt ttctttgcaa aggctc                             3936

SEQ ID NO: 37           moltype = RNA  length = 4026
FEATURE                 Location/Qualifiers
source                  1..4026
                        mol_type = other RNA
                        organism = Homo sapiens
SEQUENCE: 37
gggggtcccg gccccacaca gtgctagggt ccctctcgag tttctcatct gccttcaggt    60
cactttccac cctgatgcct tggcttgtcc tgaagctcag ggcccctgta gcttgggaaa   120
cctcccaagc tccccagcga gtggctgtag accaaggaag ggaccctgcc cggcttcagg   180
gaagaaagga agaaagttac tcccctgctg gtgcctccct ccttggcgcg cttcccacct   240
gcgatcggcg ccctcttcgc agtcacgaac tcgccagcag ctagcagcac tgactagtag   300
gagggcgggc cggaggagag gacatgctct ggagtcagaa gacagcgaaa agagaagcag   360
aagcccgggt ggcaagagtc tgaaggaagg atgactgtag cctgtggatt gtactgcagt   420
aggaaactgt cctagcaagg ctccactttg ccccagcttc aagctggaaa ggaggagaac   480
atgaaacatt gcttgaagac aatggccgag acagcaggtc ccaccctgca cagccaccag   540
catctctccc ctcagcccctg tctcctcttc tgcagttggg atctgcacat ttaagcctga   600
aattgtcctg tgaagtgaag tatgatcgga cagcctcttt tcagctttta tgacaatgga   660
```

-continued

```
gacagaggaa ttgtggctct tgccaaggtc acaggattgg aatacagagc caagccaccc    720
caggacatgc aagagcctca gaagggaaaa aagcccagca ggaagggaga acaagtagcc    780
tctgtcctga agttgtaaca gccaggggcc aggatggagg aggaggaccc cataatctgc    840
ccatctggga cttggcaggg gacctgggaa aatgtacccc aacccatccc ttaagggcct    900
ttgtctttgg cccattggcc tagcatctac ttcttcacag tgtctgttct tgtcacacct    960
agtcaggtct gtttgggtct gaggtgcatg gaacattctg ggtaggcctc cagcaaacgg   1020
aagctcttca ccgtgtttcc agcctgggac caagggcagc atactggcaa agttgccaaa   1080
gcaagggact ccagcctctt aggagttaat gactccctct ccccagctgt cctcccctttg  1140
gtgctcctct tcctccctcc tcctgctcac agcaggcagg gcctagaccc gggagccagg   1200
ctgctgtgct gttgccaggg gagcacggag gcagatctga gctatgcagg gaaaaggccc   1260
agcctgtcaa agtgtctgag atgaaccgcc gccgtccctg tgcagctggg ctcagacgtg   1320
tctcagctct tgttctgtgc ctgagaatgg cgaaacccag tgaggttcaa gggcaaactc   1380
gctattcatt agtcaggggt tcttgacgtc ccgtctctcc cagggatgag ttcccccctc   1440
ctctttctcc ccctcctatg acacattcct gggtgcctt ggtgaggact gcacaccctc    1500
ctcctgccta gccccctctc caaaggcccc tgaataaact ccccccaagg agaccaggca   1560
gggcagagac aatggctgca ggaaatcatt caggcgggac atgctggcct gccctccacc   1620
cagtccccct gtgggcccca ctcccttctg attcagggca cccttgggcc cccagcctat   1680
acaggcctgg acaggaagaa accactggga accaccctaa ggacaacatg ctagtccagt   1740
gccattcttc gctggctctg tgggtgcctt tgtggcctgt accgactggc tggctaattt   1800
tgtggtttct gtaccatcac atgcctattt taagacactc tccagcactg tcggttaggg   1860
agtgtaaatt ttgcaatatt ttctgaaatg tggcaatatc aaaatgtaaa aggcacacat   1920
acttggtcac aaacaaatgg cactatttac tctgtgggca tatttgtaaa agttgccaaa   1980
gaattatata caaggatgtt catcagagca tttctttttga agagtaaaga aatggacatg  2040
aacctgtggt ccgttcatac ggtggaatac ctatgcagct gtaaaaatca gtgtggtaga   2100
tctccgtata tgagttgatg tggaaggttg gccagttcac atgataaggt gaatagaata   2160
agttacagaa caggctgtag agtatgatct tatttgtaga tgtttaaaac tgagtcataa   2220
gtatgcttat atacagatcg tttctgaagg tatgtactga aagtctacct ctggggagtg   2280
gggatggggg agtgcactct tctatactgt tatattttct tttcatgctc ctaaggtact   2340
tttattggaa gatgtaaagc ggttcaatgt aataggctta acttctgtca actaagttgg   2400
cgtgggtgct ttaagagggt ggtagtgatg ttgctggaga aagtatccca cagtcactgg   2460
tggcttcagc cacgggccat tttgggcct aataatcaca tatcatcatg gttgctagtg     2520
ttaatcgaaa acctactaag tgccaggctt actgtctctg ggtcttgctt acgtggatgt   2580
catttttcca gttgcaccaa atcgaaagag gttaattggt ttgttggagt tcctttgtag   2640
gtgaagggca gagccaggag cttggctagg gacaggggag gtgagtgggg gatggtggat   2700
aggtcttggc tcccagtttc cttctgggca gacattgccc ctctgccctg aggacctgct   2760
tgtttggggg aagaggcctt tagaggcacc agggtcatgc caggtgttgg acatggtgaa   2820
ctgggaagtg ctcccatctg gccacagcgc agaagtatca ccgtgctggg ggatggggaa   2880
cagggctgtg aatgggccta tttgcataag cagcatgtgt ctggagagaa agacatcaca   2940
gagcagaaga gtgcgggtgc ccaggagtgc acttgccacc cctacttcat ccctgaaaga   3000
gtaaatggcc tggaaggtgt ctctgagagg taatgccgca caccaccctc cctgggggca   3060
gggtcaggct acacctgcct taggtcgggg gctgcagcag cctgagagct ctcagtaggg   3120
cctcagtagc ctgggaggga gcaggggcag ggggcaggga aagaggcgta atggggctgt   3180
ccagagggca ctgggaaacc tggtccctga ggcctggcca cagctacaat cacttcaaat   3240
tggctgtggg gccagtggac tgggaaggaa aaaagcaata agagtgacca agtgcagaag   3300
gctgtcaggt cccaggtcac atgccttagt gcagtgactc ctcatcattt tatggggtgt   3360
gggtgtcgtt ggtacaccca ttttacagat gaggacaccg aggcccagaa aagttaagtt   3420
acatgtccta agtcacacag cttgtaagtg ccagaactga gatcaaaacc aagtctcttt   3480
gactttaaag tctgtactct gaccccaaag agatcctgtt tggccactta taggaggtcc   3540
ctaaagctgc agactcccct tgccggcacc cacatataga gacattaacc cttcccctgc   3600
agggtcacct caaatagtct tttagctggg cttctcctgc aattccacct aatgccatcc   3660
cctgggtttt gcccaaacct gaactgggca gtggggtgga aggagggtt tacaggtta   3720
cagagcctca tacagatagg agccatggc tgctggtcat ctgcattcct gcaggattgg    3780
ctgttccttg gggtccttgg caggaaaatg aggattgctc cgaggcctgc tccagtactt   3840
cccagaggct ggcctggtgt ggggctctgg gaaggctgag gctggagaag cgtaagtagg   3900
agggcagaga tggcactcag gtagcttgaa tcaccaggac ccttccaagc cccacaggtt   3960
ctgagggagt actagggcca gctctgggag aggtctcttc ctatgctgtg aaccccctgc   4020
ctttct                                                              4026
SEQ ID NO: 38        moltype = RNA  length = 4334
FEATURE              Location/Qualifiers
source               1..4334
                     mol_type = other RNA
                     organism = Homo sapiens
SEQUENCE: 38
tgaggcgcca ccggtgccca gcaacctccc caggctgtgg ttgtgacctg aggacgcgtg     60
tgtccccgcc ctcaggccac cgctacgcga ccctgagtgc accttcaaga aggccgggca   120
cgtttctggg cgggcgtggg gggtgcctga tatctccgct ctatttttaca gttactcccc  180
tgctggtgcc tccctccttg gcgcgcttcc cacctgcgat cggcgccctc ttcgcagtca   240
cgaactcgcc agcagctagc agcactgact agtaggaggg cccgccggag gagaggaagc   300
cccagagaga ttggtgaggg tgatttccca ggaagacgca gtgtgctctg acttctgtga   360
cagtgagcaa cgggaccagt ggatgtccag atgctgcaa tgagtaggcc ttccctacgc    420
tgggtggcgt ccacccctc cggcttccat tgcctgggtc tcctggaggt ggtttgctgg    480
atgaataccg catgcacaga ggctggcctt gggtttgaat atggcagcca gtggacagca    540
tgtgcttcag ttatgagact gcccaggaga tgcttcttcc aaggcagagc acgtgcagag    600
tccagtgctg gagaggccgg gtgcgcagtt gacccatttc cagttctgtt ttccctctca   660
tgttcctctg tccccatcta ggacatgctc tggagtcaga agacagcgaa aagagaagca   720
gaagcccgtg tggcaagagt ctgaagctgg aaaggaggag aacatgaaac attgcttgaa   780
gacaatggcc gagacagcag gtcccaccct gcacagccac cagcatctct cccctcagcc   840
ctgtctcctc ttctgcagtt gggatctgca catttaagcc tgaaattgtc ctgtgaagtg   900
```

```
aagtatgatc ggacagcctc tttttcagctt ttatgacaat ggagacagag gaattgtggc   960
tcttgccaag gtcacaggat tggaatacag agccaagcca ccccaggaca tgcaagagcc  1020
tcagaaggga aaaaagccca gcaggaaggg agaacaagta gcctctgtcc tgaagttgta  1080
acagccaggg gccaggatgg aggaggagga ccccataatc tgcccatctg ggacttgca   1140
ggggacctgg gaaaatgtac cccaacccat cccttaaggg cctttgtctt tggcccattg  1200
gcctagcatc tacttcttca ccgtgtctgt tcttgtcaca cctagtcagg tctgtttggg  1260
tctgaggtgc atggaacatt ctgggtaggc ctccagcaaa cggaagctct tcaccgtgtt  1320
tccagcctgg gaccaagggc agcatactgg caaagttgcc aaagcaaggg actccagcct  1380
cttaggagtt aatgactccc tctccccagc tgtcctcccc ttggtgctcc tcttcctcgc  1440
tcctcctgct cacagcaggc agggcctaga cccgggagcc atgctgctgt gctgttgcca  1500
ggggagcacg gaggcagatc tgagctatgc agggaaaagg cccagcctgt caaagtgtct  1560
gagatgaacc gccgccgtcc ctgtgcagct gggctcagac gtgtctcagc tcttgttctg  1620
tgcctgagaa tggcgaaacc cagtgaggtt caagggcaaa ctcgctattc attagtcagg  1680
ggttcttgac gtcccgtctc tcccaggat gagttcccc ctcctctttc tcccctcc      1740
atgacacatt cctgggtgcc tttggtgagg actgcacacc ctcctcctgc ctagccccct  1800
ctccaaaggc ccctgaataa actccccca aggagaccag gcagggcaga gacaatggct   1860
gcaggaaatc attcaggcgg gacatgctgg cctgccctcc acccagtccc cctgtgggcc  1920
ccactccctt ctgattcagg gcaccctggg gcccccagcc tatacaggcc tggacaggaa  1980
gaaaccactg ggaaccaccc taaggacaac atgctagtcc agtgccattc ttcgctggct  2040
ctgtgggtgc ctttgtggcc tgtaccgact ggctggctaa ttttgtggtt tctgtaccat  2100
cacatgccta ttttaagaca ctctccagca ctgtcggtta gggagtgtaa attttgcaat  2160
attttctgaa atgtggcaat atcaaaatgt aaaaggcaca catacttggt cacaaacaaa  2220
tggcactatt tactctgtgg gcatatttgt aaaagttgcc aaagaattat atacaaggat  2280
gttcatcaga gcatttcttt tgaagagtaa agaaatggac atgaacctgt ggtccgttca  2340
tacggtggaa tacctatgca gctgtaaaaa tcagtgtggt agatcccgt atatgagttg    2400
atgtggaagg ttggccagtt cacatgataa ggtgaataga ataagttaca gaacaggctg  2460
tagagtatga tcttatttgt agatgtttaa aactgagtca taagtatgct tatatacaga  2520
tcgtttctgg aagtatgtac tggaagtcta cctctgggga gtggggatgg gggagtgcac  2580
tcttctatac tgttatattt tcttttcatg ctcctaaggt acttttattg gaagatgtaa  2640
agcggttcaa tgtaataggc ttaacttctg tcaactaagt tggcgttggt gctttaagag  2700
ggtggtagtg atgttgctgg agaaagtatc ccacagtcac tggtggcttc agccacgggc  2760
catttttgggg cctaataatc acatatcatc atggttgcta gtgttaatcg aaaacctact  2820
aagtgccagg cttactgtct ctgggtcttg cttacgtgga tgtcatttt ccagttgcac   2880
caaatcgaaa gaggttaatt ggtttgttgg agttcctttg taggtgaagg gcagagccag  2940
gagcttggct agggacaggg gaggtgagtg gggatggtg gataggtctt ggctcccagt   3000
ttccttctgg gcagacattg cccctctgcc ctgaggacct gcttgttggg gggaagaggc  3060
cttttagaggc accagggtca tgccaggtgt tggacatggt gaactgggaa gtgctcccat  3120
ctggccacag cgcagaagta tcaccgtgct gggggatggg aacagggct gtgaatgggc    3180
ctatttgcat aagcagcatg tgtctggaga gaaagacatc acagagcaga agagtgcggg  3240
tgcccaggag tgcacttgcc accctactt catccctgaa agagtaaatg gcctggaagg   3300
tgtctctgag aggtaatgcc gcacaccacc ctcctggg gcagggtcag gctacacctg    3360
ccttaggtcg ggggctgcag cagcctgaga gctctcagta gggcctcagt agcctgggag  3420
ggagcagggg caggggcag ggaaagaggc gtaatgggc tgtccagagg ggcctgggaa    3480
acctggtccc tgaggcctgg gcacagctac aatcacttca aattggctgt gggggccagtg  3540
gactgggaag gaaaaaagca ataagagtga ccaagtgcaa aaggctgtca ggtcccaggt  3600
cacatgcctt agtgcagtga ctcctcatca ttttatgggg tgtgggtgtc gttggtacac  3660
ccattttaca gatgaggaca ccgaggccca gaaaagttaa gttacatgtc ctaagtcaca  3720
cagcttgtaa gtgccagaac tgagatcaaa accaagtctc tttgacttta aagtctgtac  3780
tctgacccca aagagatcct gttttggccac ttataggagg tccctaaagc tgcagactcc  3840
ccttgccggc acccacatat agagacatta accccttcccc tgcagggtca cctcaaatag  3900
tcttttagct gggcttctcc tgcaattcca cctaatgcca tccccctggg ttttgcccaaa  3960
cctgaactgg gcagtggggt gagaggaggg gttttacaggg ttacagagcc tcatacagat  4020
aggagcccat ggctgctggt catctgcatt cctgcaggat tggctgttcc ttggggtcct  4080
tggcaggaaa atgaggattg ctccgaggcc tgctccagta cttcccagag gctggcctgg  4140
tgtggggctc tgggaaggct gaggctggag aagcgtaagt aggagggcag agatggcact  4200
caggtagctt gaatcaccag gacccttcca agccccacag gttctgaggg agtactaggg  4260
ccagctctgg gagaggtctc ttcctatgct gtgaacccc tgcctttctt gcagcctaca   4320
acgaataaat tttc                                                    4334
```

SEQ ID NO: 39        moltype = RNA  length = 3868
FEATURE              Location/Qualifiers
source               1..3868
                     mol_type = other RNA
                     organism = Homo sapiens
SEQUENCE: 39

```
ttactcccct gctggtgcct ccctccttgg cgcgcttccc acctgcgatc ggcgccctct    60
tcgcagtcac gaactcgcca gcagctagca gcactgacta gtaggagggc ccgccggagg   120
agaggacatg ctctggagtc agaagacagc gaaaagagaa gcagaagccc cggtggcaag   180
agtctgaagc aggaaggatg actgtagcct gtggattgta ctgcagtgag aaactgtcct   240
agcaaggctc cactttgccc cagcttcaag ctggaaagga ggagaacatg aaacattgct   300
tgaagacaat ggccgagaca gcaggtccca ccctgcacag ccaccagcat ctctcccctc   360
agccctgtct cctcttctgc agttgggatc tgcacattta agcctgaaat tgtcctgtga   420
agtgaagtat gatcggacag cctcttttca gcttttatga caatggagac agaggaattg   480
tggctcttgc caaggtcaca ggattggaat acagagccaa gccaccccca gacatgcaag   540
agcctcagaa gggaaaaaag cccagcagga agggagaaca agtagcctct gtcctgaagt   600
tgtaacagcc aggggccagg atggaggagg agaccccat aatctgccca tctgggactt    660
ggcagggac ctgggaaaat gtaccccaac ccatccctta agggcctttg tctttggccc    720
attggcctag catctacttc ttcaccgtgt ctgttcttgt cacacctagt caggtctgtt   780
tgggtctgag gtgcatggaa cattctgggt aggcctccag caaacggaag ctcttcaccg   840
```

-continued

```
tgtttccagc ctgggaccaa gggcagcata ctggcaaagt tgccaaagca agggactcca    900
gcctcttagg agttaatgac tccctctccc cagctgtcct cccccttggtg ctcctcttcc    960
tccctcctcc tgctcacagc aggcagggcc tagacccggg agccatgctg ctgtgctgtt   1020
gccaggggag cacggaggca gatctgagct atgcagggaa aaggcccagc ctgtcaaagt   1080
gtctgagatg aaccgccgcc gtccctgtgc agctgggctc aacgtgtct cagctcttgt    1140
tctgtgcctg agaatggcga aacccagtga ggttcaaggg caaactcgct attcattagt   1200
caggggttct tgacgtcccg tctctcccag ggatgagttc ccccctcctc tttctccccc   1260
tcctatgaca cattcctggg tgcctttggt gaggactgca caccctcctc ctgcctagcc   1320
ccctctccaa aggccctga ataaactccc cccaaggaga ccaggcaggg cagagacaat   1380
ggctgcagga aatcattcag gcgggacatg ctggcctgcc ctccacccag tcccctgtg   1440
ggccccactc ccttctgatt cagggcaccc ttgggccccc agcctataca ggcctggaca   1500
ggaagaaacc actgggaacc accctaagga caacatgcta gtccagtgcc attcttcgct   1560
ggctctgtgg gtgcctttgt ggcctgtacc gactggctgg ctaattttgt ggtttctgta   1620
ccatcacatg cctattttaa gacactctcc agcactgtcg gttagggagt gtaaattttg   1680
caatattttc tgaaatgtgg caatatcaaa atgtaaaagg cacacatact tggtcacaaa   1740
caaatggcac tatttactct gtgggcatat ttgtaaaagt tgccaaagaa ttatatacaa   1800
ggatgttcat cagagcattt cttttgaaga gtaaagaaat ggacatgaac ctgtggtccg   1860
ttcatacggt ggaataccta tgcagctgta aaaatcagtg tggtagatct ccgtatatga   1920
gttgatgtgg aaggttggcc agttcacatg ataaggtgaa tagaataagt tacagaacag   1980
gctgtagagt atgatcttat ttgtagatgt ttaaaactga gtcataagta tgcttatata   2040
cagatcgttt ctggaagtat gtactggaag tctacctctg gggagtgggg atgggggagt   2100
gcactcttct atactgttat attttctttt catgctccata aggtacttt attggaagat   2160
gtaaagcggt tcaatgtaat aggcttaact tctgtcaact aagttggcgt gggtgcttta   2220
agagggtggt agtgatgttg ctggagaaag tatcccacag tcactggtgg cttcagccac   2280
gggccatttt ggggcctaat aatcacatat catcatggtt gctagtgtta atcgaaaacc   2340
tactaagtgc caggcttact gtctctgggt cttgcttaag tggatgtcat ttttccagtt   2400
gcaccaaatc gaaagaggtt aattggtttg ttggagttcc tttgtaggtg aagggcagag   2460
ccaggagctt ggctagggac aggggaggtg agtgggggat ggtggatagg tcttggctcc   2520
cagtttcctt ctgggcagac attgcccctc tgccctgagg acctgcttgt ttgggggaag   2580
aggcctttag aggcaccagg gtcatgccag gtgttgaaca tggtgaactg ggaagtgctc   2640
ccatctggcc acagcgcaga agtatcaccg tgctggggga tggggaacag ggctgtgaat   2700
gggcctattt gcataagcag catgtgtctg gagagaaaga catcacagag cagaagagtg   2760
cgggtgccca ggagtgcact tgccaccct acttcatccc tgaaagagta aatgcctgg    2820
aaggtgtctc tgagaggtaa tgccgcacac cacctccct gggggcaggg tcaggctaca   2880
cctgccttag gtcgggggct gcagcagcct gagagctctc agtagggcct cagtagcctg   2940
ggagggagca ggggcagggg gcagggaaag aggcgtaatg gggctgtcca gaggggcctg   3000
ggaaacctgg tccctgaggc ctgggcacag ctacaatcac ttcaaattgg ctgtggggcc   3060
agtggactgg gaaggaaaaa agcaataaga gtgaccaagt gcagaaggct gtcaggtccc   3120
aggtcacatg ccttagtgca gtgactcctc atcattttat gggtgtggg tgtcgttgtgg   3180
acacccattt tacagatgag gacaccgagg cccagaaaag ttaagttaca tgtcctaagt   3240
cacacagctt gtaagtgcca gaactgagat caaaaccaag tctctttgac tttaaagtct   3300
gtactctgac cccaaagaga tcctgttggg ccacttatag gaggtcccta aagctgcaga   3360
ctcccctgc cggcacccac atatagagac attaacctt cccctgcagg ctcacctcaa   3420
atagtctttt agctgggctt ctcctgcaat tccacctaat gccatcccct gggttttgcc   3480
caaacctgaa ctgggcagtg gggtgagagg aggggtttac agggttacag agcctcatac   3540
agataggagc ccatggctgc tggtcatctg cattcctgca ggattggctg ttccttgggg   3600
tccttggcag gaaaatgagg attgctccga ggcctgctcc agtacttccc agaggctggc   3660
ctggtgtggg gctctgggaa ggctgaggct ggagaagcgt aagtaggagg gcagagatgg   3720
cactcaggta gcttgaatca ccaggaccct tccaagcccc acaggttctg agggagtact   3780
agggccagct ctgggagagg tctcttccta tgctgtgaac cccctgcctt tcttgcagcc   3840
tacaacgaat aaatttctt tgcaaagg                                      3868
```

| SEQ ID NO: 40 | moltype = RNA length = 3978 |
|---|---|
| FEATURE | Location/Qualifiers |
| source | 1..3978 |
| | mol_type = other RNA |
| | organism = Homo sapiens |

SEQUENCE: 40
```
ggtcgccgcg ccaagggccc gctgagcccc tcctcccatt cgtccagccg cgcggcccac     60
agaagcggaa cgcgcgtcga gagcgccctg tccgctcgcc ccagacagat gcccggttat    120
tcattaccgc gaggcctaga ggaaagagtg gctgccgtct tcctgcccac agcccgccgg    180
accctccgtc gcggctgccc ggtccccgga gccgcagccg ccgagcccgg ctgtgcgtgt    240
cgtggctgct ggggagaaag aggcttccgg acatgctctg gagtcagaag acagcgaaaa    300
gagaagcaga agccccggtg gcaagagtct gaagcaggaa gggatgactgt agcctgtgga    360
ttgtactgca gtaggaaact gtcctagcaa ggctccactt tgccccagct tcaagctgga    420
aaggaggaga acatgaaaca ttgcttgaag acaatggccg agacagcagg tcccacccctg    480
cacagccacc agcatctctc ccctcagccc tgtctcctct tctgcagttg ggatctgcac    540
atttaagcct gaaattgtcc tgtgaagtga agtatgatcg gacagcctcc tttcagcttt    600
tatgacaatg gagacagaga aattgtggct cttgccaagt tcacaggatt ggaatacaga    660
gccaagccac cccaggacat gcaagagcct cagaagggaa aaaagccag caggaaggaa    720
gaacaagtag cctctgtcct gaagttgtaa cagccagggg ccaggatgga ggaggaggac    780
cccataatct gcccatctgg gacttggcag gggacctggg aaaatgtacc caacccatc    840
ccttaagggc ctttgtcttt ggcccattgg cctagcatct acttcttcac cgtgtctgtt    900
cttgtcacac ctagtcaggt ctgttttggg tctgaggtgca tggaacattc tgggtaggcc    960
tccagcaaac ggaagctctt caccgtgttt ccagcctggg accaagggca gcatactggc   1020
aaagttgcca agcaagggga ctccagcctc ttaggagtta atgactccct ctccccagct   1080
gtcctcccct tggtgctcct cttcctcctt cctcctgctc acagcaggca gggcctagac   1140
ccgggagcca tgctgctgtg ctgttgccag gggagcacgg aggcagatct gagctatgca   1200
gggaaaaggc ccagcctgtc aaagtgtctg agatgaaccg ccgccgtccc tgtgcagctg   1260
```

```
ggctcagacg tgtctcagct cttgttctgt gcctgagaat ggcgaaaccc agtgaggttc   1320
aagggcaaac tcgctattca ttagtcaggg gttcttgacg tcccgtctct cccaggdatg   1380
agttcccccc tcctctttct cccctccta tgacacattc ctgggtgcct ttggtgagga   1440
ctgcacaccc tcctcctgcc tagcccctc tccaaaggcc cctgaataaa ctcccccca   1500
ggagaccagg cagggcagag acaatggctg caggaaatca ttcaggcagg acatgctggc   1560
ctgccctcca cccagtcccc ctgtgggccc cactccttc tgattcaggg caccttggg   1620
cccccagcct atacaggcct ggacaggaag aaaccactgg gaaccaccct aaggacaaca   1680
tgctagtcca gtgccattct tcgctggctc tgtgggtgcc tttgtggcct gtaccgactg   1740
gctggctaat tttgtggttt ctgtaccatc acatgctat tttaagacac tctccagcac   1800
tgtcggttag ggagtgtaaa ttttgcaata ttttctgaaa tgtggcaata tcaaaatgta   1860
aaggcacac atacttggtc acaaacaaat ggcactattt actctgtggg catatttgta   1920
aaagttgcca aagaattata tacaaggatg ttcatcagag catttctttt gaagagtaaa   1980
gaaatggaca tgaacctgtg gtccgttcat acggtgaat acctatgcag ctgtaaaaat   2040
cagtgtggta gatctccgta tatgagttga tgtggaaggt tggccagttc acatgataag   2100
gtgaatagaa taagttacag aacaggctgt agagtatgat cttatttgta gatgtttaaa   2160
actgagtcat aagtatgctt atatacagat cgtttctgga agtatgtact ggaagtctac   2220
ctctggggag tggggatggg ggagtgcact cttctatact gttatatttt cttttcatgc   2280
tcctaaggta cttttattgg aagatgtaaa gcggttcaat gtaataggct taacttctgt   2340
caactaagtt ggcgtgggtg ctttaagagg gtgagtagtga tgttgctgga gaaagtatcc   2400
cacagtcact ggtggcttca gccacgggcc attttggggc ctaataatca catatcatca   2460
tggttgctag tgttaatcga aaacctacta agtgccaggc ttactgtctc tgggtcttgc   2520
ttacgttggat gtcattttc cagttgcacc aaatcgaaag aggttaattg gtttgttgga   2580
gttcctttgt aggtgaaggg cagagccagg agcttggcta gggacagggg aggtgagtga   2640
gggatggtgg ataggtcttg gctcccagtt tccttctggg cagacattgc ccctctgccc   2700
tgaggacctg cttgtttggg ggaagaggcc tttagaggca ccagggtcat gccaggtgtt   2760
ggacatggtg aactgggaag tgctcccatc tggccacagc gcagaagtat caccgtgctg   2820
ggggatgggg aacagggctg tgaatgggcc tatttgcata agcagcatgt gtctggagag   2880
aaaagacatca cagagcagaa gagtgcgggg gcccaggagt gcacttgcca cccctacttc   2940
atccctgaaa gagtaaatgg cctggaaggt gtctctgaga ggtaatgccg cacaccaccc   3000
tccctggggg cagggtcagg ctacacctgc cttaggtcgg gggctgcagc agcctgagag   3060
ctctcagtag ggcctcagta gcctgggagg gagcagggga aggggcagg gaaagaggcg   3120
taatggggct gtcagagggg gcctgggaaa cctggtccct gaggcctggg cacagctaca   3180
atcacttcaa attggctgtg gggccagtgg actgggaagg aaaaaagcaa taagagtgac   3240
caagtgcaga aggctgcag gtcccaggtc acatgcctta gtgcagtgac tcctcatcat   3300
tttatggggt gtgggtgtcg ttggtacacc cattttacag atgaggacac cgaggcccaa   3360
aaaagttaag ttcatgtcc taagtcacac agcttgtaag tgccagaact gagatcaaaa   3420
ccaagtctct ttgactttaa agtctgtact ctgaccccaa agagatcctg tttggccact   3480
tataggaggt ccctaaagct gcagactccc cttgccggca cccacatata gagacattaa   3540
cccttcccct gcagggtcac ctcaaatagt cttttagctg ggcttctcct gcaattccac   3600
ctaatgccat cccctgggtt ttgcccaaac ctgaactggg cagtggggtg agaggagggg   3660
tttacangg tacagagcct catacagata ggagcccatg gctgctggtc atctgcattc   3720
ctgcaggatt ggctgttcct tggggtcctt ggcaggaaaa tgaggattgc tccgaggcct   3780
gctccagtac ttcccagagg ctggcctggt gtggggctct gtgaaggctg aggctgagga   3840
agcgtaagta ggagggcaga gatggcactc aggtagcttg aatcaccagg acccttccaa   3900
gccccacagg ttctgaggga gtactagggc cagctctggg agaggtctct tcctatgctg   3960
tgaaccccct gcctttct                                                 3978

SEQ ID NO: 41          moltype = RNA   length = 3837
FEATURE                Location/Qualifiers
source                 1..3837
                       mol_type = other RNA
                       organism = Homo sapiens
SEQUENCE: 41
ccaggcgtgt gcatttatat gcagagtgac caagaaactt cagtaatact agtttgtgtc   60
tttggagtcc cactttttgc cagggctagt gctaacagct tcaggagaat tcagcctcac   120
cttgacagga catgctctgg agtcagaaga cagcgaaaag agaagcagaa gcccggtgtg   180
caagagtctg aagcaggaag gatgactgta gcctgtggat tgtactgcag taggaaactg   240
tcctagcaag gctccacttt gccccagctt caagctggaa aggaggagaa catgaaacat   300
tgcttgaaga caatggccga gacagcaggt cccaccctgc acagccacca gcatctctcc   360
cctcagccct gtcctcctct ctgcagtttgg gatctgcaca tttaagcctg aaattgtcct   420
gtgaagtgaa gtatgatcgg acagcctctt ttcagctttt atgacaatgg agacagagga   480
attgtggctc ttgccaaggt cacaggattg aatacagag ccaagccacc ccaggacatg   540
caagagcctc agaagggaaa aaagcccagc aggaaggag aacaagtagc ctctgtcctg   600
aagttgtaac agccagggc caggatggag gaggaggacc ccataatctg cccatctgga   660
acttggcagg gacctggga aaatgtaccc caacccatcc cttaagggcc tttgtctttg   720
gcccattggc ctagcatcta cttcttcacc gtgtctgttc ttgtcacacc tagtcaggtc   780
tgtttgggtc tgaggtgcat ggaacattct gggtaggcct ccagcaaacg gaagctcttc   840
accgtgtttc cagcctggga ccaagggcag catactggca aagttgccaa agcaagggac   900
tccagcctct taggagttaa tgactccctc tccccagctg tcctccccct ggtgctcctc   960
ttcctccctc ctcctgctca cagcaggcag ggcctagacc cgggagccat gctgctgtgc  1020
tgttgccagg ggagcacgga ggcagatctg agctatgcag ggaaaaggcc cagcctgtca  1080
aagtgtctga gatgaaccgc cgccgtccct gtgcagctgg ggctcagacg tgtctcagct  1140
ttgttctgtg cctgagaatg gcgaaaccca gtgaggttca agggcaaact cgctattcat  1200
tagtcaggg gttcttgacg tccgtctctc cagggatga gttcccccc tcctctttctc  1260
ccccctccta tgacacattcc tgggtgcctt tggtgaggaa tgcacaccct cctcctgcct  1320
agcccctct ccaaaggccc ctgaataaac tccccccaag gagaccaggc agggcagaga  1380
caatggctgc aggaaatcat tcaggcggga catgctggcc tgccctccac ccagtcccc  1440
tgtgggcccc actcccttct gattcagggc accttgggc cccagccta tacaggcctg  1500
gacaggaaga aaccactggg aaccacccta aggacaacat gctagtccag tgccattctt  1560
```

```
cgctggctct gtgggtgcct ttgtggcctg taccgactgg ctggctaatt ttgtggtttc  1620
tgtaccatca catgcctatt ttaagacact ctccagcact gtcggttagg gagtgtaaat  1680
tttgcaatat tttctgaaat gtggcaatat caaaatgtaa aaggcacaca tacttggtca  1740
caaacaaatg gcactattta ctctgtgggc atatttgtaa aagttgccaa agaattatat  1800
acaaggatgt tcatcagagc atttcttttg aagagtaaag aaatggacat gaacctgtgg  1860
tccgttcata cggtggaata cctatgcagc tgtaaaaatc agtgtggtag atctccgtat  1920
atgagttgat gtggaaggtt ggccagttca catgataagg tgaatagaat aagttacaga  1980
acaggctgta gagtatgatc ttatttgtag atgtttaaaa ctgagtcata agtatgctta  2040
tatacagatc gtttctggaa gtatgtactg gaagtctacc tctggggagt ggggatgggg  2100
gagtgcactc ttctatactg ttatattttc ttttcatgct cctaaggtac ttttattgga  2160
agatgtaaag cggttcaatg taataggctt aactttctgtc aactaagttg gcgtgggtgc  2220
tttaagaggg tggtagtgat gttgctggag aaagtatccc acagtcactg gtggcttcag  2280
ccacgggcca tttggggcc taatatcac atatcatcat ggttgctagt gttaatcgaa  2340
aacctactaa gtgccaggct tactgtctct gggtcttgct tacgtggatg tcattttcc  2400
agttgcacca aatcgaaaga ggttaattgg tttgttggag ttcctttgta ggtgaagggc  2460
agagccagga gcttggctag ggacagggga ggtgagtggg ggatggtgga taggtcttgg  2520
ctcccagttt ccttctgggc agacattgcc cctctgccct gaggacctgc ttgtttgggg  2580
gaagaggcct ttagaggcac agggtcatg ccaggtgttg gacatggtga actgggaagt  2640
gctcccatct ggccacagcg cagaagtatc accgtgctgg gggatgggga acagggctgt  2700
gaatgggcct atttgcataa gcagcatgtg tctggagaga aagacatcac agagcagaag  2760
agtgcgggtc cccaggagtg cacttgccac ccctacttca tccctgaaag agtaaatggc  2820
ctggaaggtg tctctgagag gtaatgccgc acaccacct ccctggggc aggtcaggc  2880
tacacctgcc ttaggtcggg ggctgcagca gcctgagagc tctcagtagg gcctcagtag  2940
cctgggaggg agcaggggca gggggcaggg aaagaggcgt aatggggctg tccagagggg  3000
cctgggaaac ctggtccctg aggcctgggc acagctacaa tcacttcaaa ttggctgtgt  3060
ggccagtgga ctgggaagga aaaaagcaat aagagtgcag ggctgtcagg  3120
tcccaggtca catgccttag tgcagtgact cctcatcatt ttatggggtg tgggtgtcgt  3180
tggtacccc attttacaga tgaggacacc gaggcccaga aaagtaaagt tacatgtcct  3240
aagtcacaca gcttgtaagt gccagaactg agatcaaaac caagtctctt tgactttaaa  3300
gtctgtactc tgaccccaaa gagatcctgt ttggccactt ataggaggtc cctaaagctg  3360
cagactcccc ttgccggcac ccacatatag agacattaac ccttcccctg cagggtcacc  3420
tcaaatagtc ttttagctgg gcttctcctg caattccacc taatgccatc ccctgggttt  3480
tgcccaaacc tgaactgggc agtggggtga ggaggggt tacagggt acagagcctc  3540
atacagatag gagcccatgg ctgctggtca tctgcattcc tgcaggattg gctgttcctt  3600
ggggtccttg gcaggaaaat gaggattgct ccgaggcctg ctccagtact tcccagaggc  3660
tggcctggtg tggggctctg ggaaggctga ggctggagaa gcgtaagtag gagggcagag  3720
atggcactca ggtagcttga atcaccagga cccttccaag ccccacaggt tctgagggag  3780
tactagggcc agctctggga gaggtctctt cctatgctgt gaaccccctg cctttct     3837

SEQ ID NO: 42        moltype = DNA   length = 571
FEATURE              Location/Qualifiers
source               1..571
                     mol_type = other DNA
                     organism = Homo sapiens
SEQUENCE: 42
gtgcccgccc gagaaggcgg cgctgggagc cgctcagagc ccagagaagc ggcgcgcggc  60
caggagccc cgctccgcca ctgccgtgcc tgcctccgc agctgtctgc catgcgctcg  120
ccggggcagg ggcgcccgga gggcggctag agctgggcct gagcccggga acgcgcctga  180
tcaggggtgg cggagccgcg gtccccacag ccgcccacc cgccgcctg cctcgctggg  240
gcccgggccc ccttccggt ccttactccc ctgctggtgc ctccctcctt ggcgcgcttc  300
ccacctgcga tcggcgccct cttcgcagtc acgaactcgc cagcagctag cagcactgac  360
tagtaggagg gcccgccgga ggagagccgc gcggcccaca gaagcggaac gcgcgtcgag  420
agcgccctgt ccgctcgccc cagacagatg cccggttatt cattaccgcg aggcctagag  480
gaaagagtgg ctgccgtctt cctgcccaca gcccgccgga ccctccgtcg cggctgcccg  540
gtccccggag ccgcagccgc cgagcccggc t                                 571

SEQ ID NO: 43        moltype = DNA   length = 4915
FEATURE              Location/Qualifiers
source               1..4915
                     mol_type = other DNA
                     organism = Homo sapiens
SEQUENCE: 43
ccaccacacc cagactaaaa ggcagtttga ttttacaaat caaaatagca gtaatctatg  60
gagatttact tgtgagattg gtaggaaaca tcttaaatgt aatcaaacaa taacttacat  120
cttgatgaat tcacgtgtag gtttctcttc ctcagaagaa atcagatgct gttcagagca  180
cgaaggctag aatttaccc tggttctcat gctaccttgc acccaggttg gatcctgagt  240
acagtttttg gcaggtgggc ctgcatataa gttagcaatg gggataccc agctgcctct  300
cttcatacag ctgagggtttt ggggagtcat tcttatagcc cctgggttgg gcctagtcct  360
gcaaatgaat tcaccagccc taaagcccaa attgcagcct ctgtcattca ccttccagga  420
gtggaaaggg cagtaagttt catcttatta ttattgctat tttggtggtt ttgttgaggt  480
tggtgtgtgt atgttagtaa gataaagctc tcagaaatta catagcattt gtcaaggata  540
taagagggac tgtgccacat ctggctgtat agaaggtggt tccatatctt taaatagagc  600
cccaggtcct tagccaccag aaaggttttc aggggaagtg tgcaccctca gcagctgctg  660
ctggtgggca ggatgggcac gcatggaaca gctttctct ttggccagg tgaagaagcag  720
gtggtgagac acagagcagt gctgggctct gcttctgaag cctccaacct ttccttcct  780
aggaagcccc agagagattg gtgagggtga tttccagga agacgcagtg tgctctgact  840
tctgtgacag tgagcaacgg gaccagtgga tgtccagatg ctggcaatga gtaggccttc  900
cctacgctgg gtgcgtcca cacctccgg cttccattgc ctgggtctcc tggaggtggt  960
ttgctggatg aataccgcat gcacagaggc tggccttggg tttgaatatg gcagccagtg  1020
```

```
gacagcatgt gcttcagtta tgagactgcc caggagatgc ttcttccaag gcagagcacg   1080
tgcagagtcc agtgctggag aggccgggtc cgcagttgac ccatttccag ttctgttttc   1140
cctctcatgt tcctctgtcc ccatctagga catgctctgg agtcagaaga cagcgaaaag   1200
agaagcagaa gccccggtgg caagagtctg aagcaggaag gatgactgta gcctgtggat   1260
tgtactgcag taggaaactg tcctagcaag gctccacttt gccccagctt caagctggaa   1320
aggaggagaa catgaaacat tgcttgaaga caatggccga gacagcaggt cccacccctgc  1380
acagccacca gcatctctcc cctcagccct gtcctcctct ctgcagttgg gatctgcaca   1440
tttaagcctg aaattgtcct gtgaagtgaa gtatgatcgg acagcctctt ttcagctttt   1500
atgacaatgg agacagagga attgtggctc ttgccaaggt cacaggattg gaatacagag   1560
ccaagccacc ccaggacatg caagagcctc agaagggaaa aaagcccagc aggaagggag   1620
aacaagtagc ctctgtcctg aagttgtaac agccaggggc caggatggag gaggaggacc   1680
ccataatctg cccatctggg acttggcagg ggacctggga aaatgtaccc caacccatcc   1740
cttaaggggc tttgtctttg gcccattggc ctagcatcta cttcttcacc gtgtctgttc   1800
ttgtcacacc tagtcaggtc tgtttgggtc tgaggtgcat ggaacattct gggtaggcct   1860
ccagcaaacg gaagctcttc accgtgtttc cagcctggga ccaagggcag catactggca   1920
aagttgccaa agcaagggac tccagcctct taggagttaa tgactccctc tccccagctg   1980
tcctccccctt ggtgctcctc ttcctccctc ctcctgctca cagcaggcag ggcctagacc   2040
cgggagccat gctgctgtgc tgttgccagg ggagcacgga ggcagatctg agctatgcag   2100
ggaaaaggcc cagcctgtca aagtgtctga gatgaaccgc cgccgtccct gtgcagctgg   2160
gctcagacgt gtctcagctc ttgttctgtg cctgagaatg gcgaaaccca gtgaggttca   2220
agggcaaact cgctattcat tagtcagggg ttcttgacgt cccgtctctc ccagggatga   2280
gttccccct cctcttctc cccctcctat gacacattcc tgggtgcctt tggtgaggac   2340
tgcacaccct cctcctgcct agccccctct ccaaaggccc ctgaataaac tcccccaag   2400
gagaccaggc agggcagaga caatggctgc aggaaatcat tcaggcggga catgctggcc   2460
tgccctccac ccagtccccc tgtgggcccc actcccttct gattcagggc acccttgggc   2520
ccccagccta tacaggcctg gacaggaaga aaccactgga aaccacccta aggacaaacat   2580
gctagtccag tgccattctt cgctggctct gtgggtgcct ttgtggcctg taccgactgg   2640
ctggctaatt ttgtggtttc tgtaccatca catgccatt ttaagacact ctccagcact   2700
gtcggttagg gagtgtaaat tttgcaatat tttctgaaat gtggcaatat caaaatgtaa   2760
aaggcacaca tacttggtca caaacaaatg gcactattta ctctgtgggc atatttgtaa   2820
aagttgccaa agaattatat acaaggatgt tcatcagagc atttcttttg aagagtaaag   2880
aaatggacat gaactgtgg tccgttcata cggtggaata cctatgcagc tgtaaaaatc   2940
agtgtggtag atctccgtat atgagttgat gtggaaggtt ggccagttca catgataagg   3000
tgaatagaat aagttacaga acaggctgta gagtagatc ttatttgtag atgtttaaaa   3060
ctgagtcata agtatgctta tatacagatc gtttctggaa gtatgtactg gaagtctacc   3120
tctggggagt ggggatgggg gagtgcactc ttctatactg ttatatttc ttttcatgct   3180
cctaaggtac ttttattgga agatgtaaag cggttcaatg taataggctt aacttctgtc   3240
aactaagttg gcgtgggtgc tttaagaggg tggtagtgat gttgctggag aaagtatccc   3300
acagtcactg gtggcttcag ccacgggcca ttttgggcc taataatcac atatcatcat   3360
ggttgctagt gttaatcgaa aacctactaa gtgccaggct tactgtctct gggtcttgct   3420
tacgtgctgatg tcattttttcc agttgcacca aatcgaaaga ggttaattgg ttgttggag   3480
ttcctttgta ggtgaagggc agagccagga gcttggctag gacaggga ggtgagtggg   3540
ggatggtgga taggtcttgg ctcccagttt ccttctgggga agacattgcc cctctgcctt   3600
gaggacctgc ttgtttgggg aagaggcct ttagaggcac cagggtcatg ccaggtgttg   3660
gacatggtga actgggaagt gctcccatct ggccacagcg cagaagtatc accgtgctgg   3720
gggatgggga acagggctgt gaatgggcct atttgcataa gcagcatgtg tctggagaga   3780
aagacatcac agagcagaag agtgcgggtg cccaggagtg cacttgccac ccctacttca   3840
tccctgaaag agtaaatggc ctggaaggtg tctctgagag gtaatgccgc acaccaccct   3900
ccctgggggc agggtcaggc tacacctgcc ttaggtcggg ggctgcagca gcctgagagc   3960
tctcagtagg gcctcagtag cctggagggg agcaggggca gggggcaggg aaagaggcgt   4020
aatgggggta tccagagggg cctgggaaac ctggtccctg aggcctgggc acagctacaa   4080
tcacttcaaa ttggctgtgg ggccagtgga ctgggaagga aaaagcaat aagagtgacc   4140
aagtgcagaa ggctgtcagg tccaggtca catgccttag tgcagtgact cctcatcatt   4200
ttatgggtgt tgggtgtcgt tggtacaccc attttacaga tgaggacacc gaggcccaga   4260
aaagttaagt tacatgtcct aagtcacaca gcttgtaagt gccagaactg agatcaaaac   4320
caagtctctt tgacttaaa gtctgtactc tgaccccaaa gagatcctgt ttggccactt   4380
ataggaggtc cctaaagctg cagactcccc ttgccggcac ccacatatag agacattaac   4440
ccttccctg cagggtcacc tcaaatagtc ttttagctgg gcttctcctg caattccacc   4500
taatgccatc ccctgggttt tgcccaaacc tgaactgggc agtggggtga gaggagggt   4560
ttacagggtt acagagccctc atacagatag gagcccatgg ctgctggtca tctgcattcc   4620
tgcaggattg gctgttcctt ggggtccttg gcaggaaaat gaggattgct ccgaggcctg   4680
ctccagtact tcccagaggc tggcctggtg tgggctctg gaaggctga ggctggagaa   4740
gcgtaagtag gagggcagag atggcactca ggtagcttga atcaccagga cccttccaag   4800
ccccacaggt tctgagggag tactagggcc agctctggga gaggtctctt cctatgctgt   4860
gaacccctg cctttcttgc agcctacaac gaataaattt tctttgcaaa ggctt          4915
SEQ ID NO: 44           moltype = RNA   length = 4687
FEATURE                 Location/Qualifiers
source                  1..4687
                        mol_type = other RNA
                        organism = Homo sapiens
SEQUENCE: 44
ttcctcagaa gaaatcagat gctgttcaga gcacgaaggc tagaattta ccctggttct     60
catgctacct tgcacccagg ttggatcctg agtacagttt ttggcaggtg ggcctgcata   120
taagttagca atgggggata cccagctgcc tctcttcata cagctgaggt tttgggagt    180
cattcttata gcccctgggt tgggcctagt cctgcaaatg aattcaccag ccctaaagcc   240
caaattgcag cctctgtcat tcaccttcca ggagtggaaa gggcagtaag tttcatctta   300
ttattattgc tattttggtg gttttgttga ggttggtgtg tgtatgttag taagataaag   360
ctctcagaaa ttacatagca tttgtcaggg atataagagg gactgtgcca catctggctg   420
```

```
tatagaaggt ggttccatat cttaaaatag agccccaggt ccttagccac cagaaaggtt   480
ttcaggggaa gtgtgcaccc tcagcagctg ctgctggtgg gcaggatggg cacgcatgga   540
acaggctttc ctctgtggcc aggtgagaag caggtggtga gacacagagc agtgctgggc   600
tctgcttctg aagcctccaa cctttccttc cctaggaagc cccagagaga ttggtgaggg   660
tgatttccca ggaagacgca gtgtgctctg acttctgtca cagtgagcaa cgggaccagt   720
ggatgtccag atgctggcaa tgagtaggcc ttccctacgc tgggtggcgt ccacaccctc   780
cggcttccat tgcctgggtc tcctggaggt ggtttgctgg atgaataccg catgcacaga   840
ggctggcctt gggtttgaat atggcagcca gtggacagca tgtgcttcag ttatgagact   900
gcccaggaga tgcttcttcc aaggcagagc acgtgcagag tccagtgctg gagaggccgg   960
gtgcgcagtt gacccatttc cagttctgtt ttccctctca tgttcctctg tccccatcta  1020
ggacatgctc tggagtcaga agacagcgaa aagagaagca gaagcccggg tggcaagagt  1080
ctgaagctgg aaaggaggag aacatgaaac attgcttgaa gacaatggcc gagacagcag  1140
gtcccaccct gcacagccac cagcatctct ccccctcagc ctgtctcctc ttctgcagtt  1200
gggatctgca catttaagcc tgaaattgtc ctgtgaagtg aagtatgatc ggacagcctc  1260
ttttcagctt ttatgacaat ggagacagag gaattgtggc tcttgccaag gtcacaggat  1320
tggaatacag agccaagcca ccccaggaca tgcaagagcc tcagaaggga aaaaagccca  1380
gcaggaaggg agaacaagta gcctctgtcc tgaagttgta acagccaggg gccaggatgg  1440
aggaggagga ccccataatc tgcccatctg ggacttggca gggggacctgg gaaaatgtac  1500
cccaacccat cccttaaggg cctttgtctt tggcccattg gcctagcatc tacttcttca  1560
ccgtgtctgt tcttgtcaca cctagtcagg tctgtttggg tctgaggtgc atggaacatt  1620
ctgggtaggc ctccagcaaa cggaagctct tcaccgtgtt tccagcctgg gaccaagggc  1680
agcatactgg caaagttgcc aaagcaaggg actccagcct cttaggagtt aatgactccc  1740
tctcccagc tgtcctcccc ttggtgctcc tcttcctccc tcctcctgct cacagcaggc  1800
agggcctaga cccgggagcc atgctgctgt gctgttgcca ggggagcacg gaggcagatc  1860
tgagctatgc agggaaaagg cccagcctgt caaagtgtct gagatgaacc gccgccgtcc  1920
ctgtgcagct gggctcagac gtgtctcagc tgcctgagaa tggcgaaacc  1980
cagtgaggtt caagggcaaa tcgctattc attagtcagg ggttcttgac gtccgtctc  2040
tcccagggat gagttccccc ctcctctttc tccccctcct atgacacatt cctgggtgcc  2100
tttggtgagg actgcacacc ctcctcctgc ctagcccct ctccaaaggc ccctgaataa  2160
actcccccca aggagaccag gcagggcaga gacaatggct gcaggaaatc attcaggcgg  2220
gacatgctgg cctgccctcc acccagtccc cctgtgggcc ccactccctt ctgattcagg  2280
gcaccttgg gccccagcc tatacaggcc tggacaggaa gaaaccactg ggaaccaccc  2340
taaggacaac atgctagtcc agtgccattc ttcgctggct ctgtgggtgc ctttgtggcc  2400
tgtaccgact ggctggctaa ttttgtggtt tctgtaccat cacatgccta ttttaagaca  2460
ctctccagca ctgtcggtta gggagtgtaa attttgcaat attttctgaa atgtggcaat  2520
atcaaaatgt aaaaggcaca catacttggt cacaaacaaa tggcactatt tactctgtgg  2580
gcatatttgt aaaagttgcc aaagaattat atacaaggat gttcatcaga gcatttcttt  2640
tgaagagtaa agaaatggac atgaacctgt ggtccgttca tacggtggaa tacctatgca  2700
gctgtaaaaa tcagtgtggt agatctccgt atatgagttg atgtggaagg ttggccagtt  2760
cacatgataa ggtgaataga ataagttaca gaacaggctg tagagtatga tcttatttgt  2820
agatgtttaa aactgagtca taagtatgct tatatacaga tcgtttctgg aagtatgtac  2880
tggaagtcta ccctctggga gtgggatgg gggagtgcac tcttctatac tgttatattt  2940
tcttttcatg ctcctaaggt acttttattg gaagatgtaa agcggttcaa tgtaataggc  3000
ttaacttctg tcaactaagt tggcgtgggt gctttaagag ggtggtagtg atgttgctgg  3060
agaaagtatc ccacagtcac tggtggcttc agccacgggc catttggggg cctaataatc  3120
acatatcatc atgcgttgcta gtgttaatcg aaaacctact aagtgccagg cttactgtct  3180
ctgggtcttg cttacgtgga tgtcatttt ccagttgcac caaatcgaaa gaggttaatt  3240
ggttttgttgg agttcctttg taggtgaagg gcagagccag gagcttggct agggacaggg  3300
gaggtgagtg ggggatggtg gataggtctt ggctccagt ttccttctgg gcagacattg  3360
cccctctgcc ctgaggacct gcttgtttgg gggaagaggc ctttagaggc accagggtca  3420
tgccaggtgt tggacatggt gaactgggaa gtgctcccat ctggccacag cgcagaagta  3480
tcaccgtgct gggggatggg aacagggct gtgaatgggc ctatttgcat aagcagcatg  3540
tgtctggaga gaaagacatc acagagcaga agagtgcggg tgcccaggag tgcacttgcc  3600
accctactt catccctgaa agagtaaatg gcctggaagg tgtctctgag aggtaatgcc  3660
gcacaccacc ctccctgggg gcagggtcag gctacacctg cctaggtcg ggggctgcag  3720
cagcctgaga gctctcagta gggcctcagt agcctgggag ggagcagggg caggggggcag  3780
ggaaagaggc gtaatgggc tgtccagagg gcctgggaa acctggtccc tgaggcctgg  3840
gcacagctac aatcacttca aattggctgt ggggccagtg gactgggaag gaaaaaagca  3900
ataagagtga ccaagtgcag aaggctgtca ggtcccaggt cacatgcctt agtgcagtga  3960
ctcctcatca ttttatgggg tgtgggtgtc gttggtacag ccattttaca gatgaggaca  4020
ccgaggccca gaaaagttaa gttacatgtc ctaagtcaca cagcttgtaa gtgccagaac  4080
tgagatcaaa accaagtctc tttgactta aagtctgtac tctgaccca aagagatcct  4140
gtttggccac ttataggagg tccctaaagc tgcagactcc ccttgccggc acccacatat  4200
agagacatta accctcccc tgcagggtca cctcaaatag tcttttagct gggcttcctc  4260
tgcaattcca cctaatgcca tccctgggg tttgcccaaa cctgaactgg gcagtggggt  4320
gagaggaggg gtttacaggg ttacagagcc tcatacagat aggagcccat ggctgctggt  4380
catctgcatt cctgcaggat tggctgttcc ttggggtcct tggcaggaaa atgaggattg  4440
ctccgaggcc tgctccagta ctttcccgag gctggcctgg tgtgggggctc tgggaaggct  4500
gaggctggag aagcgtaagt aggagggcag agatggcact caggtagctt gaatcaccag  4560
gacccttcca agccccacag gttctgaggg agtactaggg ccagctctgg gagaggtctc  4620
ttcctatgct gtgaacccc tgcctttctt gcagcctaca acgaataaat tttctttgca  4680
aaggctt                                                            4687

SEQ ID NO: 45           moltype = RNA   length = 706
FEATURE                 Location/Qualifiers
source                  1..706
                        mol_type = other RNA
                        organism = Homo sapiens
SEQUENCE: 45
```

```
ctcagaaatt acatagcatt tgtcaaggat ataagaggga ctgtgccaca tctggctgta    60
tagaaggtgg ttccatatct ttaaatagag cccccaggtcc ttagccacca gaaaggtttt   120
caggggaagt gtgcaccctc agcagctgct gctggtgggc aggatgggca cgcatgaac    180
aggctttcct ctgtggccag gtgagaagca ggtggtgaga cacagagcag tgctgggctc   240
tgcttctgaa gcctccaacc tttccttccc taggaagcc cagagagatt ggtgagggtg    300
atttccagg aagacgcagt gtgctctgac ttctgtgaca gtgagcaacg ggaccagtga    360
atgtccagat gctggcaatg agacatgctc tggagtcaga agacagcgaa aagagaagca   420
gaagcccgg tggcaagagt ctgaaggtgg gttccttcct gacatgggca ttgggctgcg    480
catgtgtgtt cgcagttctt tccagctgct gttctgacct ctttgtgcag tgtatttatg   540
tggctgtaga tggatggtcc aaggtagatt taggttttgg aatactgttt ttttttttcta  600
cttcagggag aaaataaccc agtttgggaa ggacatttaa aaggggaaaa tattaggtat   660
gatggcacac ctgcagtccc agctattcgg gaggctaagg ctggag                  706

SEQ ID NO: 46        moltype = RNA   length = 3922
FEATURE              Location/Qualifiers
source               1..3922
                     mol_type = other RNA
                     organism = Homo sapiens
SEQUENCE: 46
cacgcatgga acaggctttc ctctgtggcc aggtgagaag caggtggtga gacacagagc    60
agtgctgggc tctgcttctg aagcctccaa ccttttccttc cctaggaagc cccagagaga   120
ttggtgaggg tgatttccca ggaagacgca gtgtgctctg acttctgtga cagtgagcaa   180
cgggaccagt ggatgtccag atgctggcaa tgagacatgc tctggagtca gaagacagcg   240
aaaagagaag cagaagcccc ggtgtgcaaga gtctgaagca ggaaggatga ctgtagcctg   300
tggattgtac tgcagtagga aactgtccta gcaaggctcc actttgcccc agcttcaagc   360
tggaaaggag gagaacatga aacattgctt gaagcaatg gccgagacag caggtcccac    420
cctgcacagc caccagcatc tctcccctca gccctgtctc ctcttctgca gttgggatct   480
gcacatttaa gcctgaaatt gtcctgtgaa gtgaagtatg atcggacagc ctcttttcag   540
cttttatgac aatggagaca gaggaattgt ggctcttgcc aaggtcacag gattggaata   600
cagagccaag ccacccccagg acatgcaaga gcctcagaag ggaaaaaagc ccagcaggaa   660
gggagaacaa gtagcctctg tcctgaagtt gtaacagcca ggggccagga tggaggagga   720
ggaccccata atctgcccat ctgggacttg cagggacc tgggaaaatg tacccccaacc   780
catcccttaa gggcctttgt ctttggccca ttggcctagc atctacttct tcaccgtgtc   840
tgttcttgtc acacctagtc aggtctgttt gggtctgagg tgcatggaac attctgggta   900
ggcctccagc aaacggaagc tcttcaccgt gtttccaagc tgggaccaag ggcagcatac   960
tggcaaagtt gccaaagcaa gggactccag cctcttagga gttaatgact ccctctcccc  1020
agctgtcctc cccttggtgc tcctcttcct ccctcctcct gctcacagca ggcagggcct  1080
agacccggga gccatgctgc tgtgctgttg caggggagc acggaggcag atctgagcta  1140
tgcagggaaa aggcccagcc tgtcaaagtg tctgagatga accgccgccg tccctgtgca  1200
gctgggctca gacgtgtctc agctcttgtt ctgtgcctga aatggcgaa acccagtgag  1260
gttcaagggc aaactcgcta ttcattagtc aggggtcctt gacgtccgt ctctcccagg   1320
gatgagttcc cccctcctct ttctccccct cctatgacac attcctgggt gcctttggtg  1380
aggactgcac accctcctcc tgcctagccc cctctccaaa ggccctgaa taaactcccg  1440
ccaaggagac caggcagggc agagacaatg gctgcaggaa atcattcagg cgggacatgc  1500
tggcctgccc tccacccagt cccccctgtgg gccccactcc cttctgattc agggcaccct  1560
tgggccccca gcctatacag gcctggacag gaagaaacca ctgggaacca ccctaaggac  1620
aacatgctag tccagtgcca ttcttgcgtg gctctgtggg tgccttttg gcctgtaccg  1680
actggctggc taatttttgtg gtttctgtac catcacatgc ctatttttaag acactctcca  1740
gcactgtcgg ttaggagtg taaattttgc aatattttct gaaatgtggc aatatcaaaa   1800
tgtaaaaggc acacatactt ggtcacaaac aaatggcact atttactctg tgggcatatt  1860
tgtaaaagtt gccaaagaat tatatacaag gatgttcatc agagcatttc ttttgaagag  1920
taaagaaatg gacatgaacc tgtggtccgt tcatacggtg gaatacctat gcagctgaaa  1980
aaatcagtgt ggtagatctc cgtatatgag ttgatggtga aggttggcca gttcacatga  2040
taaggtgaat agaataagtt acagaacagg ctgtagagta tgatcttatt tgtagatgtt  2100
taaaactgag tcataagtat gcttatatac agatcgtttc ttgaagtgta tactggaagt  2160
ctacctctgg ggagtgggga tggggagtg cactcttcta tactgttata ttttctttc    2220
atgctcctaa ggtactttta ttggaagatg taaagcggtt caatgtaata ggcttaactt  2280
ctgtcaacta agttggcgtg ggtgctttaa gagggtggta gtgatgttgc tggagaaagt  2340
atcccacagt cactggttgg ttcagccacg ggccattttg gggcctaata atcacatatc  2400
atcatggttg ctagtgttaa tcgaaaacct actaagtgcc aggcttactg tctctgggtc  2460
ttgcttacgt ggatgtcatt tttccagttg caccaaatcg aaagaggtta attggtttgt  2520
tggagttcct ttgtaggtga agggcagagc caggagcttg ctagggaca ggggaggtga   2580
gtgggggatg gtggataggt cttggctccc agtttccttc tgggcagaca ttgccctct   2640
gccctgagga cctgcttgtt tgggggaaga ggccttaga ggcaccaggg tcatgccagg   2700
tgttggacat ggtgaactgg gaagtgctcc catctggcca cagcgcagaa gtatcaccgt  2760
gctggggat ggggaacagg gctgtgaatg ggccatttg cataagcagc atgtgtctgg   2820
agagaaagac atcacagagc agaagagtgc gggtgcccag gagtgcactt gccaccccta  2880
cttcatccct gaaagagtaa atggcctgga aggtgtctct gagaggtaat gccgcacacc  2940
accctccctg gggcagggt caggctacac ctgccttagg tcgggggctg cagcagcctg   3000
agagctctca gtagggcctc agtagcctgg gagggagcag gggcaggggg caggaaaga   3060
ggcgtaatgg ggctgtccag aggggcctgg gaaacctggt ccctgaggcc tgggcacagc  3120
tacaatcact tcaaattggc tgtgggggcca gtggactggg aaggaaaaaa gcaataagag 3180
tgaccaagtg cagaaggctg tcaggtccca ggtcacatgc cttagtgcag tgactcctca  3240
tcattttatg gggtgtgggt gtcgttggta cacccatttt acagatgagg acaccaggtg  3300
ccagaaaagt taagttacat gtcctaagtc acacagcttg taagtgccag aactgagatc  3360
aaaaccaagt ctctttgact ttaaagtctg tactctgacc ccaaagagat cctgtttggc   3420
cacttatagg aggtccctaa agctgcagac tccccttgcc ggcacccaca tatagagaca   3480
ttaaccctc cctgcaggg tcacctcaaa tagtctttta gctgggcttc tcctgcaatt     3540
ccacctaatg ccatcccctg ggttttgccc aaacctgaac tgggcagtgg ggtgagagga   3600
```

```
ggggtttaca gggttacaga gcctcataca gataggagcc catggctgct ggtcatctgc  3660
attcctgcag gattggctgt tccttggggt ccttggcagg aaaatgagga ttgctccgag  3720
gcctgctcca gtacttccca gaggctggcc tggtgtgggg ctctgggaag gctgaggctg  3780
gagaagcgta agtaggaggg cagagatggc actcaggtag cttgaatcac caggacccct  3840
ccaagcccca caggttctga gggagtacta gggccagctc tgggagaggt ctcttcctat  3900
gctgtgaacc ccctgccttt ct                                          3922
```

SEQ ID NO: 47          moltype = RNA   length = 3690
FEATURE                Location/Qualifiers
source                 1..3690
                       mol_type = other RNA
                       organism = Homo sapiens
SEQUENCE: 47

```
tttaacagca ggaaggatga ctgtagcctg tggattgtac tgcagtagga aactgtccta   60
gcaaggctcc actttgcccc agcttcaagc tggaaaggag gagaacatga aacattgctt  120
gaagacaatg gccgagacag caggtcccac cctgcacagc caccagcatc tctcccctca  180
gccctgtctc ctcttctgca gttgggatct gcacatttaa gcctgaaatt gtcctgtgaa  240
gtgaagtatg atcgacagc ctcttttcag cttttatgac aatggagaca ggagaattgt  300
ggctcttgcc aaggtcacag gattggaata cagagccaag ccaccccagg acatgcaaga  360
gcctcagaag ggaaaaaagc ccagcaggaa gggagaacaa gtagcctctg tcctgaagtt  420
gtaacagcca ggggccagga tggaggagga ggaccccata atctgcccat ctgggacttg  480
gcagggggacc tgggaaaatg taccccaacc catccctaaa gggccttttgt cttttggccca  540
ttggcctagc atctacttct tcaccgtgtc tgttcttgtc acacctagtc aggtctgttt  600
gggtctgagg tgcatggaac attggtta ggcctccagc aaacggaagc tcttcaccgt  660
gtttccagcc tgggaccaag ggcagcatac tggcaaagtt gccaaagcaa gggactccag  720
cctcttagga gttaatgact ccctctcccc agctgtcctc cccttggtgc tcctcttcct  780
ccctcctcct gctcacagca ggcagggcct agaccggga gccatgctgc tgtgctgttg  840
ccaggggagc acggaggcag atctgagcta tgcaggaaa aggcccagcc tgtcaaagtg  900
tctgagatga accgccgccg tccctgtgca gctgggctca gacgtgtctc agctcttgtt  960
ctgtgcctga gaatggcgaa acccagtgag gttcaaggc aaactcgcta ttcattagtc 1020
aggggttctt gacgtccgt ctctcccagg gatgagttcc ccctcctct ttctcccct   1080
cctatgacac attcctgggt gcctttggtg aggactgcac accctcctcc tgcctagccc 1140
cctctccaaa ggccctgaa taaactcccc caaggagac caggcagggc agagacaatg 1200
gctgcaggaa atcattcagg cgggacatgc tggcctgccc tccacccagt cccccctgtgg 1260
gcccactcc cttctgattc agggcaccct tgggcccca gcctatacag gcctggacag 1320
gaagaaacca ctgggaacca ccctaaggac aacatgctag tccagtgcca ttcttcgctg 1380
gctctgtggg tgcctttgtg gcctgtaccg actggctggc taatttttgtg gtttctgtac 1440
catcacatgc ctatttttaag acactctcca gcactgtcgg ttagggagtg taaattttgc 1500
aatatttttct gaaatgtggc aatatcaaaa tgtaaaaggc acacatactt ggtcacaaac 1560
aaatggcact atttactctg tgggcatatt tgtaaaagtt gccaaagaat tatatacaag 1620
gatgttcatc agagcatttc ttttgaagag taaagaaatg gacatgaacc tgtggtccgt 1680
tcatacggtg gaatacctat gcagctgtaa aaatcagtgt ggtagatctc cgtatatgag 1740
ttgatgtgga aggttggcca gttcacatga taaggtgaat agaataagtt acagaacagg 1800
ctgtagagta tgatcttatt tgtagatgtt taaaactgag tcataagtat gcttatatac 1860
agatcgtttc tggaagtatg tactggaagt ctacctctgg ggagtgggga tgggggagtg 1920
cactcttcta tactgttata ttttcttttc atgctcctaa ggtacttttta ttggaagatg 1980
taaagcggtt caatgtaata ggcttaactt ctgtcaacta agttggcgtg ggtgctttaa 2040
gagggtggta gtgatgttgc tggagaaagt atcccacagt cactggtggc ttcagccacg 2100
ggccattttg gggcctaata atcacatatc atcatggttg ctagtgttaa tcgaaaaccct 2160
actaagtgcc aggcttactg tctctgggtc ttgcttacgt ggatgtcatt tttccagttg 2220
caccaaatcg aaagaggtta attggttttgt tggagttcct ttgtaggtga agggcagagc 2280
caggagcttg gctagggaca ggggaggtga gtggggatg gtggataggg cttggctccc 2340
agtttccttc tgggcagaca ttgccctct gccctgagga cctgcttgtt tgggggaaga 2400
ggccttttaga ggcaccaggg tcatgccagg tgttggacat ggtgaactgg gaagtgctcc 2460
catctggcca cagcgcagaa tgatcaccgt gctggggggat gggaacagg gctgtgaatg 2520
ggcctatttg cataagcagc atgtgtctgg agagaaaagac atcacagagc agaagagtgc 2580
gggtgcccag gagtgcactt gccaccccta cttcatccct gaaagagtaa atggcctgga 2640
aggtgtctct gagaggtaat gccgcacacc ccctccctg ggggcagggt caggctacac 2700
ctgccttagg tcgggggctg cagcagcctc agagctctca gtagggcctc agtagcctgg 2760
gagggagcag gggcagggg cagggaaaga ggcgtcccag aggggcctgg 2820
gaaacctggt ccctgaggcc tgggcacagc tacaatcact tcaaattggc tgtggggcca 2880
gtggactggg aaggaaaaaa gcaataagag tgaccaagtg cagaaggctg tcaggtccca 2940
ggtcacatgc cttagtgcag tgactcctca tcattttatg gggtgtgggt gtcgttggta 3000
cacccatttt acagatgagg acaccgaggc ccagaaaagt taagttacat gtcctaagtc 3060
acacagcttg taagtgccag aactgagatc aaaaccaagt ctctttgact ttaaagtctg 3120
tactctgacc ccaaagagat cctgtttggc cacttatagg aggtcctaa agctgcagac 3180
tcccccttgcc ggcaccccaca tatagagaca ttaaccctctc ccctgcaggg tcacctcaaa 3240
tagtcttttta gctgggcttc tcctgcaatt ccacctaagtc ccatcccctg ggttttgccc 3300
aaacctgaac tgggcagtgg ggtgagagga gggggttaca gggttacaga gcctcataca 3360
gataggagcc catggctgct ggtcatctgc attcctgcag gattggctgt tccttggggt 3420
ccttggcagg aaaatgagga ttgctccgag gcctgctcca gtacttccca gaggctggcc 3480
tggtgtgggg ctctgggaag gctgaggctg gagaagcgta agtaggaggg cagagatggc 3540
actcaggtag cttgaatcac caggacccct ccaagcccca caggttctga gggagtacta 3600
gggccagctc tgggagaggt ctcttcctat gctgtgaacc ccctgccttt cttgcagcct 3660
acaacgaata aattttcttt gcaaaggctt                                 3690
```

SEQ ID NO: 48          moltype = RNA   length = 4093
FEATURE                Location/Qualifiers
source                 1..4093

```
                    mol_type = other RNA
                    organism = Homo sapiens
SEQUENCE: 48
cttttagcca ccccagtgct gggcagccag ggtgtgggct tttgactgaa tgcacttgcc   60
ctcctgcatt cattacacca ttgtcagtgt gtgtgtctgg ggctgcctct gggtgtgcat  120
ggttttttt gtgtctgcgt gtcagtgtca ggctatgtgt gtctgtttct gtcggcctgt  180
ctaggcgcgc tcagtgcaac aaggagctgg gggaggtggc ggtaaagagg aagggcattt  240
caaagcccag ctgtcctcct cagggacctc aggagatgcg tgtgtgtgtg tgtgtgtgtg  300
tgtgtgtgtg tgtgtgtgta ttttttttcca tgctgctcat tgtgtggggc tgcatgcgag  360
tgtctgacca ggtgtggtgt gagcagccgc tgggctgggt gagccccatc tgccgtgagc  420
tcccagactt gccttctagc cctctgccgc catccatggg gagcctctcc cttcgcagct  480
caccgtctct tctctaattt attagctgga aaggaggaga acatgaaaca ttgcttgaag  540
acaatggccg agacagcagg tcccaccctg cacagccacc agcatctctc ccctcagccc  600
tgtctcctct tctgcagttg ggatctgcac atttaagcct gaaattgtcc tgtgaagtga  660
agtatgatcg gacagcctct tttcagcttt tatgacaatg gagacagagg aattgtggct  720
cttgccaagg tcacaggatt ggaatacaga gccaagccac cccaggacat gcaagagcct  780
cagaagggaa aaagcccag caggaaggga gaacaagtag cctctgtcct gaagttgtaa  840
cagccagggg ccaggatgga ggaggaggac cccataatct gcccatctgg gacttggcag  900
gggacctggg aaaatgtacc ccaacccatc ccttaagggc ctttgtcttt ggcccattgg  960
cctagcatct acttcttcac cgtgtctgtt cttgtcacac ctagtcaggt ctgtttgggt 1020
ctgaggtgca tggaacattc tgggtaggcc tccagcaaac ggaagctctt caccgtgttt 1080
ccagcctggg accaagggca gcatactggc aaagttgcca aagcaaggga ctccagcctc 1140
ttaggagtta atgactccct ctccccagct gtcctcccct tggtgctcct cttcctcct  1200
cctcctgctc acagcaggca gggcctagac cggggagcca tgctgctgtg ctgttgccag 1260
gggagcacgg aggcagatct gagctatgca gggaaaaggc ccagcctgtc aaagtgtctg 1320
agatgaaccg ccgccgtccc tgtgcagctg ggctcagacg tgtctcagct ccttgttctgt 1380
gcctgagaat ggcgaaaccc agtgaggttc aagggcaaac tcgctattca ttagtcaggg 1440
gttcttgacg tcccgtctct cccagggatg agttcccccc tcctctttct ccccctccta 1500
tgacacattc ctgggtgcct ttggtgagga ctgcacaccc tcctcctgcc tagcccctc  1560
tccaaaggcc cctgaataaa ctcccccaa ggagaccagg cagggcagag acaatggctg 1620
caggaaatca ttcaggcggg acatgctggc ctgccctcca cccagtcccc ctgtgggccc 1680
cactcccttc tgattcaggg cacccttggg ccccagcct atacaggcct ggacaggaag 1740
aaaccactgg gaaccaccct aaggacaaca tgctagtcca gtgccattct tcgctggctc 1800
tgtgggtgcc tttgtggcct gtaccgactg gctggctaat tttgtggttt ctgtaccatc 1860
acatgcctat tttaagacac tctccagcac tgtcggttag ggagtgtaaa ttttgcaata 1920
ttttctgaaa tgtggcaata tcaaaatgta aaaggcacac atacttggtc acaaacaaat 1980
ggcactattt actctgtggg catatttgta aagttgcca aagaattata tacaaggatg  2040
ttcatcagag catttctttt gaagagtaaa gaaatggaca tgaacctgtg gtccgttcat 2100
acggtggaat acctatgcag ctgtaaaaat cagtgtggta gatctccgta tatgagttga 2160
tgtggaaggt tggccagttc acatgataag gtgaatagaa taagttacag aacaggctgt 2220
agagtatgat cttatttgta gatgtttaaa actgagtcat aagtatgctt atatacagat 2280
cgtttctgga agtatgtact ggaagtctac ctctggggag tggggatggg ggagtgcact 2340
cttctatact gttatatttt cttttcatgc tcctaaggta tttttattgg aagatgtaaa 2400
gcggttcaat gtaataggct taacttctgt caactaagtt ggcgtgggtg ctttaagagg 2460
gtggtagtga tgttgctgga gaaagtatcc cacagtcact ggtggcttca gccacgggcc 2520
attttgggg ctaataatca catatcatca tggttgctag tgttaatcga aaacctacta 2580
agtgccagge ttactgtctc tgggtcttgc ttacgtggat gtcattttc cagttgcacc 2640
aaatcgaaag aggttaattg gtttgttgga gttcctttgt aggtgaaggg cagagccagg 2700
agcttggcta gggacagggg aggtgagtgg gggatggtgg ataggtcttg gctcccagtt 2760
tccttctggg cagacattgc ccctctgccc tgaggacctg cttgtttggg ggaagaggcc 2820
tttagaggca ccagggtcat gccaggtgtt ggacatggtg aactgggaag tgctcccatc 2880
tggccacagc gcagaagtat caccgtgctg ggggatgggg aacagggctg tgaatgggcc 2940
tatttgcata agcagcatgt gtctggagag aaagacatca cagagcagaa gagtgcgggt 3000
gcccaggagt gcacttgcca cccctacttc atccctgaaa gagtaaatgg cctggaaggt 3060
gtctctgaga ggtaatgccg cacaccaccc tccctgggg caggggtcagg ctacacctgc 3120
cttaggtcgg gggctgcagc agcctgagag ctctcagtag ggcctcagta gcctgggagg 3180
gagcaggggc aggggcagg gaaagaggcg taatgggct gtccagaggg gcctgggaaa 3240
cctggtccct gaggcctggg cacagctaca atcacttcaa attggctgtg gggccagtgg 3300
actgggaagg aaaaaagcaa taagagtgac caagtgcaga aggctgtcag gtcccaggtc 3360
acatgcctta gtgcagtgac tcctcatcat tttatggggt gtgggtgtcg ttggtacacc 3420
catttacag atgaggacac cgaggcccag aaaagttaag ttacatgtcc taagtcacac 3480
agcttgtaag tgccagaact gagatcaaaa ccaagtctct ttgactttaa agtctgtact 3540
ctgaccccaa agagatcctg tttggccact tataggaggt ccctaaagct gcagactccc 3600
cttgccggca cccacatata gagacattaa cccttccct gcagggtcac ctcaaatagt 3660
cttttagctg ggcttctcct gcaattccac ctaatgccat ccctgggtt ttgcccaaac 3720
ctgaactggg cagtggggtg agaggagggg tttacagggt tacagagcct catacagata 3780
ggagcccatg gctgctggtc atctgcattc ctgcaggatt ggctgttcct tggggtcctt 3840
ggcaggaaaa tgaggattgc tccgaggcct gctccagtac ttcccagagg ctggcctggt 3900
gtggggctct gggaaggctg aggctggaga agcgtaagta aggctggagaa gatggcactc 3960
aggtagcttg aatcaccagg acccttccaa gccccacagg ttctgaggga gtactagggc 4020
cagctctggg agaggtctct tcctatgctg tgaacccct gcctttcttg cagcctacaa 4080
cgaataaatt ttc                                                   4093

SEQ ID NO: 49           moltype = DNA    length = 957
FEATURE                 Location/Qualifiers
source                  1..957
                        mol_type = other DNA
                        organism = Homo sapiens
SEQUENCE: 49
```

```
aaggcggcgc tgggagccgc tcagagccca gagaagcggc gcgcggccag gagccccgc   60
tccgccactg ccgtgcctgc ctcccgcagc tgtctgccat gcgctcgccg ggcaggggc  120
gcccggaggg cggctagagc tgggcctgag cccgggaacg cgcctgatca ggggtggcgg  180
agccgcggtc cccacagccg ccccaccccgc gccgctgcct cgctgggcc cgggcccct  240
tcccgttact ccctgctgg tgcctccctc cttggcgtgc ttcccaccctg cgatcggcgc  300
cctcttcgca gtcacgaact cgccagcagc tagcagcact gactagtagg agggcccgcc  360
ggaggagagg acatgctctg gagtcagaag acagcgaaaa gagaagcaga agccccggtg  420
gcaagagtct gaagcaggaa ggatgactgt agcctgtgga ttgtactgca gtaggaaact  480
gtcctagcaa ggctccactt tgccccagct tcaagctgga aaggaggaga acatgaaaca  540
ttgcttgaag acaatggccg agacagcagg tcccaccctg cacagccacc agcatctctc  600
ccctcagccc tgtctcctct tctgcagttg ggatctgcac atttaagcct gaaattgtcc  660
tgtgaagtga agtatgatcg gacagcctct tttcagcttt tatgacaatg gagacagagg  720
aattgtggct cttgccaagg tcacaggatt ggaatacaga gccaagccac cccaggacat  780
gcaagagcct cagaagggaa aaaagcccag caggaaggga gaacaagtag cctctgtcct  840
gaagttgtaa cagccagggg ccaggatgga ggaggaggac cccataatct gcccatctgg  900
gacttggcag gggacctggg aaaatgtacc ccaacccatc ccttaagggc ctttgtc     957

SEQ ID NO: 50           moltype = DNA   length = 2124
FEATURE                 Location/Qualifiers
source                  1..2124
                        mol_type = other DNA
                        organism = Homo sapiens
SEQUENCE: 50
gattctcaca acttctgcgt gcgagcgccc gccccaccga ccgccccggc ccggccgca   60
agagccagag gagccgagag gagcccagcg ccggcccagc ggactccagc tcgacggagc  120
ggccgcgccc cgaccagtta ctcccctgct ggtgcctccc tccttggccg gcttccacc  180
tgcgatcggc gccctcttcg cagtcacgaa ctcgccagca gctagcagca ctgactagta  240
ggagggcccg ccggaggaga ggaagcccca gagagattgg tgagggtgat tcccaggaa  300
gacgcagtgt gctctgactt ctgtgacagt gagcaacggg accagtggat gtccagatgc  360
tggcaatgag acatgctctg gagtcagaag acagcgaaaa gagaagcaga agccccggtg  420
gcaagagtct gaagcaggaa ggatgactgt agcctgtgga ttgtactgca gtaggaaact  480
gtcctagcaa ggctccactt tgccccagct tcaagctgga aaggaggaga acatgaaaca  540
ttgcttgaag acaatggccg agacagcagg tcccaccctg cacagccacc agcatctctc  600
ccctcagccc tgtctcctct tctgcagttg ggatctgcac atttaagcct gaaattgtcc  660
tgtgaagtga agtatgatcg gacagcctct tttcagcttt tatgacaatg gagacagagg  720
aattgtggct cttgccaagg tcacaggatt ggaatacaga gccaagccac cccaggacat  780
gcaagagcct cagaagggaa aaaagcccag caggaaggga gaacaagtag cctctgtcct  840
gaagttgtaa cagccagggg ccaggatgga ggaggaggac cccataatct gcccatctgg  900
gacttggcag gggacctggg aaaatgtacc ccaacccatc ccttaagggc ctttgtc     960
ggcccattgg cctagcatct acttcttcac cgtgtctgtt cttgtcacac ctagtcaggt 1020
ctgtttgggt ctgaggtgca tggaacattc tgggtaggcc tccagcaaac ggaagctctt 1080
caccgtgttt ccagcctggg accaagggca gcatactggc aaagttgcca aagcaaggga 1140
ctccagcctc ttaggagtta atgactccct ctccccagct gtcctccccc tggtgctcct 1200
cttcctccct cctcctgctc acagcaggca gggcctagac ccgggagcca tgctgctgtg 1260
ctgttgccag gggagcacgg aggcagatct gagctatgca gggaaaaggc ccagcctgtc 1320
aaagtgtctg agatgaaccg ccgccgtccc tgtgcagctg ggctcagacg tgtctcagct 1380
cttgttctgt gcctgagaat ggcgaaaacc agtgaggttc aagggcaaac tcgctattca 1440
ttagtcaggg gttcttgacg tcccgtctct cccaggatg agttcccccc tcctcttttct 1500
cccccctccta tgacacattc ctgggtgcct tggtgagga ctgcacaccc tcctcctgcc 1560
tagcccctc tccaaaggcc cctgaataaa ctcccccaa ggagaccagg cagggcagag 1620
acaatggctg caggaaatca ttcaggcggg acatgctggc ctgcccttca cctcaaatag 1680
tcttttagct gggcttctcc tgcaattcca cctaatgcca tcccctgggt tttgcccaaa 1740
cctgaactgg gcagtgggt gagaggaggg gtttacaggg ttacagagcc tcatacagat 1800
aggagcccat ggctgctggt catctgcatt cctgcaggat tggctgttcc ttggggtcct 1860
tggcaggaaa atgaggattg ctccgaggcc tgctccagta cttcccagag gctggcctgg 1920
tgtgggctc tgggaaggct gaggctggag aagcgtaagt aggagggcag agatggcact 1980
caggtagctt gaataccag gacccttcca agcccacag gttctgaggg agtactaggg 2040
ccagctctgg gagaggtctc ttcctatgct gtgaaccccc tgcctttctt gcagcctaca 2100
acgaataaat tttctttgca aagg                                       2124

SEQ ID NO: 51           moltype = DNA   length = 576
FEATURE                 Location/Qualifiers
source                  1..576
                        mol_type = other DNA
                        organism = Homo sapiens
SEQUENCE: 51
agtgcgtggg ggtcccggcc ccacacagtg ctagggtccc tctcgagttt ctcatctgcc   60
ttcaggtcac tttccaccct gatgccttgg cttgtcctga agctcagggc cctgtagct  120
tgggaaacct cccaagctcc ccagcgagtg gctgtagacc aaggaaggga ccctgcccgg  180
cttcagggaa gaaaggaaga aagttactcc cctgctggtg cctccctcct tggcgcgctt  240
cccacctgcg atcggcgccc tcttcgcagt cacgaactcg ccagcagcta gcagcactga  300
ctagtaggag ggcccgccgg aggagagccg cgcggcccac agaagcggaa cgcgcgtcga  360
gagcgccctg tccgctcgcc ccagacagat gcccggttat tcattaccgc gaggcctaga  420
ggaaagagtg gctgctgtct tcctgcccac agccctgcgg accctccgtc gcggctgccc  480
ggtcccggga gccgcagccg ccgagcccgg ctgtgcgtgt cgtggctgct ggggagaaag  540
aggcttccgg acatgctctg gagtcagaag acagcg                           576

SEQ ID NO: 52           moltype = DNA   length = 6547
FEATURE                 Location/Qualifiers
```

| source | 1..6547 |
| | mol_type = other DNA |
| | organism = Homo sapiens |

SEQUENCE: 52

```
gagcaatgtc ctgggaggcc tggctgagct tgtgtccagg agcactggac ttgtgttaaa    60
cactgtcccc ttggatgggc ccagaagtca aacctgtcca ttagatttttt ttttttttc   120
ctttgggaga gctggtatgg gctggttgtc ctccaggaga gccctgttct cacccgaggt   180
ctgttaatga gctggggaca ggtgagcctc acacgttcca acttggctgc cttcagcggc   240
atccaggagc agtggtgagc tattaatgga aggtgccggc tttgtgctaa ttagaacttc   300
cttttcagctt ccatctgtgc agacactgga gcccctcact ggtcagcctc gccgtcccaa   360
cccccctcag tttgcaacct agttttttgtc cccccaccc cccatgaatt aggggggtgct   420
atgagtggag ctgctttcct ctagctctgg tcaaatcccg gctctttgtg tattgcagaa   480
ctgtactggg tggtatttct cagggcttct ctctcttgtt ggggtggaga tggacctgga   540
agatggagtt ggaaagggat ttgggcacca tggccaccct cctgggtagg ctggacttac   600
atcatcgacc tgagtttgtt ttgtgaaaga cctctctcct ctgccctctg gagactgtga   660
cttcagaccc ttgtcctctc cattaccccca gtcctgatgt ctcccaagtc tgatggtacc   720
cacccatgtc aactacagct gccatctttg ccatctcagg cagcctacag gtggggctg   780
tgtccttgac cctcttctga aaaagaaaaa cctattttt tccttcactt ttgctttta   840
tttcttttcac ctcaggccca atggatatat atatatatat atatatatat acatatatat   900
atatacatat atacatatat atatatatat atatatatat attttaatgg aggttgtctc   960
ttacagaggt ttcattgaaa aagaagaaac aatgtcccat taacgtcatt taaagaaaaa  1020
gcacctctca gaatggaggt tgggaaagct aggggtttctt gcctgaaatat cagttgggat  1080
gaaatcccctt gtaaggaact caagagagga gcgtttcctc agaatgcttt ctttagctcc  1140
tgagtctcct taggtctcca ctggggttgt gtgtaaaaat accaagccct ccctgacaat  1200
gcatctcatt ctcttctgct tgaattatcc tgataatgag agatcaccca cttctttgac  1260
agtgtagact aggattttaa aaattgggag tgaattattg gacagtgtgg cacttcacca  1320
gcttccctca aggttctgga tctatgctaa agaggggtgg aaatgcttct ggggtgtcca  1380
gaagggctgc agaaattcct cgtcactggt catggggaga gcaggactgg cttgcctctg  1440
tggcctcttc tgcctctgga ggtgacaatt cctgatttga ggcactaggg tggaagactc  1500
aggactatcc aggaccaggt taataaaccg gcagtccaga ttgcagaagg gcagcagctg  1560
ggggctgggg acatgcccat gcctgtggga cagagttctt ttgcatgctt tggcctttac  1620
gactctgtat ccttgacaag tcacaggcat ctctgggtga atggggaca atagtaccca  1680
tacctccaag ggttatgtga gaattaagta aaatatgcaa ataaagtgcc tggcatacag  1740
taggcactga gcaaacggta gctctttttt ccaggctggg gcaagggatg catataaatg  1800
tctggatctg aagtttgaaa ttccacctgc tggagacagt gaacacccca gtagatacc   1860
caaatcacac agaaggacgg atgaccagct gccttcttcc cccagggcat gccatacaca  1920
ctgggcctga agtgggagaa tcgggacccc aaaaaaacgg cttgtggagc ggggttgcac  1980
atgggtgtaa agttcccagc ttggctgcct ggggaggggg agcatgtaaa tgtctttaga  2040
gatttgaagg gaccaggatc tggactgatt tgcgttgcca gggggctgg ggctgggagc  2100
caaggggggtg ctgccgggag gcccaggtta gcttggggta tggcatttct aacagttggc  2160
gcctgcggaa aatggcctgg ggttccagct ctggaaggtt ccgaatctca gtattcacga  2220
gcggcgctgt ccggagcagc cagggttgtc ccttggtggt ctcgggcagg ttctccgcga  2280
tgcgcttgct gggtcgcagg tgagaacctc acggttctcc atttccggag atccagctct  2340
gagcaggcag agggtcgctc ccgtcgcctc cccctgcggt agccaagcgg gtggctggaa  2400
gcgtggctag ctgcaggta aggagctcca ggtgagacgg aacacgaccc ccaaccccct   2460
tagccggtgc cccacccgat ttctctcctg cgtcctggga gggcatggtt gaggcgccac  2520
cggtgcccag caacctcccc aggctgtggt tgtgacctga ggacgcgtgt gtccccgcac  2580
tcaggccacc gctacgcgac cctgagtgca ccttcaagaa ggccgggcac gtttctgggc  2640
gggcgtgggg ggtgcctgat atctccgctc tattttacag ttactcccct gctggtgcct  2700
ccctccttgg cgcgcttccc acctgcgatc ggcgccctct tcgcagtcac gaactcgcca  2760
gcagctagca gcactgacta gtaggagggc ccgccggagg agaggacatg ctctggagtc  2820
agaagacagc gaaaagagaa gcagaagccc cggtggcaag agtctgaagg aaggatgact  2880
gtagcctgtg gattgtactg cagtaggaaa ctgtcctagc aaggctccac tttgccccag  2940
cttcaagctg gaaaggagga gaacatgaaa cattgcttga agacaatggc cgagacagca  3000
ggtccaccc tgcacagcca ccagcatctc tcccctcagc cctgtctcct cttctgcagt  3060
tgggatctgc acatttaagc ctgaaattgt cctgtgaagt gaagtatgat cggacagcct  3120
cttttcagct tttatgacaa tggagacaga ggaattgtgg ctcttgccaa ggtcacagga  3180
ttggaataca gagccaagcc accccaggac atgcaagagc ctcagaaggg aaaaaagccc  3240
agcaggaagg gagaacaagt agcctctgtc ctgaagttgt aacagccagg ggccaggatg  3300
gaggaggagg accccataat ctgcccatct gggacttggc aggggacctg ggaaaatgta  3360
ccccaaccca tcccttaagg gcctttgtct ttggcccatt ggcctagcat ctacttcttc  3420
accgtgtctg ttcttgtcac acctagtcag gtctgtttgg gtctgaggtg catggaacat  3480
tctgggtagg cctccagcaa acggaagctc ttcaccgtgt ttcagcctg gaccaagggg  3540
cagcatactg gcaaagttgc caaagcaagg gactccagcc tcttaggagt taatgactcc  3600
ctctccccag ctgtcctccc cttggtgctc ctcttcctcc ctcctcctgc tcacagcagg  3660
cagggcctag acccgggagc catgctgctg tgctgttgcc aggggagcac ggaggcagat  3720
ctgagctatg caggggaaag gcccagcctg tcaaagtgtc tgagatgaac cgccgccgtc  3780
cctgtgcagc tgggctcaga cgtgtctcag ctcttgttct gtgcctgaga atggcgaaac  3840
ccagtgaggt tcaagggcaa actcgctatt cattagtcag gggttcttga cgtcccgtct  3900
ctcccaggga tgagttcccc cctcctcttt ctcccctcc tatgacacat tcctgggtgc  3960
ctttggtgag gactgcacac cctcctcctg cctagccccc tctccaaagg ccctgaata   4020
aactccccc aaggagacca ggcagggcag agacaatggc tgcaggaaat cattcaggcg  4080
ggacatgctg gcctgccctc cacccagtcc cctgtgggc cccactccct tctgattcag  4140
ggcaccctg ggccccagc ctatacaggc ctggacagga agaaaccact gggaaccacc  4200
ctaaggacaa catgctagtc cagtgccatt cttcgctggc tctgtgggtg cctttgtggc  4260
ctgtaccgac tggctggcta attttgtggt ttctgtacca tcacatgcct atttttaagac  4320
actccagcc actgtcggtt aggggagtgta aattttgcaa tatttttctga aatgtggcaa  4380
tatcaaaatg taaaggcac acatacttgg tcacaaacaa atggcactat ttactctgtg  4440
ggcatatttg taaaagttgc caaagaatta tatacaagga tgttcatcag agcatttctt  4500
```

```
ttgaagagta aagaaatgga catgaacctg tggtccgttc atacggtgga ataccatgc    4560
agctgtaaaa atcagtgtgg tagatctccg tatatgagtt gatgtggaag gttggccagt   4620
tcacatgata aggtgaatag aataagttac agaacaggct gtagagtatg atcttatttg   4680
tagatgttta aaactgagtc ataagtatgc ttatatacag atcgtttctg gaagtatgta   4740
ctggaagtct acctctgggg agtggggatg ggggagtgca ctcttctata ctgttatatt   4800
ttcttttcat gctcctaagg tacttttatt ggaagatgta aagcggttca atgtaatagg   4860
cttaacttct gtcaactaag ttggcgtggg tgctttaaga gggtggtagt gatgttgctg   4920
gagaaagtat cccacagtca ctggtggctt cagccacggg ccattttggg gcctaataat   4980
cacatatcat catggttgct agtgttaatc gaaaacctac taagtgccag gcttactgtc   5040
tctgggtctt gcttacgtgg atgtcatttt tccagttgca ccaaatcgaa agaggttaat   5100
tggtttgttg gagttccttt gtaggtgaag ggcagagcca ggagcttggc tagggacagg   5160
ggaggtgagt gggggatggt ggataggtct tggctcccag tttccttctg ggcagacatt   5220
gccctctgc cctgaggacc tgcttgtttg ggggaagagg cctttagagg caccagggtc    5280
atgccaggtg ttggacatgg tgaactggga agtgctccca tctggccaca gcgcagaagt   5340
atcaccgtgc tgggggatgg ggaacagggc tgtgaatggg cctatttgca taagcagcat   5400
gtgtctggaa agaaagacat cacagagcag aagagtgcgg gtgcccagga gtgcacttgc   5460
caccccctact tcatccctga aagagtaaat ggcctgaag gtgtctctga gaggtaatgc   5520
cgcacaccac cctccctggg ggcaggtca ggctacacct gccttaggtc gggggctgca    5580
gcagcctgag agctctcagt agggcctcag tagcctaggg gggagcaggg gcagggggca   5640
gggaaagagg cgtaatgggg ctgtccagag gggcctggga aacctggtcc ctgaggcctg   5700
ggcacagcta caatcacttc aaattggctg tggggccagt ggactgggaa ggaaaaaagc   5760
aataagagtg accaagtgca gaaggctgtc aggtcccagg tcacatgcct tagtgcagtg   5820
actcctcatc attttatggg gtgtgggtgt cgttggtaca cccatttac agatgaggac    5880
accgaggccc agaaaagtta agttacatgt cctaagtcac acagcttgta agtgccagaa   5940
ctgagatcaa aaccaagtct ctttgacttt aaagtctgta ctctgacccc aaagagatcc   6000
tgtttggcca cttataggag gtcccctaaag ctgcagactc ccctgccgg caccccacata   6060
tagagacatt aaccccttcc ctgcagggtc acctcaaata gtcttttagc tgggcttctc   6120
ctgcaattcc acctaatgcc atcccctggg ttttgcccaa acctgaactg ggcagtgggg   6180
tgagaggagg ggtttacagg gttacagagc ctcatacaga taggagccca tggctgctgg   6240
tcatctgcat tcctgcagga ttggctgttc cttgggggtc ttggcaggaa aatgaggatt   6300
gctccgaggc ctgctccagt acttcccaga ggctggcctg gtgtggggct ctgggaaggc   6360
tgaggctgga gaagcgtaag taggagggca gagatggcac tcaggtagct tgaatcacca   6420
ggaccccttcc aagcccccaca ggttctgagg gagtactagg gccagctctg ggagaggtct  6480
cttcctatgc tgtgaacccc ctgcctttct tgcagcctac aacgaataaa ttttctttgc   6540
aaaggct                                                             6547
```

SEQ ID NO: 53             moltype = DNA   length = 3814
FEATURE                   Location/Qualifiers
source                    1..3814
                          mol_type = other DNA
                          organism = Homo sapiens
SEQUENCE: 53

```
cacgtttctg ggcgggcgtg gggggtgcct gatatctccg ctctatttta cagttactcc   60
cctgctggtg cctccctcct tggcgcgctt cccacctgcg atcggcgccc tcttcgcagt   120
cacgaactcg ccagcagcta gcagcactga ctagtaggag ggcccgccgg aggagaggac   180
atgctctgga gtcagaagac agcgaaaaga gaagcagaag ccccggtggc aagagtctga   240
agctggaaag gaggagaaca tgaaacattg cttgaagaca atggccgaga cagcaggtcc   300
cacccctgcac agccaccagc atctctcccc tcagccctgt ctcctcttct gcagttggga   360
tctgcacatt taagcctgaa attgtcctgt gaagtgaagt atgatcggac agcctctttt   420
cagcttttat gacaatggag acagaggaat tgtggctctt gccaaggtca caggattgga   480
atacagagcc aagccacccc aggacatgca agagcctcag aaggaaaaa agcccagcag   540
gaagggagaa caagtagcct ctgtcctgaa gttgtaacag ccaggggcca ggatggagga   600
ggaggacccc ataatctgcc catctgggac ttggcagggg acctgggaaa atgtacccca   660
acccatccct taagggcctt tgtctttggc ccattggcct agcatctact tcttcaccgt   720
gtctgttctt gtcacaccta gtcaggtctg tttgggtctg aggtgcatgg aacattctgg   780
gtaggcctcc agcaaacgga agctcttcac cgtgtttcca gcctgggacc aagggcagca   840
tactggcaaa gttgccaaag caagggactc cagcctctta ggagttaatg actccctctc   900
cccagctgtc ctcccttgg tgctcctctt cctccctcct cctgctcaca gcaggcaggg    960
cctagacccg ggagccatgc tgctgtgctg ttgccagggg agcacggagg cagatctgag   1020
ctatgcaggg aaaaggccca gcctgtcaaa gtgtctgaga tgaaccgccg ccgtccctgt   1080
gcagctgggc tcagacgtgt ctcagctctt gttctgtgcc tgagaatggc gaaacccagt   1140
gaggttcaag ggcaaactcg ctattcatta gtcaggggtt cttgacgtcc cgtctctccc   1200
agggatgagt tccccctcc tctttctccc cctcctatga cacattcctg ggtgcctttg    1260
gtgaggactg cacaccctcc tcctgcctag ccccctcctc aaaggcccct gaataaactc   1320
cccccaagga gaccaggcag ggcagagaca atgctgcag gaaatcattc aggcgggaca    1380
tgctggcctg cctccacccc agtccccctg tgggccccac tccttctga ttcagggcac    1440
ccttgggccc ccagcctata caggcctgga caggaagaaa ccactgggaa ccaccctaag   1500
gacaacatgc tagtccagtg ccattcttcg ctggctctgt gggtgccttt gtggcctgta   1560
ccgactggct ggctaattt gtggtttctg taccatcca tgcctatttt aagacactct    1620
ccagcactgt cggttaggga gtgtaaattt tgcaatattt tctgaaatgt ggcaatatca   1680
aaatgtaaaa ggcacacata cttggtcaca aacaaatggc actatttact ctgtgggcat   1740
atttgtaaaa gttgccaaag aattatatac aaggatgttc atcagagcat ttcttttgaa   1800
gagtaaagaa atggacatga acctgtggtc cgttcatacg gtgaatacc tatgcagctg    1860
taaaaatcag tgtggtagat ctccgtatat gagttgattg tggaaggttg gccagttcaca   1920
tgataaggtg aatagaataa gttacagaac aggctgtaga gtatgatctt atttgtagat   1980
gtttaaaact gagtcataag tatgcttata tacagatcgt ttctgaagt atgtactgga    2040
agtctacctc tggggagtgg ggatggggga gtgcactctt ctatactgtt atattttctt   2100
tcatgctcta aggtacttt tattggaag atgtaaagcg gttcaatgta ataggcttaa     2160
cttctgtcaa ctaagttggc gtgggtgctt taagagggtg gtagtgatgt tgctggagaa   2220
```

```
agtatcccac agtcactggt ggcttcagcc acgggccatt ttggggccta ataatcacat  2280
atcatcatgg ttgctagtgt taatcgaaaa cctactaagt gccaggctta ctgtctctgg  2340
gtcttgctta cgtggatgtc atttttccag ttgcaccaaa tcgaaagagg ttaattggtt  2400
tgttggagtt cctttgtagg tgaagggcag agccaggagc ttggctaggg acaggggagg  2460
tgagtggggg atggtggata ggtcttggct cccagtttcc ttctgggcag acattgcccc  2520
tctgccctga ggacctgctt gtttggggga agaggccttt agaggcacca gggtcatgcc  2580
aggtgttgga catggtgaac tgggaagtgc tcccatctgg ccacagcgca gaagtatcac  2640
cgtgctgggg gatggggaac agggctgtga atgggcctat ttgcataagc agcatgtgtc  2700
tggagagaaa gacatcacag agcagagag tgcgggtgcc caggagtgca cttgccaccc  2760
ctacttcatc cctgaaagag taaatggcct ggaaggtgtc tctgagaggt aatgccgcac  2820
accaccctcc ctgggggcag ggtcaggcta cacctgcctt aggtcggggg ctgcagcagc  2880
ctgagagctc tcagtagggc ctcagtagcc tgggagggag caggggcagg gggcagggaa  2940
agaggcgtaa tggggctgtc cagaggggcc tgggaaacct ggtccctgag gcctgggcac  3000
agctacaatc acttcaaatt ggctgtgggg ccagtggact gggaaggaaa aaagcaataa  3060
gagtgaccaa gtgcagaagg ctgtcaggtc ccaggtcaca tgccttagtg cagtgactcc  3120
tcatcatttt atggggtgtg ggtgtcgttg gtacacccat tttacagatg aggacaccga  3180
ggcccagaaa agttaagtta catgtcctaa gtcacacagc ttgtaagtgc cagaactgag  3240
atcaaaacca agtctctttg actttaaagt ctgtactctg accccaaaga gatcctgttt  3300
ggccacttat aggaggtccc taaagctgca gactcccctt gccggcaccc acatatagag  3360
acattaaccc ttcccctgca gggtcacctc aaatagtctt ttagctgggc ttctcctgca  3420
attccaccta atgccatccc ctgggttttg cccaaacctg aactgggcag tggggtgaga  3480
ggagggsttt acagggttac agagcctcat acagatagga gcccatggct gctggtcatc  3540
tgcattcctg caggattggc tgttccttgg ggtccttggc aggaaaatga ggattgctcc  3600
gaggcctgct ccagtacttc ccagaggctg gcctggtgtg gggctctggg aaggctgagg  3660
ctggagaagc gtaagtagga gggcagagat ggcactcagg tagcttgaat caccaggacc  3720
cttccaagcc cacaggttc tgaggagta ctagggccag ctctgggaga ggtctcttcc  3780
tatgctgtga accccctgcc tttcttgcag ccta                              3814
SEQ ID NO: 54         moltype = DNA  length = 4198
FEATURE               Location/Qualifiers
source                1..4198
                      mol_type = other DNA
                      organism = Homo sapiens
SEQUENCE: 54
ttactcccct gctggtgcct ccctccttgg cgcgcttccc acctgcgatc ggcgccctct  60
tcgcagtcac gaactcgcca gcagctagca gcactgacta gtaggagggc ccgccggagg  120
agagccgcgc ggcccacaga agcggaacgc cgtcgagag cgccctgtcc gctcgcccca  180
gacagatgcc cggttattca ttaccgcgag gcctagagga aagagtggct gccgtcttcc  240
tgcccacagc ccgcccgacc ctccgtgcg gctgcccgt ccccggagcc gcagccgccg  300
agcccggctg tgcgtgtcgt ggctgctggg gagaaagagg cttccggaag ccccagagag  360
attggtgagg gtgatttccc aggaagacgc agtgtgctct gacttctgtg acagtgagca  420
acgggaccag tggatgtcca gatgctggca atgagacatg tctgtgagtc agaagacagc  480
gaaaagaga gcagaagccc cggtgccaag agtctgaagg agggaaggatg actgtagcct  540
gtggattgta ctgcagtagg aaactgtcct agcaaggctc cactttgccc cagcttcaag  600
ctggaaagga ggagaacatg aaacattgct tgaagacaat ggccgagaca gcaggtccca  660
ccctgcacag ccaccagcat ctctcccctc agccctgtct cctcttctgc agttgggatc  720
tgcacattta agcctgaaat tgtcctgtga agtgaagtat gatcggacag cctcttttca  780
gcttttatga caatggagac agaggaattg tggctcttgc caaggtcaca ggattggaat  840
acagagccaa gccacccag gacatgcaag agcctcagaa gggaaaaaag cccagcagga  900
agggagaaca agtagcctct gtcctgaagt tgtaacagcc aggggccagg atggaggagg  960
aggaccccat aatctgccca tctgggactt ggcagggac ctgggaaaat gtaccccag  1020
ccatcccta agggcctttg tctttggccc attggcctag catctactc ttcaccgtgt  1080
ctgttcttgt cacaccagt caggtctgtt gggtctgag gtgcatgaa cattctgggt  1140
aggcctccag caaacggaag ctcttcaccg tgtttccagc ctgggaccaa gggcagcata  1200
ctggcaaagt tgccaaagca agggactcca gcctcttagg agttaatgac tccctctcca  1260
cagctgtcct cccccttggtg ctcctcttcc tccctcctcc tgctcacagc aggcagggcc  1320
tagacccggg agccatgctg ctgtgctgtt gccaggggag cacggaggca gatctgagct  1380
atgcagggaa aaggcccagc ctgtcaaagt gtctgagatg aaccgccgcc gtccctgtgc  1440
agctgggctc agacgtgtct cagctcttgt tctgtgcctg agaatggcga aacccagtga  1500
ggttcaaggg caaactcgct attcattagt caggggttct tgacgtcccg tctctcccag  1560
ggatgagttc cccctcctc tttctccccc tcctatgaca cattcctggg tgcctttggt  1620
gaggactgca caccctcctc ctgcctagcc ccctctccaa aggcccctga ataaactccc  1680
cccaaggaga ccaggcaggg cagagacaat ggctgcagga aatcattcag gcgggacatg  1740
ctggcctgcc ctccacccag tcccctgtg ggccccactc cctcctgatt caggcgaccc  1800
ttgggcccc agcctataca ggctggaca ggaagaaacc actgggaacc accctaagga  1860
caacatgcta gtccagtgcc attcttcgct ggctctgtgg gtgcctttgt ggcctgtacc  1920
gactggctgg ctaattttgt ggtttctgta ccatcacatg cctatttaa gacactctcc  1980
agcactgtcg gttagggagt gtaaattttg caatatttc tgaaatgtgg caatatcaaa  2040
atgtaaaagg cacacatact tggtcacaaa caaatggcca tatttactct gtgggcatat  2100
ttgtaaaagt tgccaagaa ttatatacaa ggatgttcat cagagcattt cttttgaaga  2160
gtaaagaaat ggacatgaac ctgtggtccg ttcatacggt ggaataccta tgcagctgta  2220
aaaatcagtg tggtagatct ccgtatatga gttgatgtgg aaggttggcc agttcacatg  2280
ataaggtgaa tagaataagt tacagaacag gctgtagagt atgatcttat ttgtagatgt  2340
ttaaaactga gtcataagta tgcttatata cagatcgttt ctggaagtat gtactggaag  2400
tctacctctg ggagtggggg atgggggagt gcactcttct atactgttat attttctttt  2460
catgctccta aggtactttt attggaagat gtaaagcggt tcaatgtaat aggcttaact  2520
tctgtcaact aagttggcgt gggtgcttta agagggtggt agtgatgttg ctggagaaag  2580
tatcccacag tcactggtgg cttcagccac gggccatttt ggggcctaat aatcacatat  2640
catcatggtt gctagtgtta atcgaaaacc tactaagtgc caggcttact gtctctgggt  2700
```

```
cttgcttacg tggatgtcat ttttccagtt gcaccaaatc gaaagaggtt aattggtttg  2760
ttggagttcc tttgtaggtg aagggcagag ccaggagctt ggctagggac aggggaggtg  2820
agtgggggat ggtggatagg tcttggctcc cagtttcctt ctgggcagac attgcccctc  2880
tgccctgagg acctgcttgt ttgggggaag aggcctttag aggcaccagg gtcatgccaa  2940
gtgttggaca tggtgaactg ggaagtgctc ccatctgcc acagcgcaga agtatcaccg  3000
tgctggggga tggggaacag ggctgtgaat gggcctattt gcataagcag catgtgtctg  3060
gagagaaaga catcacagag cagaagagtg cgggtgccca ggagtgcact tgccacccct  3120
acttcatccc tgaaagagta aatggcctgg aaggtgtctc tgagaggtaa tgccgcacac  3180
caccctccct gggggcaggg tcaggcctaca cctgccttag gtcgggggct gcagcagcct  3240
gagagctctc agtagggcct cagtagcctg ggagggagca ggggcagggg gcagggaaag  3300
aggcgtaatg gggctgtcca gaggggcctg ggaaacctgg tccctgaggc ctgggcacag  3360
ctacaatcac ttcaaattgg ctgtggggcc agtggactgg gaaggaaaaa agcaataaga  3420
gtgaccaagt gcagaaggct gtcaggtccc aggtcacatg ccttagtgca gtgacctcctc  3480
atcattttat ggggtgtggg tgtcgttggt acacccattt tacagatgag gacaccgagg  3540
cccagaaaag ttaagttaca tgtcctaagt cacacagctt gtaagtgcca gaactgagat  3600
caaaaccaag tctctttgac tttaaagtct gtactctgac cccaaagaga tcctgtttgg  3660
ccacttatag gaggtcccta aagctgcaga ctcccccttgc cggcacccac atatagagac  3720
attaacccctt cccctgcagg gtcacctcaa atagtcttt agctgggctt ctcctgcaat  3780
tccacctaat gccatcccct gggttttgcc caaacctgaa ctgggcagtg gggtgagagg  3840
aggggtttac agggttacag agcctcatac agataggagc ccatggctgc tggtcatctg  3900
cattcctgca ggattggctg ttccttgggg tccttggcag gaaaatgagg attgctccga  3960
ggcctgctcc agtacttccc agaggctggc ctggtgttgg gctctgggaa ggctgaggct  4020
ggagaagcgt aagtaggagg gcagagatgg cactcaggta gcttgaatca ccaggaccct  4080
tccaagcccc acaggttctg agggagtact agggccagct ctgggagagg tctcttccta  4140
tgctgtgaac cccctgcctt tcttgcagcc tacaacgaat aaattttctt tgcaaagg    4198

SEQ ID NO: 55          moltype = DNA  length = 1402
FEATURE                Location/Qualifiers
source                 1..1402
                       mol_type = other DNA
                       organism = Homo sapiens
SEQUENCE: 55
ctgtctcaag cctccaatca acagatcaga cagcttgtac tcacaggcca aggacacgtg    60
gaaagaggct caattttcta gatgggtggc aacagccatg atcttctgtc ctctgggtcc   120
ccacaagcct ggatgaactc aagatctgac tcagtgcac agtgaggaga cctttggagc   180
ctcagtgacc atccttggac ttcacctctc acggctttca ggcagagagg ccctcccatg   240
cccacaacag gctgagccca gccttcctcg gggtttgctt ccaggcctga cttttactcc   300
cctttctaag tgaggcagcc atgactggcc acttcatgtg ctcctggaga agggcttgca   360
ccagccgttt tcaggaaagt caagcagctg ttgactcctg agtctgggtg aatttgtgtg   420
aagagcataa ggcgctgttt cttaaccaaa acgcttcctc ttgcagtgca gatgggatgt   480
gcttctccac aggaggcccc acggcttccc caccctcag aggagcgccg tgcgtgcgtc   540
tgtgtggagg attggcagct cctgcagtcg gcccttggtc ctatttggcg acgcctctgc   600
cttcccctta attatacagt catgaccgcc cctggaatca cggcagctcc ggatgatcc    660
tggatgccag aatgcagcct cagcacgggg ctgcaggaca ggagtgagcg aggggctgca   720
gagccggcgc ccgcgtggg caccatggag ggggctgccc tggcagcac gggcatgagt   780
ctcaaggccc aggtttgagt aacaggtgtt gagagcttac ttacttttcc tgagacacag   840
tttcctcatc tcgagagcac ggaaaatcat tctaacttca gggattgtt gtgaaagtta   900
aatgagatta aagaggtaaa gcccatgacg tgcttagctc gtgcttggct cttggtcaat   960
gccagttagc gctgcatttt ctcccctctc cctccctcct tctctctttc ttttcttcta  1020
ttctccattc ctgtttctc ccccaccccca ctccccaaag ctctgcgttg agaaccagat  1080
gctgtctggt gggttagggc cagaggagga aaagctgccc gccgtgggtt gcacccatac  1140
cctcttcatt ccaatgacat gagggggagg gaaaggacag aggtagactg tcctcccta  1200
cctcctccta atacaaatgg aattcctgga actggaaaac aaagaatacc cccataaaaa  1260
taagacagta cttctggtgc ggtgtaataa aggggaaagt aaccctcaat gtcaggaaac  1320
tccgcacctc ccagctcata tttgtgtgga ggaaaagtta atattaatt tggactcaac  1380
tgaatgtgga cacaaacaat gg                                          1402

SEQ ID NO: 56          moltype = DNA  length = 295
FEATURE                Location/Qualifiers
source                 1..295
                       mol_type = other DNA
                       organism = Homo sapiens
SEQUENCE: 56
tctctcatct gtgttttcag ggcatggact ggaactccca ataccctga catgggctga    60
gtcaacgtgg tcatgaacat gtgacaggag gcagcagaag ttgcagagaa gagtgaggca   120
cgtttgaaaa aggctgaaaa atgtttctgt ccaggcaagg gtgtgtgctg aatgactcaa   180
ggattttttg gtgcattgaa tgaacagcgg gacattggac acctgctgat ccatcacccc   240
gggcccgggc aggcccgtgg atgaagagag atggagaaga ccaggcatga gactg        295

SEQ ID NO: 57          moltype = DNA  length = 374
FEATURE                Location/Qualifiers
source                 1..374
                       mol_type = other DNA
                       organism = Homo sapiens
SEQUENCE: 57
gcagcagaag ttgcagagaa gagtgaggca cgtttgaaaa aggctgaaaa atgtttctgt    60
ccaggcaagg gtgtgtgctg aatgactcaa ggattttttg gtgcattgaa tgaacagcgg   120
gacattggac acctgctgat ccatcacccc gggcccgggc aggcccgtgg atgaagagag   180
atggagaaga ccaggcatga gactgtggag aagccacacc accagaaacc cctgcccat   240
```

```
gcgccgtcca gcccacacct gtggatgcac gggggattgc aggcagggct cccaccgtgg   300
actcaggaac aggcagggaa gctgctgcct caccaggcga aggggccagg aggggaggc    360
ggagaggccc gtct                                                     374

SEQ ID NO: 58           moltype = DNA  length = 2737
FEATURE                 Location/Qualifiers
source                  1..2737
                        mol_type = other DNA
                        organism = Homo sapiens
SEQUENCE: 58
gcctccaatc aacagatcag acagcttgta ctcacaggcc aaggacacgt ggaaagaggc    60
tcaattttct agatgggtgg caacagccat gatcttctgt cctctgggtc cccacaagcc   120
tggatgaact caagatctga ctcagtggca cagtgaggag acctttgagg cctcagtgac   180
catccttgga cttcacctct cacggctttc aggcagagac gctcccccat gcccacaaca   240
ggctgagccc agccttcctc gggggtttgct tccaggcctg acttttactc cccttttctaa  300
gtgtgcagat gggatgtgct tctccacagg aggcccacg gcttcccac ccctcagagg    360
agcgccgtgc gtgcgtctgt gtggaggatt ggcagctcct gcagtcggcc cttggtccta   420
tttggcgacg cctctgcctt ccccttaatt atacagtcat gagccgccct ggaatcacgg   480
cagctccgga tggatcctgg atgccagaat gcagcctcag cacggggctg caggacagga   540
gtgagcgagg ggctgcagag ccggcggccg cggtgggcac catggagggg gctgccctgg   600
gcagcacggg catgagtctc aaggcccagg tttgagtaac aggtgttgag agcttactta   660
cttttcctga gacacagttt cctcatctcg agagcacgga aaatcattct aacttcagag   720
gattgttgtg aaagttaaat gagattaaag aggtaaagcc catgacgtgc ttagctcgtg   780
cttggctctt ggtcaatgcc agttagcgct gcattttctc ccctctccct ccctccttct   840
ctctttcttt tcttctattc tccattcctg tttctcccc caccccactc cccaaagctc   900
tgcgttgaga accagatgct gtctggtggg ttagggcagg aggaggaaaa gctgcccgcc   960
gtgggctgca cccataccct cttcattcca atgacatgag gggaggggaa aggacagagg  1020
tagactgtcc tccctacct cctcctaata caaatggaat tcctggaact ggaaacaaa   1080
gaatacccc ataaaataa gacagtactt ctggtgcggt gtaataaagg ggaaagtaac   1140
cctcaatgtc aggaaactcc gcacctccca gctcatattt gtgtggagga aaagttaaat  1200
attaatttgg actcaactga atgtggacac aaacaatggt caccaagtcc cggaacaggt  1260
tgtgtgagcc tcttcagggg ttcatccagc gctgttttgg agaaatctct atttcaattt  1320
attcctatac gttagttact gaaaacaac agacaatcgc aaaagcaagt tgcccgtttt   1380
gtgttccttg agcccaatca tgaagtgccg tcgtgactgg gcctcatgac aaacaacttg  1440
taacaagtaa caacagagct caggtcccag accgactga agctctgtga gacctctcct   1500
catctgtgca tgaacgagtg tctgactctg gagcccagcc tgctgcttcc cagtctggtg  1560
gtgaatcctc cgtagtctga tggaggtttg ctcttgttgc ccaggctgga gtgcaatggc  1620
acaatctcgg ctcactgcag ccctgcctc ccggctcaa gcaattctta cgcctcagcc   1680
tcctgagtag atggaactac agggcatgga ctggaactcc caataccct gacatgggct  1740
gagtcaacgt ggtcatgaac atgtgacagg aggcagcaga agttgcagag aagagtgagg  1800
cacgtttgaa aaaggctgaa aaatgtttct gtccaggcaa gggtgtgtgc tgaatgactc  1860
aaggattttt tgggcaacac aaaccaacac gagccgtgtg aggatcaggt gacagctgcc  1920
caaaagctga cacaaggaac aagcctggag gagtgaggat gggtgctgtg aaggaggttg  1980
tgcagctggg cccgcagtcg gacctggtga gatcagagga gggggtgcca ccagtctgtg  2040
gacgaagatg agaagctgga atagagcaga aaacaggagg ctgccactct ccatctttcc  2100
caaagtcact ccaggagcaa gggtgtcatt tactgaaatg acagactctc catttcacat  2160
ttttccccca agtgcagagt gcagggaagc agatgggcta aattttttaga gtcagggtta  2220
ttaatgtata ctttacatag taaacttttcc cctttttaagt gtgcaggcct gaggtttgcc  2280
aaatatgtgt aggcatttaa tcaccaccac gatcaagatg tagaatattc ccactatcaa  2340
aaagtttgct gtgtcccttg atggtcatgc cccattccac agcccagcc ccagcccctg   2400
gagattgctg tctgcttat gttccagtgg ttttatcttt tccagactgt atggatgtga  2460
atggaatcag atgtgattcc aaggtgtttt atcttttcca gatgtgaatg gaatcagatg  2520
tacgaaatcc tatggtaggg ggtcttctga gtctagctcc ttttgtttag cgtgatgcat  2580
ttgaaattaa tccatgtctc aggcatcagg agttcatttc ttttttctgct gagtagtatt  2640
tcattgtatg gatgtactgc aatttgccta tccattcacc tgttgatgta catttgagat   2700
ttttggcaat tatgaataaa gctgctataa acagaca                            2737

SEQ ID NO: 59           moltype = DNA  length = 15706
FEATURE                 Location/Qualifiers
source                  1..15706
                        mol_type = other DNA
                        organism = Homo sapiens
SEQUENCE: 59
cagatgctaa aattgacacc aaaagcgtag gtgatgagct tgaatcaggt aagaattata    60
ttctacttcc agctaaagaa gaggatatag aagatcaata gcttaaacaa aacagaaggt   120
cttctcatgg actaaaacag tgacagtgag tgcaactcta cctatcatgt tcatattcta   180
ggtagaaact ggggaaaaga gaaaaggcgg gaaaaggcg tttctctaca aagatcacac   240
ataatcttct gtctgcatct cattggtcgg catttagtca catggccata actaccagtc   300
agggaagctg ggaaatgtag ttttttcaatg gcacattgct acccttaata aaataaggat   360
atgctaccaa caaagaatga atatgggaaa ggccctagc aatgtctgct gcatctgcca   420
ctgtggtttt ctctgatttc cacagacatt gctcttccac atagagcgca ttctgattcc   480
caagccacca ctcccaaatc acacccagtt tctgcatcta gcttgtgtgt gggcagtctg   540
ctccatcagt cccagatgtg gcttctcatg gctggtgacc tatgaactaa agacaggcc   600
attttttccc caacctaccc tacctttttct ccttgagagg aaagataaaa taaccacaat   660
ttaaaaatgt caatcttcca ttcagaaaag ggaggaaaga gaaacacaga gatcactggt   720
ttacagtgat ggaccacccc tgctaggcag gagtgaaaag gcctcccgt ccggcagtgg    780
actgggttca ttggctggcc catgtggtcc ccaccactg tctccaggag catcgccttg    840
aactgtgtct tcatggcttt tggctccgcc ttcagaaggg tcctccctgt caatcatcct    900
ccattgccac ctctgatgtg ggcactaggg agctggtcct tcccagagga tgcatgattt    960
```

```
tgacaccgtg cagtgtggga tgttggacca gggaatccag catattttcg ggcttttgta   1020
gtctcagact gggcctgaga tttctttaga aatatattaa cggttccttc aacactccaa   1080
tgggcatata gcctatttac ttctgatcat tgtaatgtgc aaataaccac agccccattt   1140
ctttgtgtcc agatgcagtt tttaggcttg aatattcatc tgttttactc actggcctct   1200
gtcactgagt ctgtcccctt agctattaaa ttaatggtga ctatgataac acttttcacc   1260
cgatccttgc tagtgcattg acttgcgttg tctgcatcga gttcttaaaa gatgcttggt   1320
aaagtcttgg gtcacagttt taacttctgc tggggttcct gctccacagc cctcatttag   1380
aactgtttca ctttggctat tgtttagctt tgggccatat ttggctgttt tttagctttg   1440
taaaaatgct catttaacgg acacaaggcc tgggttagaa catgtagtat ttccttcccc   1500
ctctgtttgc gtaggagcta gcgctagtgg aagcccatct ctcccttgca ggattttgtg   1560
gaaagtgacg aaaataactc aaaccacatc agtgttctgc ttgatttcca ccattcttgg   1620
atgctataac ttcagaaagc acatgatcta acttcccaag ggacagcagg gcctcgacca   1680
aatgccgttg tgctgagggc tgccggccgc cccgctaggc tgctgcaccc tccccgcgct   1740
gccccacacc ttgcacagag ctcaggcagc attctagcac catcagacaa attcttcatg   1800
agtcagaaat cgcacctgtc tcttaatagc gatctggcct caggtggctg aaacacacag   1860
ggttgaaatg ctgcggtgcc tgcgctcatt gtgcggtgaa gccatagagt ccgcgctgaa   1920
acccggggcg cccgcctcct gtccgcgcag gcgctgcacg ctgtcgccgg ggcagcttca   1980
ctcagcttca gcctctccat ctgcagagga ggagtaatcc cgtgctgcct catgggggcg   2040
tttcaagaag gaaatgagat gtggtataaa gtgttagagg agtatttagt gttattatta   2100
atgtgttttc tcatctggga acatgatttg catttaagc agaacttcaa catttggact   2160
caaaggagtg atgtggatgg ggagaatttc aggcatcgtg caggctggca ttagaaatgc   2220
tcaccggaaa tggagcacag gcagcaactt cagccctag aattcttcct cctatgtcac   2280
ttccgtccct caaacccttt ctgcagcccc tgtcctctct cctgcaatgg cagtgagcag   2340
gtggtctcct ggtgtctctg gaaaattccc atatggagtc ctggttgaga tgagccagaa   2400
ggctaggaag gagcctacag tcccggtctc agcgcccagg aggttttct aatggagttg   2460
gcatgcagaa gctggggcat accctgggag cagccctgtg gctggatgag ggatggacag   2520
cagcactggg cgggtggagc cgggtgcgag gtccccacag cctgcctccc agtcccactg   2580
gccagcccgg ggagggtgct gaagacaggc ttcctctctg gtcaagtctc ggctagcttg   2640
gcaagtgcag gcaggaccct ggacctgcca tatggtgcac attttgagga catcattagc   2700
aggtttggaa ggttgtgatt ctggttgtgg gagagaagga acctgggagt tgagcaggtg   2760
gtgggtggag ctatgcatgc aactgagtgt gaggagtgct ttggccatgc tagggtctcc   2820
tctgggctgg aagccttgtc ttcaagaggg ttggggtagg aggcttttta ttatagtggg   2880
aagcctcaag cctggacctg ggaaaacact ttctgggtat gaggaattaa aataaacctt   2940
gaagcactat ttaggaagaa catagtatca cttcatagat attttccccc ctaaatggtt   3000
acaaagtaaa atggcagagg tacaaagagg aaaatgaaaa ccacccaatc ccttccctga   3060
gcgatgccc tgttatcctt gggctctgtg gccatctgac ctctctctgg ggacagaagt   3120
acatgaggag aggggccact tcataagacg gagatgctct cttcctgttc cctgcctctg   3180
catcgtgctg gggatgtctg tcctcatcaa ctaagagacc catgtagacc gcagctctga   3240
gatcttctat ttttgtaaac agaacagttt gtagggagat gtgagatgtt aggtggtgct   3300
ggagagcctg ggctttgtct gtttggacaa ggctccatca aggcatcctt tgtccgacgg   3360
tgaggcatct tgagggctct ggaccccagag ctggtcctgc aagagtcctg tctgagagcc   3420
caggccccac tccactagga gggacaggag ggaacagagc agagctgagt cccttcacct   3480
acccaaaccc atacatgttt ctagagcaga gtaactgctt gtgaaacaga ccatcagagc   3540
acagggcagc accgagctgc gttctgcagg gctcggtcta ggtgatctgg agggcttggg   3600
gagctggctt ctcccctcat ccagcatgta gctacccaca gccacctgca tttcacaggg   3660
ccagtgccta gggacattgg gccagaagcc agaatttctt ttttcttttt tttttttccc   3720
tctagcattc actactagcg caagctagtg catcccaaag ttttggccct gcgtggataa   3780
tcaatccaca atttatcttc cgtctgttgc caaagtaatt tagctaaaat gcagatctca   3840
actggtcact tccctgcgta aaagcttcaa tagctttcta tcgcctacag gcaaaagtcc   3900
ctcttctgaa aagcggcttg caaagcccta gtagctggct ccatgccccc cagcaatacg   3960
tggcctcctc agacgcatct tctagcaaag gagagctgct cagtgacatc cacaaaccga   4020
gctgcttctc acctacctgt tttccttctc tttgggatgc ccccgccct caccttctgt   4080
ttctggctaa ctcctaggca tccttgaagg cttggctcag tatcctctcc tccaggaagc   4140
tgtccctcac ctttctctcct ttccctccat cccagtcacc atgcaccaca cccatatccc   4200
cattgcatcc tgcagctacc ttgtgcctgc acacgttagg ctgggcatgc atctccttct   4260
ctctcaagac ctggatccct tcactttgtg tctctggacc cccagtgtg ctgataatgt   4320
ggttggaacc catcatattt ctcttgaacg agttaatgat gggactgcta tttctctaac   4380
tgttgccttg gaggccctgt cacgtgctca tggaagagag ccagggggt ggaggtgatt   4440
cttgttaccc agaggacgtg gggtctggat acactttct gccatctgcc atctgccagc   4500
ttctttctgg ttggtagctt tggagcctgg tgcagctggg gccagtcccg agcctggact   4560
ctgctgggca gtggcaagag cactgtctgg agctctcctg aggagcccac agatccaact   4620
ccctaggcca aggctgcagc ctggggcaga gatgcagagg cctggaggag cctagggcac   4680
gcggcctgcg ggctggctgg ggttcagagt tcgtatgtgt gtggagtgac tgggcaggtg   4740
ttcagaaatg aagctggca ctgccaggta aggcccttcc ccctgatg tgagagccct   4800
ggagccaccg cagaggccca gtcagatctc tgttctaatt ctggcctggt gtggaggatg   4860
aggagagacg gcccagaaag gaaggcagac tgtgcagacc ccatgtcttc tggcccgcga   4920
ggccctcctc ctgtgcctgc ttatcttaaa gaatccggga taagaggtga cttgggcctt   4980
ggccgggagg cccctcctca gcttcagaca aggagggagc tctgggcatg aggacattga   5040
gcaagaggcg atggcagtgc ccacaactta ccctcagctc ggctctgttg ggtccgagaa   5100
gttgcatggg aagggctcct ggggggccag ttgtcagtaa gctgcagaag cctggagccg   5160
gccaggaaat aaccacgtgt aggagccttc tcagctgaga ggaaggagga ctcacgcgcg   5220
gcgagcacat gcttggagcc aggcacaggt ttgaactaag ctatttcatc tcgattctta   5280
tgacaagctc cacgtagttt gctccatttt tacagatgtg gaagctgagg ctcagagagg   5340
ttaagcgact tgtcccaaat cgcattgtca atcagtgaag gtgctgggat ttgagctagt   5400
cacctgcctc taggttcagt gtgctttcta ctctgctccc ctccatgcct gcccgaccct   5460
ttgctgatga cacattcctg agacctcaaa ggagtcctac tttgaatcat gaatggcctc   5520
gcgtttcccc agagggcatg acgcaagctt cgccacctca ctcccaccct caccactggc   5580
tggttgctct taggaagatg ctgttacag gatcacgcag tggttcaggc caccacgatg   5640
ccacttcccc tgctcttaac cccccaccaa actgcaggtg gcttccctgg gagactcggg   5700
```

```
gcaacaccct ctcgtcctgt atgaagcttg tacctttctc cacccaagtg agtgacagct   5760
ggcgggagtt ttgcactgtg gaacagggta cacaaagaca ctggagtgag aaggcagggg   5820
catggccagt ctatgtctag gaggtggtgg ctccaccttc cttgtggact cagctttgga   5880
gtcatgcagg ctgctctctg ggcactcctg tgagccattt cttctgctga tagggaggaa   5940
cgtcccactg ccccaagatg ggttctgtgc agagtctccc cagggtcaca acaggagcta   6000
gaatgtatgt catagaagga tgatctaaat ggtgacttct ggctggtgag gagaggctat   6060
ggcacctcca cggctggtgg cctcttgcta agtaagcat ggtcagcatc cccctgcac    6120
cctgtggagg tggcttaatg cattcccttg actgcaaagg actccttgcc aaagagacct   6180
tcttccccat gaggctgagg cctcctagga ccctcagtgc tcaggaaatt ataaccagcc   6240
accccatct ccattcattg gagaaggagt gacggccgcc tcagtgccat taactctgtg    6300
ctgtgattaa atggatccca aggagactcc tgctcaggga caccccctgt aggactgatg   6360
ccagggctag gcttgccgca cagtgctcta ttcctttggt tatgcacctt ccttggcaga   6420
atccacgctt accaagagga gtcactctga gctgcttgct gccagtcaca tgcttagcag   6480
tagaagatat cttgtgcttg tcaggtgact gtgagtgagg ggtgaagggg cccagcgtga   6540
agccaggtgg gacggcttct gcggggcaag acacccact ggaggaggca ggggcgcgct    6600
gtgcaggcct cagcaccagc tctggctgct gtggtgggat ctcagatcag tcactttgcc   6660
tttttggcct cagttttctc atctgtacat catggatttg ggattaaagg atttctgaag   6720
attttactca ttctgagatt atggtccctg gaaaccttta gggaaaaggg agcttcttct   6780
cttcattatt ttaacatact tgatctttta tgttctttgg tagggagaga tgataggtag   6840
ttagagaaga agcagctcag tgaaaaagct gaaagccttg tggaaaaata agttaaattg   6900
acccactgtg actccaggga cctggggaga ctttgatgtc cgtgttttg attacacatc    6960
tcttctctca gagtgaagat gcgcagttct aaggaattat gcccaatgac gaaattggca   7020
agggacaggg aactgtccag cagagaagct gctgaaaccc ttcagggaac attccattcc   7080
gccagggccc ggctctcacg ctctgctctg cagcgcatcc ggtgccaagg aggggagtag   7140
cgaacgttga ccttgtccct aaggagctta cacgcaggga ggtcagcaca gacactggaa   7200
tatctaggac tctgctatcg aaaaacacaa ttgctgacac atgggttcag aagacagaga   7260
aggaaaagag ctgtaaagag ttgggtgggc tgaggtttga aatgggcttt aattatgact   7320
ggacacaatt tggtgacaaa tgggtgaaat ttcaagcaga agaggtagca tgagcaaaaa   7380
ggggtgtgca gtctttgtga agagaagggg gagggagtgg caaggaata ggacagagag    7440
gaggagggag gagaggaagc cagagataag gagccaggga gggaagaaaa gggcagaaac   7500
gaatgtgaag gagattctga agacaagcca ctgtggtggt ccaggtggtt ccatggtgcc   7560
gcgccaagcc aggggcttgg aatttagtct gggaggatgg tgctgagtat ggatgaggaa   7620
ggagaggaat ggagagggga gaaacgggaa ggtacttcac actgattaag caagctcctc   7680
acagggctat gacttctccc ttctcagaag gaggtgccc gtggcatgcc tctaggccca    7740
gagttaaaga gctggagcca ttaggagcag caaggggctg cctccccact tgtctggtta   7800
cttctggtta cttctcccte agggtaagtc tcatgaggg atcatctctg cccatggagc    7860
tgcttccgct gcccttaggc tggtgtaaga ggaaggctgt gtaccagagg tagatcttgc   7920
tcctagtcca ccagcaaaac acatccagtt atttctatgc ctcagtctcc cttccccaca   7980
ctgatctctt tattcccta ctacctagaa atggaaggga gacaatgagg tgggaaatag    8040
agttttttcga aaggtgtttt ttggataaga caaaggcctc tcagagcaga gctggccatt   8100
ggaatggttt ccttttgtta tttaataccg gggctttcac acaggagttt agcccagctt   8160
ttaagtcttc agtatcaaat agtagttggt gtcacatccc tgctgaaata cagccatgaa   8220
aatgttttctt agtgatagat ttaggttgta ctcccttaaga aaagcccaaa tgtcaagaat  8280
tgcttcccac tggtacactt tattgggag aagggcatct caaatagaag gatggttggt    8340
ctgtctagaa atggtaagaa tactacaggt taaaggcagt ggtggtctgg actaaatgac   8400
ccctgaaact cggattttat ggtgttttca atctctggct gagtacaggt tcctccctct   8460
cccttttgtgc ctccttgggg acctgggcta ttttctcctc gtgaaagag aatggataca   8520
tccattatga aaaccaattg atataattg agcctgcatg caggtaaaaa ctatattaag    8580
aaggttata aaatcaacc ttctggctta acaagctgat tctcaaagtg gcctctcaga     8640
ccctggctga gggatggtgg tcaggggttg cagagggacc cgcacagctg ctgaggaggc   8700
tgtgggacag gaggcgctat cactgtctac ctcttccaca catgcacctg tgtgcaggtg   8760
tgagaagggc accgtgctgc aaagaagggt ccttttccacc ctctgcgggt tgctgccggc  8820
tccccgatgc ctgcctctga ggcctgagcc tggggctggg gagtgtgctg gcctcacctc   8880
tggaggatac tgcctcagtg ttacagcctg accccccacc ttgtcatcac tgcctactac   8940
agaccagagg ggacggccac agagactctg caaccatggc ctctgccctt cttccttctg   9000
cctgtgtatc tgtgaaaaac tttttttttt taaatggag aaagctacct tgacttctca    9060
gagagttgaa tggggtcagg ggatagaatc tatattttt agttatgggc acttacccat    9120
attcaaaaag atttgaggag gctggcagaa tggagctggg agaagaaaac cctcccctgg   9180
gaggaagctg tcctgtgcat gttggccagg ctgcctcttt gattagggac aatggaaacc   9240
ggcctgaggg cacgggtgaa agcagttgag tgtagaggag gctctgcagc agaagccaga   9300
ggacacagga gccagtgaag acacacaata agtcagaaag gagggatctt tgcagcccca   9360
aaagtagaaa ttcttaccat ctactgcaaa gagcaaaagt tgaaaattgg tctgattttct   9420
atctaaatgt gcttacatat tcgtgttctg ttaaatactt ctgtaacctg tgtgtctcac   9480
ataaatgcag ctttcttag ttttggaaat aaatcacatg aatcctgaat agtagtcttt    9540
aataatttgc ttagttgtag ggcagtgttg tgttttcaga aggcaagtgt atttgctaga   9600
agagtgagct gggaggtgtg aaccacatcg tcacatctgc tgtaagccta gccgttcata   9660
atacggagtt acagttagga cacgtcgccc tgaagagcta ccatcgaatg tgtgctcatc   9720
aaatgcctgg cagcgtcctc ggtgcttcac ctgccatagc cgacagtggc tgacctccca   9780
tgcctgttgc cttttcttc tgttggatca gggatacact gccatgtgtg ttaagaaaag    9840
ctggccttac ctacagggct ggccagtccc ggtcacgttt ctagtaagcc attgccttac   9900
ataagggtaa cggcatggga cgctatctta gccaatgtga taaaagtgga catgaggtga   9960
gaggcttcag agagaggttt taaaaaagag acaaagcag gacgttgcct ctcttcctcc    10020
tctccacgtg tcctacccgg atgtgaagcc aaaacagatg caggcttagt gcaaccatgg   10080
ggaacccagc ataagcacag attcaacagc agaagagtgg cagaggaagg aggtgaaagg   10140
aacctaggtt ttcctgtcct tgttgagtca ttcagttaaa aatccctgga attttcctct   10200
ctccggcagt gtgttttgtg ggataatgag ttgcttatt ggggttggct tgctagtcgg    10260
gatgtttcgc tcccatcaac atccatacgc ttgctctgtg aaccaatgac ctgatgaggt   10320
agtattagca ccaccatcat tatgctgagg atgagattta tggcacagtg gttcagtagc   10380
ttgcccaagg ccatgcggct ggtaggttct ggaggagggc tcagggcacc ccctgagcta   10440
```

```
cccctgctgg ccattgcacc accccataaa gctgctggca gtcacttctc tgagggggtta   10500
gcatgtaaga aatgtcctcc tgaatgctgg ccagacaaat ggaaatctgc cagggttggg   10560
tacccccatg acagcagcca gcctgccctc ttagtccctg acagctgcag tgacagcatc   10620
tgtgattgca aagcgtgaca atttatatct ctcatttcat cacaccatct atcagcagac   10680
agtcaggctt taaaaatcaa tcccacactg actcagtccc cagcagagat ggcctctgac   10740
aacagtatcc acactgcagg ctggacaagg gccctattaa ttttgagact cagccaaatt   10800
tccttctgac cctaagctgg tgaatccctg ctcctttgct ttggttgggg ttggtgtgag   10860
ctaaggctgt gatcccattt gctcctatgg cctccaggtg gcctgggcct ccatgaatgg   10920
gccacatggt catactgaat gcttgattac actcagacct agcagtcgtc tgggcgcagc   10980
tggtttatgg atcactttgt cacaatgttc catccttcca ggtccccatc cccgcggtgg   11040
gaaaacattg ctttaggcag tgctagagga cttcagcagg cattggcagc ttctggattc   11100
aggattagaa caaagaagga ggagtcacag caaagatagg aacagaaggc agagagaaca   11160
gacagatggg ggtgtttgag aaggagggcc tttgagacct cagggagtgg gagacactgg   11220
ctcgagaata ataataatgg caatttctct catctgtgtt ttcagggcat ggactggaac   11280
tcccaatacc cctgacatgg gctgagtcaa cgtggtcatg aacatgtgac aggaggcagc   11340
agaagttgca gagaagagtg aggcacgttt gaaaaaggct gaaaaatgtt tctgtccagg   11400
caagggtgtg tgctgaatga ctcaaggatt ttttggagag aattggagtg tctccaccaga  11460
ggagaccacg tctgaagggc tttgcatccc tccttgacca tgtctaatac ctaacactca   11520
gaaagcatcc agtaaatatt cgtggaaaga aaggagtgga gaaggggaga aaggggaaag   11580
ggagtaggcg agagagaaga aagactctgc ttcttgccca gggcctggca tggggcggag   11640
gcaaagcagt ggggtcctca gctatgtccc actgtgagtg cacagcgagt cctgaccttc   11700
agagggtgca gcccgagggg ccctggcctg tctgaaggggt gcgccagccg agtggcctgc   11760
tctgaccacc aggctcaccc atgactacct gggtggctac agccagttcc tgacaatgag   11820
tacagcactc agttatcggg gcccttccac ccacacgctg tccacttcct ggggtactgc   11880
tgtgggcatg tgagtgcttg ctccccgggg cactgctgtg ggcatgcgag tgcttgctcc   11940
ccggggcact gctgtccact tcctgggggta gctgctgtggg catgcgagtg cttgctcctc  12000
ggggcactgc tgtggacatg tgatagcttg ctccccagct ccactagtga cactggcggc   12060
ccctcgctgg ggccttcccc gcctgctccg ctccattacc gctgccgggc tcctcacgtc   12120
tctccttgct gcttcctgca ctgggtgag gagagtgggg ctggtcccct tgagaccgga    12180
gaagctccag gcttttaagg aaaactgcca gggacgaagg gaagatatca cttccccacg   12240
tggttggctt ccagattcag aaggaatgtc tgtccttgtg gattccgtac cagatgaccc   12300
cagatgctgc tcagtactca ggtccctgtg gctctggagc ctttgctggg tctgggcagt   12360
gtctcttcct ctccagttca tccttgggtc tcttcaccct tgccaggggc aggcttcctg   12420
gtgagaggtc gacctcctgc atgaaggctc tcaagaggcc agttcaaagc caagctccgg   12480
gtctgtgcct gtggggctgc tcctcgatca ggagatggtc actcccctcc tggtctgtat   12540
ctgtgggatt ctcctccatc aggagatggt ctctcccctc ctggtctata cccgtgggat   12600
tctcctccat caggagatgg tcactcccca tcctggtcta tacccgtggg attctcctcc   12660
attagatggt cactcccctc ctggtctatt cccgtgggc tgctcctcca tcaggaggtg   12720
gtcactcccc ctcctggtct ataccgtgg ggctgctcct ccatcaggag atagtcactc   12780
ccctcctggg tctataccc tgggattctc ctccatctgg agatggtcac tcccctcctg   12840
gtctataccc atgggattct cctccatctg gagatggtca ctcccctcct ggtctatacc   12900
catgggattc tcctccatct ggagatagtc actcccctcc tggtctatac ccgtggggtt   12960
ctcctcaatc aggaggttgt cactccccctc ctggtctata ccgtgggat tctcctccat   13020
caggagatgg tcactctccc tcctggtcta tacccgtggg gctgctcctc catcaggaga   13080
tggtcactcc cctcctggtc tatacctgtg ggattctcct cccctcagaag atggtcactc   13140
cccctcctgg tctatacccca tgggattctc ctccctcaga gatggtcac tcccctcct   13200
ggtctatacc cgtggggctg ctcctccatc aggagatgt cactctccct ctcggttgct   13260
cagtccaaaa acaacctctc tggaaaactg cgtggaattt ttttttaaag aattgaaact   13320
agaactagca tttgatccag ccatctgcct actgggaata cacccaaaga aaaataaatc   13380
attatatcag aaagatagaa tatgcatgtg gatgttcatt gcagcaccat ttactatagc   13440
aaagatgggc agttgagcta agtgtccaac agtggtaaga tggataaaga gaatgtgtta   13500
cacacacagt atgaatatt actcaggcat agcaaagaat gaaatcatgc cttttgcagc    13560
aacatggttg gaggtggagg tcaggagtta gagaccagcc tggccaacat ggtgaaatcg   13620
tgtctctact aaaaatacaa aaattagccg ggcatggggg tgcacacctg tagtcccagc   13680
tactctggag gctgaggcag gagaatcgct tgaacccagg aggtggagat ggcagtgagc   13740
tgagatcaca ccactgcact ccagcctggg caacagagtg aaatcctgtc tcaaaaacaa   13800
aaataaaaac aaaaaaagca tacaaaccac aggagctcct cttggtcccc ctttgtcttt   13860
cattccacct ccagaaatcc cagcagaatc accttcaaaa actcctagaa tccaattttt   13920
cccctccatt gctactgccc tgatctgagc ctccataacc cttacccaaa tgcttcctaa   13980
acgtatcctg gctggtgctg ctgaattcca tgtcttttcca gctgcccttt aaaaatacggt   14040
aggaggcaag tcttttctca aaaccctcca gtggcttctc tctcagagtt aagatcctgc   14100
agtggccttc ctggcctcag gtagtgtctg ctgtcctgta ccctcggcca ctatactcca   14160
gccacatggc tttgtgtttc ccttggacat atccagcatg tttctgcccc acggttttgg   14220
cacttgctgt cctttctgcc tggagctcct tctcctccct ctgcactgaa gaccctccct   14280
tcctttcagg atgcagagca cattatgctg tcataaccac acccccatatt cacccttaca   14340
cgatgtgtcc ctctctggcc agctagggc tcagctccat gagccccttg tcctggcaac   14400
aaagctggct ggggcggcca cctgaagtat gtctcatgga gctgactcaa tgagagacac   14460
agttcattcc atgcacagtc cacgccacag taagtcacgt ggcagcgct gacttccctt   14520
gcacaggaag aacctgcacc caccaccgc gggagaaggat ctagagctgg gatgactgag   14580
caggatgcta acaacctcaa agttcttctt agacctcatg tcttgaacag ccctaggcaa   14640
catagcaaca cacgccatga caaccccaca agaaggcaac ccgtcctctg acagcttctg   14700
gtgacaaagc caccccgctt gtgacaacct caggtcacac agcagctcct ccccctgacaa  14760
cctaaggtca cacaacaact tctcctttta aagtctcagg tgacacagca gactctcccc   14820
tgacaaactc aggtcacaca gtaacccttc agctgacctc aggtgacaca gccaccctca   14880
ccctgacaac tcaggtcac acagccaccc ctccccctgac aacctcaggt cacacagcca   14940
ccctcccct gacaacctca ggtcacacag ctacccttca actgacaacc tcaggtcaca   15000
cagccacccc tccctgaca acctcaggtc acacagccac ccctccctg acaacctcag   15060
gtcacacagc caccccctctc ctgacaactt caggtcacac agccaccct ccctgacaa    15120
cctcaggtca cacagccacc cctctcctga caacttcagg tcacacagcc acccctcccc   15180
```

```
tgacaacctc aggccacaca gccacccctc acctgacaat ctcaggtgac acagccaccc   15240
ctccccctcac aacctcaggt cacacagcca ccctcctca gacaacttct gacatagcaa    15300
ctccttgcct gacaacccta ggtaacatag caacccctccc ttgacaaccc atgtgacatg   15360
gcaatgcttc tcctgacagc cacatgtcag caacctctgc ctgacaaccc aggtgacata    15420
acagcacccc ccgacaaccg catgttacct tgccacccct ccataccgac tgtatgtggg    15480
tatccctccc tacccgcct tgggagccc atgtgaggta gccagccttt ccctggccct      15540
gggccctcca tttctgcttg ctgtctcctc tgttcctccc aagaactcac tgctctaccg    15600
tgtaatctct tgtttctctg ctgtcttagt ccgcttgggc tgccggagga gcacaccttg    15660
ggcagggagg cttagatgca cctgtgcatg gttctggagg cccagg                  15706

SEQ ID NO: 60          moltype = DNA   length = 744
FEATURE                Location/Qualifiers
source                 1..744
                       mol_type = other DNA
                       organism = Homo sapiens
SEQUENCE: 60
aagcgtaggt gatgagcttg aatcagggca tggactggaa ctcccaatac ccctgacatg    60
ggctgagtca acgtggtcat gaacatgtga caggaggcag cagaagttgc agagaagagt    120
gaggcacgtt tgaaaaaggc tgaaaaatgt ttctgtccag gcaagggtgt gtgctgaatg    180
actcaaggat ttttttggtgc attgaatgaa cagcgggaca ttggacacct gctgatccat   240
caccccgggc ccgggcaggc ccgtggatga agagagatgg agaagaccag gcatgagact    300
gtggagaagc cacaccacca gaaacccctg ccccatgcgc cgtccagccc acacctgtgg    360
atgcacgggg gattgcaggc agggctccca ccgtggactc aggaacaggc agggaagctg    420
ctgcctcacc aggcgaaggg gccaggaggg ggaggcggag aggcccgtct agcccctgcg    480
gctgtcaccg tggtgcctcc tcactggcca gtgcggtcgc gcctcagctt cgttaatagg    540
ggaggggggcc taagagtttt cacgtccagg ctcgggacgg gggaggcag gcaggagtgg    600
ccgctggttt ttcagacctc ccagggaggc cgaggaaatg gcccgtcctg gagtgggcgt    660
ggttctgtct tcagatggat gctggagggt tgggctgcgt gggaccctgg gccctgctgc    720
ttcccggagg atgcgctgtc cggg                                          744

SEQ ID NO: 61          moltype = DNA   length = 1129
FEATURE                Location/Qualifiers
source                 1..1129
                       mol_type = other DNA
                       organism = Homo sapiens
SEQUENCE: 61
aagcgtaggt gatgagcttg aatcaggtaa gaattatatt ctacttccag ctaaagaaga    60
ggatatagaa gatcaaatagc ttaaacaaaa cagaagggca tggactggaa ctcccaatac   120
ccctgacatg ggctgagtca acgtggtcat gaacatgtga caggaggcag cagaagttgc    180
agagaagagt gaggcacgtt tgaaaaaggc tgaaaaatgt ttctgtccag gcaagggtgt    240
gtgctgaatg actcaaggat ttttgggca acacaaacca acacgagccg tgtgaggatc    300
aggtgacagc tgcccaaaag ctgacacaag gaacaagcct ggaggagtga ggatgggtgc    360
tgtgaaggag gttgtgcagc tgggcccgca gtcggacctg aggatcag aggagggggt    420
gccaccagtc tgtggacgaa gatgagaagc tggaatagag cagaaaacag gaggctgcca    480
ctctccatct ttcccaaagt cactccagga gcaagggtgt catttactga aatgacagac    540
tctccatttc acattttttcc cccaagtgca gagtgcaggg aagcagatgg gctaaatttt    600
tagagtcagg gttattaatg tatactttac atagtaaact ttccccttt aagtgtgcag    660
gcctgaggtt tgccaaatat gtgtaggcat ttaatcacca ccacgatcaa gatgtagaat    720
attcccacta tcaaaaagtt tgctgtgtcc cttgatggtc atgccccatt ccacagcccc    780
agccccagcc cctggagatt gctgtctgct ttatgttcca gtggttttat cttttccaga    840
ctgtatggat gtgaatggaa tcagatgtga ttccaaggtg ttttatcttt tccagatgtg    900
aatggaatca gatgtacgaa atcctatggt aggggggtctt ctgagtctag ctccttttgt    960
ttagcgtgat gcatttgaaa ttaatccatg tctcaggcat caggagttca tttcttttttc   1020
tgctgagtag tatttcattg tatggatgta ctgcaatttg cctatccatt cacctgttga    1080
tgtacatttg agatttttgg caattatgaa taaagctgct ataaacaga               1129

SEQ ID NO: 62          moltype = DNA   length = 1843
FEATURE                Location/Qualifiers
source                 1..1843
                       mol_type = other DNA
                       organism = Homo sapiens
SEQUENCE: 62
atttagctaa aatgcagatc tcaactggtc acttccctgc gtaaaagctt caatagcttt    60
ctatcgccta caggcaaaag tccctcttct gaaaagcgc ttgcaaagcc ctagtagctg     120
gctccatgcc cccagcaat acgtggcctc ctcagacgca tcttctagca aggagagct     180
gctcagtgac atccacaaac cgagctgctt ctcacctacc tgtttttcctt ctctttggga   240
tgccccccgc cctcacctcc tgcttctggc taactcctag gcatccttga aggcttggct   300
cagtatcctc tcctccagga agctgtccct caccttctct cctttccctc catcccagtc   360
accatgcacc acacccatat ccccattgca tcctgcagct accttgtgcc tgcacacgtt   420
gggctgggca tgcatctcct tctctctcaa gacctggatc ccttcacttt gtgtctctgg   480
accccccagt gtgctgataa tggggttgga acccatcata tttctcttga acgagttaat   540
gatgggactg ctatttctct aactgttgcc ttggaggccc tgtcacgtgc tcatggaaga    600
gagccagggg ggtggaggtg attcttgtta cccagaggac gtggggtctg atacacgtt    660
tctgccatct gccatctgcc agcttctttc tggttggtag ctttggagcc tggtgcagct    720
ggggccagtc ccgagcctgg actctgctgg gcagtggcaa gagcactgtc tggagctctc    780
ctgaggagcc cacagatcca actccctagg ccaaggctgc agcctgggc agagatgcag     840
aggcctggag gagcctaggg cacgcggcct gcgggctggc tggggttcag agttcgtatg    900
tgtgtggagt gactgggcag gtgttcagaa atgaaggctg gcactgccag gtaaggccct    960
tccctccctg atgtgagagc cctggagcca ccgcagaggc ccagtcagat ctctgttcta   1020
```

```
attctggcct ggtgtggagg atgaggagag acggcccaga aaggaaggca gactgtgcag  1080
accccatgtc ttctgcccg cgaggccctc ctcctgtgcc tgcttatctt aaagaatccg   1140
ggataagagg tgacttgggc cttggccggg aggcccctcc tcagcttcag acaaggaggg   1200
agctctgggc atgaggacat tgagcaagag gcgatggcag tgcccacaac ttaccctcag   1260
ctcggctctg ttgggtccga gaagttgcat ggaaaggct ccttgggggc cagttgtcag    1320
taagctgcag aagcctggag ccggccagga aataaccacg tgtaggagcc ttctcagctg   1380
agaggaagga ggactcacgc gcggcgagca catgcttgga gccaggcaca gggcatggac   1440
tggaactccc aataccctg acatgggctg agtcaacgtg gtcatgaaca tgtgacagga   1500
ggcagcagaa gttgcagaga agagtgaggc acgtttgaaa aaggctgaaa aatgtttctg   1560
tccaggcaag ggtgtgtgct gaatgactca aggattttt ggtgcattga atgaacagcg    1620
ggacattgga cacctgctga tccatcaccc cgggcccggg caggcccgtg gatgaagaga   1680
gatggagaag accaggcatg agactgtgga gaagccacac accagaaac ccctgcccca    1740
tgcgccgtcc agcccacacc tgtggatgca cgggggattg caggcagggc tcccaccgtg   1800
gactcaggaa caggcaggga agctgctgcc tcaccaggcg aag                    1843

SEQ ID NO: 63       moltype = DNA length = 1160
FEATURE             Location/Qualifiers
source              1..1160
                    mol_type = other DNA
                    organism = Homo sapiens
SEQUENCE: 63
gagcactgtc tggagctctc ctgaggagcc cacagatcca actccctagg ccaaggctgc   60
agcctggggc agagatgcag aggcctggag gagcctaggg cacgcggcct gcgggctggc   120
tgggggttcag agttcgtatg tgtgtggagt gactgggcag gtgttcagaa atgaaggctg  180
gcactgccag gtaaggccct tccctccctg atgtgagagc cctggagcca ccgcagaggc   240
ccagtcagat ctctgttcta attctggcct ggtgtggagg atgaggagag acggcccaga   300
aaggaaggca gactgtgcag acccatgtc ttctgcccg cgaggccctc ctcctgtgcc    360
tgcttatctt aaagaatccg ggataagagg tgacttgggc cttggccggg aggcccctcc   420
tcagcttcag acaaggaggg agctctgggc atgaggacat tgagcaagag gcgatggcag   480
tgcccacaac ttaccctcag ctcggctctg ttgggtccga gaagttgcat ggaaaggct    540
ccttgggggc cagttgtcag taagctgcag aagcctggag ccggccagga aataaccacg   600
tgtaggagcc ttctcagctg agaggaagga ggactcacgc gcggcgagca catgcttgga   660
gccaggcaca gggcatggac tggaactccc aataccctg acatgggctg agtcaacgtg    720
gtcatgaaca tgtgacagga ggcagcagaa gttgcagaga agagtgaggc acgtttgaaa   780
aaggctgaaa aatgtttctg tccaggcaag ggtgtgtgct gaatgactca aggatttttt   840
gggcaacaca aaccaacacg agccgtgtga ggatcaggtg acagctgccc aaaagctgac   900
acaaggaaca agcctggagg agtgaggatg ggtgctgtga aggaggttgt gcagctgggc   960
ccgcagtcgg acctggtgag atcagaggag ggggtgccac cagtctgtgg acgaagatga   1020
gaagctggaa tagagcagaa aacaggaggc tgccactctc catctttccc aaagtcactc   1080
caggagcaag ggtgtcattt actgaaatga cagactctcc atttcacatt tttcccccaa   1140
gtgcagagtg cagggaagca                                              1160

SEQ ID NO: 64       moltype = DNA length = 572
FEATURE             Location/Qualifiers
source              1..572
                    mol_type = other DNA
                    organism = Homo sapiens
SEQUENCE: 64
cgctctgctc tgcagcgcat ccggtgccaa ggaggggagt agcgaacgtt gaccttgtcc   60
ctaaggagct tacacgcagg gagggcatgg actggaactc ccaatacccc tgacatgggc   120
tgagtcaacg tggtcatgaa catgtgacag gaggcagcag aagttgcaga gaagagtgag   180
gcacgtttga aaaaggctga aaaatgtttc tgtccaggca agggtgtgtg ctgaatgact   240
caaggatttt tgggcaaca caaaccaaca cgagccgtgt gaggatcagg tgacagctgc    300
ccaaaagctg acacaaggaa caagcctgga ggagtgagga tgggtgctgt gaaggaggtt   360
gtgcagctgg gcccgcagtc ggacctggtg agatcagagg gggtgccac accagtctgt    420
ggacgaagat gagaagctgg aatagagcag aaaacaggag gctgccactc tccatctttc   480
ccaaagtcac tccaggagca agggtgtcat ttactgaaat gacagactct ccatttcaca   540
tttttcccc aagtgcagag tgcagggaag ca                                 572

SEQ ID NO: 65       moltype = DNA length = 4435
FEATURE             Location/Qualifiers
source              1..4435
                    mol_type = other DNA
                    organism = Homo sapiens
SEQUENCE: 65
caaatgcctg gcagcgtcct cggtgcttca cctgccatag ccgacagtgg ctgacctccc   60
atgcctgttg ccttttcttt ctgttggatc agggatacac tgccatgtgt gttaagaaaa   120
gctggcctta cctacagggc tggccagtcc cggtcacgtt tctagtaagc cattgcctta   180
cataaggta acggcatggg acgctatctt agccaatgta ataaagtgg acatgaggtg     240
agaggcttca gagagaggtt ttaaaaaaga gacaaaagca ggacgttgcc tctcttcctc   300
ctctccacgt gtcctacccg gatgtgaagc caaaacagat gcaggcttag tgcaaccatg   360
gggaacccag cataagcaca gattcaacag cagaagagtg gcagagggag aaggtgaaag   420
gaacctaggt ttttcctgtcc ttgttgagtc attcagttaa aaatccctgg aattttcctc    480
tctccggcag tgtgttttgt ggggataatga gttgccttat tgggggttggc ttgctagtcg   540
ggatgtttcg ctcccatcaa catccatacg cttgctctgt gaaccaatga cctgatgagg   600
tagtattagc accaccatca ttatgctgag gatgagattt atggcacagt ggttcagtag   660
cttgcccaag gccatgcggc tggtaggttc tggaggaggg ctcagggcac ccctgagct    720
accctgctg gccattgcac caccccataa agctgctggg agtcacttct ctgaggggtt    780
agcatgtaag aaatgtcctc ctgaatgctg gccagacaaa tggaaatctg ccaggggttgg  840
```

```
gtaccccat   gacagcagcc   agcctgccct   cttagtccct   gacagctgca   gtgacagcat    900
ctgtgattgc  aaagcgtgac   aatttatatc   tctcatttca   tcacaccatc   tatcagcaga    960
cagtcaggct  ttaaaaatca   atcccacact   gactcagtcc   ccagcagaga   tggcctctga   1020
caacagtatc  cacactgcag   gctggacaag   ggccctatta   attttgagac   tcagccaaat   1080
ttccttctga  ccctaagctg   gtgaatccct   gctccttgtc   tttggttggg   gttggtgtga   1140
gctaaggctg  tgatcccatt   tgctcctatg   gcctccaggt   ggcctgggcc   tccatgaatg   1200
ggccacatgg  tcatactgaa   tgcttgatta   cactcagacc   tagcagtcgt   ctgggcgcag   1260
ctggtttatg  gatcactttg   tcacaatgtt   ccatccttcc   aggtcccat    ccccgcggtg   1320
ggaaaacatt  gcttaggca    gtgctagagg   acttcagcag   gcattggcag   cttctggatt   1380
caggattaga  acaaagaagg   aggagtcaca   gcaaagatag   gaacagaagg   cagagagaac   1440
agacagatgg  gggtgtttga   gaaggagggc   ctttgagacc   tcaggagtg    ggagacactg   1500
gctcgagaat  aataataatg   gcaatttctc   tcatctgtgt   tttcagggca   tggactggaa   1560
ctcccaatac  ccctgacatg   ggctgagtca   acgtggtcat   gaacatgtga   caggaggcag   1620
cagaagttgc  agagaagagt   gaggcacgtt   tgaaaaaggc   tgaaaaatgt   ttctgtccag   1680
gcaagggtgt  gtgctgaatg   actcaaggat   ttttggtgc    attgaatgaa   cagcgggaca   1740
ttggacacct  gctgatccat   caccccgggc   ccgggcaggc   ccgtggatga   agagagatgg   1800
agaagaccag  gcatgagact   gtggagaagc   acaccacca    gaaaccctg    ccccatgcgc   1860
cgtccagccc  acacctgtgg   atgcacgggg   gattgcaggc   aggctcccca   ccgtggactc   1920
aggaacaggc  agggaagctg   ctgcctcacc   aggcgaaggg   gccaggaggg   ggaggcggag   1980
aggcccgtct  agccctgcg    gctgtcaccg   tggtgcctcc   tcactggcca   gtgcggtcgc   2040
gcctcagctt  cgttaatagg   ggaggggggcc  taagagttttt  cacgtccagg   ctcgggcagt   2100
ggggaggcag  gcaggagtgg   ccgctggttt   ttcagacctc   cagggaggc    cgaggaaatg   2160
gcccgtcctg  gagtgggcgt   ggttctgtct   tcagatggat   gctggagggt   tgggctgcgt   2220
gggaccctgg  gccctgctgc   ttcccggagg   atgcgctgtc   cggggctgca   caggttggct   2280
gtgtttttttg dgatgcttgat  attttgtttt   ttcttctctt   cactctgtca   tgaaactggc   2340
aatagtagtt  tgtaaataaa   tatgtgttat   agatgaatat   ttgctatgag   taaattaata   2400
aaggagtgaa  taaatgagcg   attgatgtag   ggcctgtcct   gtctcaggga   gcccacgaa    2460
ggcctgcgcg  ccgccagag    cctgcctgcc   tgccagggta   ctgggacgtc   actctcaaag   2520
cggcgggacc  cagccgctga   tcttgctgag   gaggcccggt   ctcagaaaac   tgagcggctg   2580
cttctgcaga  ccctgcatcc   tccccctccct ggagaaagaa   gctctggctg   agtcctggga   2640
ccgaacccct  gggtgccaca   gaaacgggct   ttgctgcctg   tcagtcaagc   ggcgggagaa   2700
acagacctgg  ggaggaggag   gctgggaggg   ctgtgttttc   tgcacagcga   gtagctcctt   2760
agcctggtgc  catttctctc   caaacaccct   gaaggttgag   tccagggtga   agatgtagag   2820
gcaagttttg  gggggatgga   gtgggcttgg   agggatgctg   gcgccttagc   aggctgtgct   2880
cctgaggtgc  ccagtgtctg   cgggcacagg   aacatgttgc   cgagggcatt   tgggtgtggg   2940
tggggtgggg  aaagggagac   agggctgtct   cttttaatgg   gtatctgcga   gcatgtgatt   3000
gtaagagagg  aagaagtagg   ggaggaagaa   ggcctccttg   ggaggtgcgt   catcctgagg   3060
aaggctgaac  aatgagggtc   ttggagagtc   aattcagaag   cacaaccttg   cagagcaggc   3120
aaaaacaata  gggcttcttg   aggctgcccg   ggcactcatg   caatcaccat   ttcctgctgt   3180
gaatgagcct  acattttgtt   ggggaagaga   cgcaacgacg   ccaaacgatg   gactctgagt   3240
caacgataag  atgaaacaaa   attaaaacaa   agtaggaaat   caagagtggc   tgctgtgatg   3300
gcgttgcgga  gatgatgttt   gctttgagaa   ctggacaagt   gagcccctga   gctgcatctg   3360
cacccagagg  ctgagccggt   gcacaggact   tgcagaggca   tgggctggg   cttgtagagc   3420
agcacaacgg  ccccaggcct   ggaggagcaa   gggtgggaag   gggggcaggc   cagctcctgc   3480
caggctggag  aaggactcgg   acctcaggcc   acctgtgcct   gggtgattgt   gaacttgtaa   3540
caaatgtgat  cttatttatg   ttttgaaaaa   ggcaacacaa   accaacacga   gccgtgtgag   3600
gatcaggtga  cagctgccca   aaagctgaca   caaggaagca   gcctggagga   gtgaggatgg   3660
gtgctgtgaa  ggaggttgtg   cagctgggcc   cgcagtcgga   cctggtgaga   tcagaggagg   3720
gggtgccacc  agtctgtgga   cgaagatgag   aagctggaat   agagcagaaa   acaggaggct   3780
gccactctcc  atctttccca   aagtcactcc   aggagcaagg   gtgtcattta   ctgaaatgac   3840
agactctcca  tttcacattt   ttcccccaag   tgcagagtgc   agggaagcag   atgggctaaa   3900
tttttagagt  cagggttatt   aatgtatact   ttacatagta   aactttcccc   ttttaagtgt   3960
gcaggcctga  ggtttgccaa   atatgtgtag   gcatttaatc   accaccacga   tcaagatgta   4020
gaatattccc  actatcaaaa   agtttgctgt   gtccttgat    ggtcatgccc   cattccacag   4080
ccccagcccc  agccccttgga  gattgctgtc   tgctttatgt   tccagtggtt   ttatctttttc  4140
cagactgtat  ggatgtgaat   ggaatcagat   gtgattccaa   ggtgttttat   cttttccaga   4200
tgtgaatgga  atcagatgta   cgaaatccta   tggtagggg    tcttctgagt   ctagctcctt   4260
ttgtttagcg  tgatgcattt   gaaattaatc   catgtctcag   gcatcaggag   ttcatttctt   4320
tttctgctga  gtagtatttc   attgtatgga   tgtactgcaa   tttgcctatc   cattcacctg   4380
ttgatgtaca  tttgagattt   ttggcaatta   tgaataaagc   tgctataaac   agaca        4435

SEQ ID NO: 66             moltype = DNA   length = 374
FEATURE                   Location/Qualifiers
source                    1..374
                          mol_type = other DNA
                          organism = Homo sapiens
SEQUENCE: 66
cttctgtcct  ctgggtcccc   acaagcctgg   atgaactcaa   gatctgactc   agtggcacag    60
tgaggagacc  tttgaggcct   cagtgaccat   ccttggactt   cacctctcac   ggctttcagg   120
cagagaggcc  ctcccatgcc   cacaacaggc   tgagcccagc   cttcctcggg   gtttgcttcc   180
aggcctgact  tttactcccc   tttctaagtg   tgctcccggg   aatgctgtct   acttgttgcg   240
attttactcc  cgtggcctgt   gctagctgcc   tgcttggccg   ttgggactga   agggatgctc   300
atccacttgg  cacactgact   gcaagcctgg   caccggcctt   gcctttgttc   tcccatgagt   360
cctcttgaag  gcaa                                                             374

SEQ ID NO: 67             moltype = DNA   length = 1245
FEATURE                   Location/Qualifiers
source                    1..1245
                          mol_type = other DNA
```

```
                        organism = Homo sapiens
SEQUENCE: 67
aaatgtcctc ctgaatgctg gccagacaaa tggaaatctg ccagggttgg gtacccccat    60
gacagcagcc agcctgccct cttagtccct gacagctgca gtgacagcat ctgtgattgc   120
aaagcgtgac aatttatatc tctcatttca tcacaccatc tatcagcaga cagtcaggct   180
ttaaaaatca atcccacact gactcagtcc ccagcagaga tggcctctga caacagtatc   240
cacactgcag gctggacaag ggccctatta attttgagac tcagccaaat ttccttctga   300
ccctaagctg tgaatccct gctcctttgc tttggttggg gttggtgtga gctaaggctg    360
tgatcccatt tgctcctatg gcctccaggt ggcctgggcc tccatgaatg ggccacatgg   420
tcatactgaa tgcttgatta cactcagacc tagcagtcgt ctgggcgcag ctggtttatg   480
gatcactttg tcacaatgtt ccatccttcc aggtccccat ccccgcggtg ggaaaacatt   540
gctttaggca gtgctagagg acttcagcag gcattggcag cttctggatt caggattaga   600
acaaagaagg aggagtcaca gcaaagatag gaacagaagg cagagagaac agacagatgg   660
gggtgtttga gaaggagggc ctttgagacc tcagggagtg ggagacactg gctcgagaat   720
aataataatg gcaatttctc tcatctgtgt tttcaggggca tggactggaa ctcccaatac   780
ccctgacatg ggctgagtca acgtggtcat gaacatgtga caggaggcag cagaagttgc   840
agagaagagt gaggcacgtt tgaaaaggc tgaaaatgt ttctgtccag gcaagggtgt     900
gtgctgaatg actcaaggat tttttgggca acacaaacca acacgaccg tgtgaggatc    960
aggtgacagc tgcccaaaag ctgacacaag gaacaagcct ggaggagtga ggatgggtgc  1020
tgtgaaggag gttgtgcagc tgggcccgca gtcggacctg gtgagatcag aggaggggt   1080
gccaccagtc tgtggacgaa gatgagaagc tggaatagag cagaaaacag gaggctgcca  1140
ctctccatct ttcccaaagt cactccagga gcaagggtgt catttactga aatgacagac  1200
tctccatttc acattttcc cccaagtgca gagtgcaggg aagca                    1245

SEQ ID NO: 68           moltype = DNA   length = 537
FEATURE                 Location/Qualifiers
source                  1..537
                        mol_type = other DNA
                        organism = Homo sapiens
SEQUENCE: 68
aatgcttgat tacactcaga cctagcagtc gtctgggcgc agctggttta tggatcactt    60
tgtcacaatg ttccatcctt ccaggtcccc atccccgcgg tgggaaaaca ttgctttagg   120
cagtgctaga ggacttcagc aggcattggc agcttctgga ttcaggatta gaacaaagaa   180
ggaggagtca cagcaaagat aggaacagaa ggcagagaga acagacagat gggggtgttt   240
gagaaggagg gcctttgaga cctcaggga tgggagacac tggctcgaga ataataataa    300
tggcaatttc tctcatctgt gttttcaggg catggactgg aactcccaat acccctgaca   360
tgggctgagt caacgtggtc atgaacatgt gacaggaggc agcagaagtt gcagagaaga   420
gtgaggcacg ttttgaaaaag gctgaaaaat gtttctgtcc aggcaagggt gtgtgctgaa   480
tgactcaagg atttttggc ctctgcctgt gtcctggccc tcactgcacc cccaaga       537

SEQ ID NO: 69           moltype = DNA   length = 1863
FEATURE                 Location/Qualifiers
source                  1..1863
                        mol_type = other DNA
                        organism = Homo sapiens
SEQUENCE: 69
cttcctcggg gtttgcttcc aggcctgact tttactcccc tttctaagtg tgcagatggg    60
atgtgcttct ccacaggagg ccccacggct tccccacccc tcagaggagc gccgtgcgtg   120
cgtctgtgtg gaggattggc agctcctgca gtcggccctt ggtcctattt ggcgacgcct   180
ctgccttccc cttaattata cagtcatgag ccgcctgga atcacggcag ctccggatgg   240
atcctggatg ccagaatgca gcctcagcac ggggctgca gacaggagtg agcgagggc    300
tgcagagccg gcggccgcgg tgggcaccat ggagggggct gccctgggca gcacgggcat   360
gagtctcaag gcccagggtt gagtaacagg tgttgagagc ttacttactt ttcctgagac   420
acagtttcct catctcgaga gcacggaaaa tcattctaac ttcagaggat tgttgtgaaa   480
gttaaatgag attaaagagg taaagcccat gacgtgctta gctcgtgctt ggctcttggt   540
caatgccagt tagcgctgca ttttctcccc tctccctccc tccttctctc tttctttcct   600
tctattctcc attcctgttt tctccccac cccactcccc aaagctctgc gttgagaacc    660
agatgctgtc tggtgggtta gggccagagg aggaaaagct gcccgccgtg ggctgcaccc   720
ataccctctt cattccaatg acatgagggg aggggaaagg acagaggtag actgtcctcc   780
cctacctcct cctaatacaa atggaattcc tggaactgga aaacaaagaa taccccata    840
aaaataagac agtacttctg gtgcggtgta ataagggga aagtaaccct caatgtcagg    900
aaactccgca cctcccagct catatttgtg tggaggaaaa gttaaatatt aattttggact   960
caactgaatg tggacacaaa caatggtcac caagtcccgg aacaggttgt gtgagcctct  1020
tcagggggttc atccagcgct gttttggaga atctctatt tcaatttatt cctatacgtt  1080
agttactgaa aaacaacaga caatcgcaaa agcaagttgc ccgttttgtg ttccttgagc  1140
ccaatcatga agtgccgtcg tgactgggcc tcatgacaaa caacttgtaa caagtaacaa  1200
cagagctcag gtcccagacc gcactgaagc tctgtgagac ctctcctcat ctgtgcatga  1260
acgagtgtct gactctggag cccagcctgc tgcttcccag tctggtggtg aatcctccgt  1320
agtctgatgg aggtttgctc ttgttgccca ggctggagtg caatggcaca atctcggctc  1380
actgcagccc ctgcctccca ggctcaagca attcttacgc ctcagcctcc tgagtagatg  1440
gaactacagg gcatggactg gaactcccaa tacccctgac atgggctgag tcaacgtggt  1500
catgaacatg tgcagggagg cagcagaagt tgcagagaag agtgaggcac gtttgaaaaa  1560
ggctgaaaaa tgtttctgtc caggcaaggg tgtgtgctga atgactcaag gatttttggg  1620
gcaacacaaa ccaacacgag ccgtgtgagg atcaggtgac agctgcccaa aagctgacac  1680
aaggaacaag cctggaggag tgaggatggg tgctgtgaag gaggttgtgc agctgggccc  1740
gcagtcggac ctggtgagat cagaggaggg ggtgccacca gtctgtggac gaagatgaga  1800
agctggaata gagcagaaaa caggaggctg ccactctcca tctttcccaa agtcactcca  1860
gga                                                               1863
```

| SEQ ID NO: 70 | moltype = DNA length = 3679 |
|---|---|
| FEATURE | Location/Qualifiers |
| source | 1..3679 |
| | mol_type = other DNA |
| | organism = Homo sapiens |

SEQUENCE: 70
```
gaggcagcca tgactggcca cttcatgtgc tcctggagaa gggcttgcac cagccgtttt    60
caggaaagtc aagcagctgt tgactcctga gtctgggtga atttgtgtga agagcataag   120
gcgctgtttc ttaaccaaaa cgcttcctct tgcagtgcag atgggatgtg cttctccaca   180
ggaggcccca cggcttcccc acccctcaga ggagcgccgt gcgtgcgtct gtgtggagga   240
ttggcagctc ctgcagtcgg cccttggtcc tatttggcga cgcctctgcc ttccccttaa   300
ttatacagtc atgagccgcc ctggaatcac ggcagctccg gatggatcct ggatgccaga   360
atgcagcctc agcacggggc tgcaggacag gagtgagcga ggggctgcag agccggcggc   420
cgcggtgggc accatggagg gggctgccct gggcagcacg ggcatgagtc tcaaggccca   480
ggtttgagta acaggtgttg agagcttact tactttcct gagacacagt ttcctcatct   540
cgagagcacg gaaaatcatt ctaacttcag aggattgttg tgaaagttaa atgagattaa   600
agaggtaaag cccatgacgt gcttagctcg tgcttggctc ttggtcaatg ccagttagcg   660
ctgcatttt tcccctctcc ctccctcctt ctctctttct tttcttctat tctccattcc   720
tgtttctcc cccaccccac tccccaaagc tctgcgttga gaaccagatg ctgtctggtg   780
ggttagggcc agaggaggaa aagctgcccg ccgtgggctg cacccatacc ctcttcattc   840
caatgacatg aggggagggg aaaggacaga ggtagactgt cctcccctac ctcctcctaa   900
tacaaatgga attcctggaa ctgaaaaaca aagaatacca ccataaaaat aagacagtac   960
ttctggtgcg gtgtaataaa ggggaaagta accctcaatg tcaggaaact ccgcacctcc  1020
cagctcatat ttgtgtggag gaaaagttaa atattaattt ggactcaact gaatgtggac  1080
acaaacaatg gtcaccaagt cccggaacag gttgtgtgag cctcttcagg ggttcatcca  1140
gcgctgtttt ggagaaatct ctatttcaat ttattcctat acgttagtta ctgaaaaaca  1200
acagacaatc gcaaaagcaa gttgcccgtt ttgtgttcct tgagcccaat catgaagtgc  1260
cgtcgtgact gggcctcatg acaaacaact tgtaacaagt aacaacagag ctcaggtccc  1320
agaccgcact gaagctctgt gagacctctc ctcatctgtg catgaacgag tgtctgactc  1380
tggagcccag cctgctgctt cccagtctgg tggtgaatcc tccgtagtct gatggaggtt  1440
tgctcttgtt gcccaggctg gagtgcaatg gcacaatctc ggctcactgc agccctgcc  1500
tcccaggctc aagcaattct tacgcctcag cctcctgagt agatggaact acagggcatg  1560
gactggaact cccaatacccc ctgacatggg ctgagtcaac gtggtcatga acatgtgaca  1620
ggaggcagca gaagttgcag agaagagtga ggcacgtttg aaaaaggctg aaaaatgttt  1680
ctgtccaggc aagggtgtgt gctgaatgac tcaaggattt tttgagaga attgagtgt  1740
ctcaccagag gagaccacgt ctgaagggct ttgcatccct ccttggacat gtctaatacc  1800
taacactcag aaagcatcca gtaaatattc gtggaaagaa aggagtggag aaggggagaa  1860
aggggaaagg gagtaggcga gagagaagaa agactctgct tcttgcccag ggctggcat  1920
ggggcggagg caaagcagtg gggtcctcag ctatgtccca ctgtgagtgc acagcgagtc  1980
ctgaccttca gagggtgcag cccgagggc cctggcctgt ctgaagggtg cgccagccga  2040
gtggcctgct ctgaccacca ggctcaccca tgactacctg ggtggctaca gccagttcct  2100
gacaatgagt acagcactca gttatcgggg cccttccacc cacacgctgt ccacttcctg  2160
gggtactgct gtgggcatgt gagtgcttgc tccccgaggtg actgctgggc catgcgagt  2220
gcttgctccc cggggcactg ctgtccactt cctggggtac tgctgtgggc atgcgagtgc  2280
ttgctcccg gggcactgct gtggacatgt gatagcttgc tccccagctc cactagtgac  2340
actggcggcc cctcgctggg gccttcccg cctgctccgc tccattaccg ctgccgggct  2400
cctcacgtct ctccttgctg cttcctgcac tggggtgagg agagtggggc tggtcccctt  2460
gagaccggag aagctccagg cttttaagga aaactgccag ggacgaagag aagatatcac  2520
ttccccacgt ggttggcttc cagattcaga aggaatgtct gtccttgtgg attccgtacc  2580
agatgacccc agatgctgcc tcagtactag gtccctgtgg ctctggagcc tttgctgggt  2640
ctgggcagtg tctcttcctc tccagttcat ccttgggtct cttcacccctt gccagggca  2700
ggcttcctgg tgagaggtcg acctcctgca tgaaggctct caagaggcca gttcaaagcc  2760
aagctccggg tctgtgcctg tggggctgct cctcgatcag gagatggtca ctcccctcct  2820
ggtctgtatc tgtgggattc tcctccatca ggagatggtc tctcccctcc tggtctatac  2880
ccgtggggatt ctcctccatc aggagatggt cactcccctt cctggtctat accgtggga   2940
ttctcctcca ttagatggtc actcccctcc tggtctattc ccgtggggct gctcctccat  3000
caggaggtgg tcactcccccc tcctggtcta taccgtggg gctgctcctc catcaggaga  3060
tagtcactcc cctcctggt ctataccgt gggattctcc tccatctgga gatggtcact  3120
cccctcctgg tctataccca tggattctc tccatctg gagatagtca ctccccctcct  3180
gtctataccc atgggattct cctccatctg gagatagtca ctccccctcct ggtctatacc  3240
cgtggggttc tcctcaatca ggaggtggtc actcccctcc tggtctatac ccgtgggatt  3300
ctcctccatc aggagatggt cactctcct ctggtctat accgtgggg ctgctcctcc  3360
atcaggagat ggtcactccc ctcctggtct atacctgtgg gattcctc cctcagaaga  3420
tggtcactcc ccctcctggt ctatacccat gggattctcc tccctcagaa tggtcactccc  3480
ccctcctg gtctataccc gtggggctgc tcctccatca ggagatggtc actctccctc   3540
tcggttgctc agtccaaaaa caacctctct ggaaaactgc gtgaattt ttttttaaga   3600
attgaaacta gaactagcat ttgatccagc catctgccta ctgggaatac acccaaagaa  3660
aaataaatca ttatatcag                                              3679
```

| SEQ ID NO: 71 | moltype = DNA length = 3620 |
|---|---|
| FEATURE | Location/Qualifiers |
| source | 1..3620 |
| | mol_type = other DNA |
| | organism = Homo sapiens |

SEQUENCE: 71
```
gaggcagcca tgactggcca cttcatgtgc tcctggagaa gggcttgcac cagccgtttt    60
caggaaagtc aagcagctgt tgactcctga gtctgggtga atttgtgtga agagcataag   120
gcgctgtttc ttaaccaaaa cgcttcctct tgcagtgcag atgggatgtg cttctccaca   180
ggaggcccca cggcttcccc acccctcaga ggagcgccgt gcgtgcgtct gtgtggagga   240
```

```
ttggcagctc ctgcagtcgg cccttggtcc tatttggcga cgcctctgcc ttcccottaa    300
ttatacagtc atgagccgcc ctggaatcac ggcagctccg gatggatcct ggatgccaga    360
atgcagcctc agcacggggc tgcaggacag gagtgagcga ggggctgcag agccggcggc    420
cgcggtgggc accatggagg gggctgccct gggcagcacg gcatgagtc tcaaggccca     480
ggtttgagta acaggtgttg agagcttact tactttttct gagacacagt ttcctcatct    540
cgagagcacg gaaaatcatt ctaacttcag aggattgttg tgaaagttaa atgagattaa    600
agaggtaaag cccatgacgt gcttagctcg tgcttggctc ttggtcaatg ccagttagcg    660
ctgcattttc tccctctcc ctccctcctt ctctctttct tttcttctat tctccattcc     720
tgttttctcc cccaccccac tccccaaagc tctgcgttga gaaccagatg ctgtctggtg    780
ggttagggcc agaggaggaa aagctgcccg ccgtgggctg cacccatacc ctcttcattc    840
caatgacatg aggggagggg aaaggacaga ggtagactgt cctcccctac ctcctcctaa    900
tacaaatgga attcctggaa ctggaaaaca aagaatacccc ccataaaaat aagacagtac   960
ttctggtgcg gtgtaataaa ggggaaagta accctcaatg tcaggaaact ccgcacctcc    1020
cagctcatat ttgtgtggag gaaaagttaa atattaattt ggactcaact gaatgtggac    1080
acaaacaatg gtcaccaagt cccggaacag gttgtgtgag cctcttcagg ggttcatcca    1140
gcgctgtttt ggagaaatct ctatttcaat ttattcctat acgttagtta ctgaaaaaca    1200
acagacaatc gcaaaagcaa gttgccgtt ttgtgttcct tgagcccaat catgaagtgc     1260
cgtcgtgact gggcctcatg acaaacaact tgtaacaagt aacaacagag ctcaggtccc    1320
agaccgcact gaagctctgt gagacctctc ctcatctgtg catgaacgag tgtctgactc    1380
tggagcccag cctgctgctt cccagtctgg tggtgaatcc tccgtagtct gatggaggtt    1440
tgctcttgtt gcccaggctg gagtgcaatg gcacaatctc ggctcactgc agccctgcc    1500
tcccaggctc aagcaattct tacgcctcag cctcctgagt agatgaact acagggcatg    1560
gactggaact cccaatacccc ctgacatggg ctgagtcaac gtggtcatga acatgtgaca    1620
ggaggcagca gaagttgcag agaagagtga ggcacgtttg aaaaaggctg aaaaatgttt    1680
ctgtccaggc aagggtgtgt gctgaatgac tcaaggattt tttggagaga attggagtgt    1740
ctcaccagag gagaccacgt ctgaagggct ttgcatccct ccttggacat gtctaatacc    1800
taacactcag aaaagcatcca gtaaatattc gtgaaagaa aggagtggag aaggggagaa    1860
agggggaagg gagtaggcga gagagaagaa agactctgct tcttgcccag ggcctggcat    1920
ggggcggagg caaagcagtg gggtcctcag ctatgtccca ctgtgagtgc acagcgagtc    1980
ctgaccttca gagggtgcag cccgagggggc cctggcctgt ctgaagggtg cgccagccga    2040
gtggcctgct ctgaccacca ggctcaccca tgactacctg ggtggctaca gccagttcct     2100
gacaatgagt acagcactca gttatcgggg cccttccacc cacacgctgt ccacttcctg    2160
gggtactgct gtgggcatgt gagtgcttgc tccccgggggc actgctgtgg gcatgcgatg    2220
cttgctcccc ggggcactgc tgtggacatg tgatagcttc ctgctgctccg ccactagtga    2280
cactggcggc ccctcgctgg ggccttcccc gcctgctccg ctccattacc gctgccgggc    2340
tcctcacgtc tctccttgct gcttcctgca ctggggtgag gagagtgggg ctggtcccct    2400
tgagaccgga gaagctccag gcttttaagg aaaactgcca gggacgaaga gaagatatca    2460
cttcccccacg tggttggctt ccagattcag aaggaatgtc tgtccttgtg gattccgtac    2520
cagatgaccc cagatgctgc ctcagtacta ggtccctgtg gctctggagc ctttgctggg    2580
tctgggcagt gtctcttcct ctccagttca tccttgggtc tcttcacctct tgccaggggc    2640
aggcttcctg gtgagaggtc gacctcctgc atgaaggctc tcaagaggcc agttcaaagc    2700
caagctccgg gtctgtgcct gtgggggctgc tcctcgatca ggagatggtc actccccctcc    2760
tggtctgtat ctgtgggatt ctcctccatc aggagatggt ctctccccctc ctggtctata     2820
cccgtgggat tctcctccat caggagatgg tcactcccca tcctggtcta tacccgtggg     2880
attctcctcc attagatggt cactcccctc ctggtctatt cccgtggggc tgctcctcca     2940
tcaggaggtg gtcactcccc ctcctggtct atacccgtgg ggctgctcct ccatcaggag     3000
atagtcactc ccctcctgg tctataccccg tgggattctc ctccatctgg agatggtcac    3060
tcccctcctg gtctataccc atgggattct cctccatctg gagatggtca ctcccctcct     3120
ggtctatacc catgggattc tcctccatct ggagatagtc actcccctcc tggtctatac    3180
ccgtgggggtt ctcctcaatc aggaggtggt cactcccctc ctggtctata cccgtgggat    3240
tctcctccat caggagatgg tcactctccc tcctggtcta taccgtggg gctgctccta     3300
catcaggaga tggtcactcc cctcctggtc tatacctgtg ggattctcct ccctcagaag    3360
atggtcactc cccctcctgg tctataccca tgggattctc ctcccctcaga agatggtcac     3420
tcccctcctg gtctatacc cgtgggggctg ctcctccatc aggagatggt cactctcctc    3480
ctcggttgct cagtccaaaa acaacctctc tggaaaactg cgtggaattt ttttttaaag    3540
aattgaaact agaactagca tttgatccag ccatctgcct actgggaata caccaaaga    3600
aaaataaatc attatatcag                                                 3620

SEQ ID NO: 72         moltype = DNA   length = 720
FEATURE               Location/Qualifiers
source                1..720
                      mol_type = other DNA
                      organism = Homo sapiens
SEQUENCE: 72
ctggagctct cctgaggagc ccacagatcc aactccctag gccaaggctg cagcctgggg     60
cagagatgca gaggcctgga ggagcctagg gcacgcggcc tgcgggctgg ctggggttca    120
gagttcgtat gtgtgtggag tgactgggca ggtgttcaga aatgaaggct ggcactgcca    180
ggtaaggccc ttccctccct gatgtgagag ccctggagcc accgcagagg cccagtcaga    240
tctctgttct aattctggcc tggtgtggag gatgaggaga gacggcccag aaaggaaggc    300
agactgtgca gaccccatgt cttctggccc gcgaggccct cctcctgtgc ctgcttatct    360
taaagaatcc gggataagag gtgacttggg ccttggccgg gaggcccctc ctcagcttca    420
gacaaggagg gagctctggg catgaggaca ttgagcaaga ggcgatggca gtgcccacaa    480
cttaccctca gctcggctct gttgggtccg agaagttgca tggaaagggc tccttggggg    540
ccagttgtca gtaagctgca gaagcctgga gccggccagg aaataaccac gtgtaggagc    600
cttctcagct gagaggaagg aggactcacg cgcggcgagc acatgcttgg agccaggcac    660
agggcatgga ctggaactcc caatacccct gacatgggct gagtcaacgt ggtcatgaac    720

SEQ ID NO: 73         moltype = DNA   length = 4387
FEATURE               Location/Qualifiers
```

| source | 1..4387 |
| --- | --- |
| | mol_type = other DNA |
| | organism = Homo sapiens |

SEQUENCE: 73

```
caaatgcctg gcagcgtcct cggtgcttca cctgccatag ccgacagtgg ctgacctccc    60
atgcctgttg ccttttcttt ctgttggatc agggatacac tgccatgtgt gttaagaaaa   120
gctggcctta cctacagggc tggccagtcc cggtcacgtt tctagtaagc cattgcctta   180
cataagggta acggcatggg acgctatctt agccaatgtg ataaaagtgg acatgaggtg   240
agaggcttca gagagaggtt ttaaaaaaga gacaaaagca ggacgttgcc tctcttcctc   300
ctctccacgt gtcctacccg gatgtgaagc caaaacagat gcaggcttag tgcaaccatg   360
gggaacccag cataagcaca gattcaacag cagaagagtg gcagagggag aaggtgaaag   420
gaacctaggt tttcctgtcc ttgttgagtc attcagttaa aaatccctgg aattttcctc   480
tctccggcag tgtgttttgt gggataatga gttgccttat tggggttggc ttgctagtcg   540
ggatgtttcg ctcccatcaa catccatacg cttgctctgt gaaccaatga cctgatgagg   600
tagtattagc accaccatca ttatgctgag gatgagattt atggcacagt ggttcagtag   660
cttgcccaag gccatgcggc tggtaggttc tggaggaggg ctcagggcac ccctgagct   720
acccctgctg gccattgcac caccccataa agctgctggc agtcacttct ctgaggggtt   780
agcatgtaag aaatgtcctc ctgaatgctg gccagacaaa tggaaatctg ccaggggttgg   840
gtacccccat gacagcagcc agcctgccct cttagtccct gacagctgca gtgacagcat   900
ctgtgattgc aaagcgtgac aatttatatc tctcatttca tcacaccatc tatcagcaga   960
cagtcaggct ttaaaaatca atcccacact gactcagtcc ccagcagaga tggcctctga  1020
caacagtatc cacactgcag gctggacaag ggccctatta attttgagac tcagccaaat  1080
ttccttctga ccctaagctg gtgaatccct gctcctttgc tttggttggg gttggtgtga  1140
gctaaggctg tgatcccatt tgctcctatg gcctccaggt ggcctgggcc tccatgaatg  1200
ggccacatgg tcatactgaa tgcttgatta cactcagacc tagcagtcgt ctgggcgcag  1260
ctggtttatg gatcactttg tcacaatgtt ccatcctctc aggtccccat ccccgcggtg  1320
ggaaaacatt gctttaggca gtgctagagg acttcagcag gcattggcag cttctgatt   1380
caggattaga acaaagaagg aggagtcaca gcaaagatag gaacagaagg cagagagaac  1440
agacagatgg gggtgtttga gaaggagggc ctttgagacc tcagggagtg ggagacactg  1500
gctcgagaat aataaatg gcaattttctc tcatctgtgt tttcagggga tggactggaa  1560
ctcccaatac ccctgacatg ggctgagtca acgtggtcat gaacatgtga caggaggcag  1620
cagaagttgc agaagaagt gaggcacgtt tgaaaaaggc tgaaaatgt ttctgtccag  1680
gcaagggtgt gtgctgaatg actcaaggat ttttggtgc attgaatgaa cagcgggaca  1740
ttggacacct gctgatccat caccccgggc ccggcaggcc ccgtggactg agagatggg  1800
agaagaccag gcatgagact gtggagaagc cacaccacca gaaaccctg ccccatgcgc  1860
cgtccagccc acacctgtgg atgcacgggg gattgcaggc agggctccca ccgtggactc  1920
aggaacaggc agggaagctg ctgcctcacc aggcgaaggg gccaggaggg ggaggcggag  1980
aggcccgtct agccctgcg gctgtcaccg tggtgcctcc tcactggcca gtgcggtcgc  2040
gcctcagctt cgttaatagg ggagggggcc taagagtttt cacgtccagg ctcgggcagt  2100
ggggaggcag gcaggagtgg ccgctggttt tcagacctc ccaggaggc cgaggaaatg  2160
gcccgtcctg gagtgggcgt ggtctgtct tcagatggat gctggaggt tgggctgcgt  2220
gggaccctgg gccctgctgc ttcccggagg atgcgctgtc cggggctgca caggttggct  2280
gtgttttttg gatgcttgat attttgtttt ttcttctctt cactctgtca tgaaactgcc  2340
aatagtagtt tgtaaataaa tatgtgttat agatgaatat ttgctatgag taaattaata  2400
aaggagtgaa taaatgagcg attgatgtag ggcctgtcct gtctcaggga gcccacgaa  2460
ggcctgcgcg ccggccagag cctgcctgcc tgccagggta ctgggacgtc actctcaaag  2520
cggcgggacc cagccgctga tcttgctgag gaggcccggt ctcagaaaac tgagcggctg  2580
cttctgcaga ccctgcatcc tcccctccct ggagaaagaa gctctggctg agtcctggga  2640
ccgaacccctt gggtgccaca gaaacgggct ttgctgcctg tcagtcaagc ggcgggagaa  2700
acagacctgg ggaggaggag gctggagggg ctgtgttttc tgcacagcga gtagctcctt  2760
agcctggtgc catttctctc caaacaccct gaaggttgag tccaggggtga agatgtagag  2820
gcaagttttg gggggatgga gtgggcttgg agggatgctg gcgccttagc aggctgtgct  2880
cctgaggtgc ccagtgtctg cgggcacagg aacatgttgc cgagggcatt tgggtgtggg  2940
tggggtgggg aaagggagac agggctgtct cttttaatgg gtatctgcga gcatgtgatt  3000
gtaagagagg aagaagtagg ggaggaagaa ggcctccttg gggggtgct catcctgagg  3060
aaggctgaac aatgagggtc ttggagagtc aattcagaag cacaaccttg cagagcaggc  3120
aaaaacaata gggcttcttg aggctgcccg ggcactcatg caatcaccat ttcctgctgt  3180
gaatgagcct acattttgtt ggggaagaga cgcaacgacg ccaaacgatg gactctgagt  3240
caacgataag atgaaacaaa attaaaacaa agtaggaaat caagagtggc tgctgtgatg  3300
gcgttgcgga gatgatgttt gctttgaaga ctggacaagt gagcccctga gctgcatctg  3360
cacccagagg ctgagccggt gcacaggact tgcagaggga tgggcctggg cttgtagagc  3420
agcacaacgg ccccaggcct ggaggagcaa gggtgggaag gggggcaggc cagctcctgc  3480
caggctggag aaggactcgg acctcaggcc acctgtgcct gggtgattgt gaacttgtaa  3540
caaatgtgat cttatttatg ttttgaaaaa ggcaacacga accaacacga ggtgttttat ctttccaga  3600
gatcaggtga cagctgccca aaagctgaca caaggaacaa gcctggagga gtgaggatgg  3660
gtgctgtgaa ggaggttgtg cagctgggcc cgcagtcgga cctggtgaga tcagaggagg  3720
gggtgccacc agtctgtgga cgaagatgag aagctgaat agagcagaaa acaggaggct  3780
gccactctcc atctttccca aagtcactcc aggagcaagg gtgtcattta ctgaaatgac  3840
agactctcca tttcacattt ttccccccaag tgcagagtgc agggaagcag atgggctaaa  3900
ttttttagagt cagggttatt aatgtatact ttacatagta aactttcccc ttttaagtgt  3960
gcaggcctga ggtttgccaa atatgtgtag gcatttaatc accaccacga tcaagatgta  4020
gaatattccc actatcaaaa agtttgctgt gtcccttgat ggtcatgccc cattccacag  4080
ccccagcccc agccctgga gattgctgtc tgctttatgt tccagtggtt ttatcttttc  4140
cagactgtat ggatgtgaat ggaatcagat gtgattccaa ggtgtttat cttttccaga  4200
tgtgaatgaa atcagatgta cgaaatccta tggtaggggg tcttctgagt ctagctcctt  4260
ttgtttagcg tgatgcattt gaaattaatc catgtctcag gcatcaggag ttcatttctt  4320
tttctgctga gtagtatttc attgtatgga tgtactgcaa tttgcctatc cattcacctg  4380
ttgatgt                                                             4387
```

| SEQ ID NO: 74 | moltype = DNA length = 1398 |
| --- | --- |
| FEATURE | Location/Qualifiers |
| source | 1..1398 |
| | mol_type = other DNA |
| | organism = Homo sapiens |

SEQUENCE: 74

```
cgggatgttt cgctcccatc aacatccata cgcttgctct gtgaaccaat gacctgatga    60
ggtagtatta gcaccaccat cattatgctg aggatgagat ttatggcaca gtggttcagt   120
agcttgccca aggccatgcg gctggtaggt tctggaggag ggctcagggc acccctgag    180
ctaccctgc tggccattgc accaccccat aaagctgctg gcagtcactt ctctgaggg     240
ttagcatgta agaaatgtcc tcctgaatgc tggccagaca aatggaaatc tgccagggtt   300
gggtaccccc atgacagcag ccagcctgcc ctcttagtcc ctgacagctg cagtgacagc   360
atctgtgatt gcaaagcgtg acaatttata tctctcattt catcacacca tctatcagca   420
gacagtcagg cttttaaaaat caatcccaca ctgactcagt ccccagcaga gatggcctct   480
gacaacagta tccacactgc aggctggaca agggccctat taattttgag actcagccaa   540
atttccttct gaccctaagc tggtgaatcc ctgctccttt gctttggttg gggttggtgt   600
gagctaaggc tgtgatccca tttgctccta tggcctccag gtggcctggg cctccatgaa   660
tgggccacat ggtcatactg aatgcttgat tacactcaga cctagcagtc gtctgggcgc   720
agctggttta tggatcactt tgtcacaatg ttccatcctt ccaggtcccc atccccgcgg   780
tgggaaaaca ttgctttagg cagtgctaga ggacttcagc aggcattggc agcttctgga   840
ttcaggatta gaacaaagaa ggaggagtca cagcaaagat aggaacagaa ggcagagaga   900
acagacagat ggggtgtttt gagaaggagg gcctttgaga cctcagggag tgggagacac   960
tggctcgaga ataataataa tggcaatttc tctcatctgt gttttcaggg catggactgg  1020
aactcccaat acccctgaca tgggctgagt caacgtggtc atgaacatgt gacaggaggc  1080
agcagaagtt gcagagaaga gtgaggcacg tttgaaaaag gctgaaaaat gtttctgtcc  1140
aggcaagggt gtgtgctgaa tgactcaagg attttttggg tatgtcattt cccatttctc  1200
accctcaaat aggactccgc ttcccatcta agcatttgta taaatattga ttattggtta  1260
gtgtgtatca gagagctatt gagtaaaaat tatatcagaa aaattaagaa tctctagaga  1320
tggcaaggtg tgaaacaaaa aacgccagga aggtaaatgc tcaaagttca ccacacacca  1380
cagtgagaag tgttgggg                                                1398
```

| SEQ ID NO: 75 | moltype = DNA length = 939 |
| --- | --- |
| FEATURE | Location/Qualifiers |
| source | 1..939 |
| | mol_type = other DNA |
| | organism = Homo sapiens |

SEQUENCE: 75

```
acagcatctg tgattgcaaa gcgtgacaat ttatatctct catttcatca caccatctat    60
cagcagacag tcaggctttta aaaatcaatc ccacactgac tcagtcccca gcagagatgg   120
cctctgacaa cagtatccac actgcaggct ggacaagggc cctattaatt ttgagactca   180
gccaaatttc cttctgaccc taagctggtg aatcccctgct cctttgcttt ggttggggtt   240
ggtgtgagct aaggctgtga tcccatttgc tcctatggcc tccaggtggc ctgggcctcc   300
atgaatgggc cacatggtca tactgaatgc ttgattacac tcagacctag cagtcgtctg   360
ggcgcagctg gtttatggat cactttgtca caatgttcca tccttccagg tccccatccc   420
cgcggtggga aacattgct ttaggcagtg ctagaggact tcagcaggca ttggcagctt   480
ctggattcag gattagaaca agaaggagg agtcacagca agataggaa cagaaggcag   540
agagaacaga cagatggggg tgtttgagaa ggagggcctt tgagacctca gggagtggga   600
gacactggct cgagaataat aataatggca atttctctca tctgtgtttt cagggcatgg   660
actggaactc ccaataccc tgacatgggc tgagtcaacg tggtcatgaa catgtgcag   720
gaggcagcag aagttgcaga gaagtgag gcacgtttga aaaggctga aaatgtttc   780
tgtccaggca agggtgtgtg ctgaatgact caaggatttt ttgggctgatt tagtaaacaa   840
acaagaatga agaaggaaac catagctgag tggcagagcg tgcctggctg tttacacagg   900
actccagggc agggctcctg gagagggacg tgccagagg                          939
```

| SEQ ID NO: 76 | moltype = DNA length = 138 |
| --- | --- |
| FEATURE | Location/Qualifiers |
| misc_feature | 1..138 |
| | note = primer |
| source | 1..138 |
| | mol_type = other DNA |
| | organism = synthetic construct |

SEQUENCE: 76

```
ctggaaagga ggagaacatg aaacattgct tgaagacaat ggccgagaca gcaggtccca    60
ccctgcacag ccaccagcat ctctcccctc agccctgtct cctcttctgc agttgggatc   120
tgcacattta agcctgaa                                                 138
```

| SEQ ID NO: 77 | moltype = DNA length = 147 |
| --- | --- |
| FEATURE | Location/Qualifiers |
| misc_feature | 1..147 |
| | note = primer |
| source | 1..147 |
| | mol_type = other DNA |
| | organism = synthetic construct |

SEQUENCE: 77

```
attgtcctgt gaagtgaagt atgatcggac agcctctttt cagctttat gacaatggag    60
acagaggaat tgtggctctt gccaaggtca caggattgga atacagagcc aagccacccc   120
aggacatgca agagcctcag aagggaa                                        147
```

| SEQ ID NO: 78 | moltype = DNA length = 19 |
| --- | --- |

```
FEATURE                  Location/Qualifiers
misc_feature             1..19
                         note = primer
source                   1..19
                         mol_type = other DNA
                         organism = synthetic construct
SEQUENCE: 78
acagccacca gcatctctc                                                       19

SEQ ID NO: 79            moltype = DNA  length = 27
FEATURE                  Location/Qualifiers
misc_feature             1..27
                         note = primer
source                   1..27
                         mol_type = other DNA
                         organism = synthetic construct
SEQUENCE: 79
tgaagtgaag tatgatcgga cagcctc                                              27

SEQ ID NO: 80            moltype = DNA  length = 22
FEATURE                  Location/Qualifiers
misc_feature             1..22
                         note = primer
source                   1..22
                         mol_type = other DNA
                         organism = synthetic construct
SEQUENCE: 80
ccacaattcc tctgtctcca tt                                                   22

SEQ ID NO: 81            moltype = DNA  length = 90
FEATURE                  Location/Qualifiers
misc_feature             1..90
                         note = primer
source                   1..90
                         mol_type = other DNA
                         organism = synthetic construct
SEQUENCE: 81
tctctcatct gtgttttcag ggcatggact ggaactccca atacccctga catgggctga          60
gtcaacgtgg tcatgaacat gtgacaggag                                           90

SEQ ID NO: 82            moltype = DNA  length = 101
FEATURE                  Location/Qualifiers
misc_feature             1..101
                         note = primer
source                   1..101
                         mol_type = other DNA
                         organism = synthetic construct
SEQUENCE: 82
gcagcagaag ttgcagagaa gagtgaggca cgtttgaaaa aggctgaaaa atgtttctgt          60
ccaggcaagg gtgtgtgctg aatgactcaa ggattttttg g                             101

SEQ ID NO: 83            moltype = DNA  length = 21
FEATURE                  Location/Qualifiers
misc_feature             1..21
                         note = primer
source                   1..21
                         mol_type = other DNA
                         organism = synthetic construct
SEQUENCE: 83
catggactgg aactcccaat a                                                    21

SEQ ID NO: 84            moltype = DNA  length = 25
FEATURE                  Location/Qualifiers
source                   1..25
                         mol_type = other DNA
                         organism = Homo sapiens
SEQUENCE: 84
tgcagagaag agtgaggcac gtttg                                                25

SEQ ID NO: 85            moltype = DNA  length = 21
FEATURE                  Location/Qualifiers
misc_feature             1..21
                         note = primer
source                   1..21
                         mol_type = other DNA
                         organism = synthetic construct
SEQUENCE: 85
ccttgcctgg acagaaacat t                                                    21
```

```
SEQ ID NO: 86           moltype = DNA  length = 1434
FEATURE                 Location/Qualifiers
source                  1..1434
                        mol_type = other DNA
                        organism = Homo sapiens
SEQUENCE: 86
gttcgttgca acaaattgat gagcaatgct tttttataat gccaactttg tacaaaaaag    60
ttggcatgag ccggtcaagg cacctgggca aaatccggaa gcgtctggaa gatgtcaaga   120
gccagtgggt ccggccagcc agggctgact ttagtgacaa cgagagtgcc cggctggcca   180
cggacgccct cttggatggg ggttctgaag cctactggcg ggtgctcagc caggaaggcg   240
aggtggactt cttgtcctcg gtggaggccc agtacatcca ggcccaggcc agggagcccc   300
cgtgtccccc agacaccctg ggaggggcgg aagcaggccc taaggactg gactccagct    360
ccctacagtc cggcacctac ttccctgtgg cctcagaggg cagcgagccg ccctactgc    420
acagctgggc ctcagctgag aagccctacc tgaaggaaaa atccagcgcc actgtgtact   480
tccagaccgt caagcacaac aacatcagag acctcgtccg ccgctgcatc acccggacta   540
gccaggtcct ggtcatcctg atggatgtgt tcacggatgt ggagatcttc tgtgacattc   600
tagaggcagc caacaagcgt ggggtgttcg tttgtgtgct cctggaccag ggaggtgtga   660
agctcttcca ggagatgtgt gacaaagtcc agatctctga cagtcacctc aagaacattt   720
ccatccggag tgtggaagga gagatatact gtgccaagtc aggcaggaaa ttcgctggcc   780
aaatccggga gaagttcatc atctcggact ggagatttgt cctgtctgga tcttacagct   840
tcacctggct ctgcggacac gtgcaccgga acatcctctc caagttcaca ggccaggcgg   900
tggagctgtt tgacgaggag ttccgccacc tctacgcctc ctccaagcct gtgatgggcc   960
tgaagtcccc gcggctggtc gccccgtcc cgcccggagc agccccggcc aatggccgcc   1020
ttagcagcag cagtggctcc gccagtgacc gcacgtcctc caacccctc agcggccgct   1080
cggcaggcag ccaccccggt acccgaagtg tgtccgcgtc ttcagggccc tgtagcccg    1140
cggccccaca cccgcctcca ccgcccggt tccagcccca ccaaggccct tgggagccc    1200
cgagtcccca ggcccacctc tcccgcggc cccacgacgg cccgcccgcc gctgtctaca    1260
gcaacctggg ggcctacagg cccacgcggc tgcagctgga gcagctgggc ctggtgccga   1320
ggctgactcc aacctggagg cccttcctgc aggcctcccc tcacttctgc ccaactttct   1380
tgtacaaagt tggcattata agaaagcatt gcttatcaat ttgttgcaac gaac         1434

SEQ ID NO: 87           moltype = DNA  length = 3535
FEATURE                 Location/Qualifiers
source                  1..3535
                        mol_type = other DNA
                        organism = Homo sapiens
SEQUENCE: 87
gcggccgcgg cgccgatccc ggctgaggcg cagcggcgag aggtcgcggg cagggccatg    60
gccccggggg gccgctagcg cggaccggcc caacgggagc cgctccgtgc cgccgccgcc   120
gcccgggcgc ccaggccccg ccgctgcgga agaggttct agagagtgga gcctgcttcc   180
tgggccctag gccccctccca caatgcttgt cgccggtctt cttctctggg cttccctact   240
gaccggggcc tggccatcct tccccaccca ggaccacctc ccggccacgc ccggggtccg   300
gctctcattc aaagagctga aggccacagg caccgcccac ttcttcaact tcctgctcaa   360
cacaaccgac taccgaatct tgctcaagga cgaggaccac gaccgcatgt acgtgggcag   420
caaggactac gtgctgtccc tggacctgca cgacatcaac cgcgagcccc tcattataca   480
ctgggcagcc tccccacagc gcatcgagga atgcgtgctc tcaggcaagg atgtcaacgg   540
cgagtgtggg aacttcgtca ggctcatcca gcctgaacc cgaacacac tgtatgtgtg    600
cgggacaggt gcctacaacc ccatgtgcac ctatgtgaac gcggacgcc gcgcccaggc   660
cacaccatgg acccagactc aggcggtcag aggccgcggc agcagagcca cggatggtgc   720
cctccgcccg atgcccacag ccccacgcca ggattacatc ttctacctgg agcctgagcg   780
actcgagtca gggaagggca agtgtccgta cgatcccaag ctggacacag catcggcct   840
catcaatgag gagctctatg ctggtgtgta atcgatttt atgggcactg atgcagccat   900
cttccgcaca cttggaaagc agacagccat gcgcacggat cagtacaact cccggtggct   960
gaacgaccg tcgttcatcc atgctgagct cattcctgac agtgcggagc gcaatgatga  1020
taagctttac ttcttcttcc gtgagcggtc ggcagaggc gcagaggcc ccggtgta     1080
cgcccgcatc gggcgcattt gcctgaacga tgcggtggt cactgttgcc tggtcaacaa   1140
gtggagcaca ttcctgaagg cgcggctcgt ctgctctgtc ccgggcgagg atggcattga  1200
gactcacttt gatgagctcc aggacgtgtt tgtccagcag accaggacg tgaggaaccc   1260
tgtcatttac gctgtcttta cctcctctgg ctccgtgttc caggctctg ccgtgtgtgt   1320
ctactccatg gctgatattc gcatggtctt caacggggcc tttgccccaca aagagggccc   1380
caactaccag tggatgcct tctcagggaa gatgcctac ccacggccgg gcacgtgccc   1440
tggtggaacc ttcacgccat ctatgaagtc caccaaggat tatcctgatg aggtgatcaa   1500
cttcatgcgc agccacccac tcatgtacca ggccgtgtac cctctgcagc ggcggcccct   1560
ggtagtccgc acaggtgctc cctaccgcct taccactatt gccgtggacc aagttggatgc   1620
agccgacggg cgctatgagg tgctttttcct gggcacagac cgcggacag tgcagaaggt   1680
cattgtgctg cccaaggatg accaggagtt ggaggagctc atgctgagg aggtggaggt   1740
cttcaaggat ccagcacccg tcaagaccat gaccatctct tctaagaggc aacaactcta   1800
cgtggcgtca gccgtgggtg tcacacacct gagcctgcac cgctgccagg cgtatgggc   1860
tgcctgtgct gactgctgcc ttgccccggga cccttactgt gcctgggatg gccaggcctg   1920
ctccgctat acagcatcct ccaagaggcg gagccgccgg caggacgtcc ggcacgaaa    1980
cccatcagg cagtgccgtg ggtcaactc caatgccaac aagaatgccg tggagtctgt    2040
gcagtatggc gtgccggca gcgcagcctt ccttgagtgc cagccccgct cgccccaagc   2100
cactgttaag tggctgttcc agcgagatc tggtgaccgg cgcgagaga ttcgtgcaga   2160
ggaccgcttc ctgcgcacag agcagggctt gttgctccgt gacgctggc tcagcgatcg   2220
tggcctctac tcctgcacag ccactgaaaa caacttaag cacgtcgtca cacgagtgca   2280
gctgcatgta ctgggccggg acgccgtcca tgctgccct ttcccaccac tgtccatgag   2340
cgccccgcca cccccaggcg caggccccc aacgcctcct taccaggagt tagcccagct   2400
gctgcccag ccagaagtgg gcctcatcca ccagtactgc cagggttact ggcgccatgt   2460
gccccccagc cccagggagg ctccaggggc acccggtct cctgagccc aggaccagaa    2520
```

```
aaagccccgg aaccgccggc accaccctcc ggacacatga ggccagctgc ctgtgcctgc    2580
catgggccag cctagccctt gtcccttta atataaaaga tatatatata tatatatata    2640
tataaaatat ctatattcta tacacaccct gcccctgcaa agacagtatt tattggtggg    2700
ttgaatatag cctgcctcag tggcagcatc ctccaaaact tagacccatg ctggtcagag    2760
acggcagaaa acagagcctg cctaaccagg cccagccagt tggtggggcc aggccaggac    2820
cacacagtcc ccagactcag ctggaagtct acctgctgga cagcctccgc caagatctac    2880
aggacaaagg gagggagcaa gccctactcg gatgggcac  ggactgtcca ccttttctga    2940
tgtgtgttgt cagcctgtgc tgtggcatag acatggatgc gaggaccact ttggagactg    3000
gggtggcctc aagagcacac agagaaggga agaaggggcc atcacaggat gccagccctc    3060
gcctggggttg ggggcactca gccacgacca gccccttcct gggtatttat tctctattta    3120
ttggggatag gagaagaggc atcctgcctg ggtgggacag cctcttcagc cccttctccc    3180
ctccccgcct ggccagggca gggccacccc actctacctc cttagctttc cctgtgccac    3240
tttgactcag aggctgggag catagcgag  gggccaggcc caggcagagc tgacgggagg    3300
cccagctct  gaggggaggg ggtccgtggt agaggcctgg ggccggtaga ggctccccag    3360
ggctcccta  tgtccaccac ttcaggggat gggtgtggat gtaattagct ctgggggca    3420
gttgggtaga tgggtgggg  ctcctggtgg ccttctgctg cccaggccac agccgccttt    3480
gggttccatc ttgctaataa acactggctc tgggactaga aaaaaaaaaa aaaaa         3535

SEQ ID NO: 88          moltype = DNA   length = 3558
FEATURE                Location/Qualifiers
source                 1..3558
                       mol_type = other DNA
                       organism = Homo sapiens
SEQUENCE: 88
ctgactggtg ctccctctct tccatcttgg gctgtctgca tgtgtctcat tcccccactc      60
tctcctgtgc ctccccctcta ccgtaataat caggtccagg tttctctgta ctgggagaag   120
acctgtggct ggagcaggca gggatgcacc ctatctgttc cccattcctc caggtgggga   180
ggagaaggag taacccactt tattggccac agatgcaggg gagaaaggag aaagcatgct   240
gggagctgga aagagcccta agatcacctg gtttctagag agtggagcct gcttcctggg   300
ccctaggccc ctcccacaat gcttgtcgcc ggtcttcttc tctgggcttc cctactgacc   360
ggggcctggc catccttccc cacccaggac cacctcccgg ccacgccccg ggtccggctc   420
tcattcaaag agctgaaggc cacaggcacc gcccactttct tcaacttcct gctcaacaca   480
accgactacc gaatcttgct caaggacgag gaccacgacc gcatgtacgt gggcagcaag   540
gactacgtgc tgtccctgga cctgcacgac atcaaccgcg agccctctat tatacactgg   600
gcagcctccc cacagcgcat cgaggaatgc gtgctctcga gcaaggatgt caacgccgag   660
tgtgggaact tcgtcaggct catccagccc tggaaccgaa cacacctgta tgtgtgcggg   720
acaggtgcct acaaccccat gtgcacctat gtgaaccgcg gacgccgcgc ccaggattac   780
atcttctacc tggagcctga gcgactcgag tcagggaagg gcaagtgtcc gtacgatccc   840
aagctggaca cagcatcggc cctcatcaat gaggagctct atgctggtgt gtacatcgat   900
tttatgggca ctgatgcagc catcttccgc acacttggaa agcagacagc catgcgcacg   960
gatcagtaca actcccggtg gctgaacgac ccgtcgttca tccatgctga gctcattcct  1020
gacagtgcgg agcgcaatga tgataagctt tacttcttct tccgtgagcg gtcggcagag  1080
gcgccgcaga gccccgcggt gtacgcccgc acgggcgcg tttgcctgaa cgatgacgat  1140
ggtcactgtt gcctggtcaa caagtgagc  cattcctga aggcgcggct cgtctgctct   1200
gtcccggggcg aggatggcat tgagactcac tttgatgagc tccaggacgt gtttgtccag  1260
cagacccagg acgtgaggaa ccctgtcatt tacgctgtct ttacctcctc tggctccgtg  1320
ttccgaggct ctgcgtgtgt tgtctactcc atggctgata ttcgcatggt cttcaacggg  1380
cccttttgccc acaaagaggg gcccaactac cagtggatgc ccttctcagg gaagatgccc  1440
tacccacggc cgggcacgtg ccctggtgga accttcacgc catctatgaa gtccaccaag  1500
gattatcctg atgaggtgat caacttcatg cgcagccacc cactcatgta ccaggccgtg  1560
taccctctgc agcggcggcc cctggtagtc cgcacaggtg ctccctaccg ccttaccact  1620
attgccgtgg accaggtgga tgcagccgac gggcgctatg aggtgctttt cctgggcaca  1680
gaccgcggga cagtgcagaa ggtcattgtg ctgcccaagg atgaccagga gttggaggag  1740
ctcatgctgg aggaggtgga ggtcttcaag gatccagcac ccgtcaagac catgaccatc  1800
tcttctaaga ggcaacaact ctacgtggcg tcagccgtg gtcacacaca cctgagcctg  1860
caccgctgcc aggcgtatgg ggctgcctgt gctgactgct gccttgcccg ggacccttac  1920
tgtgcctggg atgccaggc  ctgctcccgc tatacagcat cctccaagag gcggagccgc  1980
cggcaggacg tccggcacgg aaaccccatc aggcagtgcc gtgggttcaa ctccaatgcc  2040
aacaagaatg ccgtggagtc tgtgaagtat ggcgtggccg gacgcgcagc cttccttgag  2100
tgccagcccc gctcgcccca agccactgtt aagtgggtgt tccagcgaga tcctggtgac  2160
cggcgccgag agattcgtgc agaggaccgc ttcctgcgca cagagcaggg cttgttgctc  2220
cgtgcactgc agctcagcga tcgtggcctc tactcctgca cagccactga gaacaacttt  2280
aagcacgtcg tcacacgagt gcagctgcat gtactgggcg gggacgccgt ccatgctgcc  2340
ctcttcccac cactgtccat gagcgccccg ccacccccga ccaggcccc cccaacgcct  2400
ccttaccagg agttagccca gctgctggcc cagccagaag tgggcctcat ccaccagtac  2460
tgccaggtt  actggcgcca tgtgcccccc agccccaggg aggctccagg gcacccccgg  2520
tctcctgagc cccaggacca gaaaaagccc cggaaccgcc ggcaccaccc tccggacaca  2580
tgaggccagc tgcctgtgcc tgccatgggc cagctagcc  cttgtccctt ttaatataaa  2640
agatatatat atatatatat atatataaaa tatctatact cctgcccctg  2700
caaagacagt atttattggt gggttgaata tagcctgcct cagtggcagc atcctccaaa  2760
acttagaccc atgctggtca gagacggcag aaaacagagc ctgcctaacc aggcccagcc  2820
agttggtggg gccaggccag gaccacacag tccccagact cagctggaag tctacctgct  2880
ggacagcctc cgcaagatc  tacaggacaa agggagggag caagccctac tcggatgggg  2940
cacggactgt ccaccttttc tgatgtgtgt tgtcagcctg tgctgtggca tagacatgga  3000
tgcgaggacc actttggaga ctggggtggc ctcaagagca cacagagaag ggaagaaggg  3060
gccatcacag gatgccagcc cctgcctggg ttggggcac tcagccacga ccagcccctt  3120
cctgggtatt tattctctat ttattgggga taggagaaga ggcatcctgc ctgggtggga  3180
cagcctcttc agccccttct cccctccccg cctggccagg gcagggccac cccactctac  3240
ctccttagct ttccctgtgc cactttgact cagaggctgg gagcatagca gaggggccag  3300
```

```
gcccaggcag agctgacggg aggcccagc  tctgaggga  gggggtccgt ggtagaggcc 3360
tggggccggt agaggctccc cagggctccc ttatgtccac cacttcaggg gatgggtgtg 3420
gatgtaatta gctctggggg gcagttgggt agatgggtgg gggctcctgg tggccttctg 3480
ctgcccaggc cacagccgcc tttgggttcc atcttgctaa taaacactgg ctctgggact 3540
agaaaaaaaa aaaaaaaa                                              3558

SEQ ID NO: 89           moltype = DNA   length = 3274
FEATURE                 Location/Qualifiers
source                  1..3274
                        mol_type = other DNA
                        organism = Homo sapiens
SEQUENCE: 89
cccgcgcggc tctgagcgcc ccgtcccgcc ggcggccgcg agaccagagc gagcgaacga 60
accgcggcgg tccggagagc cccgagcgca gcgcaggacc tgggaccacc tcccggccac 120
gccccgggtc cggctctcat tcaaagagct gaaggccaca ggcaccgccc acttcttcaa 180
cttcctgctc aacacaaccg actaccgaat cttgctcaag gacgaggacc acgaccgcat 240
gtacgtgggc agcaaggact acgtgctgtc cctggacctg cacgacatca accgcgagcc 300
cctcattata cactgggcag cctccccaca gcgcatcgag gaatgcgtgc tctcaggcaa 360
ggatgtcaac ggcgagtgtg ggaacttcgt caggctcatc cagccctgga accgaacaca 420
cctgtatgtg tgcgggacag gtgcctacaa ccccatgtgc acctatgtga accgcggacg 480
ccgcgcccag gattacatct tctacctgga gcctgagcga ctcgagtcag ggaagggcaa 540
gtgtcgtac  gatcccaagc tggacacagc atcggccctc atcaatgagg agctctatgc 600
tggtgtgtac atcgatttta tgggcactga tgcagccatc ttccgcacac ttggaaagca 660
gacagccatg cgcacggatc agtacaactc ccggtggctg aacgaccgt  cgttcatcca 720
tgctgagctc attcctgaca gtgcggagcg caatgatgat aagctttact tcttcttccg 780
tgagcggtcg gcagaggcgc cgcagagccc gcggttgtac gcccgcatcg ggcgcatttg 840
cctgaacgat gacggtggtc actgttgcct ggtcaacaag tggagcacat tcctgaaggc 900
gcggctcgtc tgctctgtcc cggccgagga tggcattgag actcactttg atgagctcca 960
ggacgtgttt gtccagcaga cccaggacgt gaggaaccct gtcatttacg ctgtctttac 1020
ctcctctggc tccgtgttcc gaggctctgc cgtgtgtgtc tactccatgg ctgatattcg 1080
catggtcttc aacgggccct tgcccacaa  agagggggcc aactaccagt ggatgccctt 1140
ctcagggaag atgccctacc cacggccggg cacgtgccct ggtggaacct tcacgccatc 1200
tatgaagtcc accaaggatt atcctgatga ggtgatcaac ttcatgcgca gccacccact 1260
catgtaccag gccgtgtacc ctctgcagcg gcggcccctg gtagtccgca caggtgctcc 1320
ctaccgcctt accactattg ccgtggacca ggtggatgca gccgacgggc gctatgaggt 1380
gcttttcctg ggcacagacc gcgggacagt gcagaaggtc attgtgctgc ccaaggatga 1440
ccaggagttg gaggagctca tgctggagga ggtggaggtc ttcaaggatc cagcaccccgt 1500
caagaccatg accatctctt ctaagaggca acaactctac gtggcgtcag ccgtgggtgt 1560
cacacacctg agcctgcacc gctgccaggc gtatggacct gcctgtgctg actgctgcct 1620
tgccccgggac ccttactgtg cctgggatgg ccaggcctgc tcccgctata cagcatcctc 1680
caagaggcgg agccgccggc aggacgtccg gcacggaaac cccatcaggc agtgccgtgg 1740
gttcaactcc aatgccaaca agaatgccgt ggagtctgtg cagtatggcg tggccggcag 1800
cgcagccttc cttgagtgcc agccccgctc gccccaagcc actgttaagt ggctgttcca 1860
gcgagatcct ggtgaccggc gccgagagat tcgtgcagag gaccgcttcc tgcgcacaga 1920
gcagggcttg ttgctccgtg cactgcagct cagcgatcgt ggcctctact cctgcacagc 1980
cactgagaac aactttaagc acgtcgtcac acgagtgcag ctgcatgtac tgggccggga 2040
cgccgtccat gctgccctct tcccaccact gtccatgagc gcccgccac  ccccaggcgc 2100
aggccccca  acgcctcctt accaggagtt agcccagctg ctggcccagc cagaagtggg 2160
cctcatccac cagtactgcc agggttactg cgccatgtgc cccccagcc  ccagggaggc 2220
tccagggca  ccccggtctc ctgagcccca ggaccagaaa aagccccgga accgccggca 2280
ccaccctccg gacacatgag gccagctgcc tgtgcctgcc atgggccagc ctagccctt  2340
tcccttttaa tataaaagat atatatatat atatatatat ataaaatatc tatattctat 2400
acacaccctg cccctgcaaa gacagtattt attggtgggt tgaatatagc ctgcctcagt 2460
ggcagcatcc tccaaaactt agaccatgc  tggtcagaga cggcagaaaa cagagcctgc 2520
ctaaccaggc ccagccagtt ggtggggcca ggcaggacc  acacagtcca cagactcagc 2580
tggaagtcta cctgctggac agcctccgcc aagatctaca ggacaaaggg agggagcaag 2640
ccctactcgg atggggcacg gactgtccac cttttctgat gtgtgttgtc agcctgtgct 2700
gtggcataga catggatgcg aggaccactt tggagactgg ggtggcctca agagcacaca 2760
gagaagggaa gaagggggcca tcacaggatg ccagcccctg cctgggttgg gggcactcag 2820
ccacgaccag cccctttctg ggtatttatt tctatttat  ctgggatagg agaagggca  2880
tcctgcctgg gtgggacagc ctcttcagcc ccttctcccc tccccgcctg gccagggcag 2940
ggccaccca  ctctacctcc ttagctttcc ctgtgccact ttgactcaga ggctgggagc 3000
atagcagagg ggccaggccc aggcagagct gacgggaggc cccagctctg aggggagggg 3060
gtccgtggta gaggctgggg gccggtagag gctcccaggg gctcccttat gtccaccttg 3120
tcaggggatg ggtgtggatg taattagctc tggggggcag ttgggtagat gggtgggggc 3180
tcctggtggc cttctgctgc ccaggccaca gccgcctttg gttccatct  tgctaataaa 3240
cactggctct gggactagaa aaaaaaaaa  aaaa                             3274

SEQ ID NO: 90           moltype = DNA   length = 2658
FEATURE                 Location/Qualifiers
source                  1..2658
                        mol_type = other DNA
                        organism = Homo sapiens
SEQUENCE: 90
aataaatatc cgtgtagaaa atcagaacga ctctttcagg ccatctttaa aatgtcattg 60
gtaaaccata cttgatccta aattcctgta cttcctcagg ccatccgagc atgaaacgct 120
gtcacctacc cacatccgct ggctgtgacg cttgtcaaag tgttctctat cggctgcatg 180
cctagaccac caaagcgttc tgaccggaca gtgtcactgg agaaggcggc gcgacatgtc 240
cagggcgcag atctgggctc tggtgtctgg tgtcggaggg tttggagctc tcgttgctgc 300
```

```
taccacgtcc aatgagtgga aagtgaccac gcgagcctcc tcggtgataa cagccacttg    360
ggtttaccag ggtctgtgga tgaactgcgc aggtaacgcg ttgggttctt tccattgccg    420
accgcatttt actatcttca aagtagcagg ttatatacag gcatgtagag gacttatgat    480
cgctgctgtc agcctgggct tctttggttc catatttgcg ctctttggaa tgaagtgtac    540
caaagtcgga ggctccgata aagccaaagc taaaattgct tgtttggctg ggattgtatt    600
catactgtca gggctgtgct caatgactgg atgttcccta tatgcaaaca aaatcacaac    660
ggaattcttt gatcctctct ttgttgagca aaagtatgaa ttaggagccg ctctgtttat    720
tggatgggca ggagcctcac tgtgcataat tggtggtgtc atattttgct tttcaatatc    780
tgacaacaac aaaacaccca gatacacata caacggggcc acatctgtca tgtcttctg    840
gacaaagtat catggtggag aagattttaa aacaacaaac ccttcaaaac agtttgataa    900
aaatgcttat gtctaaaaga gctcgctggc aagctgcctc ttgagtttgt tataaaagcg    960
aactgttcac aaaatgatcc catcaaggcc ctcccataat taacactcaa aactattttt   1020
aaaatatgca tttgaagcat ctgttgattg tatggatgta agtgttctta catgttagt   1080
tatatactaa tcattttctg ttgtggcttt ctataaaaaa taaacagttt atttacagga   1140
tttgtaaaat gttttctaca tttatataga acatgaaaag catttagtac caaaggttca   1200
agaagtattc gtactctagc cttttttaatc attcatagat agaagtcttt gtacccactc   1260
cttatgtttc ttttcattca taaacaggtg tataaggaac aatgtcttat aaacagcatg   1320
ggggcaatct gagaatattc ctcaaaaggt gtccaggtta aatagacatg ttactggctg   1380
cacacaggca aattctagtt tgtttttttt aagtattcta caacatttat ttaaaaaggt   1440
aaatcttttt gttgaagcag caagttatct ggtagaactt aacttctaca ggatcagaga   1500
ggatcttgct cattcatggc catatccaca tgcccatggc cactcagtag attgttgaaa   1560
aagcaaagcc acaccattct ctttgatgta tgcagagatt tacgtagcag gggatgttct   1620
ctgatttatt ccactggcac cattagtgaa tatttagttg ttttcataaa cgatgctgtg   1680
atgaagactc atgtacatat ttagcaaatt ttggtttctt acatgtgcct gtcatgactg   1740
taattcatta tgactgctcc aggaagggct aatgggccca atatattatt gcctgtcatg   1800
tggcacatcc atgttaaggg gctgagcgt ccctggcacg gaatgcagag ccctgagcta   1860
gggcatcagc agaagctgag atagagatat tggtcatggt tgactgagga gccaattaaa   1920
acctgtttat gcctagtgtt ccattattgg aacactaagc atgtgggagt tatttatatc   1980
ctactgctca aggtcatcgc caaggtgtga ttggaaaaat tcaaaaaatt gcaacctcag   2040
gcataaatgg gttaaggaca tcccaagccc aagtggtacg tgcctcactc agaactgacg   2100
ggccgagttc tatctaggtg tgtcttccag aacctgttta cggctaactg gataactgag   2160
agacttgtca tttctaaaga catttaagtt gctccaggga tttctgaaaa aagacacagg   2220
cttcttccta gagccagccc tatataacat gcccacaagg gcaacagtta tcacagttca   2280
tacacacctt tcatgtcctg tctcactcac tcctcacage catcctagga gatacatatt   2340
gttttcatcc tgcatttaca gaaaaagaaa tgaaacagaa gagcttaaat aatttgccac   2400
agtaatgtcg aaactaggcc tttgaaccaa ggcagtctag ggtaaaatat agtttcaaag   2460
tatgaataag aattggtatt tgtgttatct ttgagtaaga aactgtccga tatgaatcac   2520
aacgtgggtg aatgtagtat tttcctgaag tgtgaaagac ttaaaaaaaa gaatcacatt   2580
gttcagaggt gctcaatgga aagaaaagga aatgaacaag tttgttaaaa gataaaaaat   2640
aaaaaaatt ccatacct                                                  2658
SEQ ID NO: 91          moltype = DNA  length = 2490
FEATURE                Location/Qualifiers
source                 1..2490
                       mol_type = other DNA
                       organism = Homo sapiens
SEQUENCE: 91
gagtgcgggg gtcgcggcgc agagtgggag ccggagagcg agcgcggctg cagccggcgg     60
catggctagc acggcttcgg agatcatcgc cttcatggtc tccatctcag gctgggtact    120
ggtgtcctcc acgctgccca ccgactactg gaaggtgtct accatcgacg gcacggtcat    180
cacaaccgca acctattggg ccaacctgtg gaaggcgtgc gttaccgact ccacgggcgt    240
ctccaactgc aaggacttcc cctccatgct ggcgctggac ggttatatac aggcatgtag    300
aggacttatg atcgctgctg tcagcctggg cttctttggt tccatatttg cgctctttgg    360
aatgaagtgt accaaagtcg gaggctccga taaagccaaa gctaaaattg cttgtttggc    420
tgggattgta ttcatactgt cagggctgtg tcaatgact ggatgttccc tatatgcaaa    480
caaaatcaca acggaattct tgatcctctc ctttgttgag caaaagtatg aattaggagc    540
cgctctgttt attggatggg caggagcctc actgtgcata attggtggtg tcatattttg    600
cttttcaata tctgacaaca acaaaacacc cagatacaca tacaacgggg ccacatctgt    660
catgtcttct cggacaaagt atcatggtgg agaagatttt aaaacaacaa accttcaaa    720
acagtttgat aaaaatgctt atgtctaaaa gagctcgctg gcaagctgcc tcttgagttt    780
gttataaaag cgaactgttc acaaaatgat cccatcaagg ccctcccata attaacactc    840
aaaactattt ttaaaatatg catttgaagc atctgttgat tgtatggatg taagtgttct    900
tacatagtta gttatatact aatcatttc tgttgtggct ttctataaaa aataaacagt    960
ttatttacag gatttgtaaa atgttttcta catttatata gaacatgaaa agcatttaca   1020
accaaaggtt caagaagtat tcgtactcta gcctttttaa tcattcatag atagaagtct   1080
ttgtacccac tccttatgtt tcttttcatt cataaacagg tgtataagga acaatgtctt   1140
ataaacagca tgggggcaat ctgagaatat tcctcaaaag gtgtccaggt taaatagaca   1200
tgttactggc tgcacacagg caaattctag tttgttttt taagtattc tacaacattt   1260
atttaaaaag gtaaatcttt ttgttgaagc agcaagttat ctggtagaac ttaacttcta   1320
caggatcaga gaggatcttg ctcattcatg gccatatcca catgcccatg gccactcagt   1380
agattgttga aaaagcaaag ccacaccatt ctctttgatg tatgcagaga ttacgtagc   1440
aggggatgtt ctctgattta ttccactggc accattagtg aatatttagt tgttttcata   1500
aacgatgctg tgatgaagac tcatgtacat atttagcaaa ttttggtttc ttacatgtgc   1560
ctgtcatgac tgtaattcat tatgactgct ccaggaaggg ctaatgggcc aatatatta   1620
ttgcctgtca tgtggcacat ccatgttaag gggctgagcg tccctggca cggaatgcag   1680
agccctgagc tagggcatca gcagaagctg agatagagat attggtcatg gttgactgag   1740
gagccaatta aaacctgttt atgcctagtg ttccattatt ggaacactaa gcatgtggga   1800
gttatttata tcctactgct caaggtcatc gccaaggtgt gattggaaaa attcaaaaaa   1860
ttgcaacctc aggcataaat gggttaagga catcccaagc ccaagtggta cgtgcctcac   1920
```

```
tcagaactga cgggccgagt tctatctagg tgtgtcttcc agaacctgtt tacggctaac   1980
tggataactg agagacttgt catttctaaa gacatttaag ttgctccagg gatttctgaa   2040
aaaagacaca ggcttcttcc tagagccagc cctatataac atgcccacaa gggcaacagt   2100
tatcacagtt catacacacc tttcatgtcc tgtctcactc actcctcaca gccatcctag   2160
gagatacata ttgtttttcat cctgcattta cagaaaaaga aatgaaaaca gagagcttaa   2220
ataatttgcc acagtaatgt cgaaactagg cctttgaacc aaggcagtct agggtaaaat   2280
atagttttcaa agtatgaata agaattggta tttgtgttat ctttgagtaa gaaactgtcc   2340
gatatgaatc acaacgtggg tgaatgtagt attttcctga agtgtgaaag acttaaaaaa   2400
aagaatcaca ttgttcagag gtgctcaatg gaaagaaaag gaaatgaaca agtttgttaa   2460
aagataaaaa ataaaaaaaa ttccatacct                                    2490

SEQ ID NO: 92           moltype = DNA   length = 2424
FEATURE                 Location/Qualifiers
source                  1..2424
                        mol_type = other DNA
                        organism = Homo sapiens
SEQUENCE: 92
gttccccgcg tgccaccagg aagctcgggc cggccaagag cgtagactct tgagaggagt   60
gagacaggtg cgcgccagcc ggccttcggg gctttatggg aactgggccg tgcggcggtc   120
ccgcccctcgt gcgcaggcgc agaaccgttg tgaccagagc ggttgcgggc tgagcggttt   180
cgagccggct cgggagcg gcggtaccgg gcggctgcgg ggctggctcg acccagcttg   240
aggtctcggc gtccgcgtcc tgcggtgccc tggggtctcc cgaggacctt gtacccgcgc   300
ggcttccttg ggctggcttt ggacgacgct ttcgccttcc tgctgcctag gatccgccga   360
catgaatccc atcgtagtgg tccacggcgg cggagccggt cccatctcca aggatcggaa   420
ggagcgagtg caccagggca tggtcagagc cgccaccgtg ggctacggca tcctccggga   480
gggcgggagc gccgtggatg cccgtagaggg agctgtcgtc gccctggaag acgatccgga   540
gttcaacgca ggttgtgggt ctgtcttgaa cacaaatggt gaggttgaaa tggatgctag   600
tatcatggat ggaaaagacc tgtctgcagg agcagtgtcc gcagtccagt gtatagcaaa   660
tcccattaaa cttgctcggc ttgtcatgga aagacacct cattgctttc tgactgacca   720
aggcgcagcg cagtttgcag cagctatggg ggttccagaa attcctggag aaaaactggt   780
gacagagaga aacaaaaagc gcctggaaaa agagaagcat gaaaaaggtg ctcagaaaac   840
agattgtcaa aaaaacttgg gaaccgtggg tgctgttgcc ttggactgca aagggaatgt   900
agcctacgca acctccacag gcggtatcgt taataaaatg gtcggccgcg ttggggactc   960
accgtgtcta ggagctggag gttatgccga caatgacatc ggagccgtct caaccacagg   1020
gcatgggaa agcatcctga aggtgaacct ggctagactc accctgttcc acatagaaca   1080
aggaaagacg gtagaagagg ctgcggacct atcgttgggt tatatgaagt caagggttaa   1140
aggtttaggt ggcctcatcg tggttagcaa aacaggagac tgggtggcaa agtggacctc   1200
cacctccatg ccctgggcag ccgccaagga cggcaagctg cacttcggaa ttgatcctga   1260
cgatactact atcaccgacc ttccctaagc cgctggaaga ttgtattcca gatgctagct   1320
tagaggtcaa gtacagtctc ctcatgagac atagcctaat caattagatc tagaattgga   1380
aaaattgtcc cgtctgtcac ttgttttgtt gccttaataa gcatcgaat gtttggttgt   1440
ggggcgggtt ctgaagcgat gagagaaatg cccgtattag gaggattact tgagcccagg   1500
aggtcaaagc tgaggtgagc catgattact ccactgcact ccagcctggg caacagagcc   1560
aggccctgta tcaaaaaaaa aaaaaaaag aaaagggaaa aagaaagaa agcagcagca   1620
tgatcctgac atgacagatg tgggagaccc acagcctgca gacactgtgg gctgaaggt   1680
gggaagggag gggccggtgg aggtggagct gtttgaaagt gacacagcag cagtagaagc   1740
agtggtgggc gaagcccagg tgaccctcag aacgttgcac aagaacatca gggaaaagaa   1800
ccagaatcct ttaaggaaaa tgttcttcat gtatgagaga ctaaagtgat tttttctaaga   1860
aagttcagcc cttctctgac ttaccttggac atttctagat acttccaaag gacctctctgg   1920
gaatccatag cttcctaatc tggagatggg aggtcataag ggagacgctg tggggttcct   1980
tgaagtttct tgggttcaca gaggagcccc ctcacttggt gttctcccgt gagccagcct   2040
ccacctgcca aagacactct ggtcctcgta tagtgagtaa tggggctcag ggcctctcca   2100
acaacagaga ggagctgatg ctgtagggct gaccccgtga cttcctgagt cctcaccctg   2160
tccagtgctt tgagattctt cccacctccc catcctcacc agccggatcg ggcgctgtgc   2220
agtgtggtca gcatggtgaa gaaagtcatt tcctcggtgg gcagtattcc tctttatctc   2280
tcattacact ggaaatgtta tttctgctgt atcatccgtg ctcaacgttt tagtctgtca   2340
ggctcacctt ctctctggaa agaatttgct taacttgaca ttccatgtgc cgctaataaa   2400
atatattttg aaagaataaa aaaa                                          2424

SEQ ID NO: 93           moltype = DNA   length = 2347
FEATURE                 Location/Qualifiers
source                  1..2347
                        mol_type = other DNA
                        organism = Homo sapiens
SEQUENCE: 93
gttccccgcg tgccaccagg aagctcgggc cggccaagag cgtagactct tgagaggagt   60
gagacaggtg cgcgccagcc ggccttcggg gctttatggg aactgggccg tgcggcggtc   120
ccgcccctcgt gcgcaggcgc agaaccgttg tgaccagagc ggttgcgggc tgagcggttt   180
cgagccgcg tcgggagcg gcggtaccgg gcggctgcgg ggctggctcg acccagcttg   240
aggtctcggc gtccgcgtcc tgcggtgccc tgggatccgc cgacatgaat cccatcgtag   300
tggtccacgg cggcggagcc ggtcccatct ccaaggatcg gaaggagcga gtgcaccagg   360
gcatggtcag agccgccacc gtgggctacg gcatcctccg ggagggcggg agcgccgtgg   420
atgccgtaga gggagctgtc gtcgccctgg aagacgatcc cgagttcaac gcaggttgtg   480
ggtctgtctt gaacacaaat ggtgaggttg aaatggatgc tagtatcatg gatggaaaag   540
acctgtctgt aggagcagtg tccgcagtcc agtgtatagc aaatcccatt aaacttgctc   600
ggcttgtcat ggaaaagaca cctcattgct ttctgactga ccaaggcgca gcgcagtttg   660
cagcagctat gggggttcca gagattcctg gagaaaaact ggtgacagag agaaacaaaa   720
agcgcctgga aaaagagaag catgaaaaag gtgctcagaa aacagattgt caaaaaaact   780
tgggaaccgt gggtgctgtt gccttggact gcaaagggaa tgtagcctac gcaacctcca   840
```

```
caggcggtat cgttaataaa atggtcggcc gcgttgggga ctcaccgtgt ctaggagctg    900
gaggttatgc cgacaatgac atcggagccg tctcaaccac agggcatggg gaaagcatcc    960
tgaaggtgaa cctggctaga ctcaccctgt tccacataga acaaggaaag acggtagaag   1020
aggctgcgga cctatcgttg ggttatatga agtcaagggt taaaggttta ggtggcctca   1080
tcgtggttag caaaacagga gactgggtgg caaagtggac ctccacctcc atgccctggg   1140
cagccgccaa ggacggcaag ctgcacttcg gaattgatcc tgacgatact actatccaccg   1200
accttcccta agccgctgga agattgtatt ccagatgcta gcttagaggt caagtacagt   1260
ctcctcatga gacatagcct aatcaattag atctagaatt ggaaaaattg tcccgtctgt   1320
cacttgtttt gttgccttaa taagcatctg aatgtttggt tgtggggcgg gttctgaagc   1380
gatgagagaa atgcccgtat taggaggatt acttgagccc aggaggtcaa agctgaggtg   1440
agccatgatt actccactgc actccagcct gggcaacaga gccaggccct gtatcaaaaa   1500
aaaaaaaaaa aagaaaaggg aaaaaagaaa gaaagcagca gcatgatcct gacatgacag   1560
atgtgggaga cccacagcct gcagacactg tgggctggaa ggtgggaagg gaggggccgg   1620
tggaggtgga gctgtttgaa agtgacacag cagcagtaga agcagtggtg ggcgaagccc   1680
aggtgaccct cagaacgttg cacaagaaca tcagggaaaa gaaccagaat cctttaagga   1740
aaatgttctt catgtatgag agactaaagt gattttttcta agaaagttca gcccttctct   1800
gacttacctg gacatttcta gatacttcca aaggaccctc tgggaatcca tagcttccta   1860
atctggagat gggaggtcat aagggagacg ctgtgggggtt ccttgaagtt tcttgggttc   1920
acagaggagc cccctcactt ggtgttctcc cgtgagccag cctccacctg ccaaagacac   1980
tctggtcctc gtatagtgag taatgggggct cagggcctct ccaacaacag agaggagctg   2040
atgctgtagg gctgacccccg tgacttcctg agtcctcacc ctgtccagtg ctttgagatt   2100
cttcccacct ccccatcctc accagccgga tcgggcgcta tcgcagtgtgg tcagcatggt   2160
gaagaaagtc atttcctcgg tgggcagtat tcctctttat ctctcattac actgaaatg   2220
ttatttctgc tgtatcatcc gtgctcaacg ttttagtctg tcaggctcac cttctctctg   2280
gaaagaattt gcttaacttg acattccatg tgccgctaat aaaatatatt ttgaaagaat   2340
aaaaaaa                                                             2347

SEQ ID NO: 94          moltype = DNA  length = 2205
FEATURE                Location/Qualifiers
source                 1..2205
                       mol_type = other DNA
                       organism = Homo sapiens
SEQUENCE: 94
tccccctggac ccgcccccat ctgcccaaga taattttagt ttccttgggc ctggaatctg     60
gacacacagg gctccccccc gcctctgact tctctgtccg aagtcgggac accctcctac    120
cacctgtaga gaagcgggag tggatctgaa ataaaatcca ggaatctggg ggttcctaga    180
cggagccaga cttcggaacg ggtgtcctgc tactcctgct ggggctcctc caggacaagg    240
gcacacaact ggttccgtta agcccctctc ttgctcagac gccatggagc tggatctgtc    300
tccacctcat cttagcagct ctccggaaga cctttgccca gccctctggga ccctcctgg    360
gactccccgg cccccctgata cccctctgcc tgaggaggta aagagagtccc agcctctcct    420
catcccaacc accggcagga aacttcgaga ggaggagagg cgtgccacct ccctcccctc    480
tatccccaac cccttccctg agctctgcag tcctccctca cagagcccaa ttctcggggg    540
cccctccagt gcaaggggc tgctcccccg cgatgccagc cgcccccatg tagtaaaggt    600
gtacagtgag gatgggggcct gcaggtctgt ggaggtggca gcaggtgcca cagctcgcca    660
cgtgtgtgaa atgctggtgc agcgagctca cgccttgagc gacgagacct gggggctggt    720
ggagtgccac ccccaccctag cactggagcg gggtttggag gaccacgagt ccgtggtgga    780
agtgcaggct gcctggcccg tgggcggaga tagccgcttc gtcttccgga aaaacttcga    840
caagtacgaa ctgttcaaga gctccccaca ctccctgttc ccagaaaaaa tggtctccag    900
ctgtctcgat gcacacactg gtatatccca tgaagacctc atccagaact tcctgaatgc    960
tggcagcttt cctgagatcc agggcttttct gcagctgcgg ggttcaggac ggaagctttg   1020
gaaacgtttt ttctgcttct tgcgccgatc tggcctctat tactccacca agggcacctc   1080
taaggatccg aggcacctgc agtacgtggc agatgtgaac gagtccaacg tgtacggtgt   1140
gacgcagggc cgcaagctct acgggatgcc cactgacttc ggtttctgtg tcaagcccaa   1200
caagcttcga aatggccaca aggggctttcg gatcttctgc agtgaagatg agcagagccg   1260
cacctgctgg ctggctgcct tccgcctctt caagtacggg gtgcagctgt acaagaatta   1320
ccagcaggca cagtctcgcc atctgcatcc atcttgtttg ggctcccac ccttgagaag   1380
tgcctcagat aataccctgg tggccatgga cttctctggc catgctgggc gtgtcattga   1440
gaaccccgg gaggctctga gtgtggccct ggaggaggcc caggcctgga ggaagaagac   1500
aaaccaccgc ctcagcctgc ccatgccagc ctccggcacg agcctcagtg cagcctgttc   1560
ctggtccggg agagtcagcg gaaccccag ggctttgtcc tctctttgtg ccacctgcag   1620
aaagtgaagc attatctcat cctgccgagc gaggaggagg gccgcctgta cttcagcatg   1680
gatgatggcc agacccgctt cactgacctg ctgcagctcg tggagttcca ccagctgaac   1740
cgcggcatcc tgccgtgctt gctgcgcat tgctgcacgc gggtggccct ctgaccaggc   1800
cgtggactgg ctcatgcctc agcccgcctt caggctggcc caggccccctc cacccatcca   1860
gtggactctg gggcgcggcc acaggggacg ggatgaggag cgggagggtt ccgccactcc   1920
agtttttctcc tctgcttctt tgcctccctc agatagaaaa cagcccccac tccagtccac   1980
tcctgacccc tctcctcaag ggaaggcctt gggtggcccc ctctcttct cctagctctg   2040
gaggtgctgc tctagggcag ggaattatgg gagaagtggg ggcagcccag gcggtttcac   2100
gccccacact ttgtacagac cgagaggcca gttgatctgc tctgttttat actagtgaca   2160
ataaagatta ttttttgata caaaaaaaaa aaaaaaaaaa aaaaa                    2205

SEQ ID NO: 95          moltype = DNA  length = 1210
FEATURE                Location/Qualifiers
source                 1..1210
                       mol_type = other DNA
                       organism = Homo sapiens
SEQUENCE: 95
ctctcccttc tccactctct cccctgtct cctttcttct tcttctttca ccctccgtct     60
ctcacacccc ctccattccc ctgtctcctt tctgacactg cactgcagct gctcctcagc    120
```

-continued

```
cctgccccct ccccagtgag aacaaaccag caacattgct tttttccta aagagattta   180
tattgatccg attaaaaaaa aaaaacctta agaaacccca aacgcaaaaa aaaaaaaaaa   240
aaaaaaagaa aaaagaaaag aaaaagccaa aacaaaaggg agaaccttct cccggtagca   300
gcggcaggaa ctgcaaacat gatggcggca gctcccatcc agcagaacgg gacccacact   360
ggggttccca tagacctgga cccgccggac tcgcggaaaa ggccgctgga agcccccct    420
gaagccggca gcaccaagag gaccaatacg ggcgaagacg gccagtattt tctaaaggtt   480
ctcataccta gttatgctgc tggatctata attgggaagg gaggacagac aattgttcag   540
ttgcaaaaag aaactggagc caccatcaag ctgtctaagt ccaaagattt ttacccaggt   600
actactgagc gagtgtgctt gatccaggga acggttgaag cactgaatgc agttcatgga   660
ttcattgcag aaaaaattcg agaaatgccc caaaatgtgg ccaagacaga accagtcagc   720
attctacaac cccagaccac cgttaatcca gatcgcatca aacaaacatt gccatcttcc   780
ccaactacca ccaagtcctc tccatctgat cccatgacca cctccagagc taatcagaag   840
cataatatct cctggatatc atgaagcaag ataagagaga agaacaaaac aaaatccgta   900
attcattgaa agaattgtaa tcatcaatct ttcatattat taatactttg taattatttt   960
ctcccaaca gtattttcca gtagattcta atcatgtggt agggcagaag gaaatgtgtt  1020
ttttgttgtt catttgtttc ttgtcaatag tcctgattaa tttagctttg ctatactgac  1080
ttatatctgg aagtatataa ccaagataag aaaataggtt ttaatatgat catcttaagc  1140
taattgtaat gaaaagaact aatggactgt caatattcag aaaaccaaaa ataaaaaata  1200
cagaaaacta                                                          1210
```